United States Patent
Takeda et al.

(10) Patent No.: US 12,065,419 B2
(45) Date of Patent: Aug. 20, 2024

(54) ORGANIC COMPOUND, LIGHT-EMITTING DEVICE, LIGHT-EMITTING APPARATUS, ELECTRONIC DEVICE, DISPLAY DEVICE, AND LIGHTING DEVICE

(71) Applicant: Semiconductor Energy Laboratory Co., Ltd., Kanagawa-ken (JP)

(72) Inventors: Kyoko Takeda, Kanagawa (JP); Hiroshi Kadoma, Kanagawa (JP); Yusuke Takita, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 914 days.

(21) Appl. No.: 17/052,937

(22) PCT Filed: Apr. 30, 2019

(86) PCT No.: PCT/IB2019/053511
§ 371 (c)(1),
(2) Date: Nov. 4, 2020

(87) PCT Pub. No.: WO2019/215540
PCT Pub. Date: Nov. 14, 2019

(65) Prior Publication Data
US 2021/0139445 A1    May 13, 2021

(30) Foreign Application Priority Data

May 11, 2018 (JP) ................ 2018-092186

(51) Int. Cl.
*C07D 307/79* (2006.01)
*H10K 50/15* (2023.01)
*H10K 85/60* (2023.01)

(52) U.S. Cl.
CPC .......... *C07D 307/79* (2013.01); *H10K 85/636* (2023.02); *H10K 85/6574* (2023.02); *H10K 50/15* (2023.02)

(58) Field of Classification Search
CPC .. C07D 307/79; H10K 85/633; H10K 85/636; H10K 85/6572; H10K 85/6574; H10K 85/6576
See application file for complete search history.

(56) References Cited

U.S. PATENT DOCUMENTS

| | | |
|---|---|---|
| 9,412,953 B2 | 8/2016 | Inoue et al. |
| 9,447,111 B2 | 9/2016 | Kitamura et al. |

(Continued)

FOREIGN PATENT DOCUMENTS

| | | |
|---|---|---|
| CN | 101659593 A | 3/2010 |
| CN | 102924217 A | 2/2013 |

(Continued)

OTHER PUBLICATIONS

International Search Report (Application No. PCT/IB2019/053511) dated Jul. 16, 2019.

(Continued)

*Primary Examiner* — Kregg T Brooks
(74) *Attorney, Agent, or Firm* — Husch Blackwell LLP

(57) ABSTRACT

A novel organic compound is provided. Alternatively, an organic compound that exhibits light emission with favorable chromaticity is provided. Alternatively, an organic compound that exhibits blue light emission with favorable chromaticity is provided. Alternatively, a light-emitting device with favorable emission efficiency is provided. Alternatively, an organic compound having a high carrier-transport property is provided. Alternatively, an organic compound with favorable reliability is provided. An organic compound having at least one amino group in which any one (Continued)

of a substituted or unsubstituted dibenzofuranyl group, a substituted or unsubstituted dibenzothiophenyl group, and a substituted or unsubstituted carbazolyl group is bonded to any one of a substituted or unsubstituted naphthobisbenzofuran skeleton, a substituted or unsubstituted naphthobisbenzothiophene skeleton, and a substituted or unsubstituted naphthobenzothienobenzofuran skeleton is provided.

23 Claims, 46 Drawing Sheets

(56) References Cited

U.S. PATENT DOCUMENTS

| | | |
|---|---|---|
| 9,496,503 B2 | 11/2016 | Takeda et al. |
| 9,586,972 B2 | 3/2017 | Kitamura et al. |
| 9,634,263 B2 | 4/2017 | Ogita et al. |
| 10,003,031 B2 | 6/2018 | Jang et al. |
| 11,618,757 B2 | 4/2023 | Koo et al. |
| 2010/0032658 A1 | 2/2010 | Lee et al. |
| 2011/0248246 A1 | 10/2011 | Ogita et al. |
| 2015/0108440 A1 | 4/2015 | Jung et al. |
| 2015/0166560 A1 | 6/2015 | Kitamura et al. |
| 2015/0218184 A1 | 8/2015 | Kitamura et al. |
| 2015/0349276 A1 | 12/2015 | Jang et al. |
| 2018/0201621 A1 | 7/2018 | Park et al. |
| 2018/0282276 A1 | 10/2018 | Mun et al. |
| 2019/0378992 A1 | 12/2019 | Skulason et al. |
| 2020/0181165 A1 | 6/2020 | Koo et al. |

FOREIGN PATENT DOCUMENTS

| | | |
|---|---|---|
| CN | 109153685 A | 1/2019 |
| EP | 2 145 936 A2 | 1/2010 |
| JP | 2010-059147 A | 3/2010 |
| JP | 2013-232521 A | 11/2013 |
| JP | 2013-234151 A | 11/2013 |
| JP | 2014-045099 A | 3/2014 |
| JP | 2014-082247 A | 5/2014 |
| JP | 2014-237682 A | 12/2014 |
| JP | 2016-503761 | 2/2016 |
| KR | 2010-0007780 A | 1/2010 |
| KR | 2014-0023407 A | 2/2014 |
| KR | 2014-0023408 A | 2/2014 |
| KR | 2014-0024438 A | 2/2014 |
| KR | 2014-0024439 A | 2/2014 |
| KR | 2014-0024440 A | 2/2014 |
| KR | 2015-0046639 A | 4/2015 |
| KR | 2015-0048182 A | 5/2015 |
| KR | 2016-0115114 A | 10/2016 |
| KR | 2017-0022505 A | 3/2017 |
| KR | 2019-0044561 A | 4/2019 |
| TW | 201009046 | 3/2010 |
| TW | 201408670 | 3/2014 |
| TW | 201414717 | 4/2014 |
| WO | WO 2014/034393 A1 | 3/2014 |
| WO | WO 2014/061464 A1 | 4/2014 |
| WO | WO 2014/092362 A1 | 6/2014 |
| WO | WO 2016/153198 A1 | 9/2016 |
| WO | WO 2017/030307 A1 | 2/2017 |
| WO | WO 2018/185571 A1 | 10/2018 |
| WO | WO 2019/078692 A1 | 4/2019 |

OTHER PUBLICATIONS

Written Opinion (Application No. PCT/IB2019/053511) dated Jul. 16, 2019.

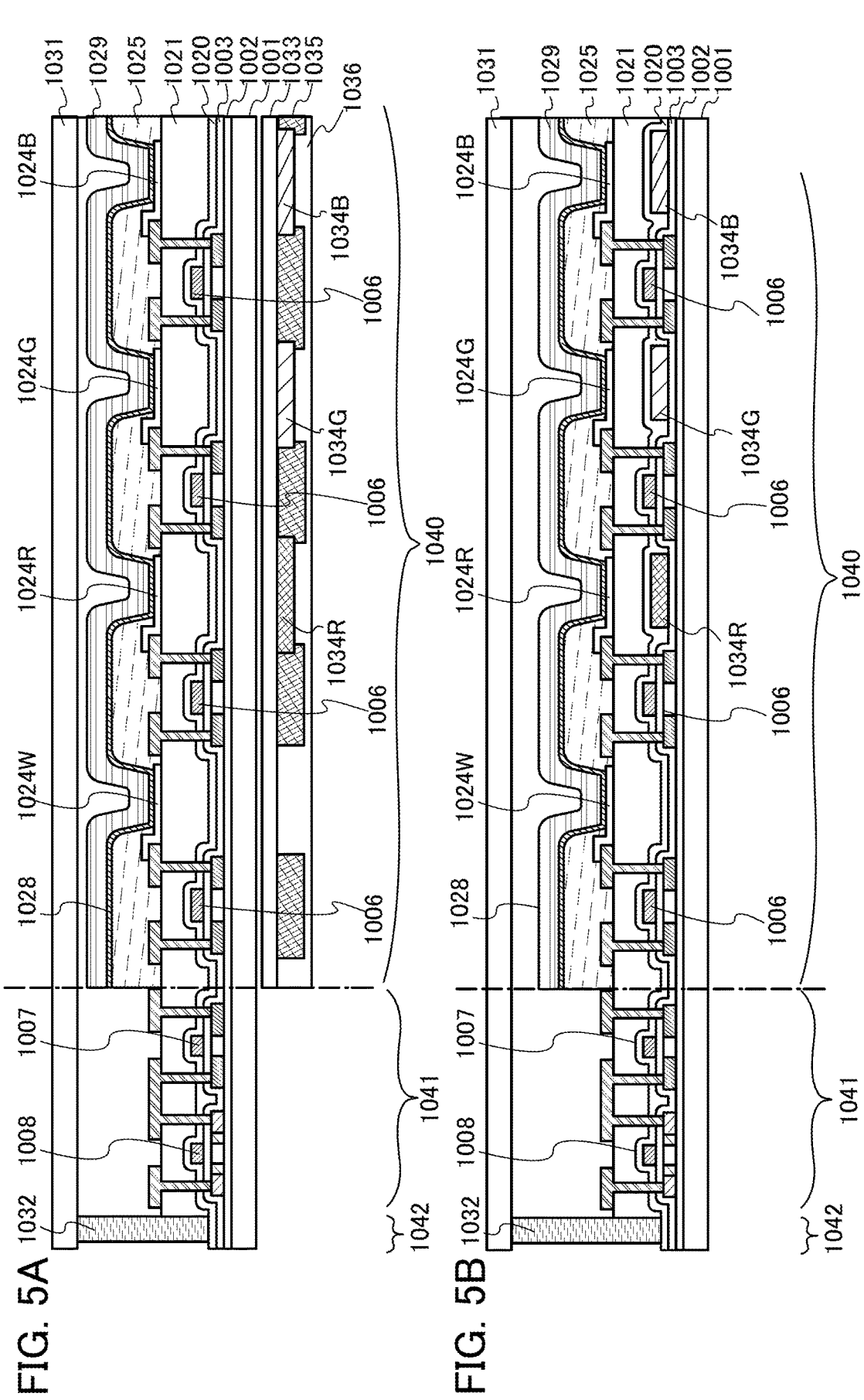

FIG. 9A
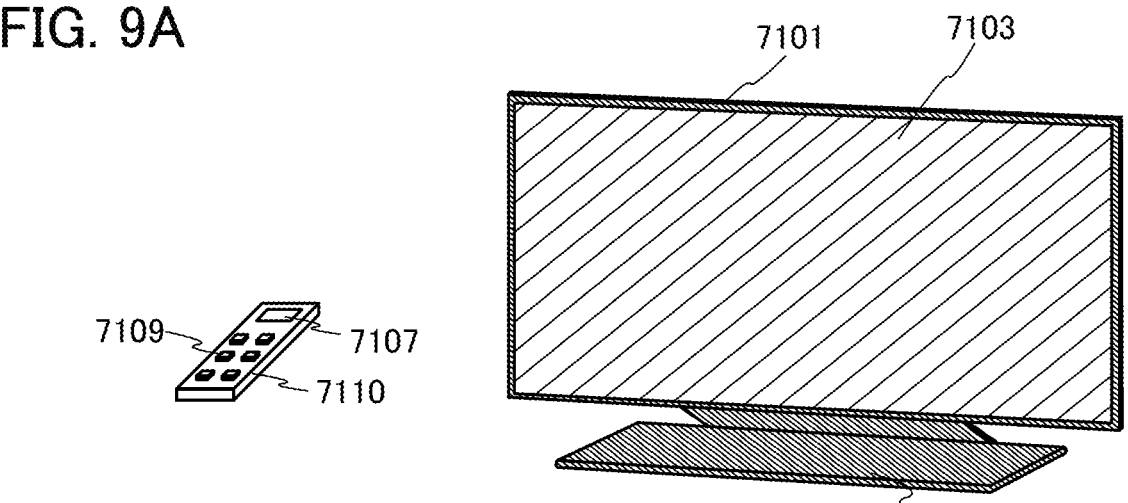
FIG. 9B1
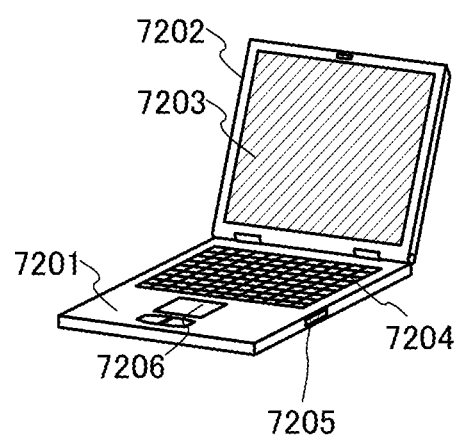
FIG. 9B2
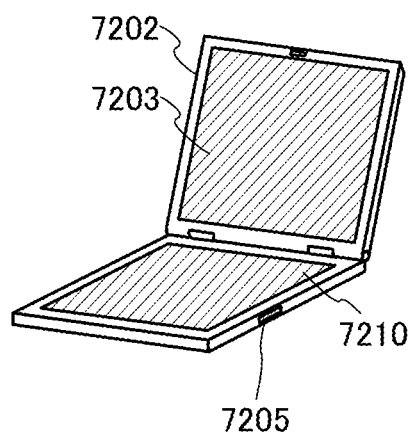
FIG. 9C
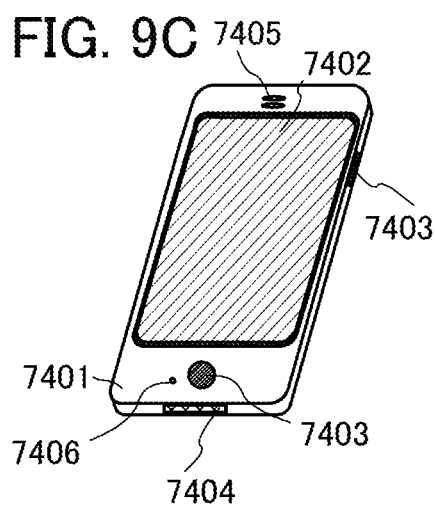
FIG. 9D
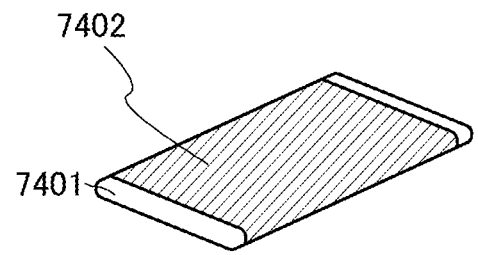

ORGANIC COMPOUND, LIGHT-EMITTING DEVICE, LIGHT-EMITTING APPARATUS, ELECTRONIC DEVICE, DISPLAY DEVICE, AND LIGHTING DEVICE

This application is a 371 of international application PCT/IB2019/053511 filed on Apr. 30, 2019 which is incorporated herein by reference.

TECHNICAL FIELD

One embodiment of the present invention relates to an organic compound, and a light-emitting device, a display module, a lighting module, a display device, a light-emitting apparatus, an electronic device, and a lighting device each using the organic compound. Note that one embodiment of the present invention is not limited to the above technical field. The technical field of one embodiment of the invention disclosed in this specification and the like relates to an object, a method, or a manufacturing method. Alternatively, one embodiment of the present invention relates to a process, a machine, manufacture, or a composition of matter. Accordingly, the following can be given as an example of the technical field of one embodiment of the present invention that is more specifically disclosed in this specification: a semiconductor device, a display device, a liquid crystal display device, a light-emitting apparatus, a lighting device, a power storage device, a memory device, an imaging device, a method for driving any of them, or a method for manufacturing any of them.

BACKGROUND ART

Display devices and light-emitting apparatuses including organic EL elements, some of which have been practically used, are finding wider applications. In recent years, liquid crystal displays have greatly progressed; thus, high quality is naturally required for organic EL displays that are regarded as next-generation displays.

Although a variety of substances has been developed as materials for organic EL displays, not so many of them have sufficient properties to withstand practical use. In light of diversity, affinity, and the like of combinations, there is no doubt that the number of options is preferably as large as possible.

Organic EL elements have a function-separated structure in which a plurality of functions are given to different substances. Demands for light-emitting materials, especially regarding emission efficiency that affects power consumption and emission colors to improve display quality, are higher than for others.

Patent Document 1 to Patent Document 4 disclose an organic compound having a naphthobisbenzofuran skeleton.

REFERENCES

Patent Documents

[Patent Document 1] Japanese Published Patent Application No. 2014-237682
[Patent Document 2] Japanese Published Patent Application No. 2010-59147
[Patent Document 3] Japanese Published Patent Application No. 2013-232521
[Patent Document 4] Japanese Translation of PCT International Application No. 2016-503761

SUMMARY OF THE INVENTION

Problems to be Solved by the Invention

An object of one embodiment of the present invention is to provide a novel organic compound. Another object is to provide an organic compound that emits light with excellent chromaticity. Another object is to provide an organic compound that emits blue light with excellent chromaticity. Another object is to provide a light-emitting device with high emission efficiency. Another object is to provide an organic compound with an excellent carrier-transport property. Another object is to provide an organic compound with high reliability.

Another object of one embodiment of the present invention is to provide a novel light-emitting device. Another object is to provide a light-emitting device with high emission efficiency. Another object is to provide a light-emitting device that emits light with excellent chromaticity. Another object is to provide a light-emitting device that emits blue light with excellent chromaticity. Another object is to provide a light-emitting device with an excellent lifetime. Another object is to provide a light-emitting device with low driving voltage.

Another object of one embodiment of the present invention is to provide a light-emitting apparatus, an electronic device, and a display device each having low power consumption. Another object of one embodiment of the present invention is to provide a light-emitting apparatus, an electronic device, and a display device each having high reliability. Another object of one embodiment of the present invention is to provide a light-emitting apparatus, an electronic device, and a display device each having high display quality.

It is only necessary that at least one of the above-described objects be achieved in the present invention.

Means for Solving the Problems

One embodiment of the present invention is an organic compound represented by a general formula (G1) below.

[Chemical Formula 1]

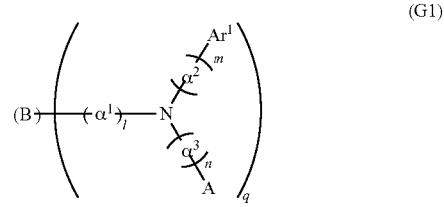

(G1)

Note that, in the formula, B is any of a substituted or unsubstituted naphthobisbenzofuran skeleton, a substituted or unsubstituted naphthobisbenzothiophene skeleton, and a substituted or unsubstituted naphthobenzothienobenzofuran skeleton.

Furthermore, $Ar^1$ is any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group. Note that the substituted or unsubstituted dibenzofuranyl group, the substituted or unsubstituted dibenzothiophenyl group, and the substituted or unsubstituted carbazolyl group may have a structure in which a benzene ring is further condensed.

A is any of a substituted or unsubstituted dibenzofuranyl group in which at least one benzene ring is condensed, a substituted or unsubstituted dibenzothiophenyl group in which at least one benzene ring is condensed, and a substituted or unsubstituted carbazolyl group in which at least one benzene ring is condensed, and $\alpha^1$ to $\alpha^3$ are each independently a substituted or unsubstituted divalent aromatic hydrocarbon group having 6 to 25 carbon atoms. l, m, and n each independently represent an integer of 0 to 2, and q is 1 or 2.

Another embodiment of the present invention is an organic compound represented by a general formula (G1) below.

[Chemical Formula 2]

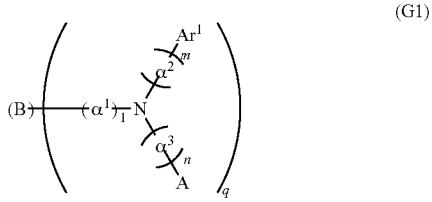
(G1)

Note that, in the formula, B is any of a substituted or unsubstituted naphthobisbenzofuran skeleton, a substituted or unsubstituted naphthobisbenzothiophene skeleton, and a substituted or unsubstituted naphthobenzothienobenzofuran skeleton. $Ar^1$ is any of a substituted or unsubstituted aromatic hydrocarbon group having 6 to 25 carbon atoms and groups represented by general formulae (g1) to (g3) below, and A is any of the groups represented by the general formulae (g1) to (g3) below. $\alpha^1$ to $\alpha^3$ are each independently any of substituted or unsubstituted divalent aromatic hydrocarbon groups having 6 to 14 carbon atoms. l, m, and n each independently represent an integer of 0 to 2, and q is 1 or 2.

[Chemical Formulae 3]

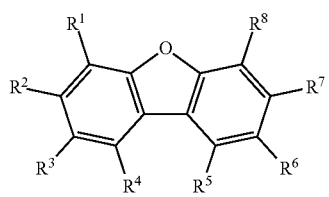
(g1)

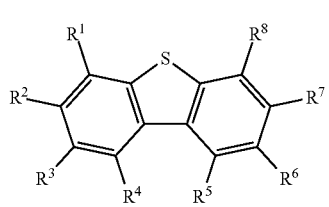
(g2)

-continued

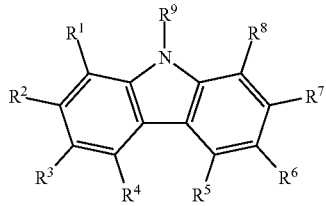
(g3)

In the general formulae (g1) to (g3), any one of $R^1$ to $R^9$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms.

Note that A is any of the general formulae (g1) to (g3), and has a structure in which condensation occurs in at least one of combinations of $R^1$ and $R^2$, $R^2$ and $R^3$, $R^3$ and $R^4$, $R^5$ and $R^6$, $R^6$ and $R^7$, and $R^7$ and $R^8$ among $R^1$ to $R^8$ in the general formulae (g1) to (g3) and a benzene ring is formed. When A is represented by the general formula (g3) and $R^9$ in the general formula (g3) represents a single bond, n is 1 or 2.

When $Ar^1$ is the group represented by the general formulae (g1) to (g3), $R^1$ and $R^2$, $R^2$ and $R^3$, $R^3$ and $R^4$, $R^5$ and $R^6$, $R^6$ and $R^7$, and $R^7$ and $R^8$ among $R^1$ to $R^8$ in the general formulae (g1) to (g3) may each have a structure in which they are condensed to form a benzene ring. When $Ar^1$ is represented by the general formula (g3) and $R^9$ in the general formula (g3) represents a single bond, m is 1 or 2.

Another embodiment of the present invention is the organic compound with the above structure, in which the B is any of skeletons represented by a general formula (B1) to a general formula (B4) below.

[Chemical Formulae 4]

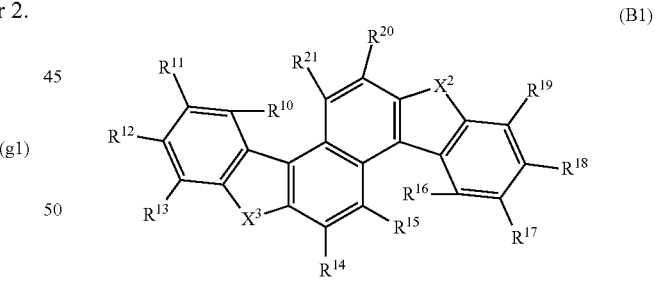
(B1)

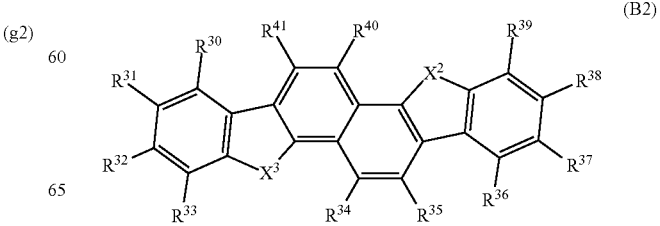
(B2)

-continued

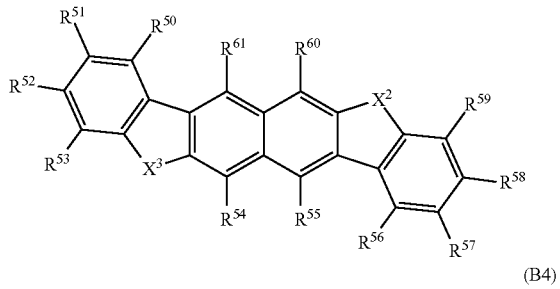
(B3)

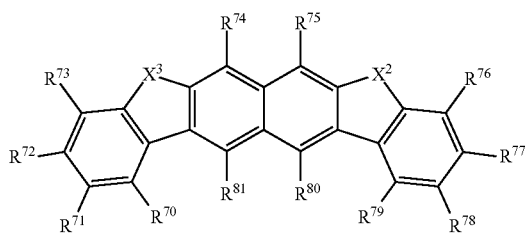
(B4)

Note that, in the formulae, X² and X³ each independently represent an oxygen atom or a sulfur atom.

Note that, in the general formula (B1), any one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B2), any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B3), any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B4), any one or two of $R^{70}$ to $R^{81}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Another embodiment of the present invention is the organic compound with the above structure, in which q in the general formula (G1) is 2.

Another embodiment of the present invention is the organic compound with the above structure, in which q in the general formula (G1) is 2 and the B is any of skeletons represented by a general formula (B1) to a general formula (B4) below.

[Chemical Formulae 5]

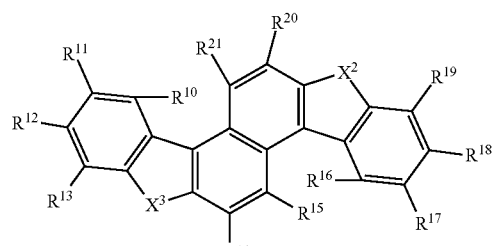
(B1)

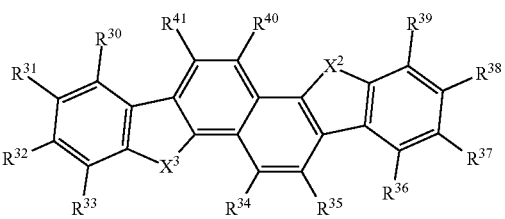
(B2)

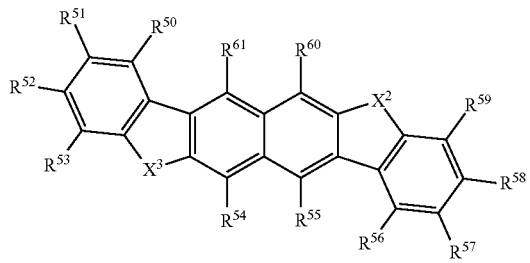
(B3)

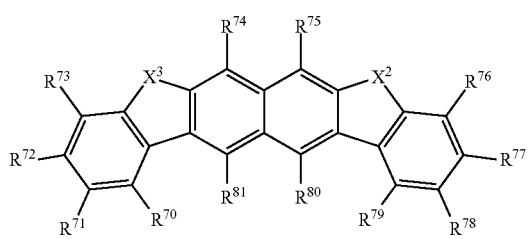
(B4)

Note that, in the formulae, X² and X³ each independently represent an oxygen atom or a sulfur atom.

Note that, in the general formula (B1), $R^{12}$ and $R^{18}$ represent a single bond and $R^{10}$, $R^{11}$, $R^{13}$ to $R^{17}$, and $R^{19}$ to $R^{21}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B2), $R^{32}$ and $R^{38}$ represent a single bond and $R^{30}$, $R^{31}$, $R^{33}$ to $R^{37}$, and $R^{39}$ to $R^{41}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B3), $R^{52}$ and $R^{58}$ represent a single bond and $R^{50}$, $R^{51}$, $R^{53}$ to $R^{57}$, and $R^{59}$ to $R^{61}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

In the general formula (B4), $R^{72}$ and $R^{77}$ represent a single bond and $R^{70}$, $R^{71}$, $R^{73}$ to $R^{76}$, and $R^{78}$ to $R^{81}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Another embodiment of the present invention is an organic compound represented by a general formula (G1-1) below.

[Chemical Formula 6]

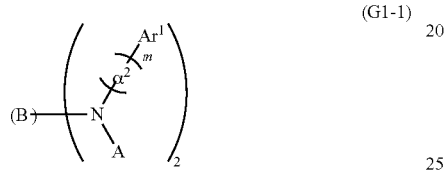

(G1-1)

Note that, in the general formula (G1-1), B represents a general formula (B1-1) or (B3-1) below. $Ar^1$ is a substituted or unsubstituted aromatic hydrocarbon group having 6 to 25 carbon atoms, and A is a group represented by a general formula (g0) below. m represents an integer of 0 to 2. $\alpha^2$ is a substituted or unsubstituted divalent aromatic hydrocarbon group having 6 to 14 carbon atoms.

[Chemical Formulae 7]

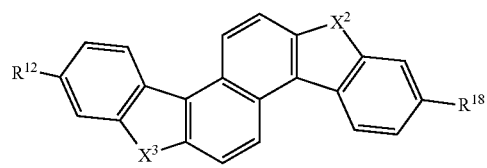

(B1-1)

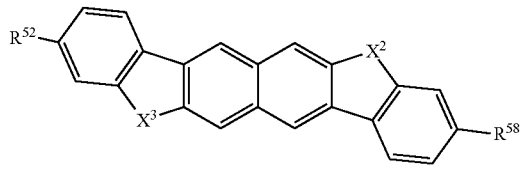

(B3-1)

Note that, in the general formula (B1-1) or (B3-1), $X^2$ and $X^3$ each independently represent an oxygen atom or a sulfur atom. $R^{12}$, $R^{18}$, $R^{52}$, and $R^{58}$ represent a single bond.

[Chemical Formula 8]

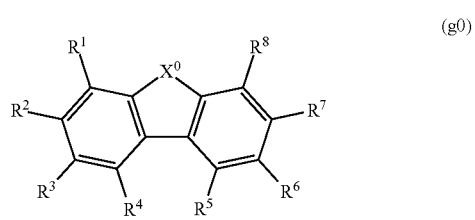

(g0)

Note that, in the general formula (g0), $X^0$ is an oxygen atom, a sulfur atom, or a nitrogen atom to which a substituted or unsubstituted phenyl group is bonded. Furthermore, $R^2$ represents a single bond. Among $R^3$ to $R^8$, condensation occurs in at least one of combinations of $R^3$ and $R^4$, $R^5$ and $R^6$, $R^6$ and $R^7$, and $R^7$ and $R^8$ and a benzene ring is formed, and the others represent a hydrogen atom.

Another embodiment of the present invention is the organic compound with the above structure, in which a molecular weight is less than or equal to 1300.

Another embodiment of the present invention is an organic compound represented by either of structural formulae below.

[Chemical Formula 9]

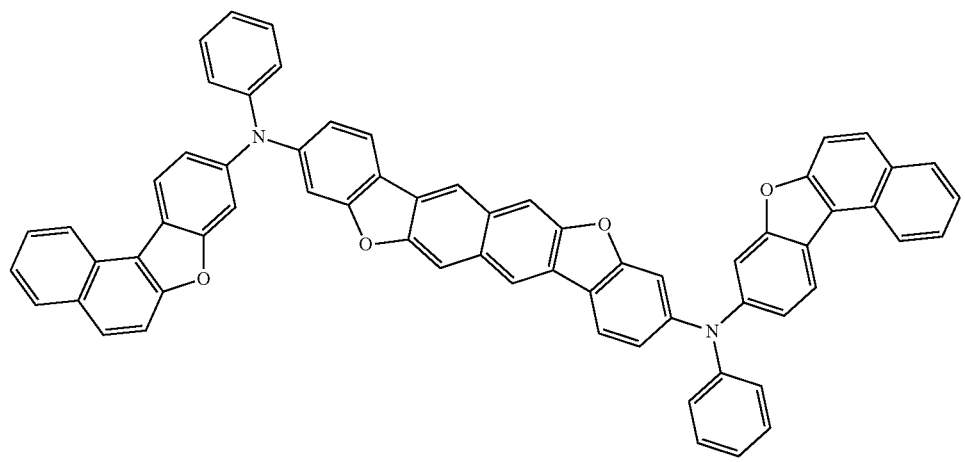

-continued

[Chemical Formula 10]

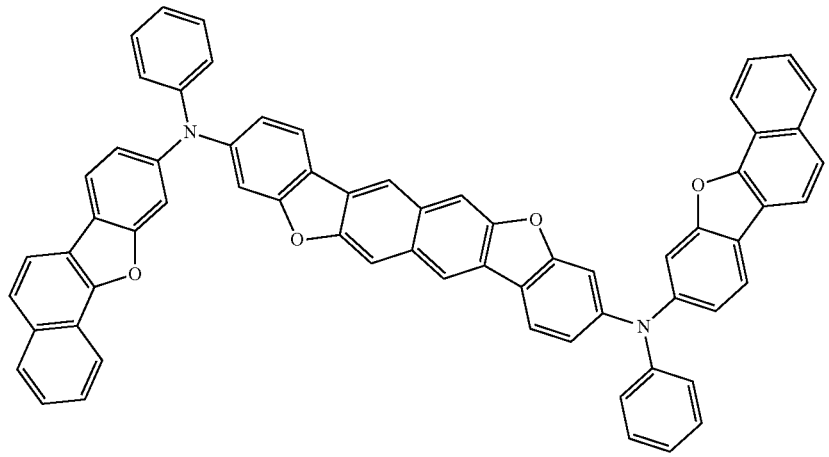

Another embodiment of the present invention is a light-emitting device containing the organic compound with the above structure.

Another embodiment of the present invention is a light-emitting apparatus including the light-emitting device with the above structure, and a transistor or a substrate.

Another embodiment of the present invention is an electronic device including the light-emitting apparatus with the above structure, and a sensor, an operation button, a speaker, or a microphone.

Another embodiment of the present invention is a lighting device including the light-emitting apparatus with the above structure and a housing.

Another embodiment of the present invention is an electronic device containing the organic compound with the above structure.

Note that the light-emitting apparatus in this specification includes an image display device that uses a light-emitting device. Moreover, the light-emitting apparatus may also include a module in which a connector such as an anisotropic conductive film or a TCP (Tape Carrier Package) is connected to a light-emitting device, a module in which a printed wiring board is provided on the tip of a TCP, or a module in which an IC (integrated circuit) is directly mounted on a light-emitting device by a COG (Chip On Glass) method. Furthermore, a lighting device or the like may include the light-emitting apparatus.

Effect of the Invention

According to one embodiment of the present invention, a novel organic compound can be provided. An organic compound that emits light with excellent chromaticity can be provided. An organic compound that emits blue light with excellent chromaticity can be provided. A light-emitting device with high emission efficiency can be provided. An organic compound with an excellent carrier-transport property can be provided. An organic compound with high reliability can be provided.

According to one embodiment of the present invention, a novel light-emitting device can be provided. A light-emitting device with high emission efficiency can be provided. A light-emitting device that emits light with excellent chromaticity can be provided. A light-emitting device that emits blue light with excellent chromaticity can be provided. A light-emitting device with an excellent lifetime can be provided. A light-emitting device with low driving voltage can be provided.

According to another embodiment of the present invention, a light-emitting apparatus, an electronic device, and a display device each having low power consumption can be provided. According to another embodiment of the present invention, a light-emitting apparatus, an electronic device, and a display device each having high reliability can be provided. According to another embodiment of the present invention, a light-emitting apparatus, an electronic device, and a display device each having high display quality can be provided.

Note that the description of the effects does not disturb the existence of other effects. Note that one embodiment of the present invention does not necessarily have all of these effects. Effects other than these will be apparent from the description of the specification, the drawings, the claims, and the like, and effects other than these can be derived from the description of the specification, the drawings, the claims, and the like.

BRIEF DESCRIPTION OF THE DRAWINGS

FIGS. 5A and 5B are schematic diagrams of active matrix light-emitting apparatuses.

Diagrams

FIGS. 9A-9D are diagrams illustrating electronic devices.

Emission

Emission

MODE FOR CARRYING OUT THE INVENTION

Figure 1A:
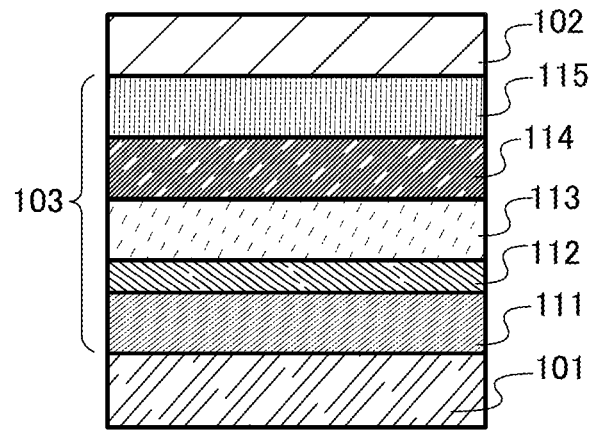
FIGS. 1A-1C are schematic diagrams of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

An organic compound of one embodiment of the present invention is an organic compound represented by a general formula (G1) below.

[Chemical Formula 11]

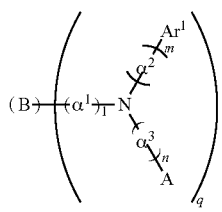

(G1)

In the above general formula (G1), a skeleton B represents any of a substituted or unsubstituted naphthobisbenzofuran skeleton, a substituted or unsubstituted naphthobisbenzothiophene skeleton, and a substituted or unsubstituted naphthobenzothienobenzofuran skeleton.

One or two arylamino groups are bonded to the skeleton B (i.e., q is 1 or 2), and the arylamino group has any one of a dibenzofuranyl group, a dibenzothiophenyl group, and a carbazolyl group, each of which has a structure in which one or more benzene rings are condensed.

That is, A in the above general formula (G1) represents any of three groups of a dibenzofuranyl group having a structure in which at least one benzene ring is condensed, a dibenzothiophenyl group having a structure in which at least one benzene ring is condensed, and a carbazolyl group having a structure in which at least one benzene ring is condensed. Note that these groups do not necessarily have a substituent, and the number of benzene rings condensed with these groups is preferably 1 or 2.

Furthermore, in the above general formula (G1), $Ar^1$ represents any of an aromatic hydrocarbon group having 6 to 25 carbon atoms, a dibenzofuranyl group, a dibenzothiophenyl group, and a carbazolyl group. Note that in the case where AO is any of a dibenzofuranyl group, a dibenzothiophenyl group, and a carbazolyl group, a benzene ring may be condensed with these groups and these groups do not necessarily have a substituent.

Note that in the case where A or $Ar^1$ is any of a dibenzofuranyl group, a dibenzothiophenyl group, and a carbazolyl group, each of which has a structure in which a benzene ring is condensed, the benzene ring is condensed at a position of a benzene skeleton originally included in these groups, i.e., A or AO has at least what is called a naphthalene skeleton, a skeleton in which two benzene rings are condensed.

In the above general formula (G1), $\alpha^1$, $\alpha^2$, and $\alpha^3$ are each independently any one of substituted or unsubstituted divalent aromatic hydrocarbon groups having 6 to 25 carbon atoms, and l, m, and n are each independently a numerical value of any of 0, 1, and 2.

The substituted or unsubstituted naphthobisbenzofuran skeleton, the substituted or unsubstituted naphthobisbenzothiophene skeleton, or the substituted or unsubstituted naphthobenzothienobenzofuran skeleton is a very useful skeleton as a luminophore. An organic compound having the skeleton has high emission efficiency and exhibits favorable blue light emission; thus, a light-emitting device using the organic compound can be a blue light-emitting device with favorable emission efficiency. While a variety of substances have been developed as blue fluorescent materials, this organic compound is a highly promising material as a blue light-emitting material for representing a color gamut covering the ITU-R BT.2020 standard, which is an international standard of a super wide color gamut conforming to 8K displays, because of its significantly excellent chromaticity of blue light emission.

The present inventors have found that a light-emitting device using, for these skeletons useful as a luminophore, an organic compound having unique arylamine including any one or more of a dibenzofuranyl group having a structure in which a benzene ring is condensed, a dibenzothiophenyl group having a structure in which a benzene ring is condensed, and a carbazolyl group having a structure in which a benzene ring is condensed can be a light-emitting device with especially favorable characteristics. Specifically, effects such as more favorable emission efficiency and favorable color purity can be provided.

The dibenzofuranyl group, the dibenzothiophenyl group, and the carbazolyl group, which are some of the choices for A and AO in the above general formula (G1), can also be represented by a general formula (g1) to a general formula (g3) below.

[Chemical Formulae 12]

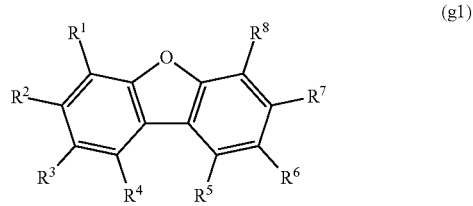

(g1)

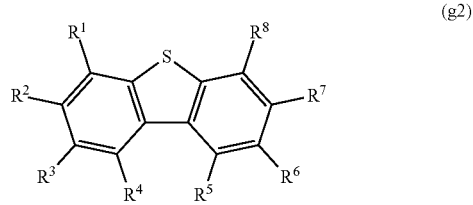

(g2)

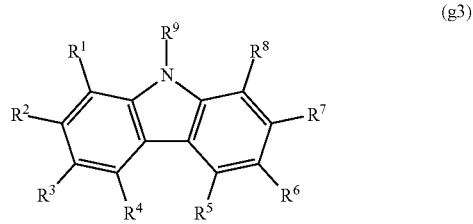

(g3)

In the above general formula (g1) to general formula (g3), any one of $R^1$ to $R^9$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms.

Note that the groups represented by the above general formulae (g1) to (g3) can also be represented by a general formula (g0) below.

[Chemical Formula 13]

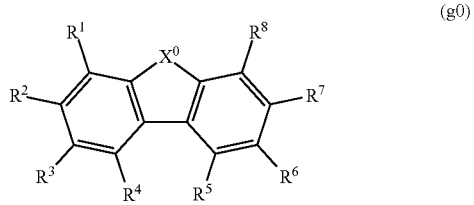

(g0)

In the above general formula (g0), $X^0$ is an oxygen atom, a sulfur atom, or a nitrogen atom to which a substituted or unsubstituted phenyl group is bonded. Furthermore, any one of $R^1$ to $R^8$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms.

Note that in the case where A is the group represented by any one of the general formula (g0) and the general formulae (g1) to (g3), A is a group having a condensed polycyclic structure in which condensation occurs in at least one of combinations of $R^1$ and $R^2$, $R^2$ and $R^3$, $R^3$ and $R^4$, $R^5$ and $R^6$, $R^6$ and $R^7$, and $R^7$ and $R^8$ and a benzene ring is formed.

In the case where $Ar^1$ is the group represented by any one of the general formula (g0) and the general formulae (g1) to (g3), $R^1$ and $R^2$, $R^2$ and $R^3$, $R^3$ and $R^4$, $R^5$ and $R^6$, $R^6$ and $R^7$, and $R^7$ and $R^8$ out of $R^1$ to $R^8$ may have a condensed polycyclic structure in which they are condensed to form a benzene ring.

Note that in the case where A is the group represented by the above general formula (g3) and $R^9$ in the group represented by the above general formula (g3) represents a single bond, n in the above general formula (G1) is preferably 1 or 2. Furthermore, in the case where AO is the group represented by the above general formula (g3) and $R^9$ in (g3) represents a single bond, m in the above general formula (G1) is 1 or 2.

In the case where one or both of $Ar^1$ and A are the group represented by the above general formula (g1), any one of $R^1$ to $R^3$ is preferably a single bond. Similarly, in the case where one or both of AO and A are the group represented by the above general formula (g2), any one of $R^1$ to $R^3$ is preferably a single bond. In the case where one or both of $Ar^1$ and A are the group represented by the above general formula (g3), $R^2$ or $R^3$ is preferably a single bond.

Note that the above general formulae (g0) to (g3) are bonded to $\alpha^2$, $\alpha^3$, or N in the above general formula (G1) with a single bond, which is any one of $R^1$ to $R^8$.

Unless A in the above general formula (G1) is the group represented by the above general formula (g3) and $R^9$ is a single bond, a structure where n is 0 is a preferable mode because the number of synthesis steps is small and the sublimation temperature is low. Furthermore, l and n are each preferably 0 regardless of A because the number of synthesis steps is small and the sublimation temperature is low.

In the case where A in the above general formula (G1) is the group represented by the above general formula (g3) and $R^9$ is a single bond, a structure where n is 1 is a preferable mode because synthesis is facilitated and chemical stability is achieved. Also in the case where AO is the group represented by the above general formula (g3) and $R^9$ is a single bond, a structure where m is 1 is preferable for the same reason.

Furthermore, one or both of A and AO in the general formula (G1) are preferably the group represented by the above general formula (g1) or the group represented by the above general formula (g2), preferably the group represented by the above general formula (g1), in which case the organic compound represented by the above general formula (G1) emits light with a short wavelength.

In that case, the position of the single bond bonded to $\alpha^2$, $\alpha^3$, or N in the group represented by the above general formula (g1) or the group represented by the above general formula (g2) is preferably $R^1$ or $R^2$ because shorter wavelength light emission is obtained. Furthermore, the position of the single bond bonded to $\alpha^2$, $\alpha^3$, or N in the group represented by the above general formula (g1) or the group represented by the above general formula (g2) is preferably $R^2$ or $R^3$ because the emission quantum yield becomes higher. Furthermore, the position of the single bond is preferably $R^2$ because the emission spectrum becomes narrower.

Furthermore, one or both of AO and A in the general formula (G1) are preferably the group represented by the above general formula (g3) because the reliability can be favorable.

Furthermore, $Ar^1$ is preferably a substituted or unsubstituted aromatic hydrocarbon group having 6 to 25 carbon atoms because the sublimation temperature can be low.

Furthermore, q of 2 is preferable, in which case the quantum yield can be higher. Moreover, q of 1 is preferable, in which case the sublimation temperature can be lower.

Note that in this specification, the sublimation temperature also means an evaporation temperature.

Typical examples of a group represented by A in the above general formula (G1) are shown in the following structural formulae (Ar-200) to (Ar-284). Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 14]

(Ar-200)

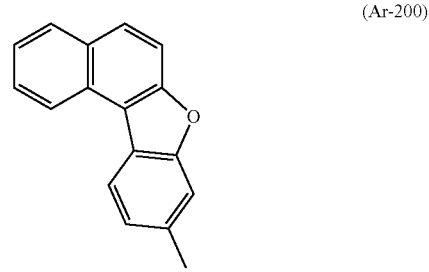

(Ar-201)
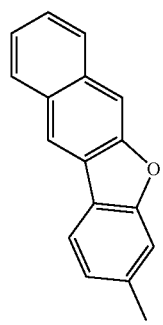
(Ar-202)
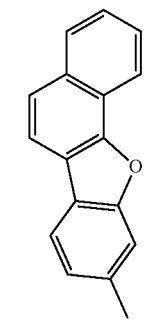
(Ar-203)
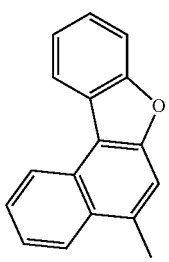
(Ar-204)
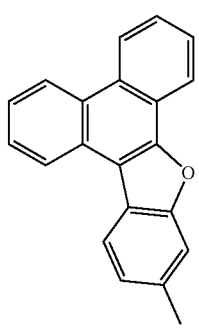
(Ar-205)
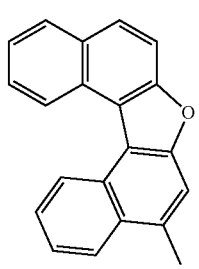
(Ar-206)
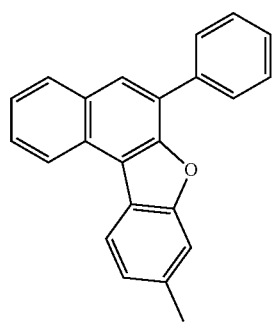
(Ar-207)
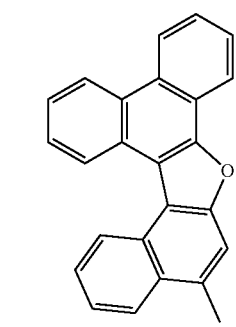
(Ar-208)
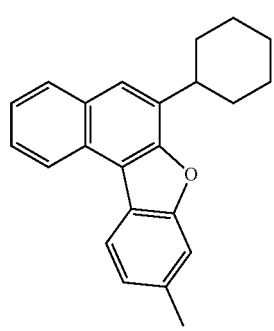
(Ar-209)
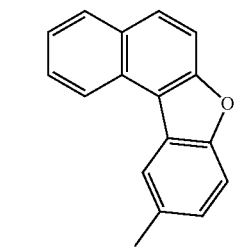
(Ar-210)
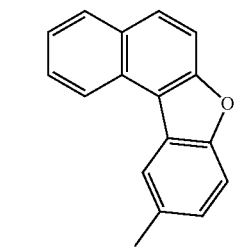

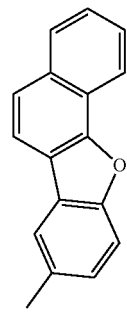 (Ar-211)
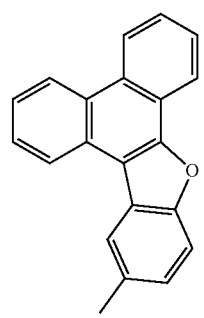 (Ar-212)
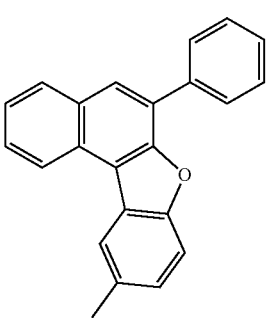 (Ar-213)
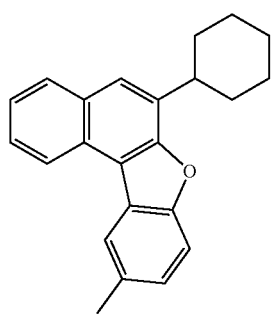 (Ar-214)
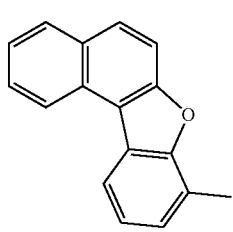 (Ar-215)
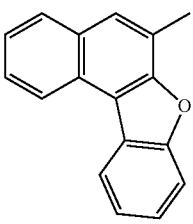 (Ar-216)
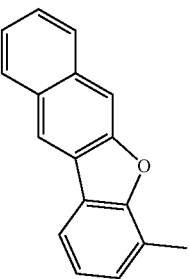 (Ar-217)
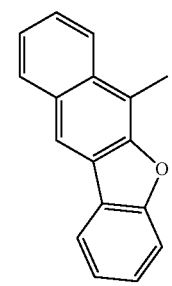 (Ar-218)
[Chemical Formulae 15]
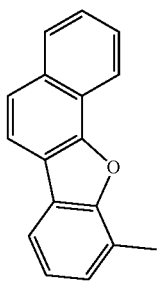 (Ar-219)
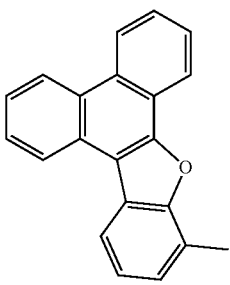 (Ar-220)

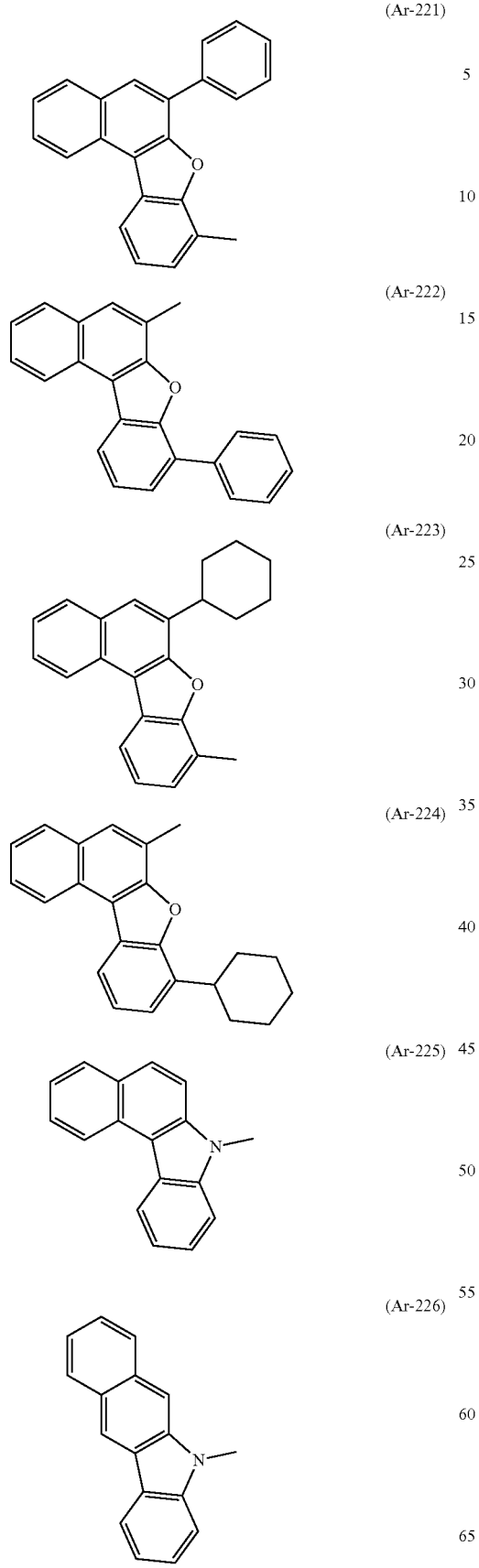
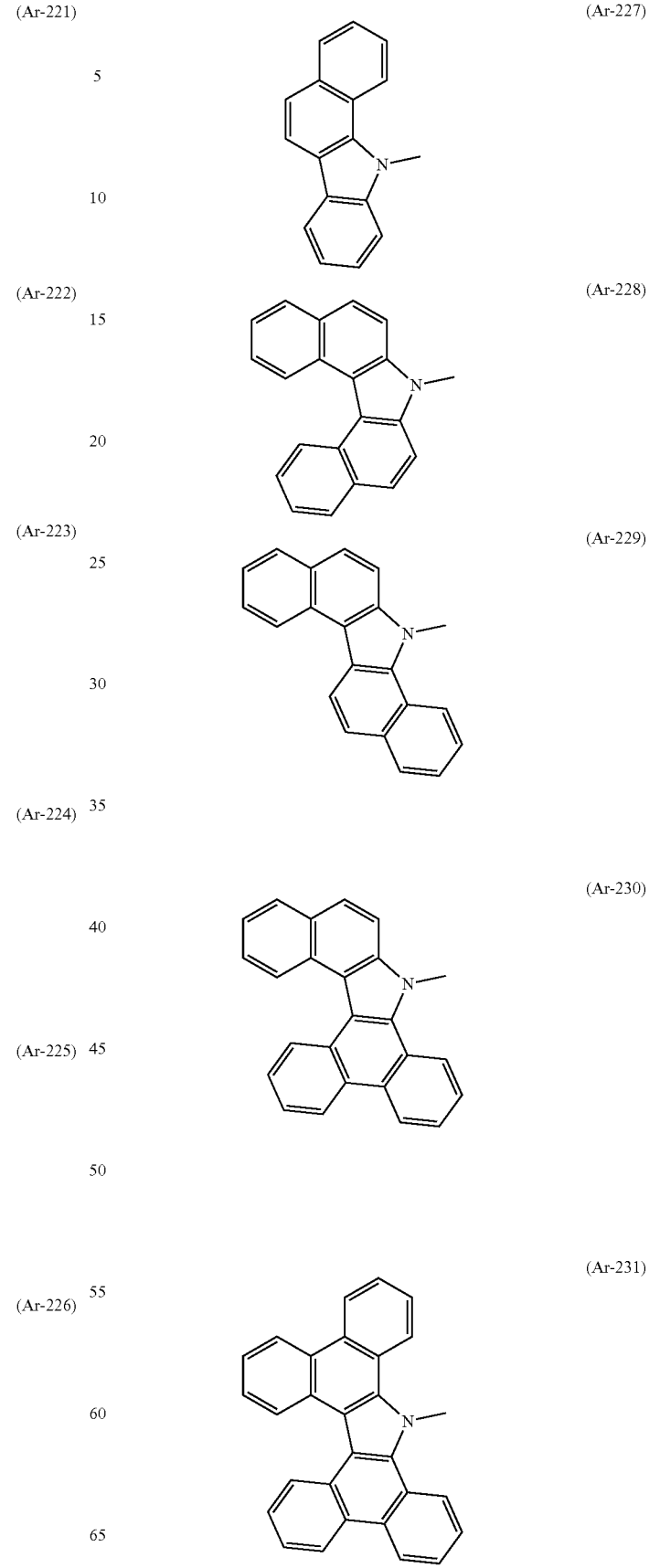

-continued
(Ar-232)
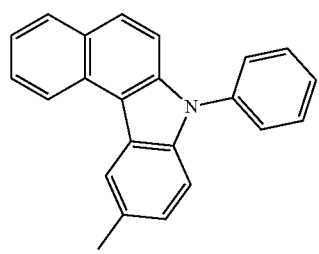
(Ar-233)
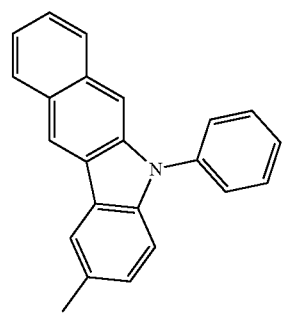
(Ar-234)
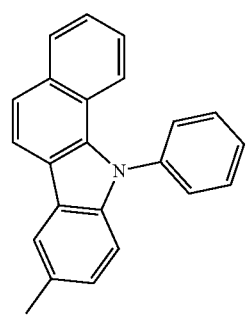
(Ar-235)
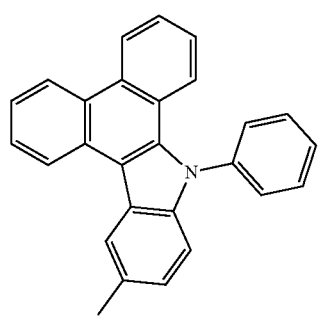
[Chemical Formulae 16]
(Ar-236)
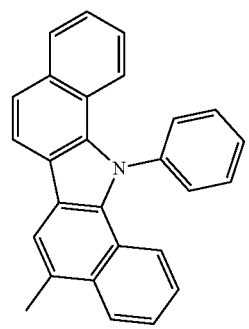
(Ar-237)
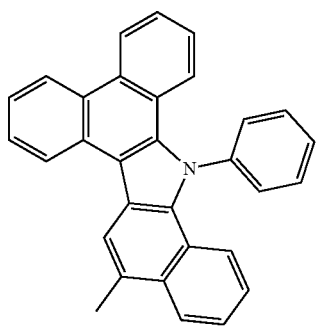
(Ar-238)
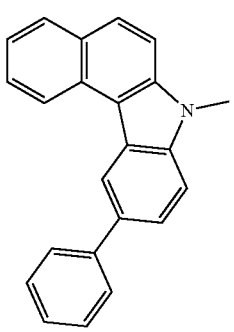
(Ar-239)
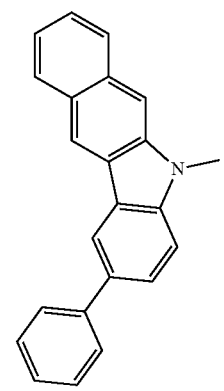
(Ar-240)
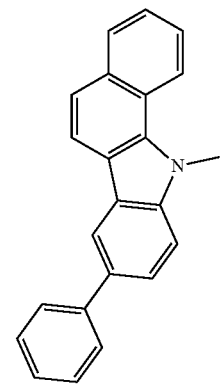

(Ar-241) 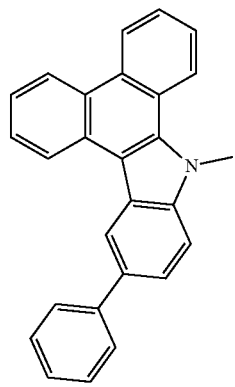
(Ar-242) 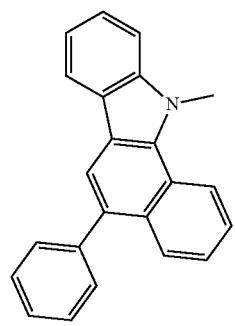
(Ar-243) 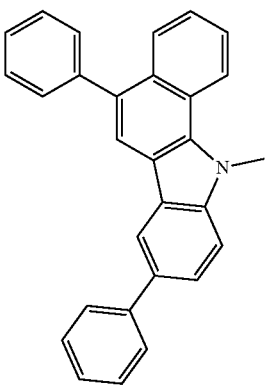
(Ar-244) 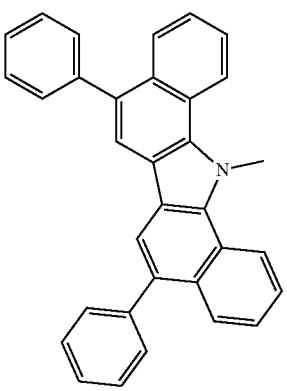
(Ar-245) 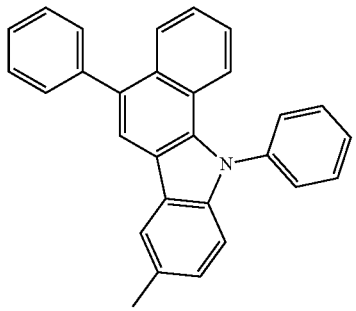
(Ar-246) 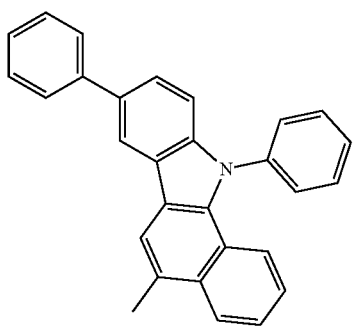
(Ar-247) 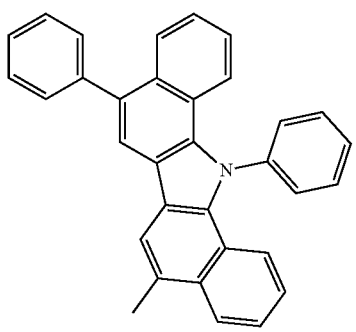
(Ar-248) 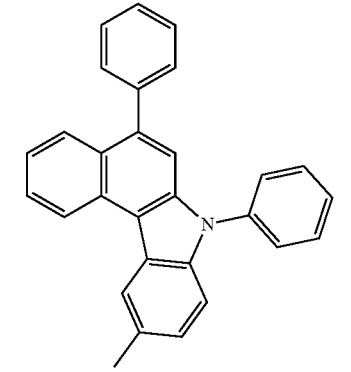

-continued
(Ar-249)
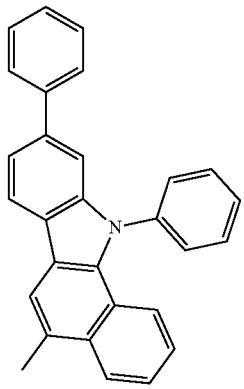
(Ar-250)
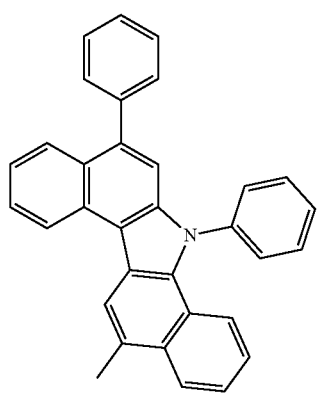
[Chemical Formulae 17]
(Ar-251)
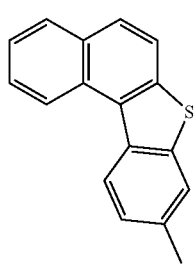
(Ar-252)
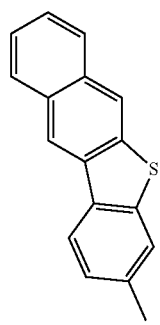
-continued
(Ar-253)
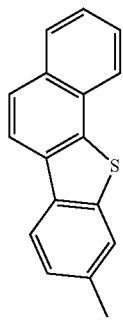
(Ar-254)
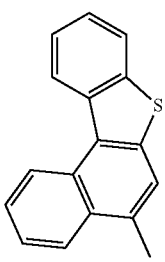
(Ar-255)
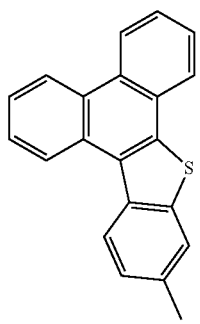
(Ar-256)
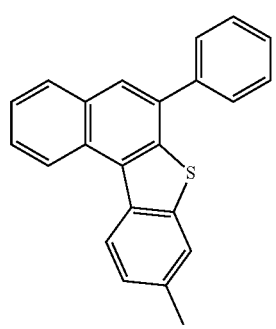
(Ar-257)
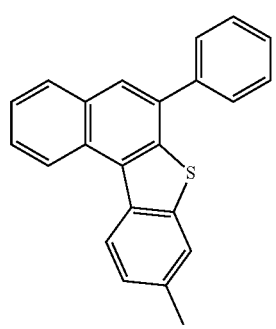

-continued
(Ar-258)
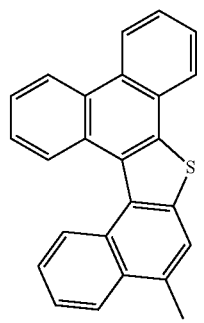
(Ar-259)
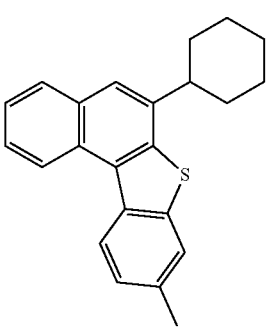
(Ar-260)
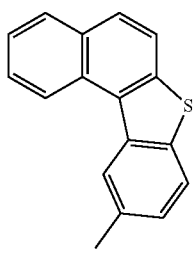
(Ar-261)
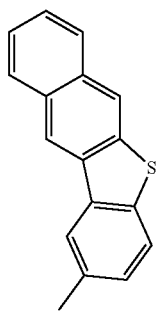
(Ar-262)
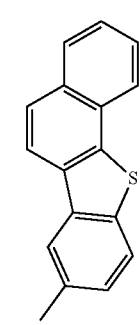
(Ar-263)
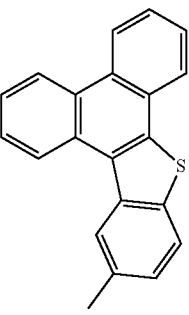
(Ar-264)
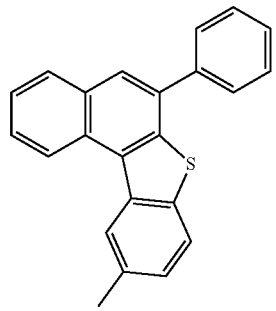
(Ar-265)
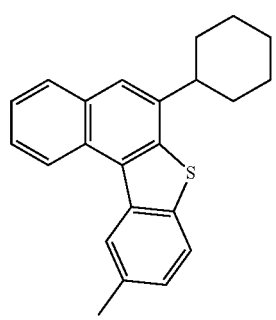
(Ar-266)
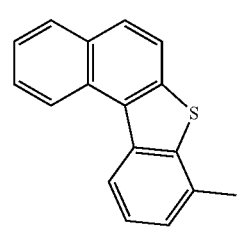
(Ar-267)
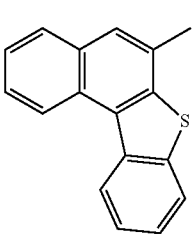

(Ar-268)
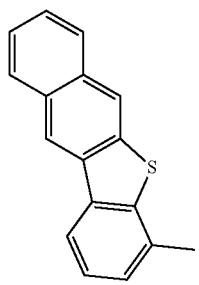
(Ar-269)
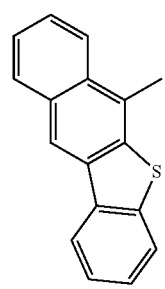
[Chemical Formulae 18]
(Ar-270)
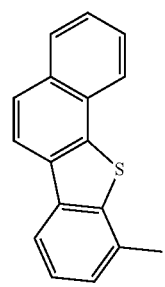
(Ar-271)
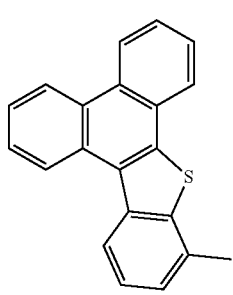
(Ar-272)
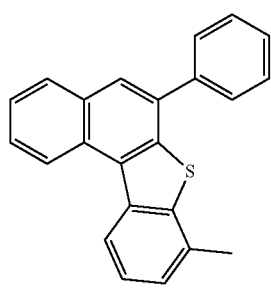
(Ar-273)
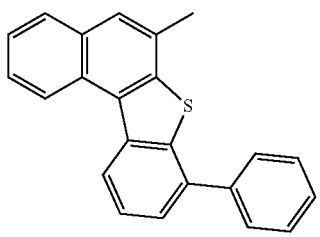
(Ar-274)
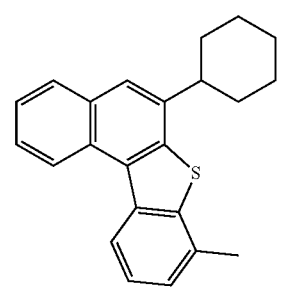
(Ar-275)
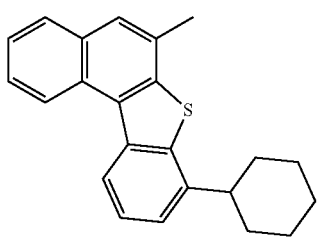
(Ar-276)
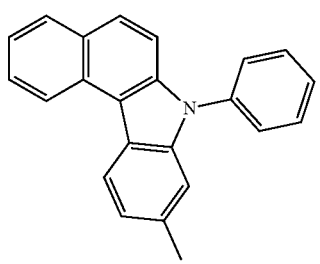
(Ar-277)
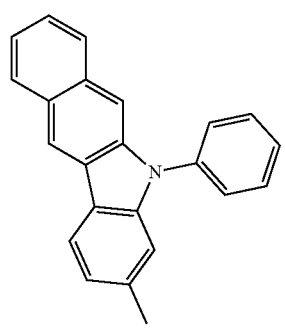

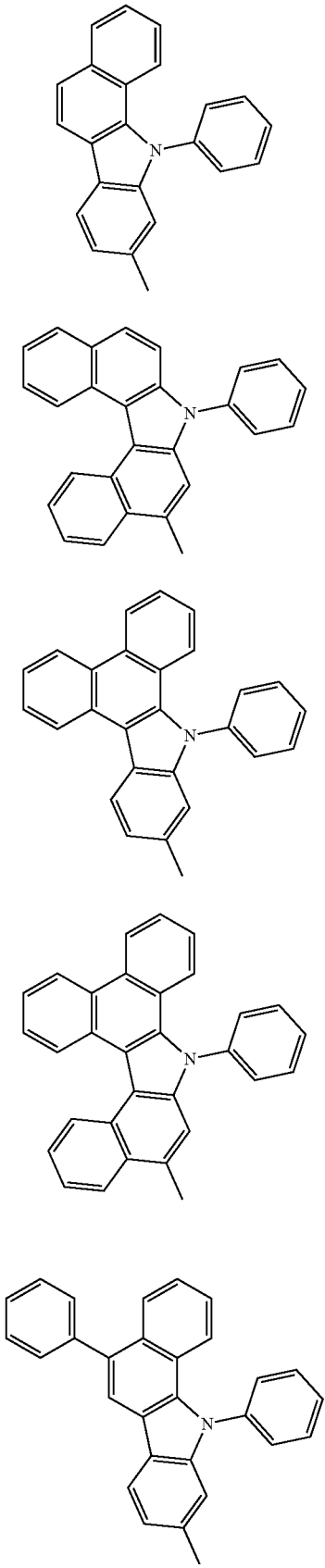

(Ar-278)
(Ar-279)
(Ar-280)
(Ar-281)
(Ar-282)

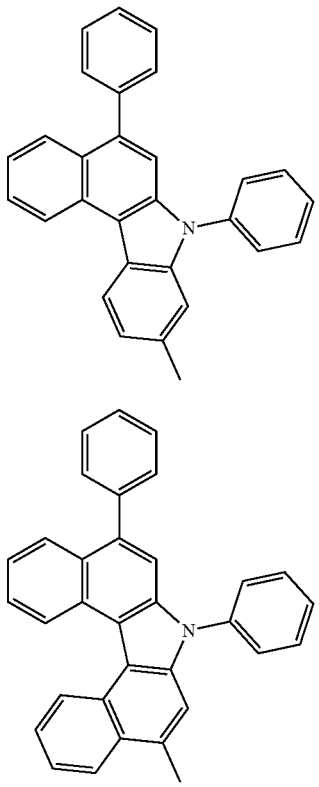

(Ar-283)
(Ar-284)

Furthermore, $Ar^1$ in the above general formula (G1) represents any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group, and a benzene ring may be condensed with these groups. Specific examples of the substituted or unsubstituted aromatic hydrocarbon group having 6 to 25 carbon atoms include a phenyl group, a biphenyl group, a terphenyl group, a naphthyl group, a fluorenyl group, a dimethylfluorenyl group, a spirofluorenyl group, a diphenylfluorenyl group, a phenanthryl group, an anthryl group, a dihydroanthryl group, a triphenylenyl group, and a pyrenyl group. Typical examples of $Ar^1$ are shown in the following structural formulae (Ar-50) to (Ar-66), (Ar-100) to (Ar-119), (Ar-130) to (Ar-140), and (Ar-200) to (Ar-284). Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 19]

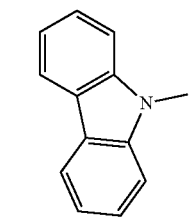

(Ar-50)

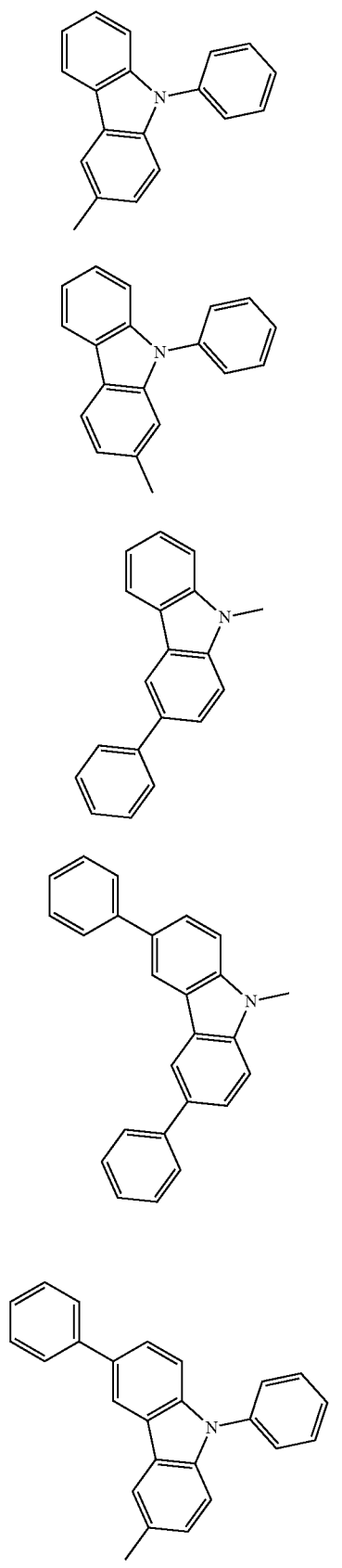
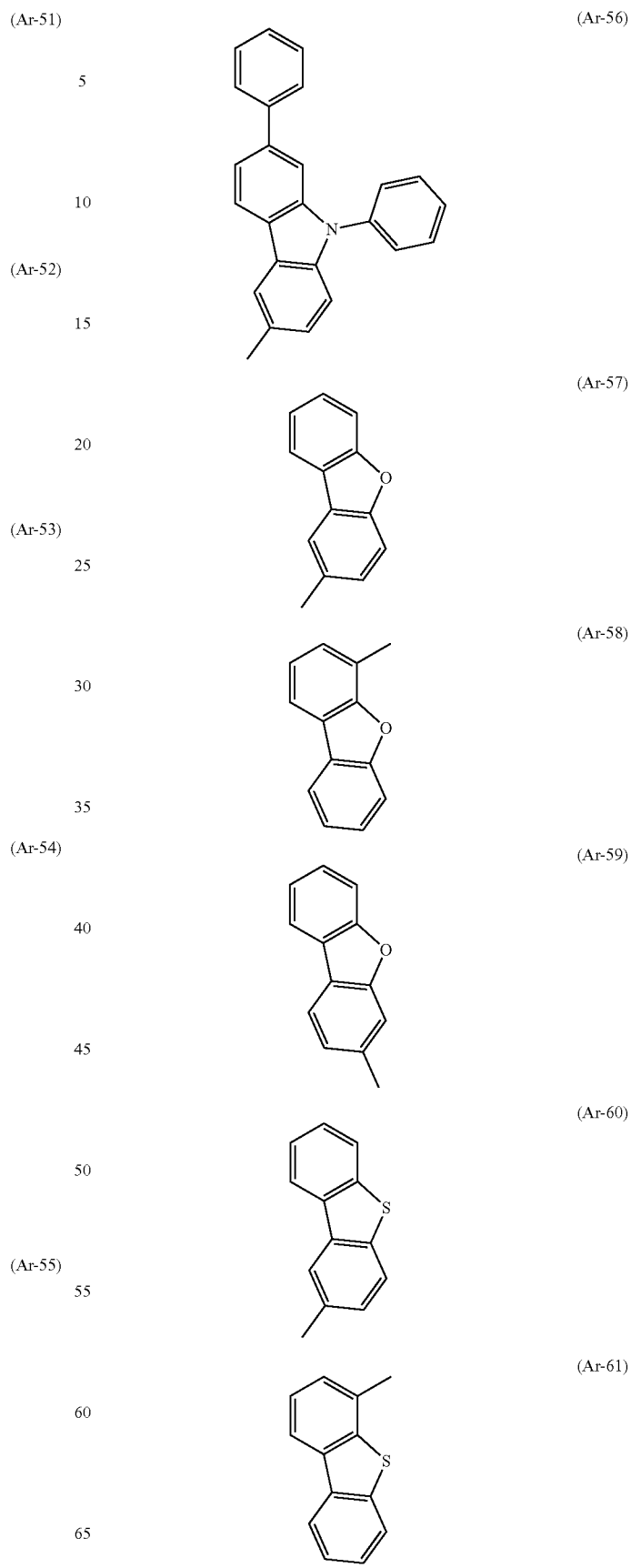

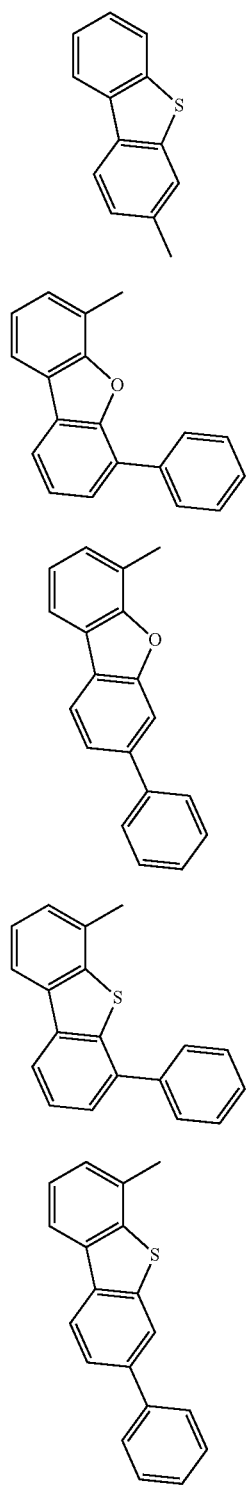
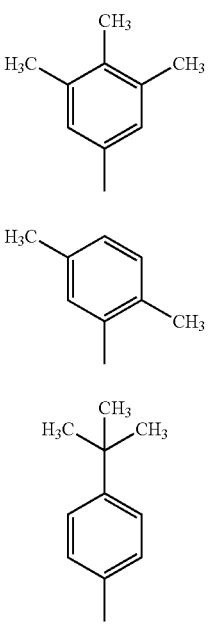
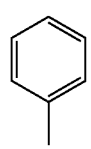
[Chemical Formulae 20]

(Ar-108) 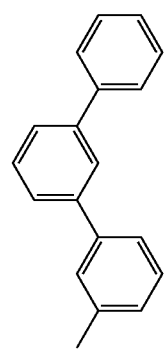
(Ar-109) 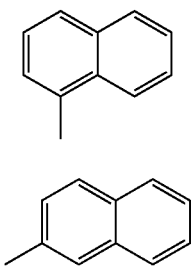
(Ar-110) 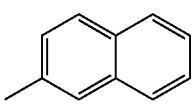
(Ar-111) 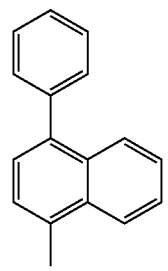
(Ar-112) 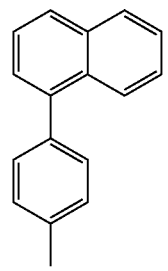
(Ar-113) 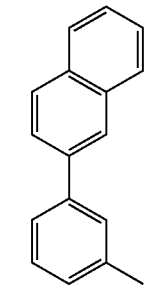
(Ar-114) 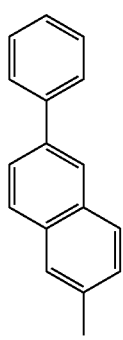
(Ar-115) 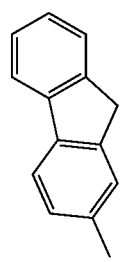
(Ar-116) 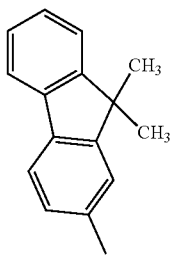
(Ar-117) 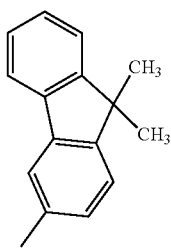
(Ar-118) 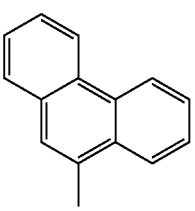
(Ar-119) 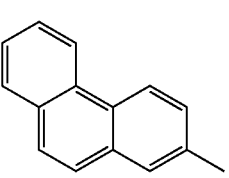

[Chemical Formulae 21]
(Ar-130)
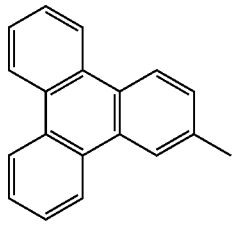
(Ar-131)
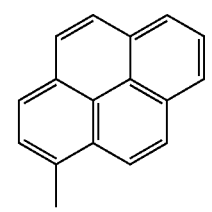
(Ar-132)
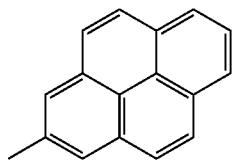
(Ar-133)
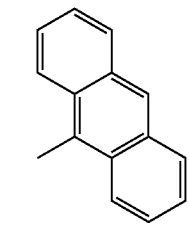
(Ar-134)
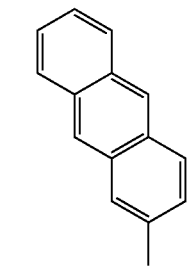
(Ar-135)
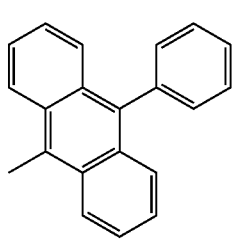
(Ar-136)
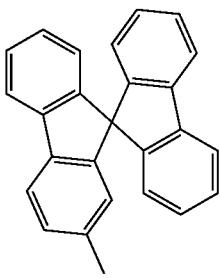
(Ar-137)
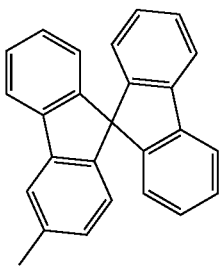
(Ar-138)
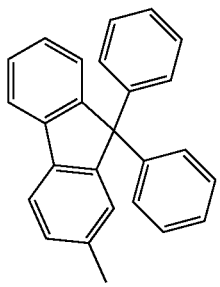
(Ar-139)
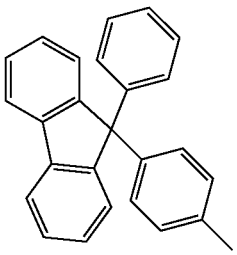
(Ar-140)
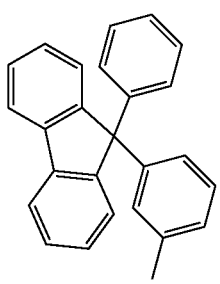

[Chemical Formulae 22]
(Ar-200)
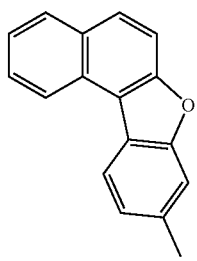
(Ar-201)
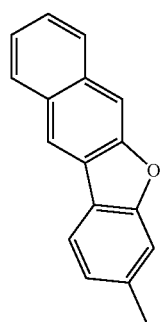
(Ar-202)
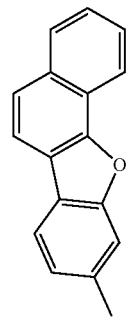
(Ar-203)
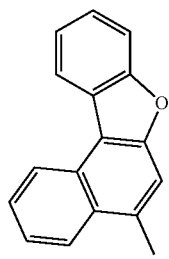
(Ar-204)
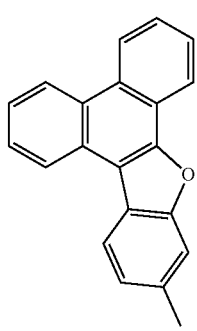
(Ar-205)
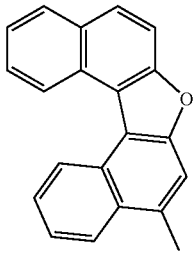
(Ar-206)
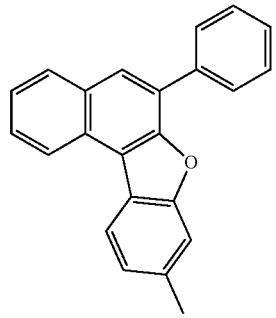
(Ar-207)
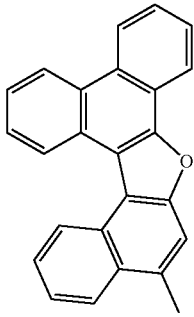
(Ar-208)
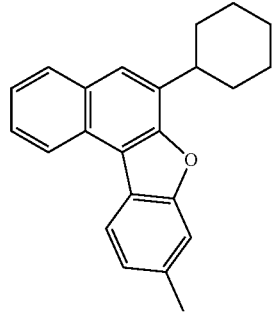
(Ar-209)
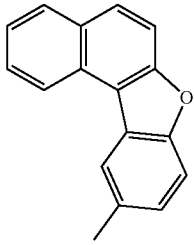

(Ar-210)
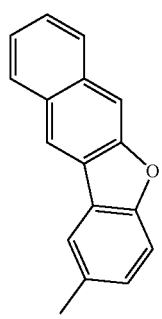
(Ar-211)
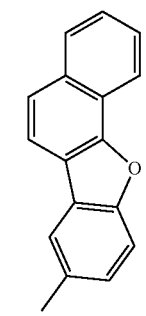
(Ar-212)
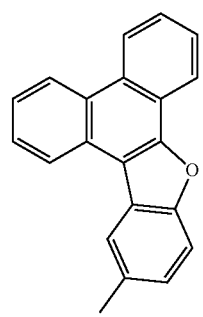
(Ar-213)
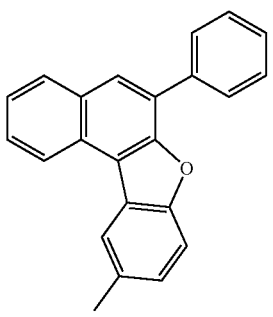
(Ar-214)
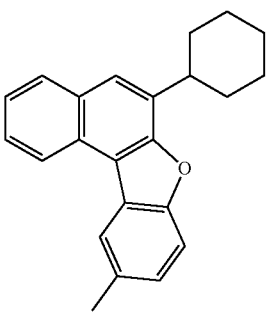
(Ar-215)
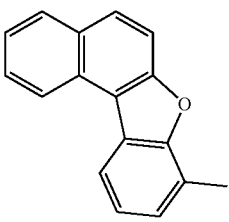
(Ar-216)
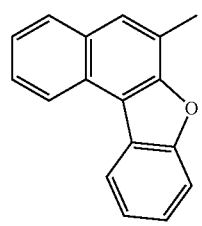
(Ar-217)
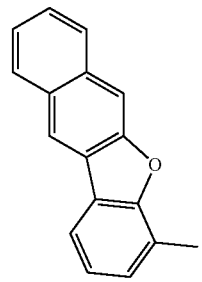
(Ar-218)
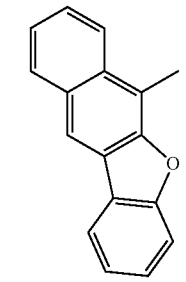
[Chemical Formulae 23]
(Ar-219)
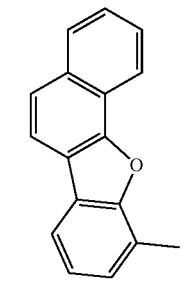
(Ar-220)
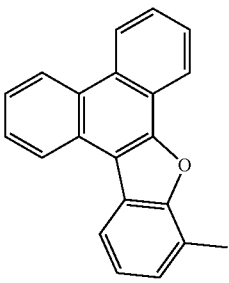

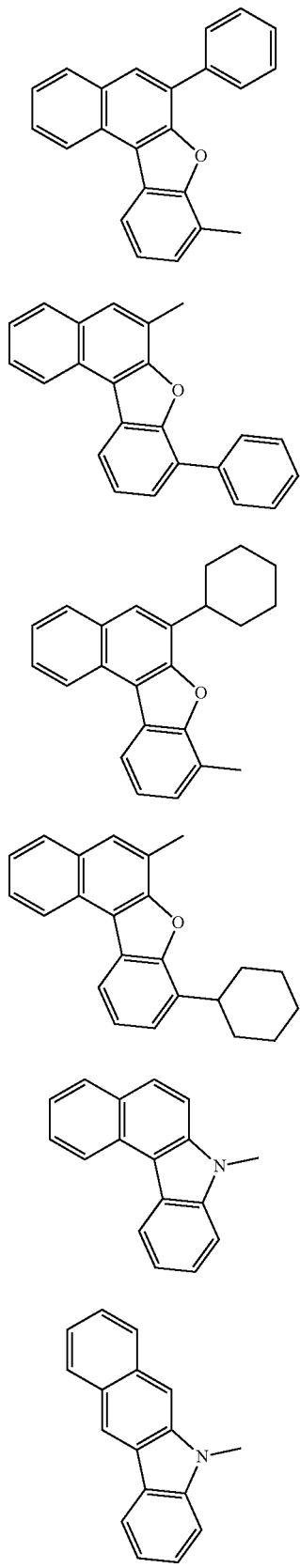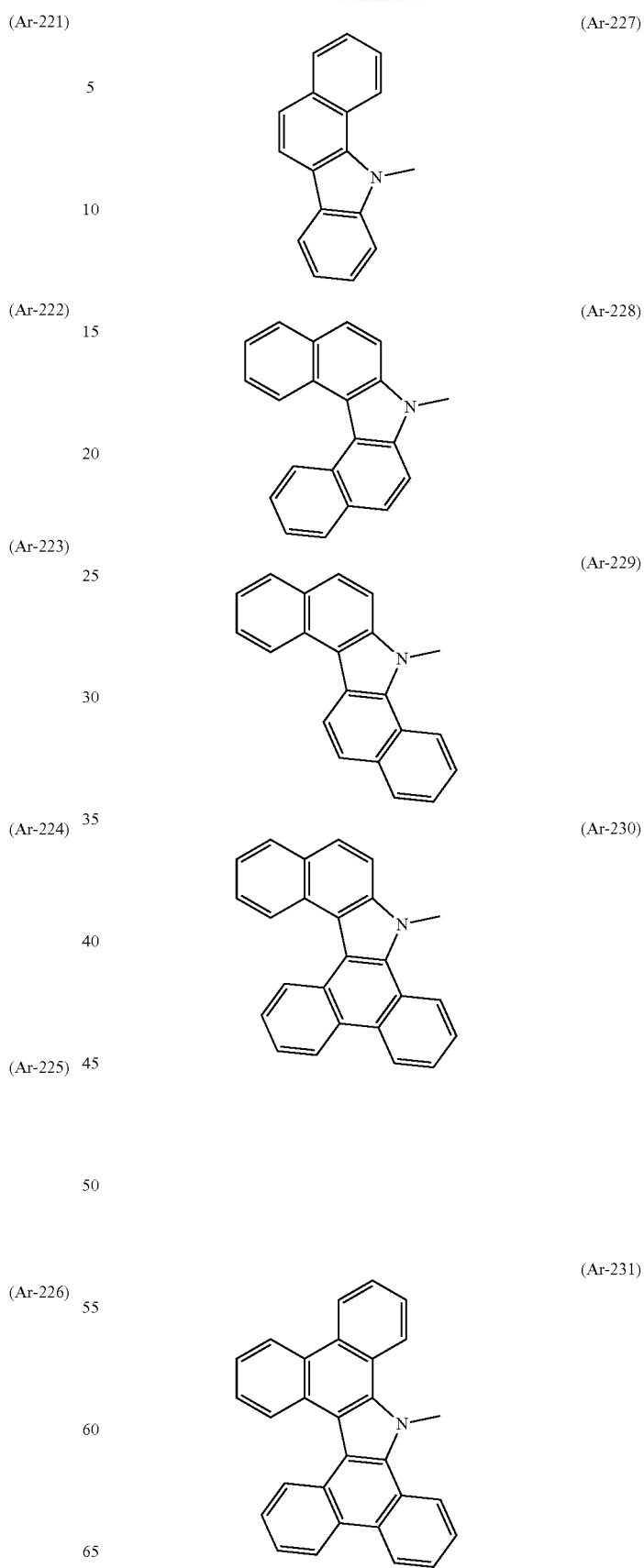

(Ar-232) 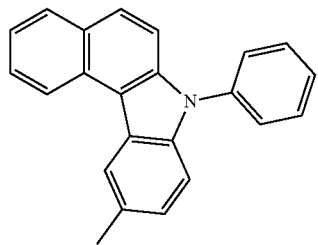
(Ar-233) 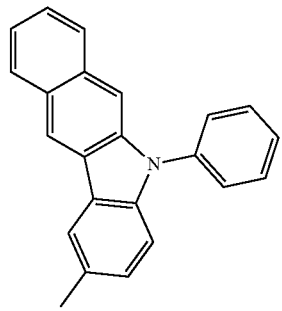
(Ar-234) 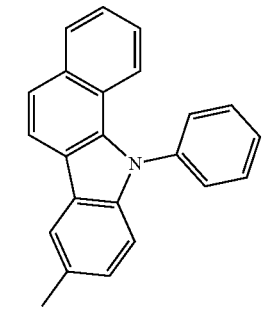
(Ar-235) 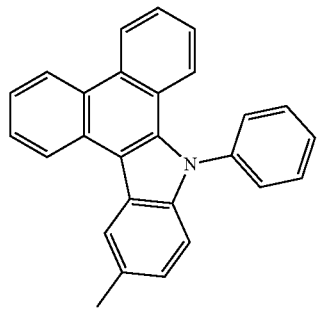
[Chemical Formulae 24]
(Ar-236) 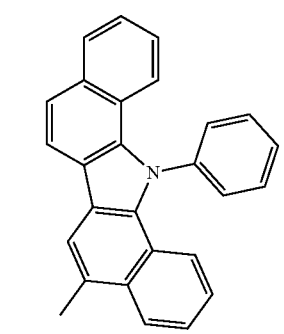
(Ar-237) 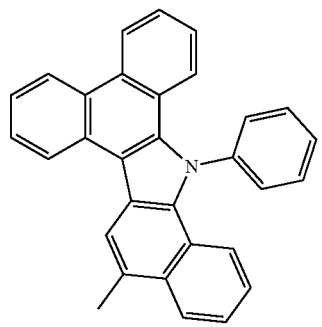
(Ar-238) 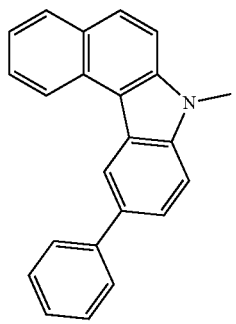
(Ar-239) 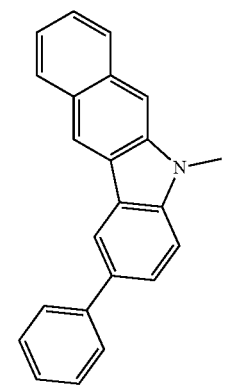
(Ar-240) 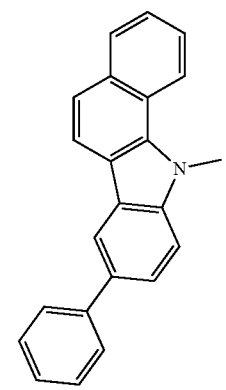

(Ar-241) 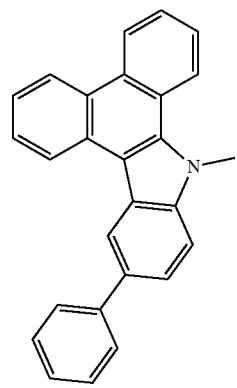
(Ar-242) 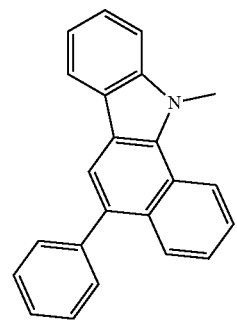
(Ar-243) 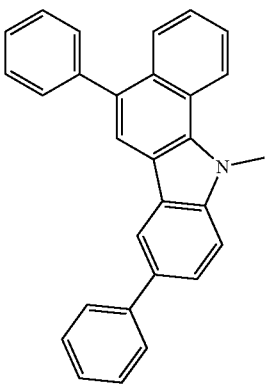
(Ar-244) 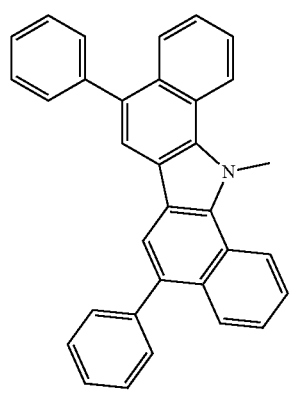
(Ar-245) 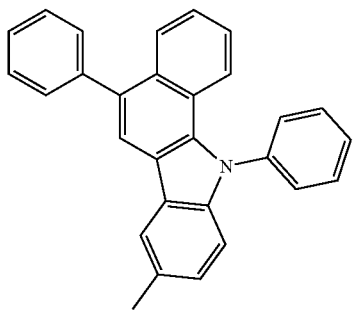
(Ar-246) 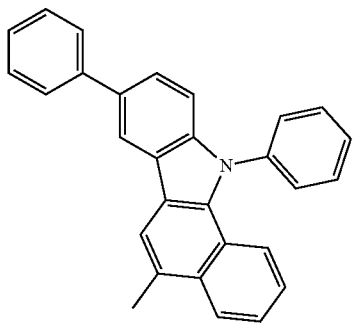
(Ar-247) 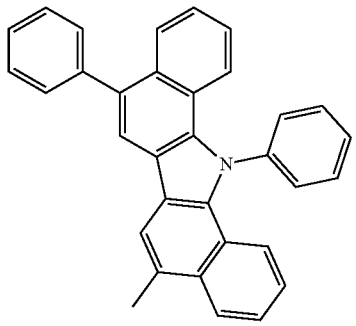
(Ar-248) 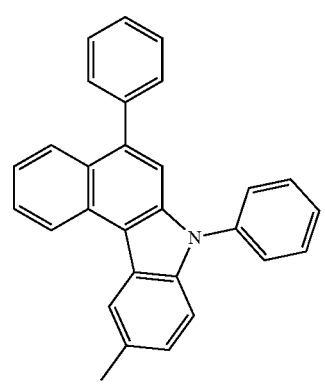

(Ar-249)
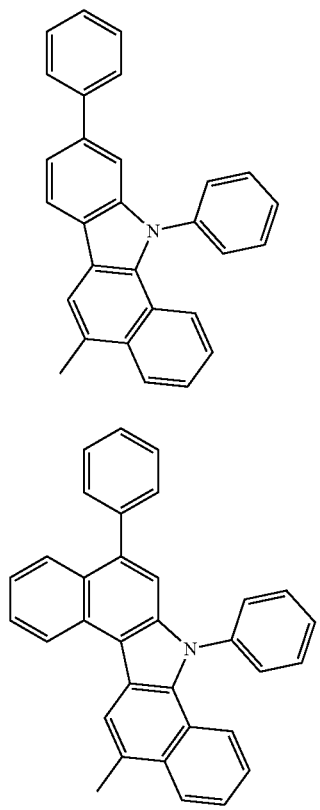
(Ar-250)
[Chemical Formulae 25]
(Ar-251)
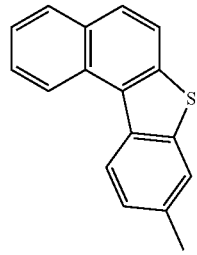
(Ar-252)
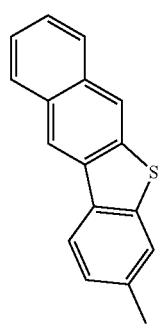
(Ar-253)
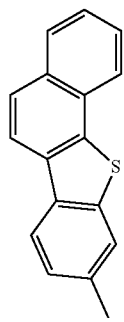
(Ar-254)
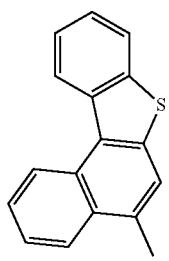
(Ar-255)
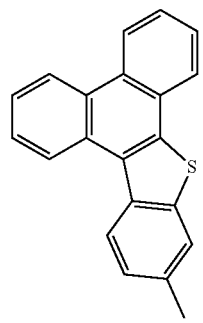
(Ar-256)
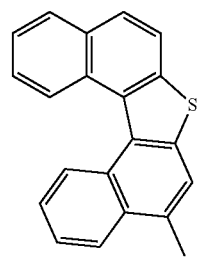
(Ar-257)
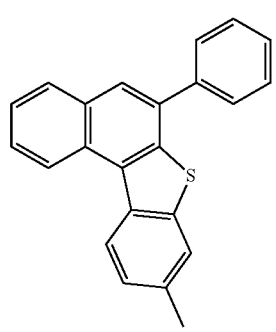

(Ar-258) 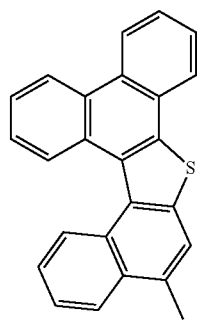
(Ar-259)
(Ar-260)
(Ar-261)
(Ar-262) 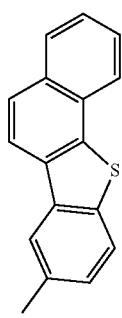
(Ar-263) 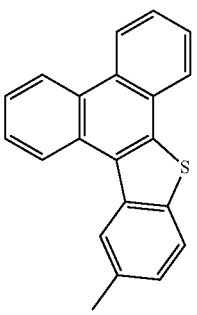
(Ar-264) 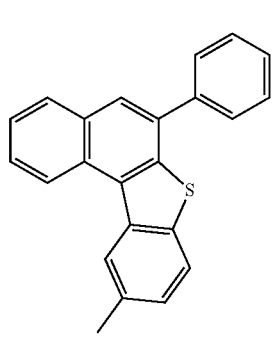
(Ar-265) 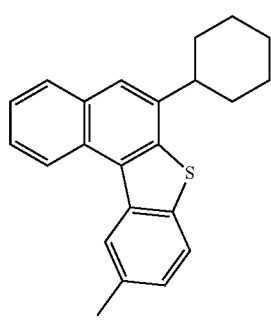
(Ar-266) 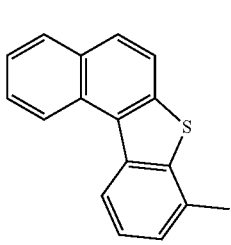
(Ar-267) 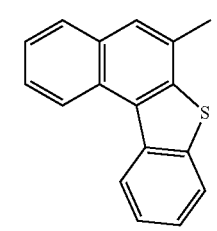

(Ar-268) 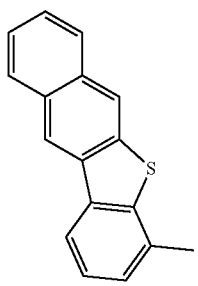
(Ar-269) 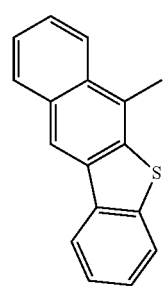
[Chemical Formulae 26]
(Ar-270) 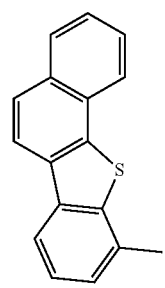
(Ar-271) 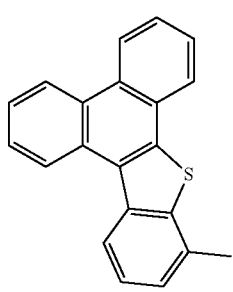
(Ar-272) 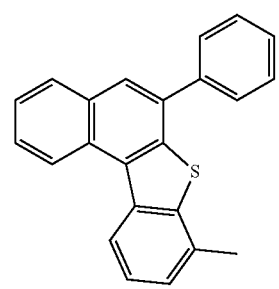
(Ar-273) 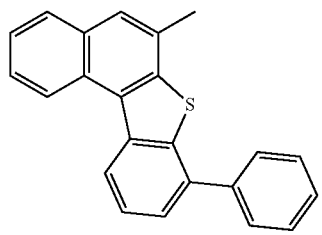
(Ar-274) 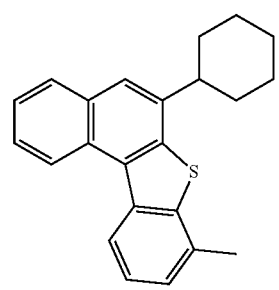
(Ar-275) 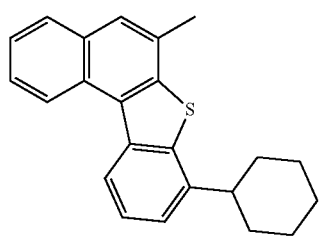
(Ar-276) 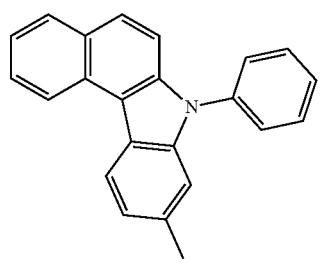
(Ar-277) 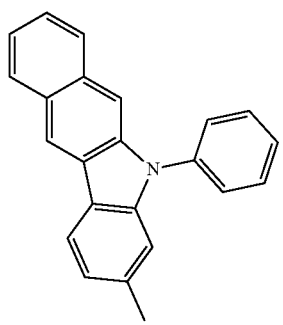

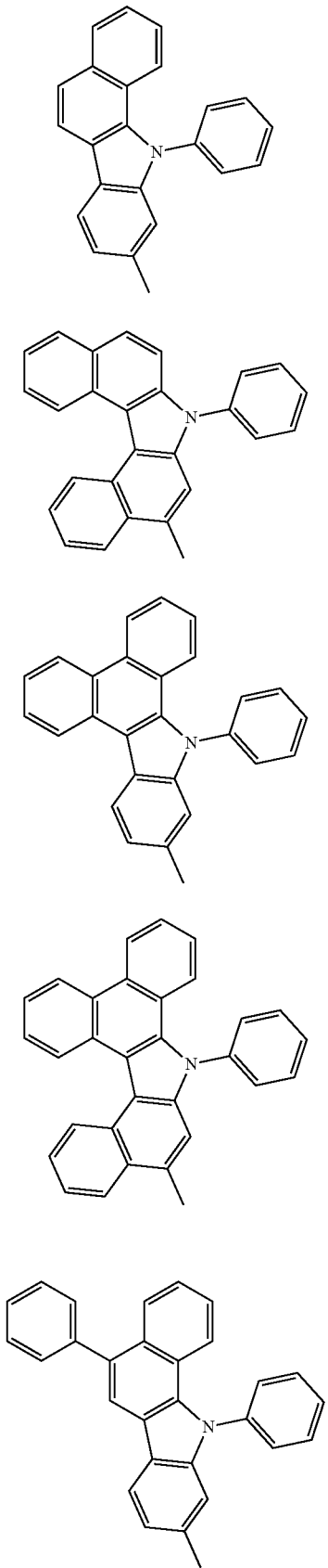

(Ar-278)
(Ar-279)
(Ar-280)
(Ar-281)
(Ar-282)

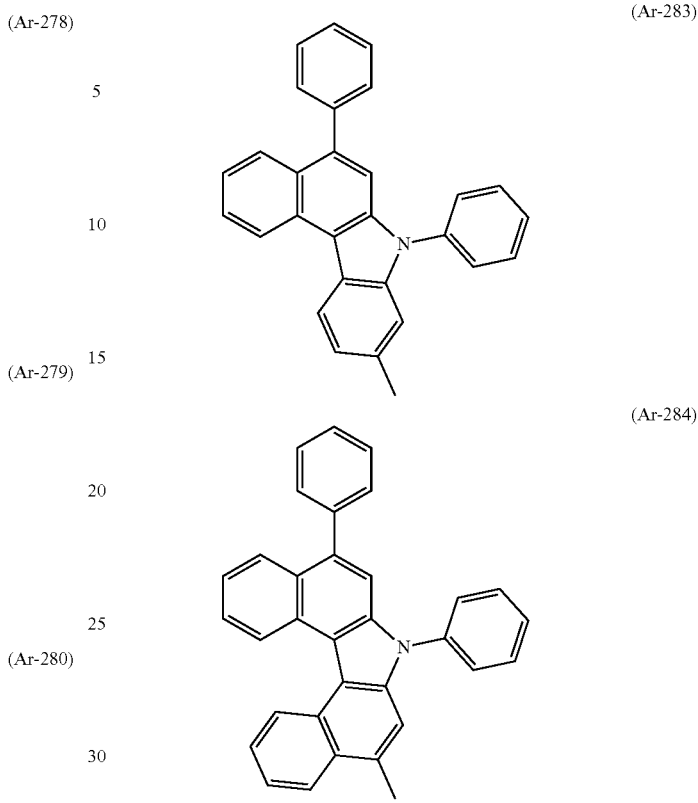

(Ar-283)
(Ar-284)

Note that an organic compound having a structure in which, like (Ar-50), (Ar-53), (Ar-54), (Ar-225) to (Ar-231), and (Ar-238) to (Ar-244), $Ar^1$ is bonded to $\alpha^2$ or nitrogen (amine) in the general formula (G1) with $R^9$ in the general formula (g3) is preferable, in which case conjugation is unlikely to extend and short-wavelength light emission can be obtained.

As shown in (Ar-51), (Ar-55), (Ar-56), (Ar-57), (Ar-60), (Ar-209) to (Ar-214), (Ar-232) to (Ar-237), (Ar-245) to (Ar-250), and (Ar-260) to (Ar-265), an organic compound in which $\alpha^2$ is bonded to nitrogen (amine) in the general formula (G1) and $R^3$ in the general formulae (g1) to (g3) is bonded to $\alpha^2$ is preferable, in which case effects such as a high hole-transport property, long-wavelength light emission, and high reliability can be obtained. In particular, those effects are prominent in the case of the carbazolyl group.

As shown in (Ar-52), (Ar-59), (Ar-62), (Ar-200) to (Ar-208), (Ar-251) to (Ar-259), and (Ar-276) to (Ar-284), an organic compound in which $\alpha^2$ is bonded to nitrogen (amine) in the general formula (G1) and $R^2$ in the general formulae (g1) to (g3) is bonded to $\alpha^2$ is preferable, in which case a carrier-transport property is high and thus driving voltage should be reduced.

As shown in (Ar-51), (Ar-52), (Ar-55), (Ar-56), (Ar-232) to (Ar-237), (Ar-245) to (Ar-250), and (Ar-276) to (Ar-284), an aryl group is preferably bonded to $R^9$ in the general formula (g3), in which case an effect such as high reliability can be obtained.

An organic compound in which, like (Ar-58), (Ar-61), (Ar-63) to (Ar-66), (Ar-214) to (Ar-224), and (Ar-266) to (Ar-275), the general formulae (g1) and (g2) are bonded to $\alpha^2$ or nitrogen (amine) in the general formula (G1) with $R^1$ is preferable, in which case conjugation is unlikely to extend, short-wavelength light emission can be obtained, and reliability is high.

Furthermore, the one to which a phenyl group is connected as in (Ar-100) to (Ar-104) and (Ar-106) to (Ar-108) is preferable, in which case conjugation is unlikely to extend and the light emission has a short wavelength.

As in (Ar-100) to (Ar-119), the one is preferably composed of hydrocarbon with two or less condensed six-membered rings, such as a benzene ring, a naphthalene ring, or a fluorene ring, or hydrocarbon such as a phenanthrene ring having three or more condensed six-membered rings, in which one six-membered ring is condensed at the b-position and d-position with respect to the other six-membered rings, in which case conjugation is unlikely to extend and the light emission has a short wavelength.

In the above general formula (G1), $\alpha^1$ to $\alpha^3$ each independently represent a substituted or unsubstituted divalent aromatic hydrocarbon group having 6 to 25 carbon atoms; specifically, a phenylene group, a biphenylene group, a terphenylene group, a naphthylene group, a fluorenylene group, a dimethylfluorenyl group, and the like can be given. As typical examples of $\alpha^1$ to $\alpha^3$, groups represented by the following structural formulae (Ar-1) to (Ar-27) can be given. Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 27]

-continued
(Ar-11)
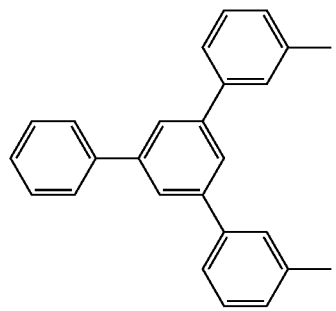
[Chemical Formulae 28]
(Ar-12)
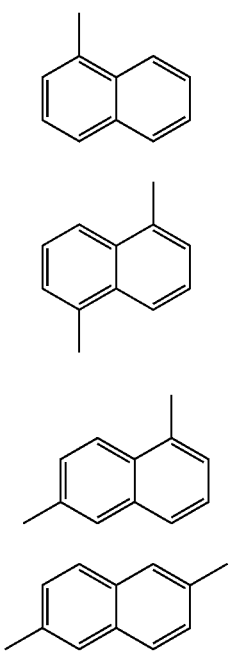
(Ar-13)
(Ar-14)
(Ar-15)
(Ar-16)
(Ar-17)
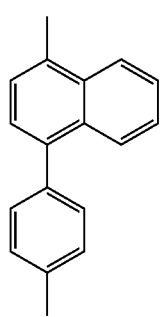
(Ar-18)
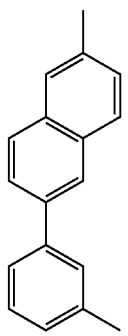
(Ar-19)
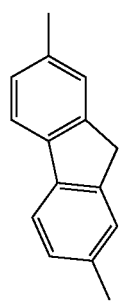
(Ar-20)
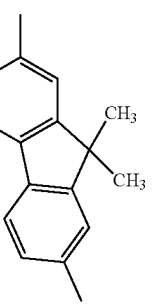
(Ar-21)
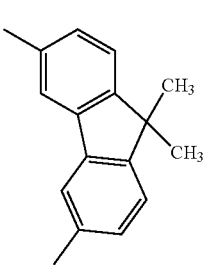
(Ar-22)
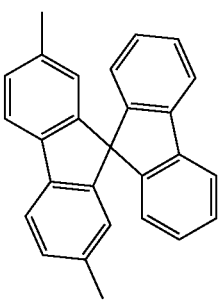

-continued (Ar-23)
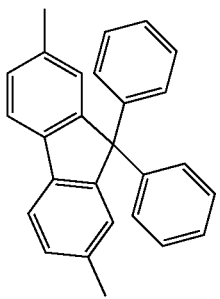

(Ar-24)
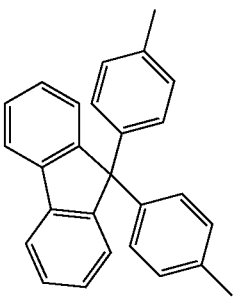

(Ar-25)
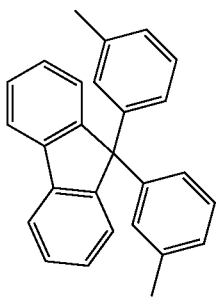

(Ar-26)
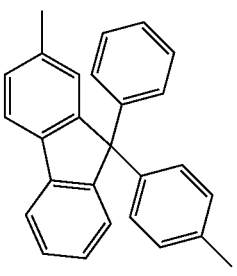

(Ar-27)
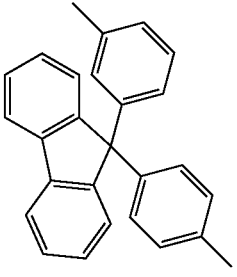

Note that $\alpha^1$ to $\alpha^3$ are preferably a phenylene group or a group in which some phenylene groups are connected as in (Ar-1) to (Ar-11), in which case conjugation is unlikely to extend and the singlet excitation level is kept high. In particular, a structure containing a meta-phenylene group is a preferable mode because of its significant effect. Furthermore, a structure in which $\alpha^1$ to $\alpha^3$ are each a para-phenylene group has improved reliability as a light-emitting material, and thus is a preferable mode. When connection of a substituent is made by carbon at the 9-position of fluorene having a sigma bond as in (Ar-24) to (Ar-27), conjugation is unlikely to extend and the S1 level is kept high, which leads to a shorter light emission wavelength and thus is a preferable structure.

In the case where l, m, and n in the above general formula (G1) are each 2, different substituents may be connected to each other as $\alpha^1$, $\alpha^2$, and $\alpha^3$. For example, in (Ar-17) and (Ar-18), naphthylene and phenylene are connected to each other.

In the organic compound represented by the above general formula (G1), a substituted or unsubstituted naphthobisbenzofuran skeleton, a substituted or unsubstituted naphthobisbenzothiophene skeleton, or a substituted or unsubstituted naphthobenzothienobenzofuran skeleton, which is represented by B, is preferably any of skeletons represented by general formulae (B1) to (B4) below.

[Chemical Formulae 29]

(B1)
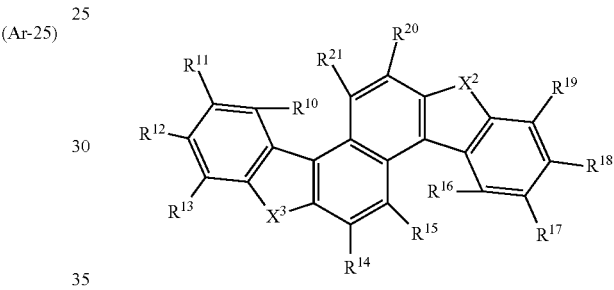

(B2)
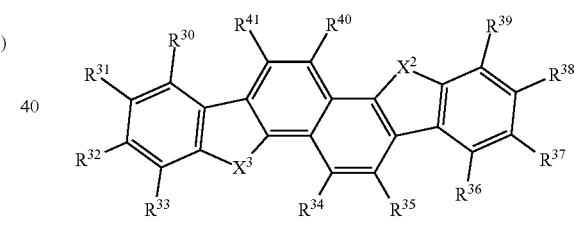

(B3)
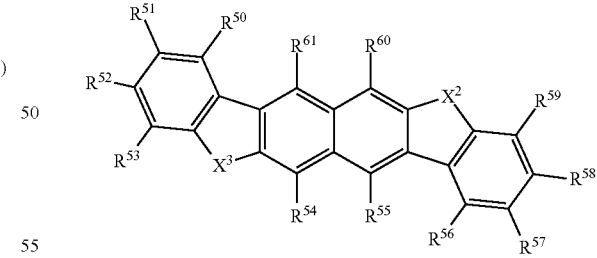

(B4)
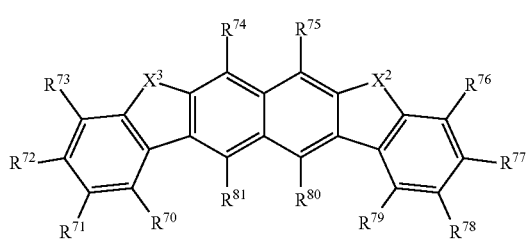

In the above general formulae (B1) to (B4), $X^1$ and $X^3$ each independently represent an oxygen atom or a sulfur atom. Note that both of them are preferably the same atoms for easy synthesis. A structure where both of them are oxygen atoms is a preferable mode because there are effects such as easy synthesis, availability of light emission with a shorter wavelength due to a high singlet excitation level, and acquisition of a high emission quantum yield. Note that $X^2$ and $X^3$ with more oxygen atoms contribute to light emission with a shorter wavelength, whereas $X^2$ and $X^3$ with more sulfur atoms contribute to light emission with a longer wavelength; thus, the number of oxygen atoms or sulfur atoms can be appropriately selected depending on the target singlet excitation level and emission wavelength.

The emission wavelength of the organic compound represented by the above general formula (G1) shows tendency depending on the skeleton represented by B. The emission wavelength becomes longer in the order that B is a skeleton represented by the general formula (B2), a skeleton represented by the general formula (B4), a skeleton represented by the general formula (B1), and a skeleton represented by the general formula (B3). Thus, in the case where blue light emission with a shorter wavelength is desired, a compound represented by the general formula (B2) is preferable. In the case where blue light emission with a relatively long wavelength is desired, a compound represented by the general formula (B3) is preferable.

In the organic compound represented by the above general formula (G1), the skeleton represented by B is preferably the skeleton represented by the general formula (B3) because the emission spectrum becomes narrower and light emission with high color purity can be obtained.

In the skeleton represented by the above general formula (B1), any one or two of $R^{10}$ to $R^{21}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{11}$, $R^{12}$, $R^{17}$ and $R^{18}$ of $R^{10}$ to $R^{21}$ are preferably a single bond for easy synthesis.

In the case where any two of $R^{10}$ to $R^{21}$ in the above general formula (B1) are a single bond (that is, in the case where q in the above general formula (G1) is 2), one of $R^{11}$ and $R^{12}$ and one of $R^{17}$ and $R^{18}$ are preferably a single bond for easy synthesis. In that case, $R^{11}$ and $R^{17}$ are preferably a single bond in terms of obtaining light emission with a long wavelength; $R^{12}$ and $R^{18}$ are preferably a single bond to obtain light emission with a short wavelength, favorable light emission quantum efficiency, a high molar absorption coefficient, and favorable reliability in light emission.

Furthermore, in the above general formula (B2), any one or two of $R^{30}$ to $R^{41}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{31}$, $R^{32}$, $R^{37}$, and $R^{38}$ of $R^{30}$ to $R^{41}$ are preferably a single bond for easy synthesis.

In the case where any two of $R^{30}$ to $R^{41}$ in the above general formula (B2) are a single bond (that is, in the case where q in the above general formula (G1) is 2), one of $R^{31}$ and $R^{32}$ and one of $R^{37}$ and $R^{38}$ are preferably a single bond for easy synthesis. In that case, $R^{31}$ and $R^{37}$ are preferably a single bond in terms of obtaining light emission with a long wavelength; $R^{32}$ and $R^{38}$ are preferably a single bond to obtain light emission with a short wavelength, favorable light emission quantum efficiency, a high molar absorption coefficient, and favorable reliability in light emission.

Furthermore, in the above general formula (B3), any one or two of $R^{50}$ to $R^{61}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group. Note that any one or two of $R^{51}$, $R^{52}$, $R^{57}$ and $R^{58}$ of $R^{50}$ to $R^{61}$ are preferably a single bond for easy synthesis.

In the case where any two of $R^{50}$ to $R^{61}$ in the above general formula (B3) are a single bond (that is, in the case where q in the above general formula (G1) is 2), one of $R^{51}$ and $R^{52}$ and one of $R^{57}$ and $R^{58}$ are preferably a single bond for easy synthesis. In that case, $R^{51}$ and $R^{57}$ are preferably a single bond in terms of obtaining light emission with a long wavelength; $R^{52}$ and $R^{58}$ are preferably a single bond to obtain light emission with a short wavelength, favorable light emission quantum efficiency, a high molar absorption coefficient, and favorable reliability in light emission.

Furthermore, in the above general formula (B4), any one or two of $R^{70}$ to $R^{81}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{71}$, $R^{72}$, $R^{77}$, and $R^{78}$ of $R^{70}$ to $R^{81}$ are preferably a single bond for easy synthesis.

In the case where any two of $R^{70}$ to $R^{81}$ in the above general formula (B4) are a single bond (that is, in the case where q in the above general formula (G1) is 2), one of $R^{71}$ and $R^{72}$ and one of $R^{77}$ and $R^{78}$ are preferably a single bond for easy synthesis. In that case, $R^{71}$ and $R^{78}$ are preferably a single bond in terms of obtaining light emission with a long wavelength; $R^{72}$ and $R^{77}$ are preferably a single bond to obtain light emission with a short wavelength, favorable light emission quantum efficiency, a high molar absorption coefficient, and favorable reliability in light emission.

Note that a single bond here refers to an atomic bonding with $\alpha^1$ or nitrogen (amine) in the above general formula (G1).

Among the substituents represented by $R^{10}$ to $R^{21}$, $R^{30}$ to $R^{41}$, $R^{50}$ to $K^{61}$, and $R^{70}$ to $R^{81}$ in the above general formula (B1) to general formula (B4), the ones other than the single bond are preferably hydrogen because the synthesis is easy and the sublimation temperature is low. However, with the use of substituents other than hydrogen, the heat resistance, the solubility in a solvent, and the like can be improved, and the emission wavelength can be shifted to a long wavelength.

Note that the organic compound represented by the above general formula (G1) is preferably an organic compound represented by a general formula (G1-1) below.

[Chemical Formula 30]

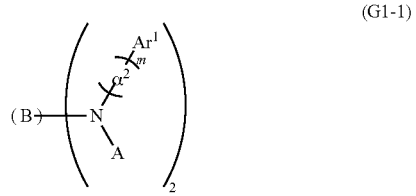

(G1-1)

Note that, in the above general formula (G1-1), B is a skeleton represented by a general formula (B1-1) or (B3-1) below. Furthermore, $Ar^1$ is a substituted or unsubstituted aromatic hydrocarbon group having 6 to 25 carbon atoms, and A is a group represented by the following general formula (g0). Furthermore, m represents an integer of 0 to 2. Furthermore, $\alpha^2$ is a substituted or unsubstituted divalent aromatic hydrocarbon group having 6 to 14 carbon atoms.

[Chemical Formulae 31]

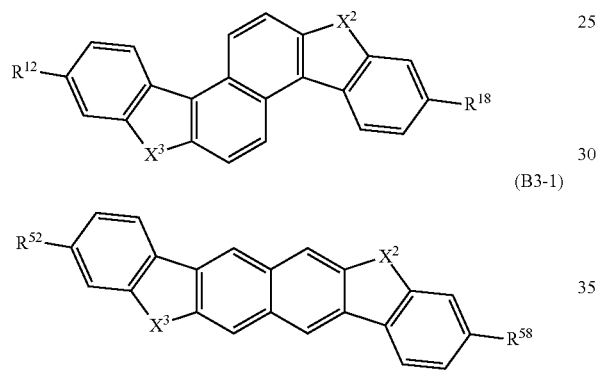

(B1-1)

(B3-1)

Note that, in the above general formula (B1-1) or (B3-1), $X^2$ and $X^3$ each independently represent an oxygen atom or a sulfur atom. Furthermore, $R^{12}$, $R^{18}$, $R^{52}$, and $R^{58}$ represent a single bond.

[Chemical Formula 33]

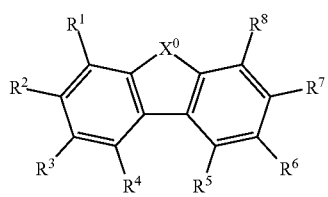

(g0)

In the above general formula (g0), $X^0$ is any of an oxygen atom, a sulfur atom, and a nitrogen atom to which a substituted or unsubstituted phenyl group is bonded. $X^0$ is preferably an oxygen atom for easy synthesis.

Among $R^1$ to $R^8$, $R^2$ represents a single bond, and the others each independently represent any one of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms. Note that $R^1$ and $R^3$ to $R^8$ are preferably hydrogen for easy synthesis.

Note that the group represented by the above general formula (g0) is a group having a condensed polycyclic structure in which condensation occurs in at least one of combinations of $R^3$ and $R^4$, $R^5$ and $R^6$, $R^6$ and $R^7$, and $R^7$ and $R^8$ and a benzene ring is formed.

The group represented by the above general formula (g0) is preferably a group represented by general formulae (g0-1) to (g0-3) below.

[Chemical Formulae 33]

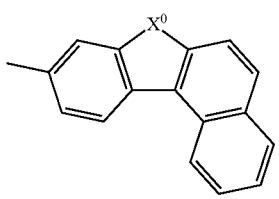

(g0-1)

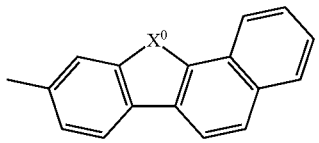

(g0-2)

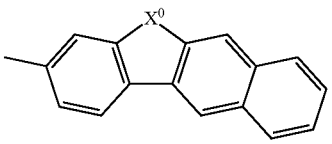

(g0-3)

Note that the molecular weight of the organic compound represented by the above general formula (G1) or (G1-1) is 1300 or less, preferably 1000 or less in consideration of the sublimation property. The molecular weight is preferably 650 or more in consideration of the film quality.

Note that in the case where a skeleton or a group bonded to the above organic compound has a substituent, the substituent is preferably any of a hydrocarbon group having 1 to 10 carbon atoms, a cyclic hydrocarbon group having 3 to 10 carbon atoms, and an aromatic hydrocarbon group having 6 to 14 carbon atoms.

Examples of a hydrocarbon group having 1 to 10 carbon atoms of the above substituent represented by R or a substituent further bonded to the substituent include a methyl group, an ethyl group, a propyl group, an isopropyl group, a butyl group, a tert-butyl group, a pentyl group, a hexyl group, a heptyl group, an octyl group, a nonyl group, and a decyl group. Examples of a cyclic hydrocarbon group having 3 to 10 carbon atoms include a cyclopropyl group and a cyclohexyl group. Examples of an aromatic hydrocarbon group having 6 to 14 carbon atoms include a phenyl group, a biphenyl group, a naphthyl group, a phenanthryl group, an anthryl group, and a fluorenyl group.

In the case where the above substituent represented by R5 is a diarylamino group having 12 to 32 carbon atoms, it is further preferable that two aryl groups included in the diarylamino group be each independently an aromatic hydrocarbon group having 6 to 16 carbon atoms. Examples of the aromatic hydrocarbon group include a phenyl group, a biphenyl group, a naphthyl group, a phenanthryl group, an anthryl group, a fluorenyl group, and a naphthyl phenyl group.

Among them, the aromatic hydrocarbon group having 6 to 14 carbon atoms and the diarylamino group having 12 to 32 carbon atoms may further have, as a substituent, an aliphatic hydrocarbon group having 1 to 6 carbon atoms, an alicyclic hydrocarbon group having 3 to 6 carbon atoms, or the like.

Examples of the organic compound of the present invention with the above structure are shown below.

[Chemical Formulae 34]

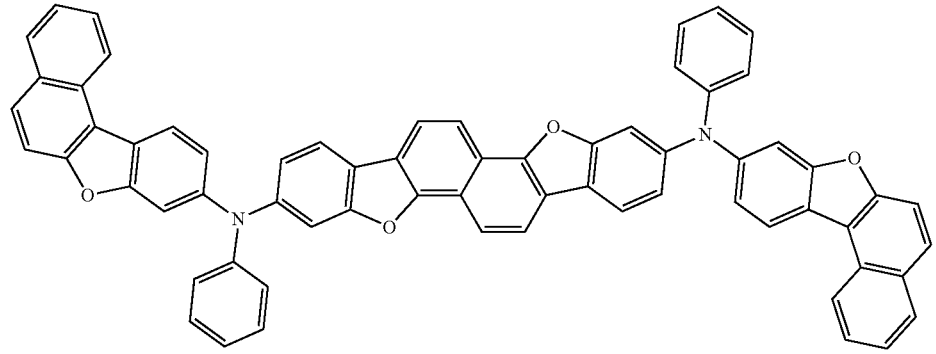

(100)

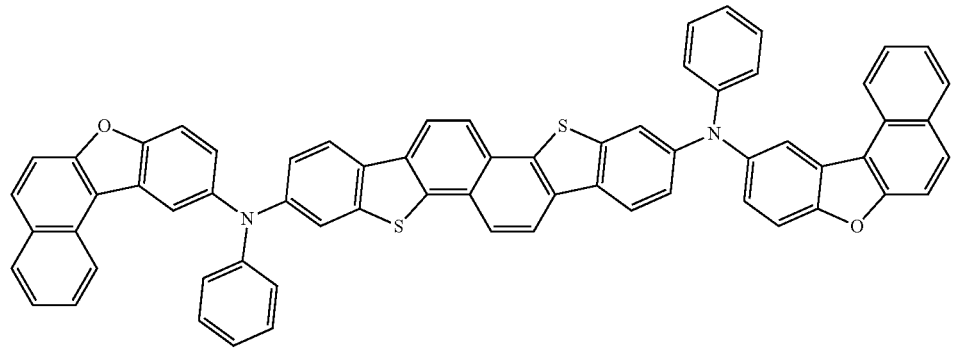

(101)

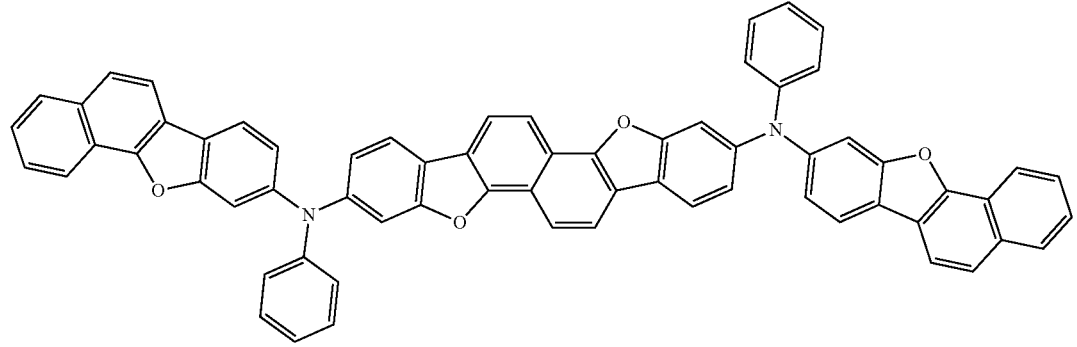

(102)

-continued
(103)
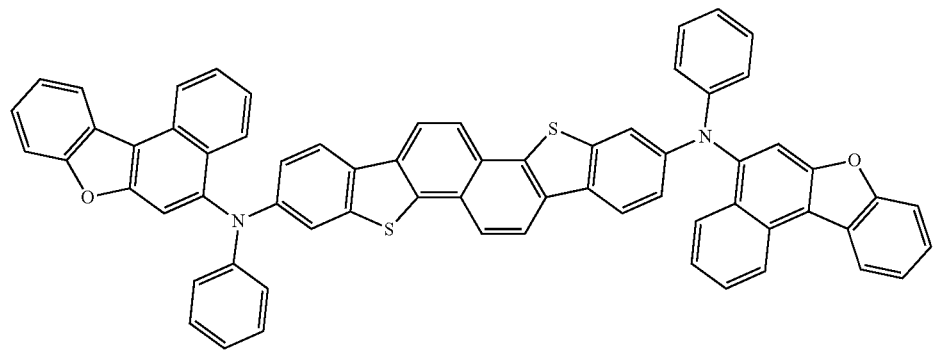
(104)
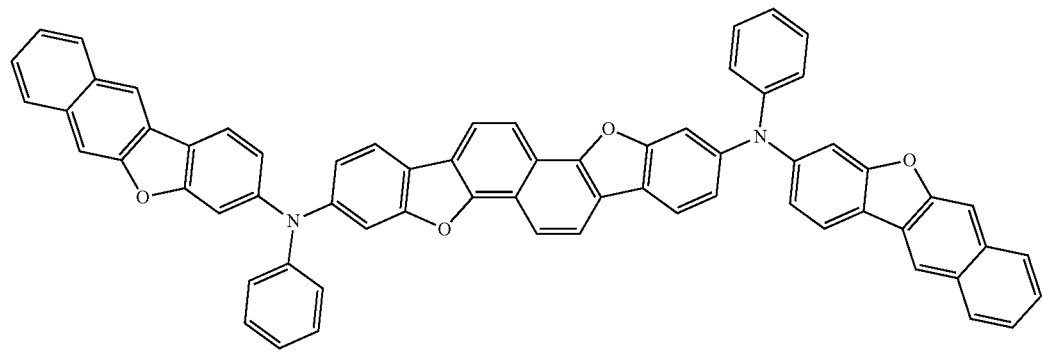
(105)
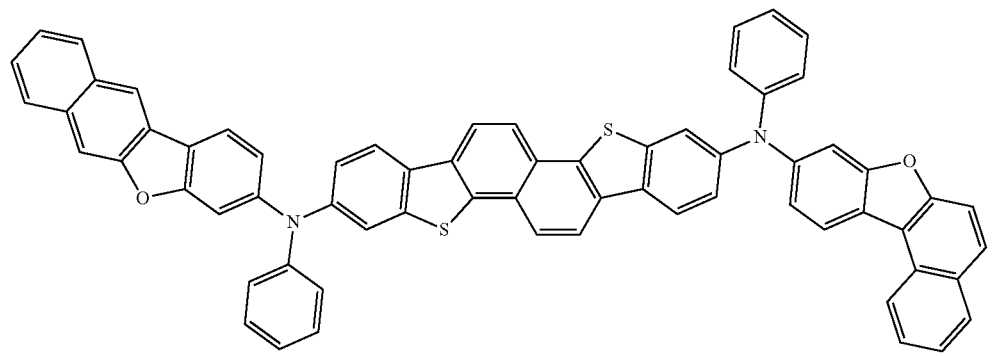
(106)
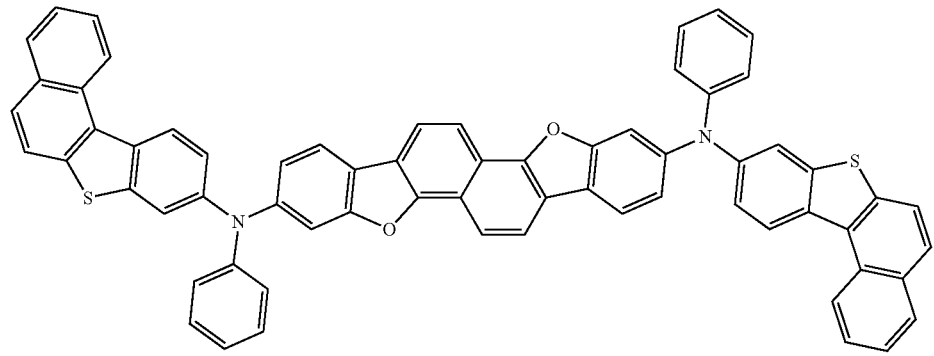

[Chemical formulae 35]
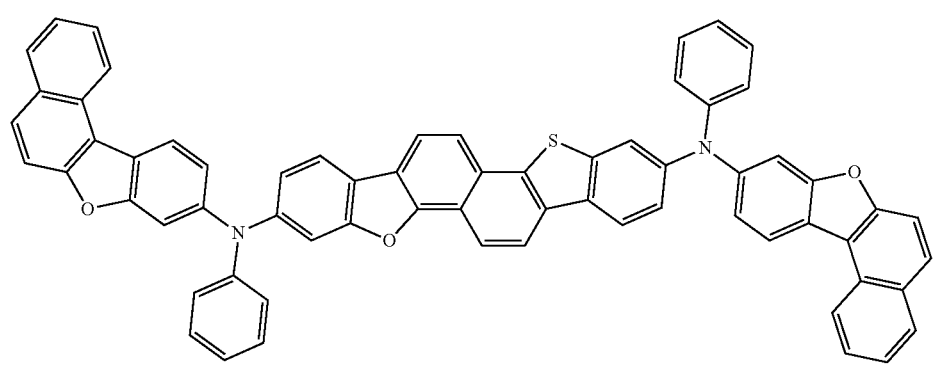
(107)
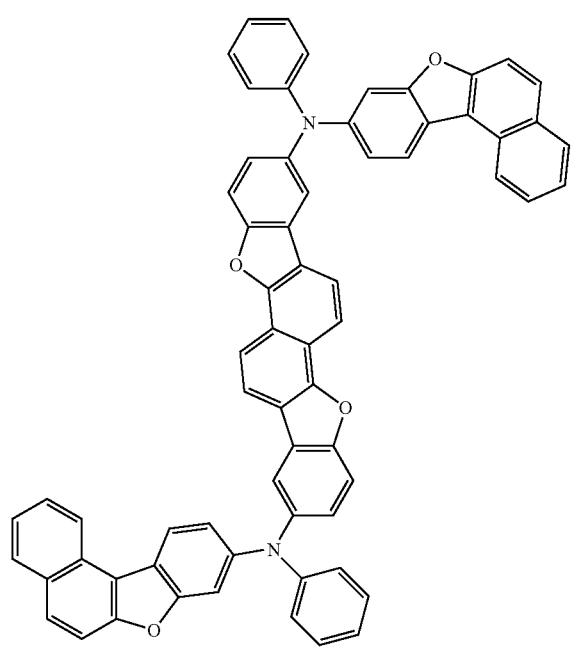
(108)

(109)
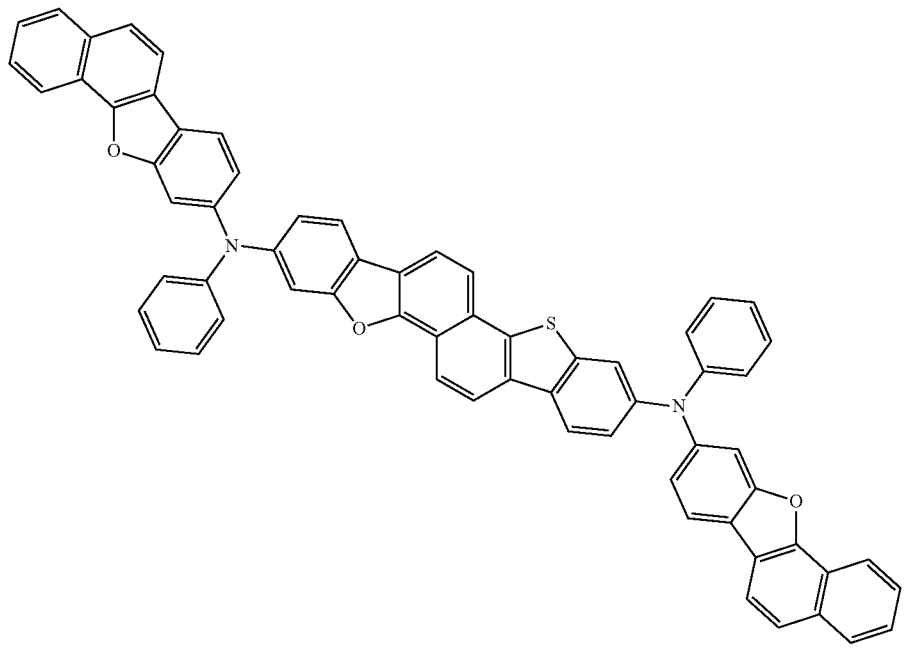
(110)
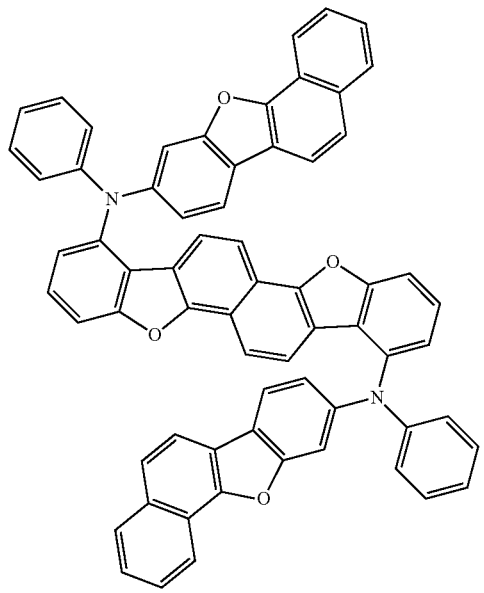

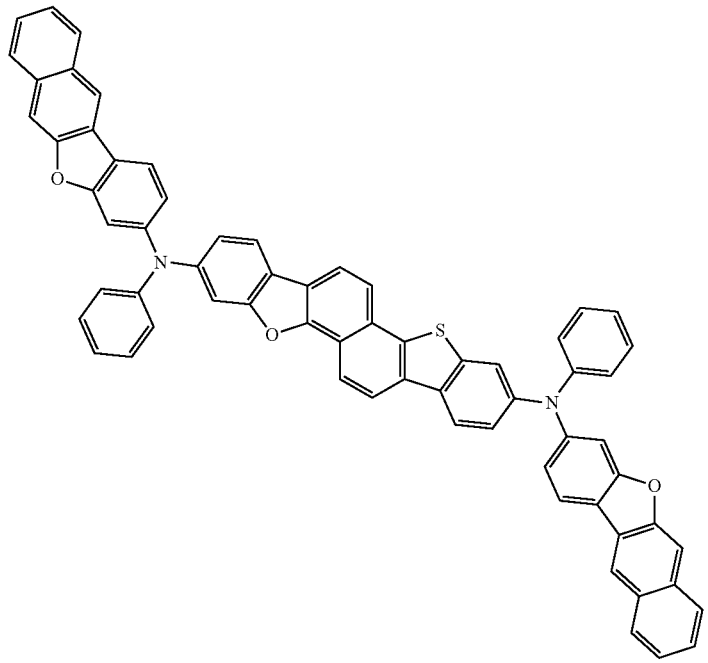
(111)
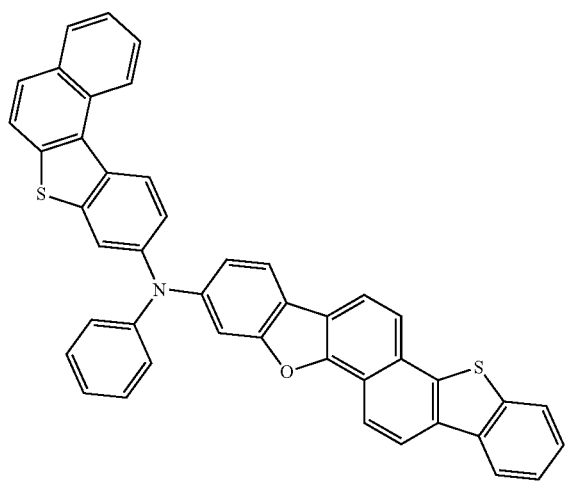
(112)

(113)
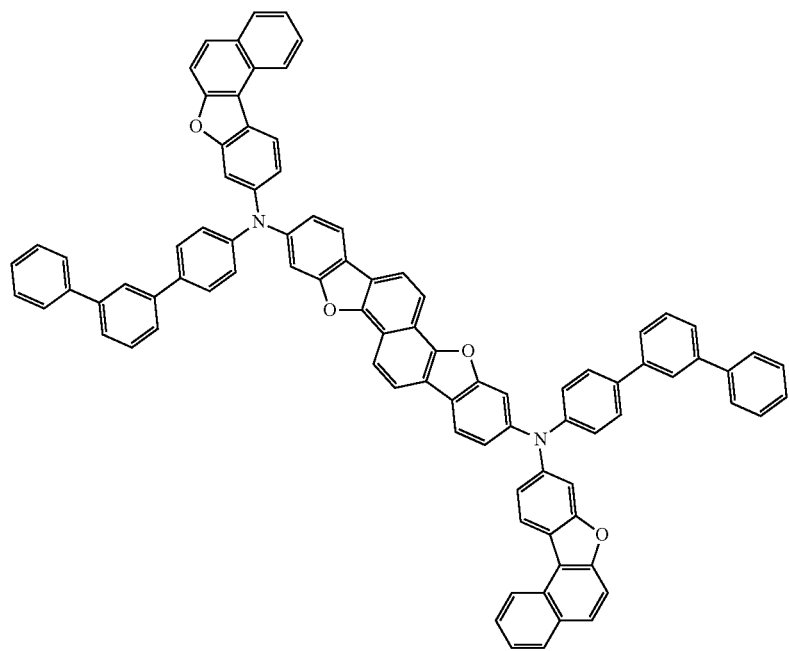
(114)
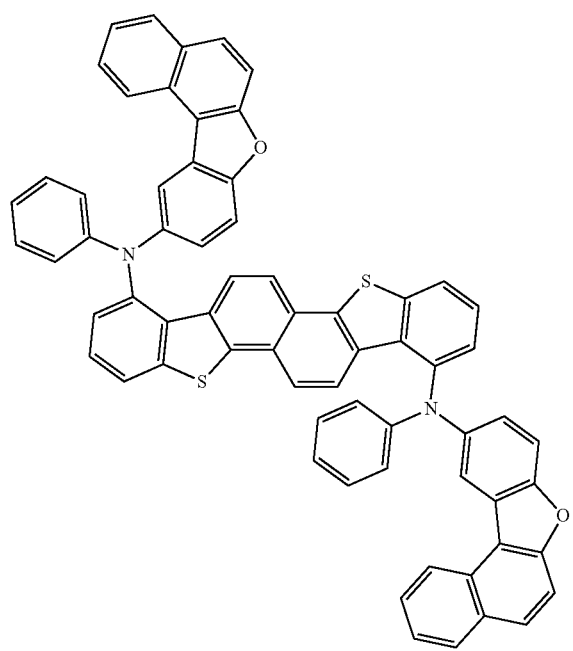

-continued
[Chemical Formulae 36]
(115)
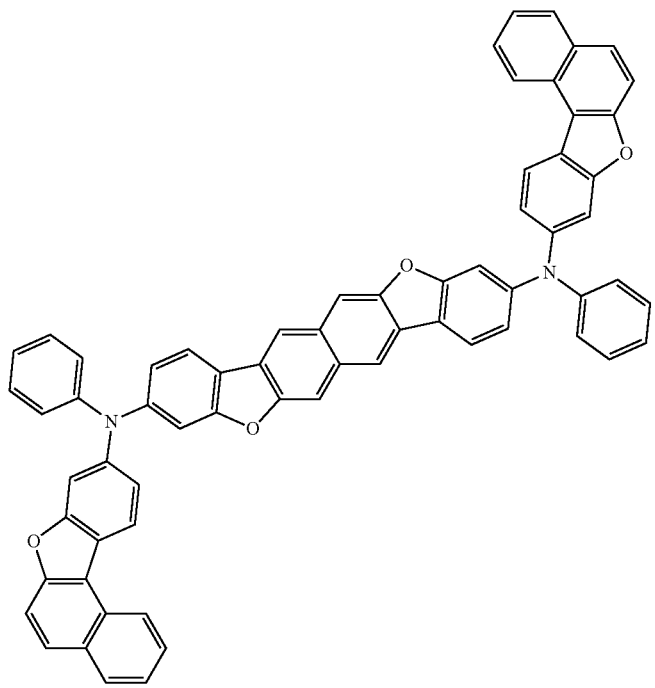
(116)
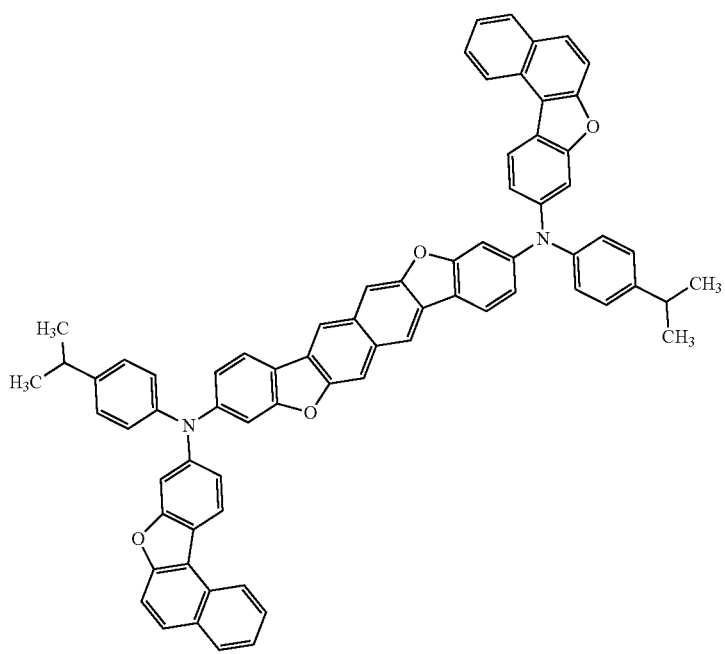

(117)
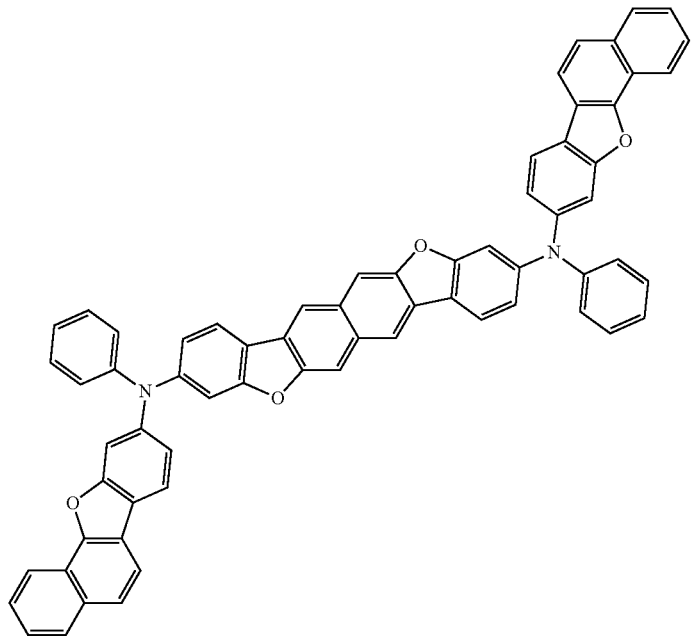
(118)
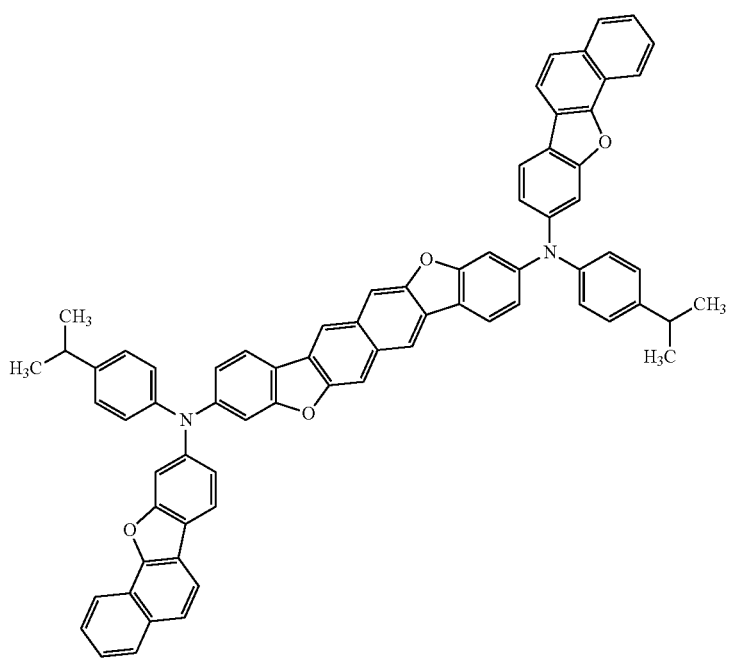

(119)
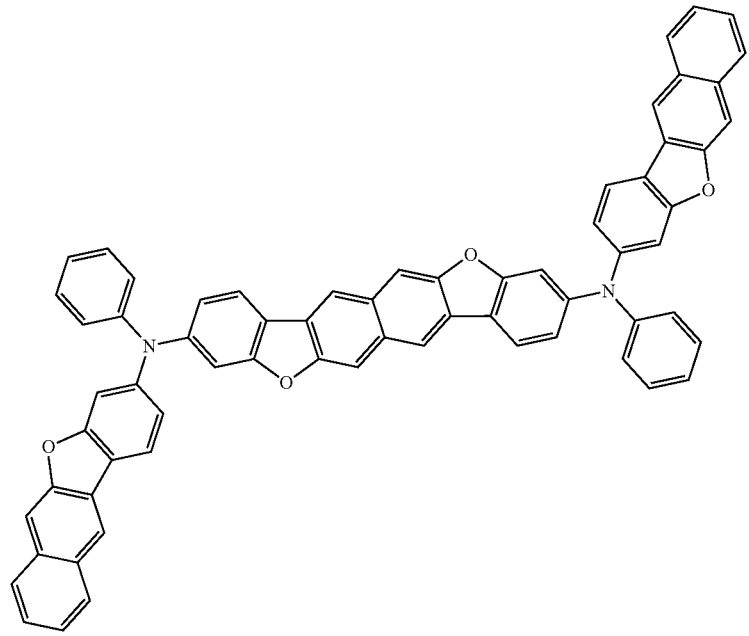
(120)
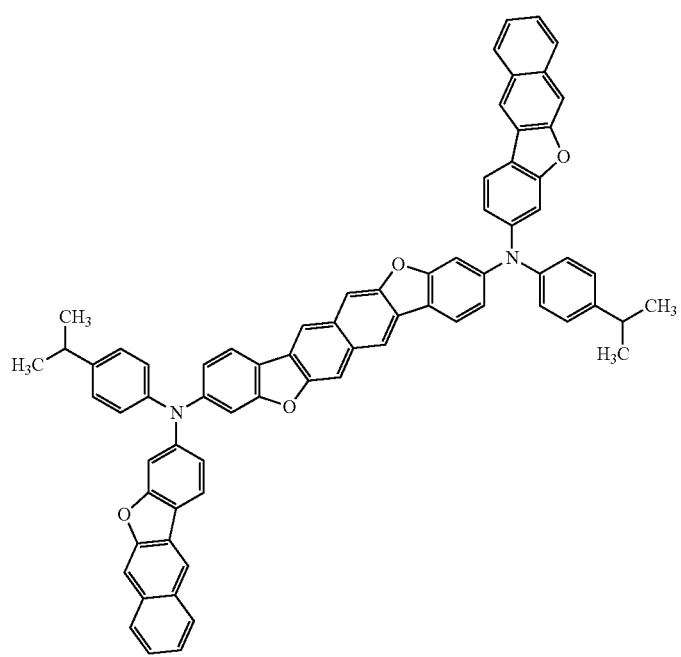

[Chemical Formulae 37]
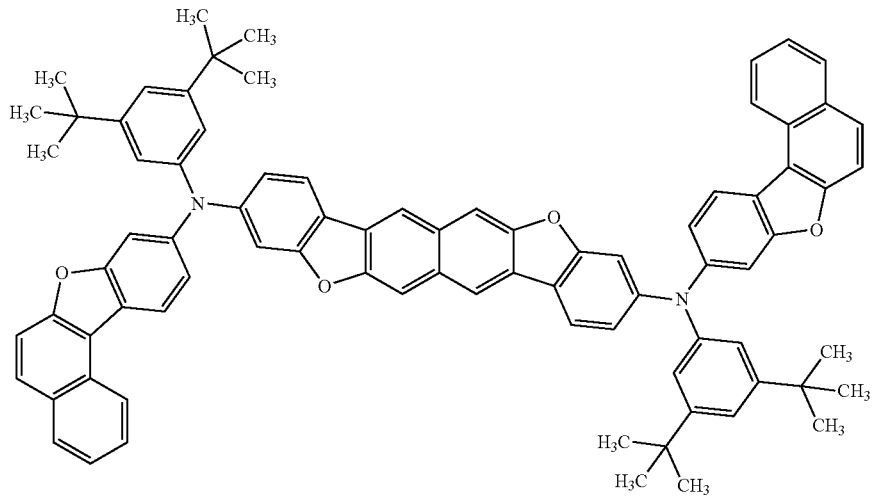
(121)
(122)

(123)
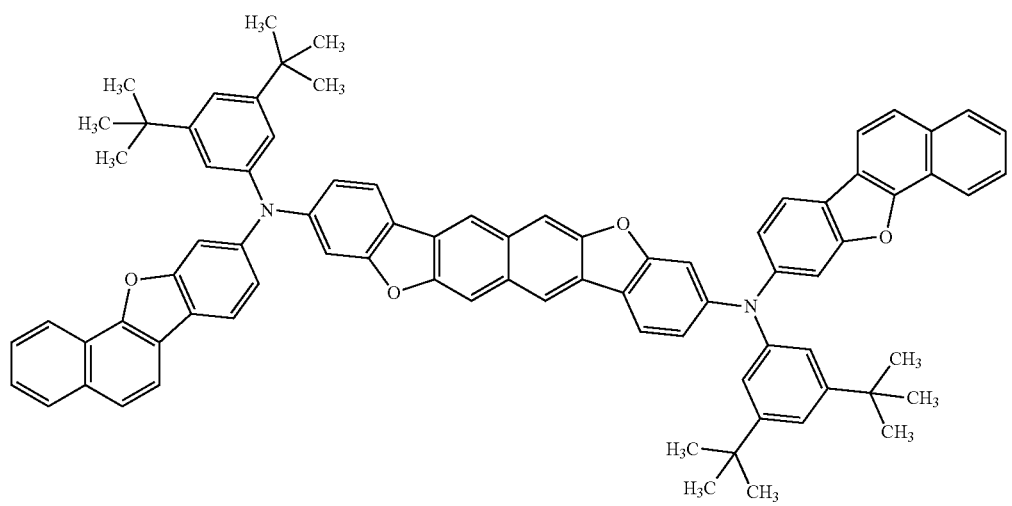
(124)
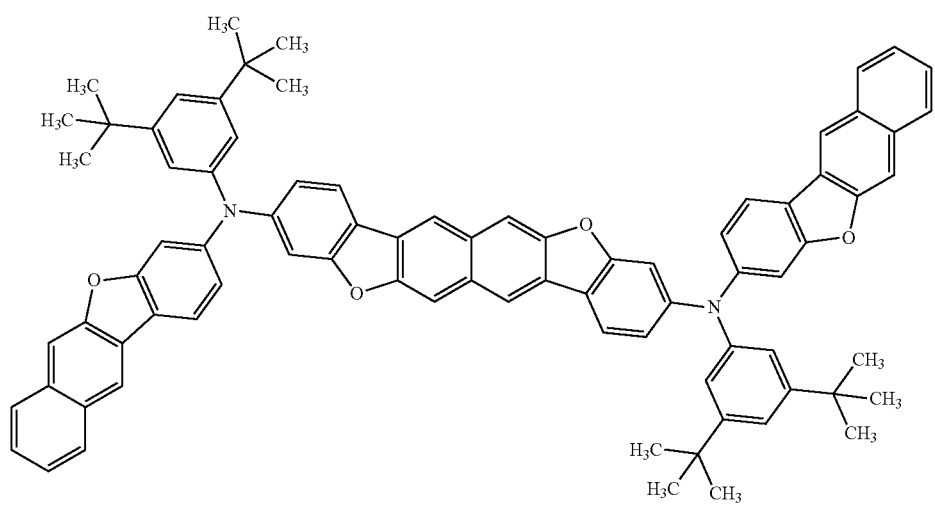
(125)
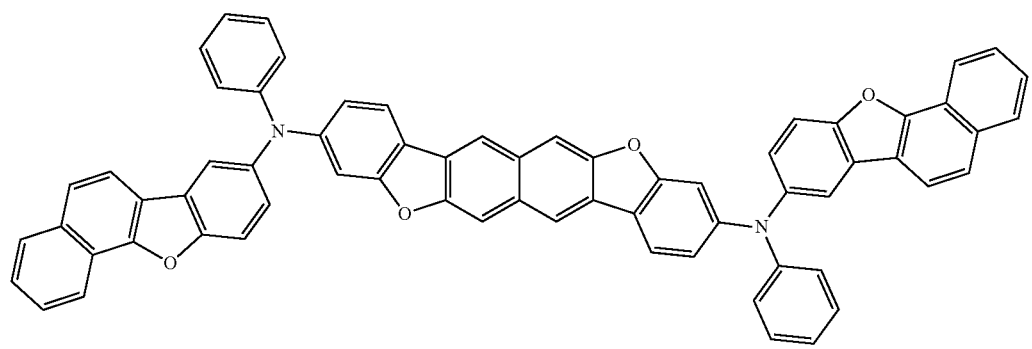

-continued
(126)
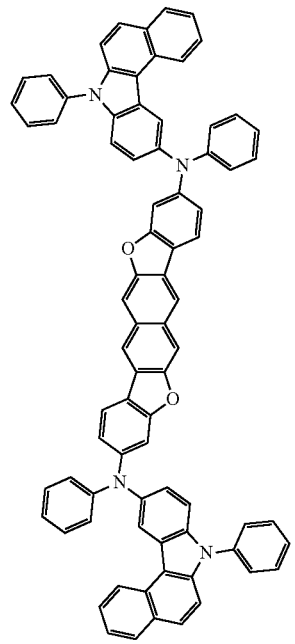
(127)
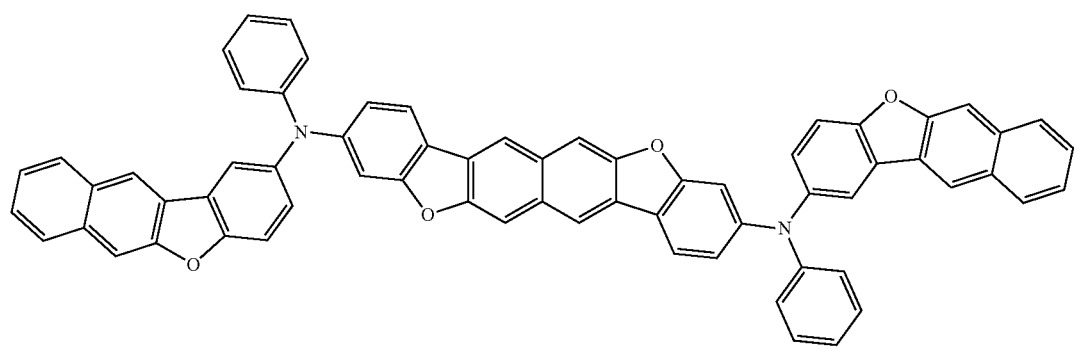
[Chemical Formulae 38]
(128)
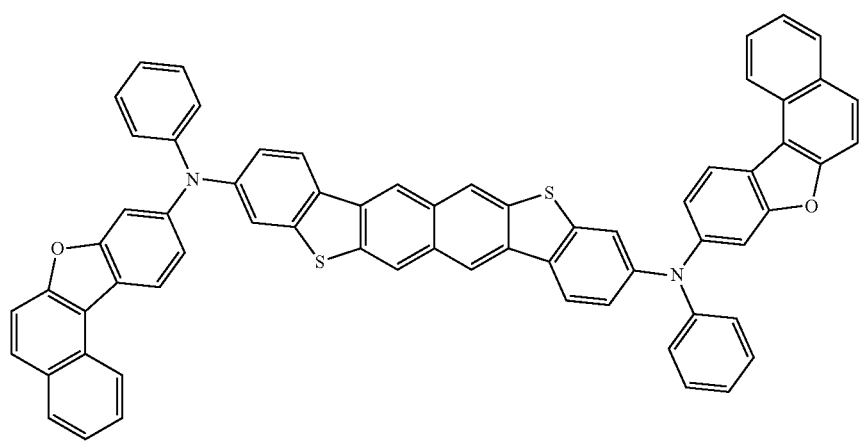

(129)
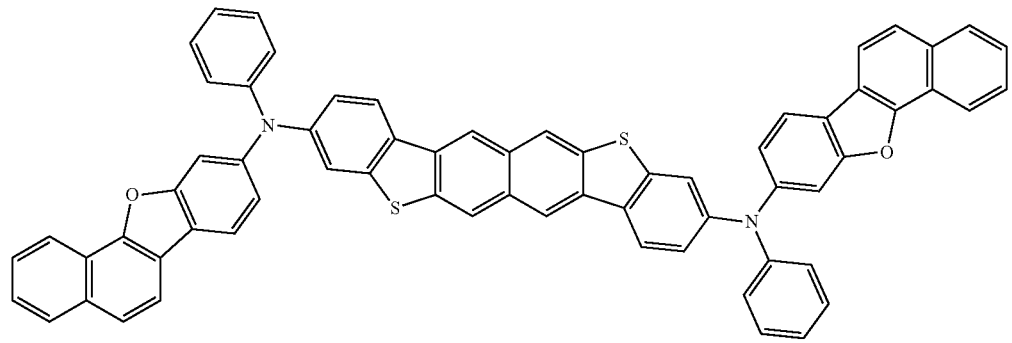
(130)
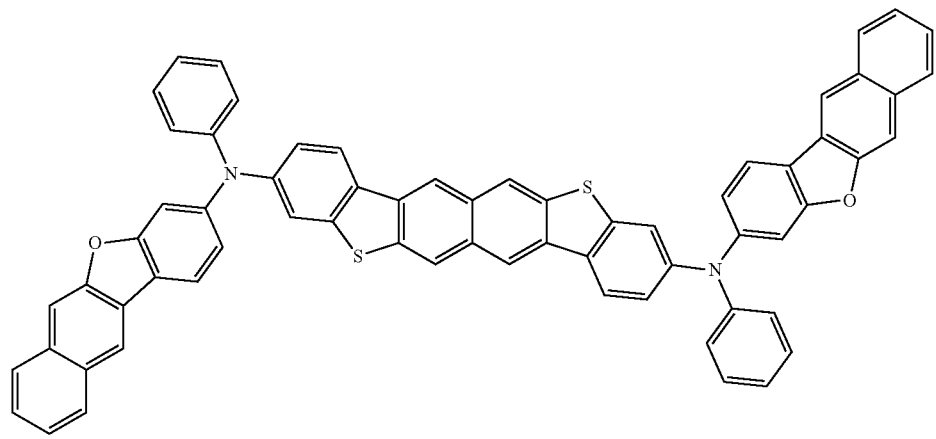
(131)
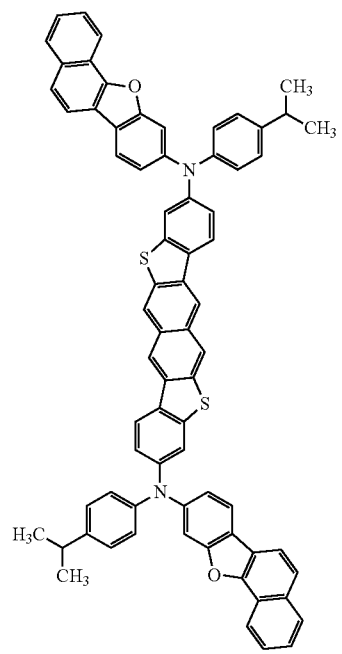

(132)
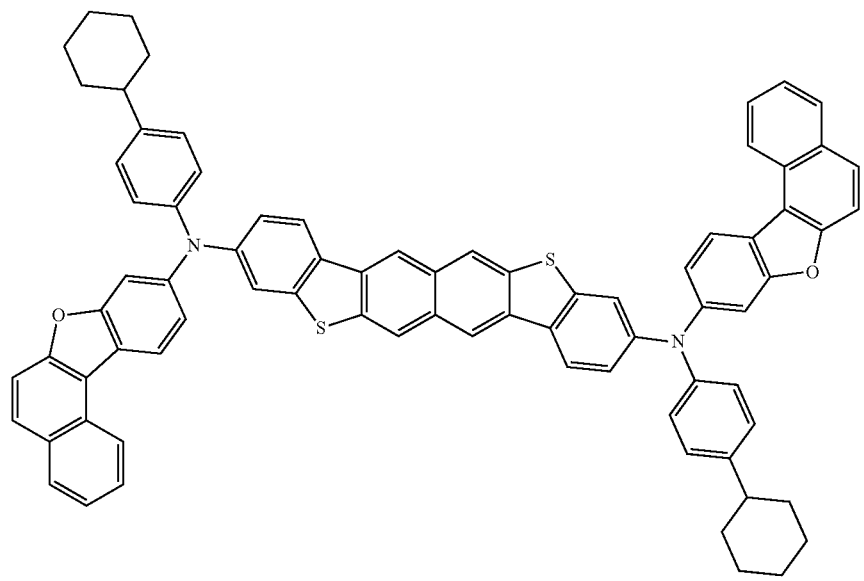
(133)
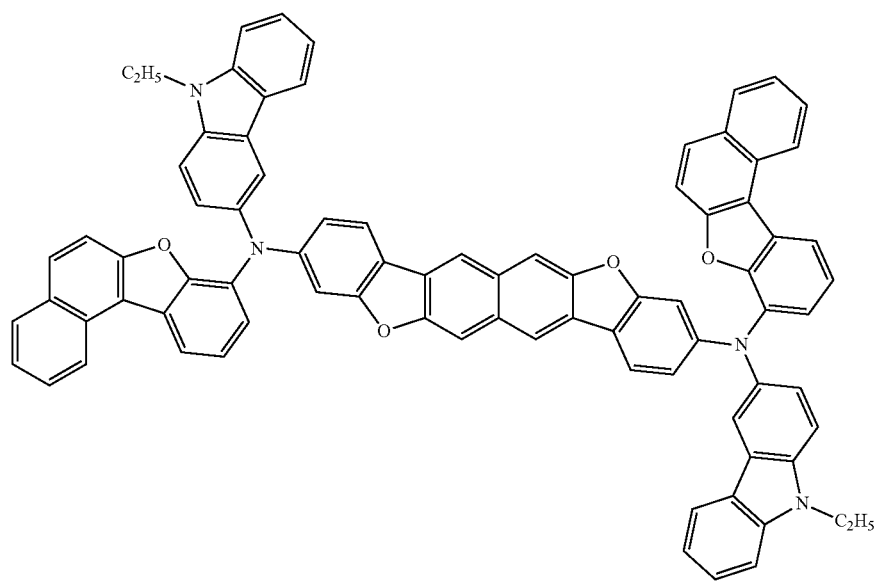

(134)
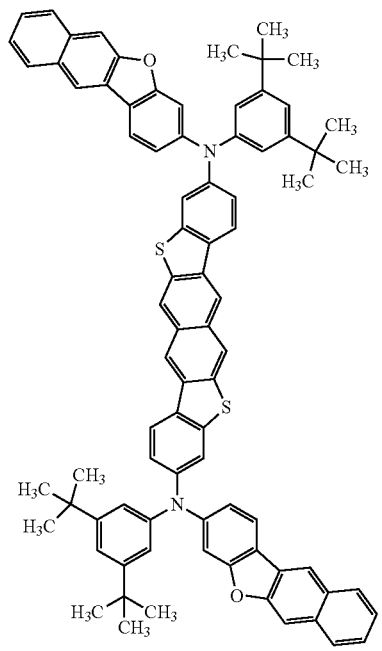
[Chemical Formulae 39]
(135)
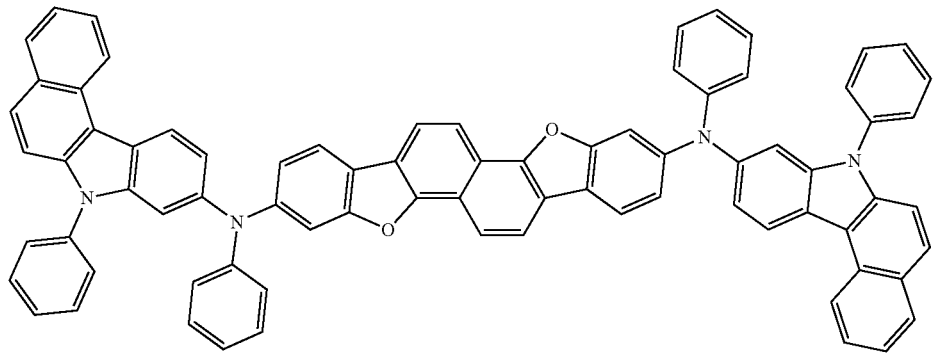
(136)
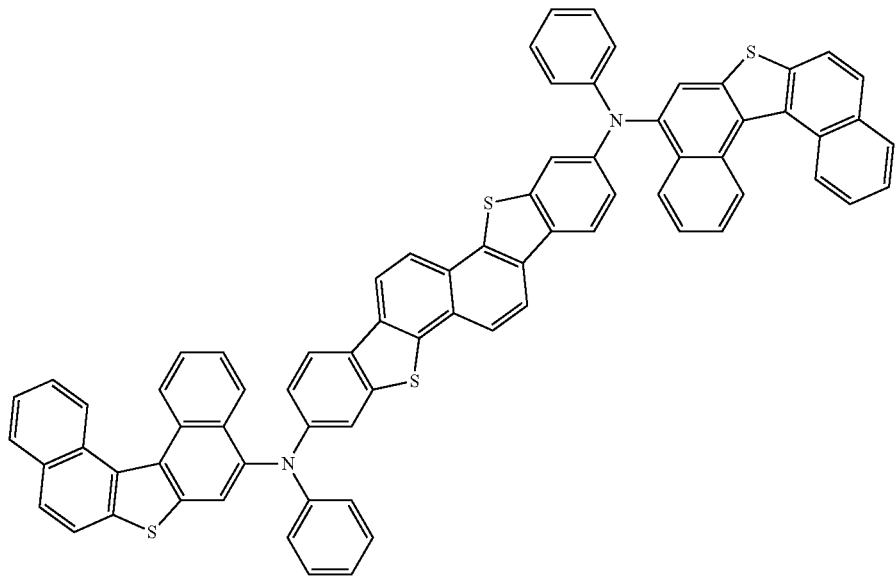

-continued
(137)
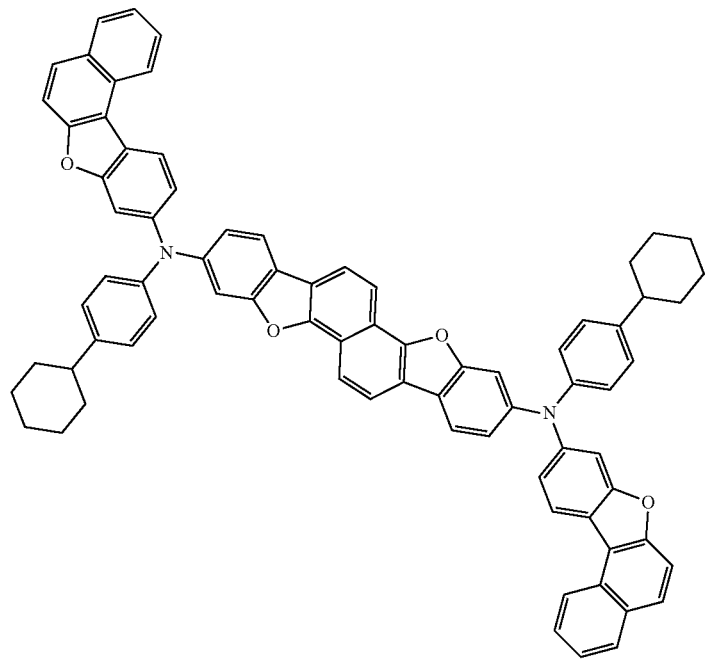
(138)
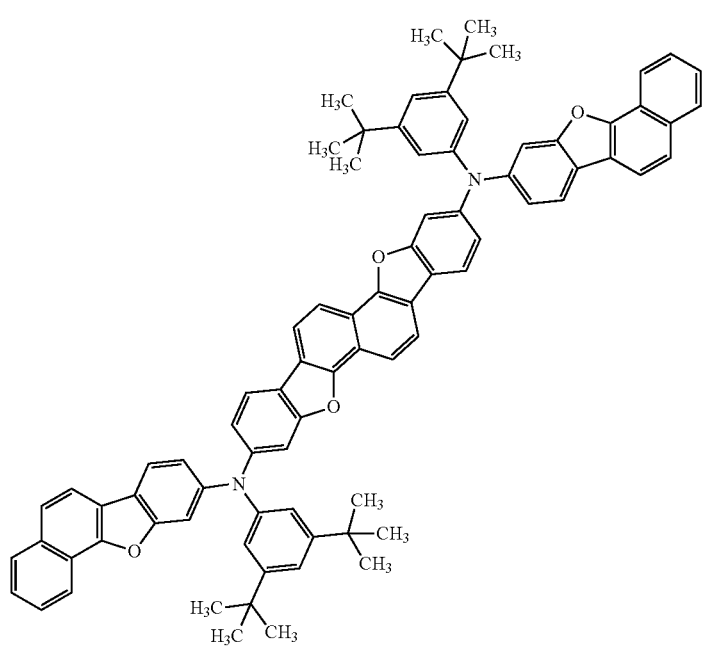

-continued
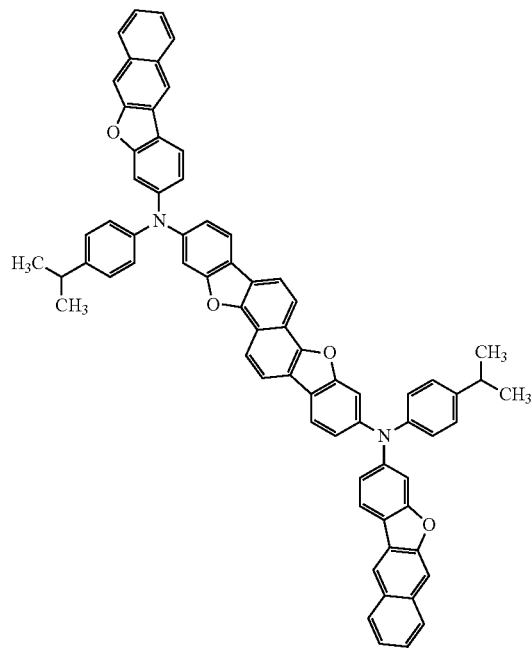
(139)
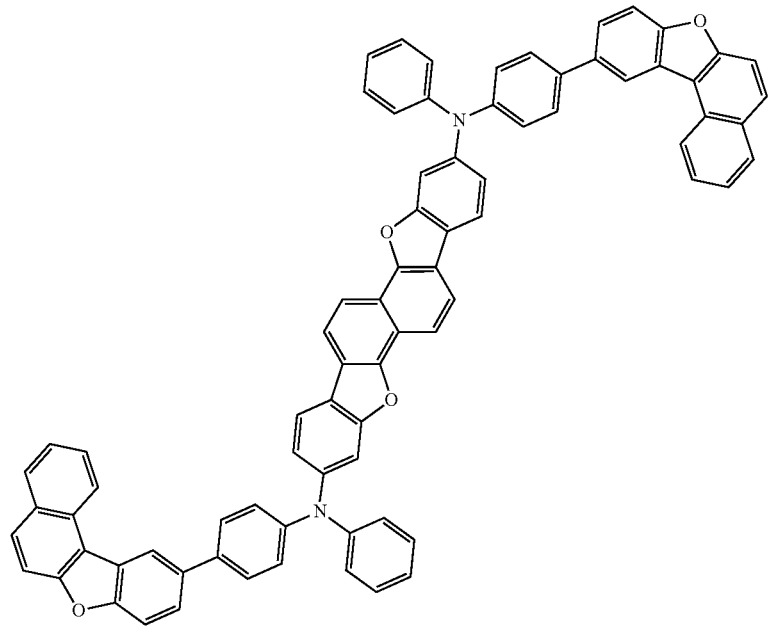
(140)
[Chemical Formulae 40]
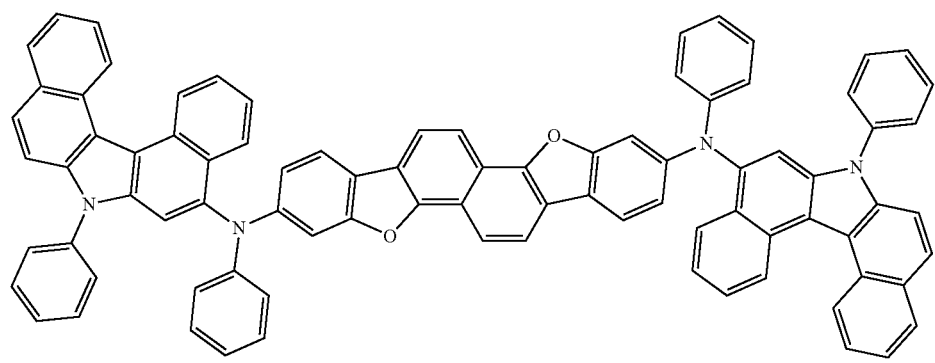
(141)

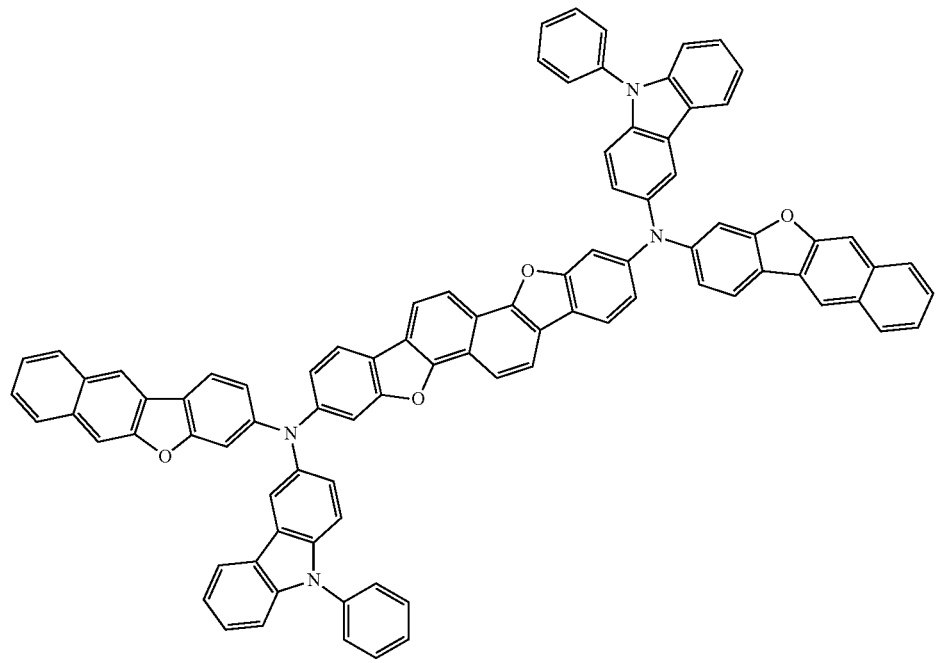
(142)
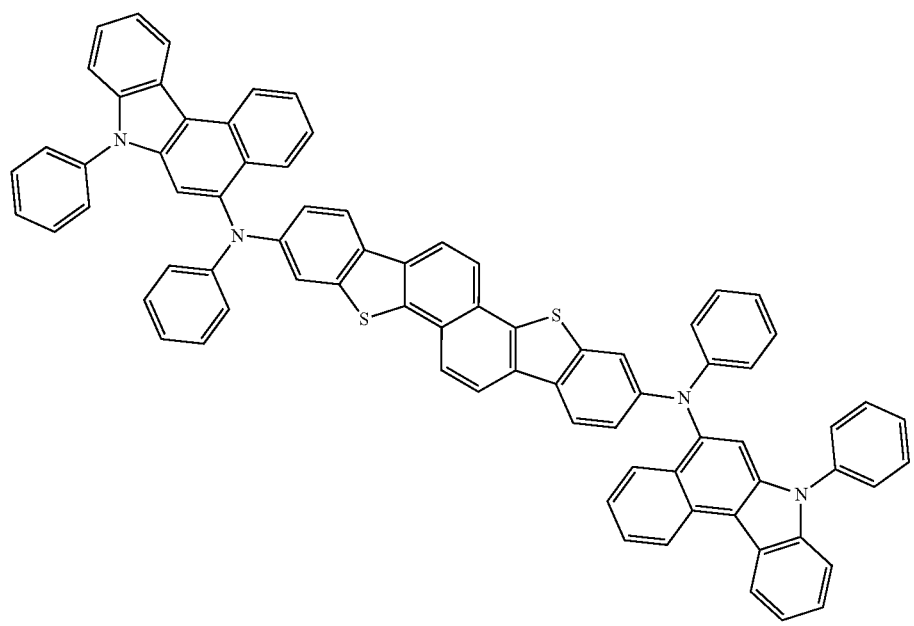
(143)

-continued
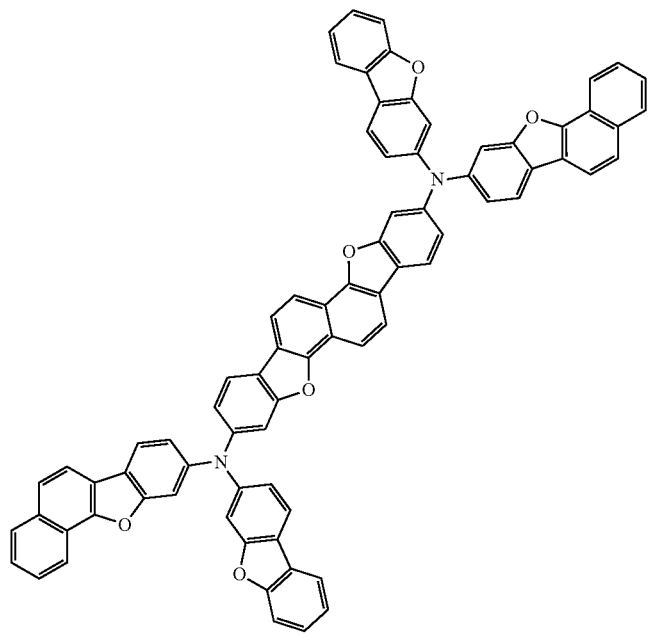
(144)
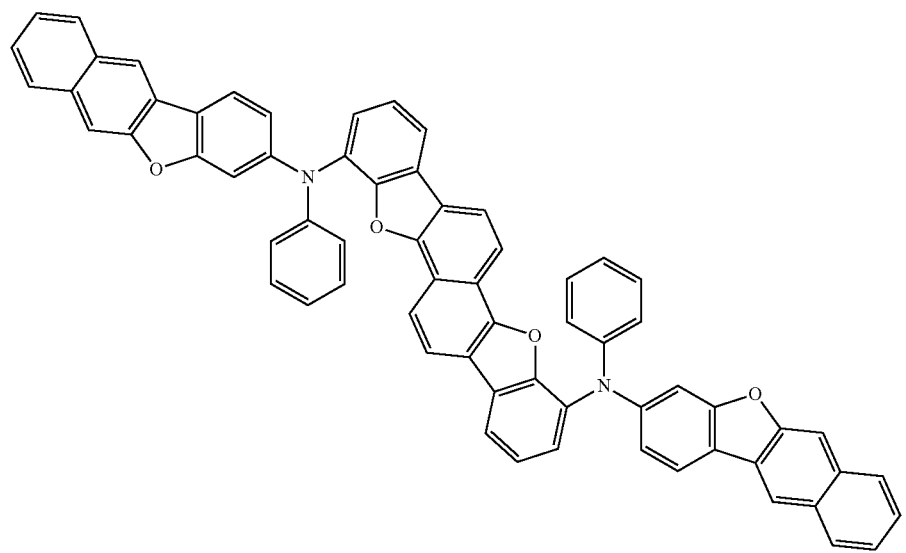
(145)

-continued
(146)
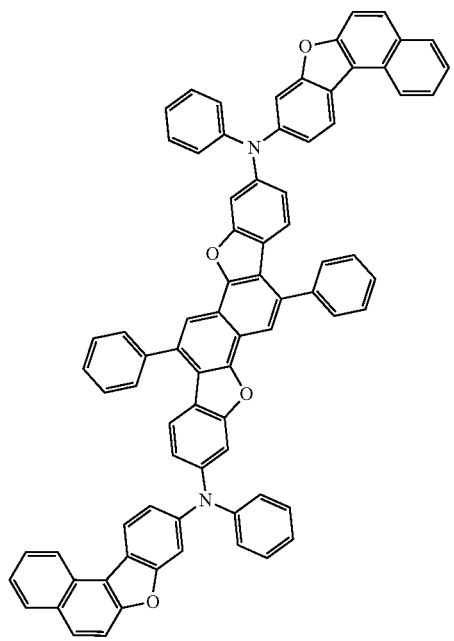
(147)
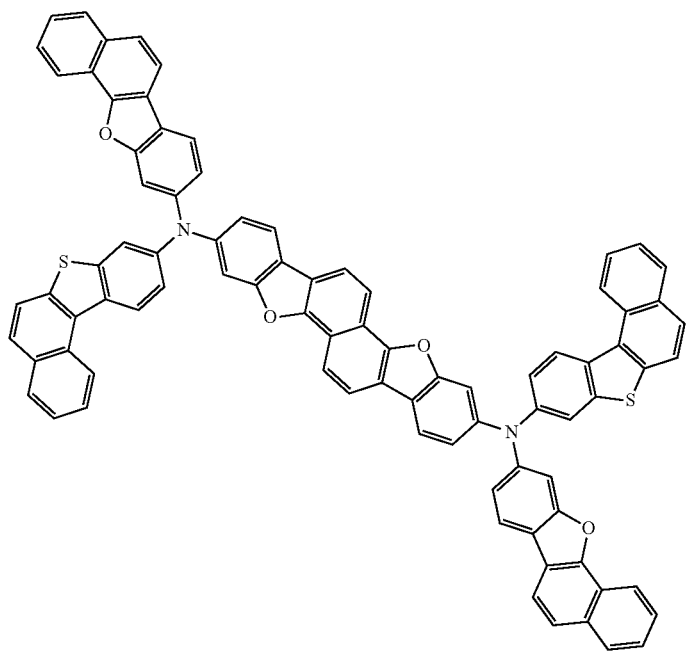

[Chemical Formulae 41]
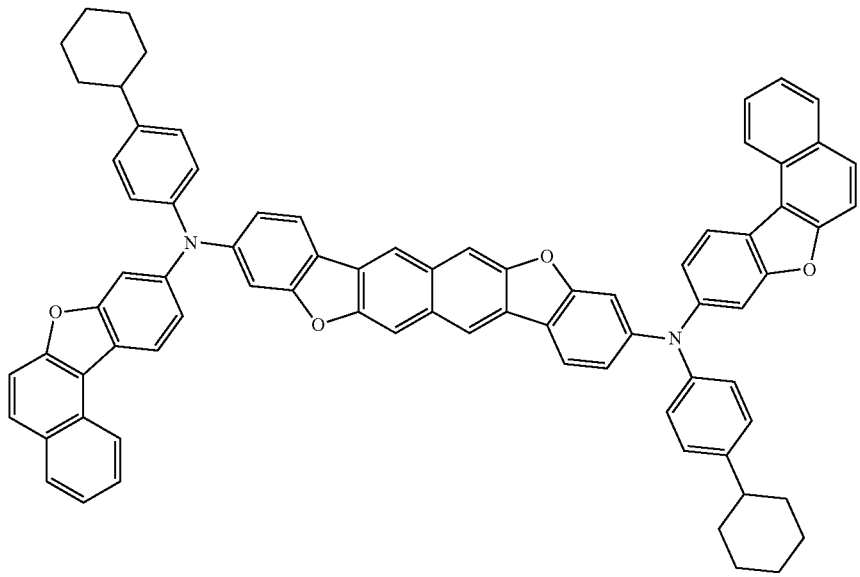
(148)
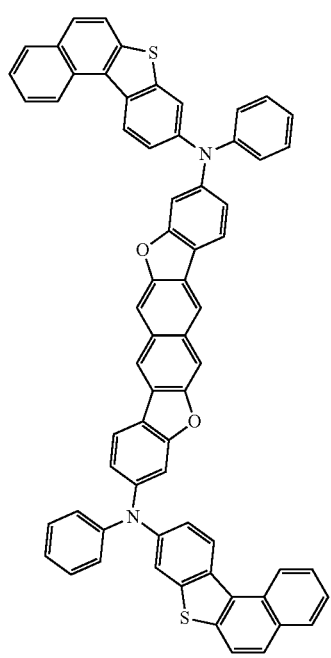
(149)

-continued
(150)
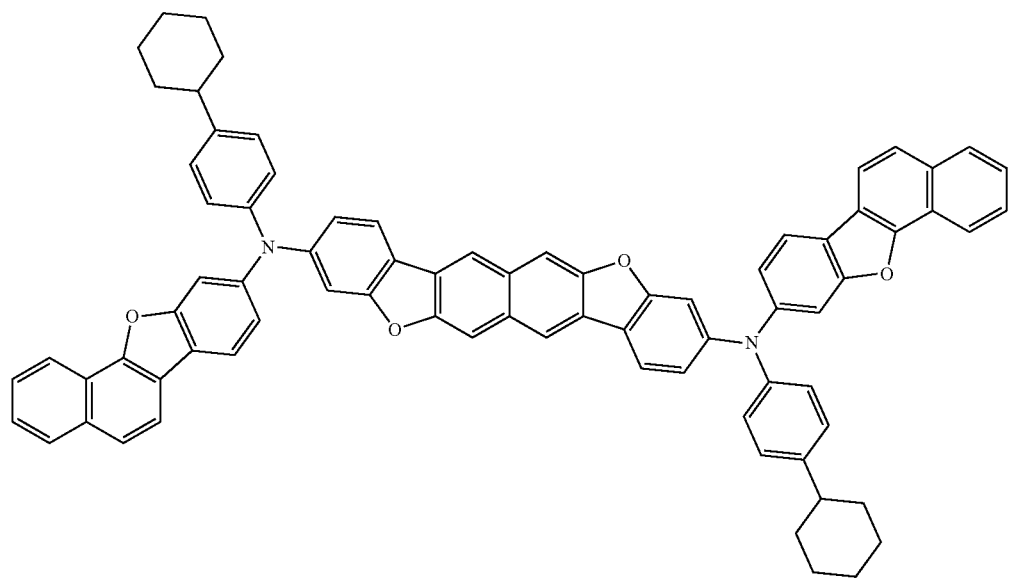
(151)
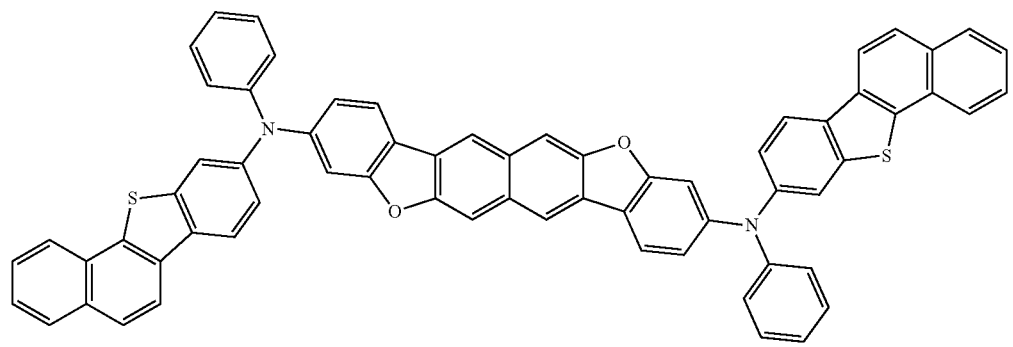
(152)
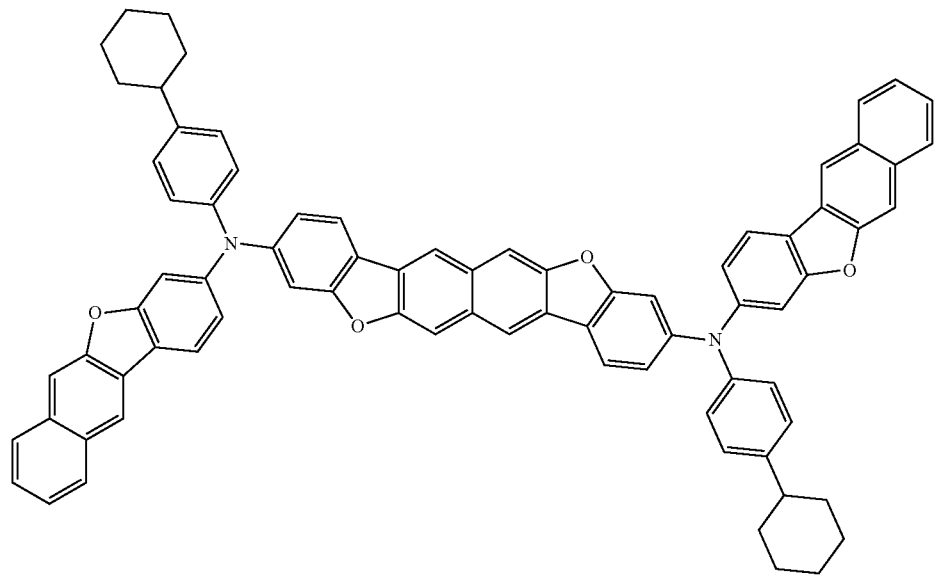

(153)
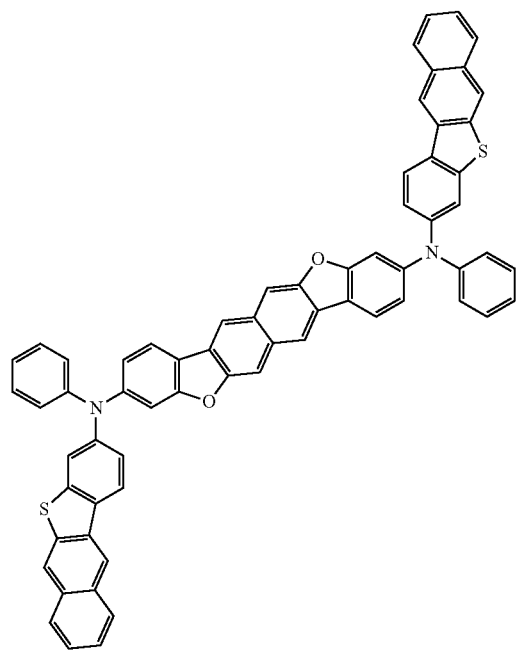
[Chemical Formulae 42]
(154)
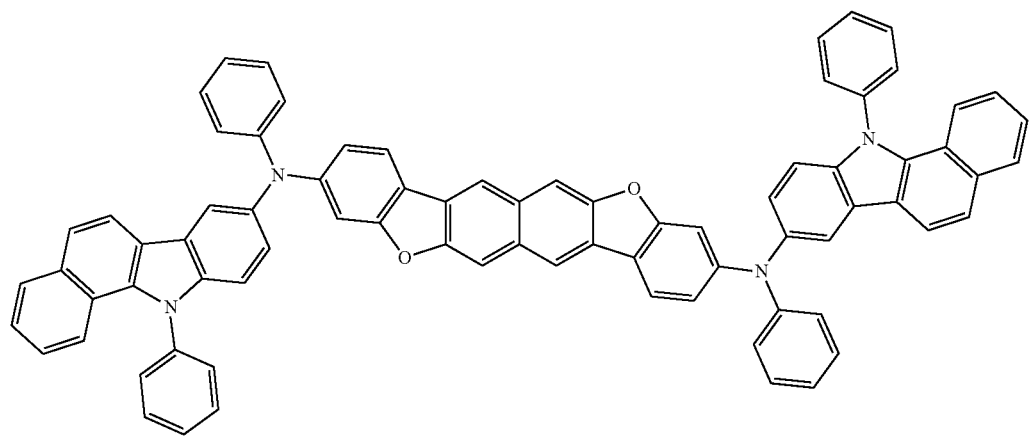

-continued
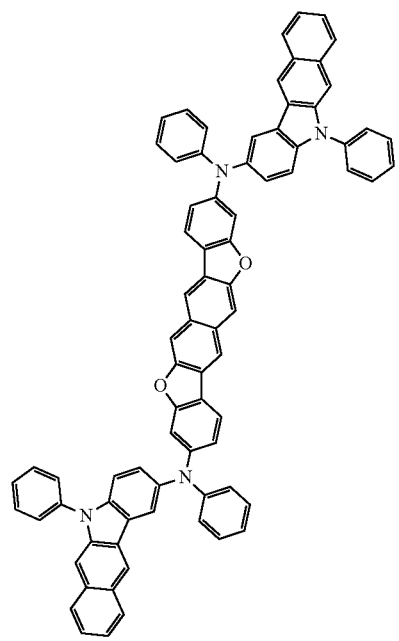
(155)
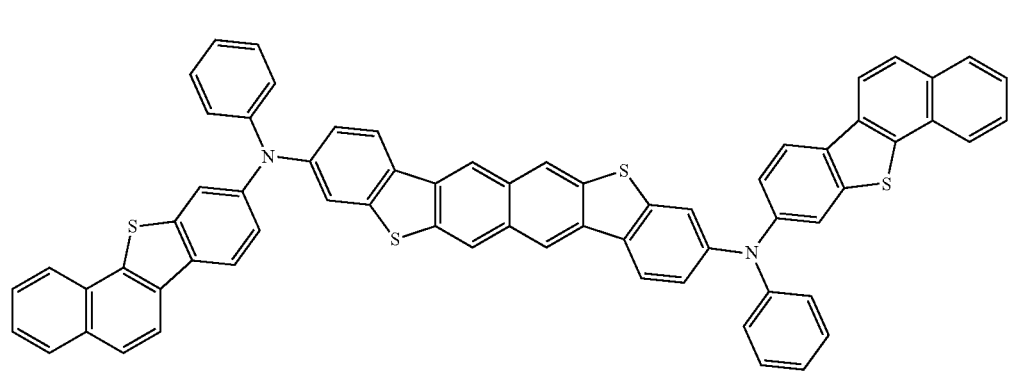
(156)
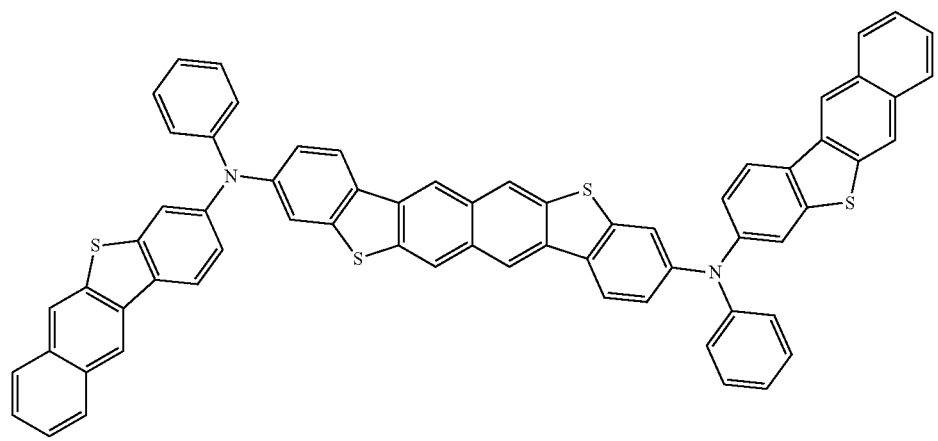
(157)

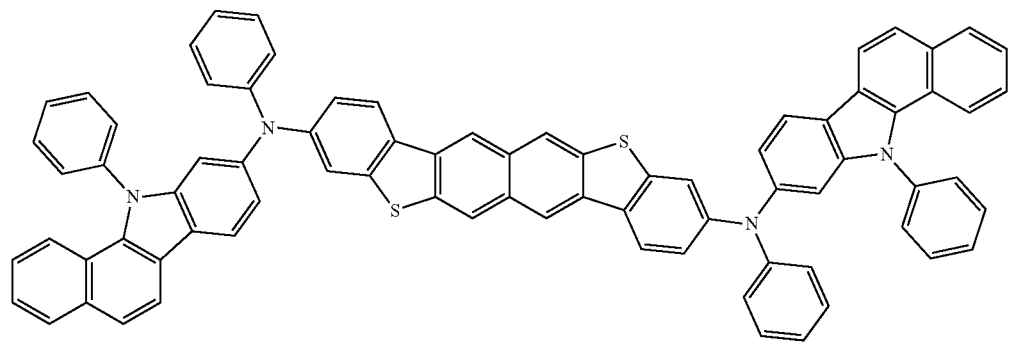
(158)
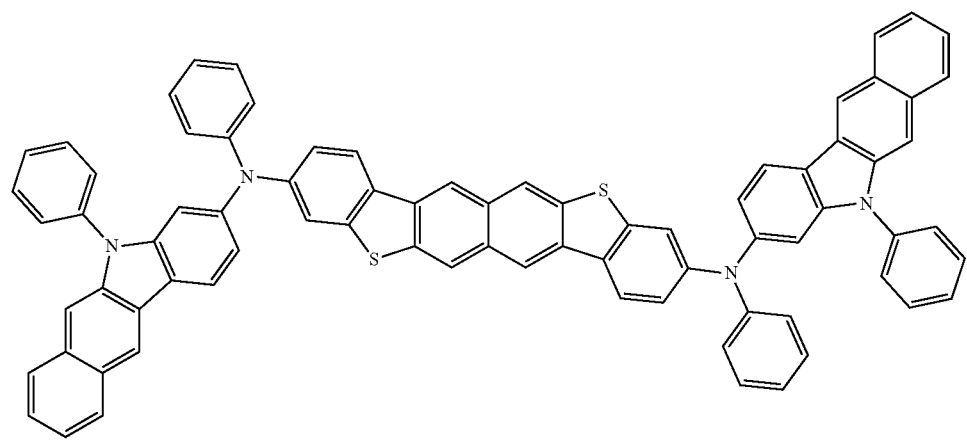
(159)
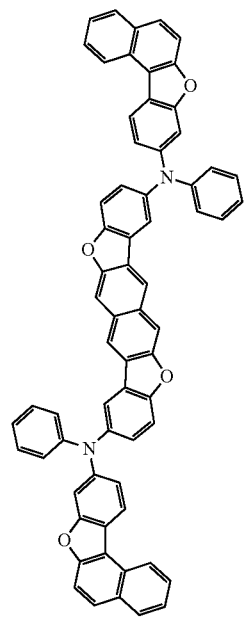
(160)

[Chemical Formulae 43]
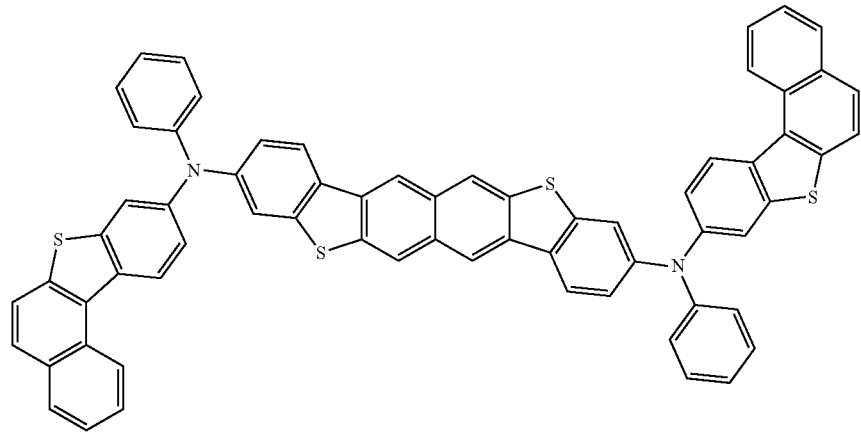
(161)
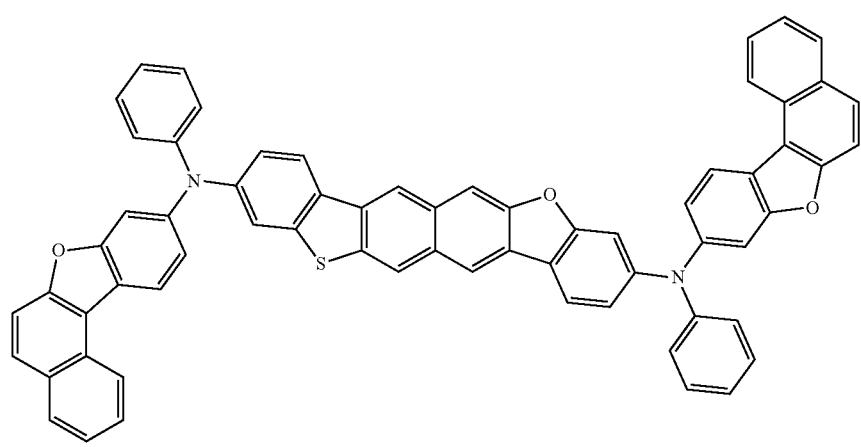
(162)
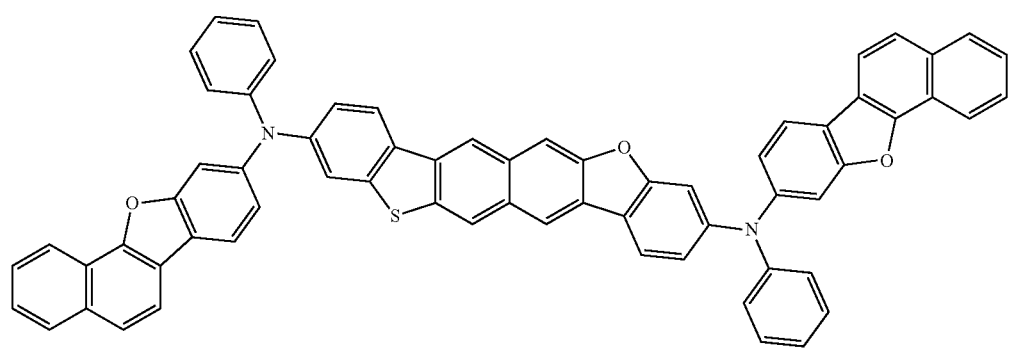
(163)

(164)
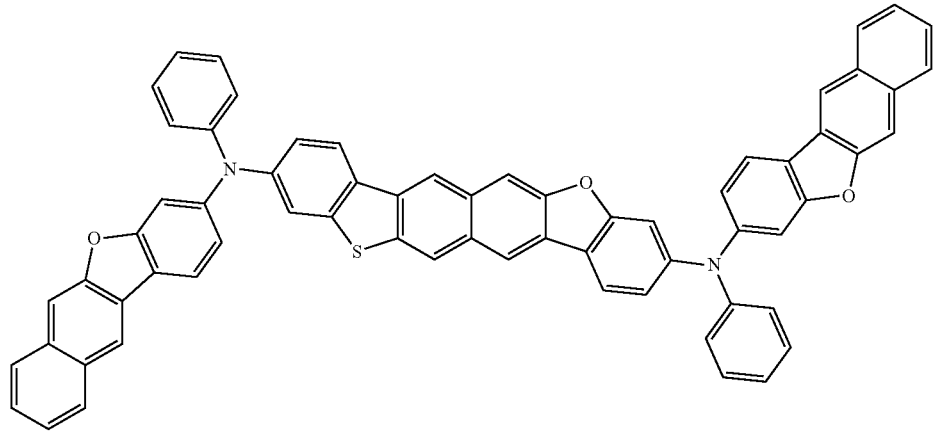
(165)
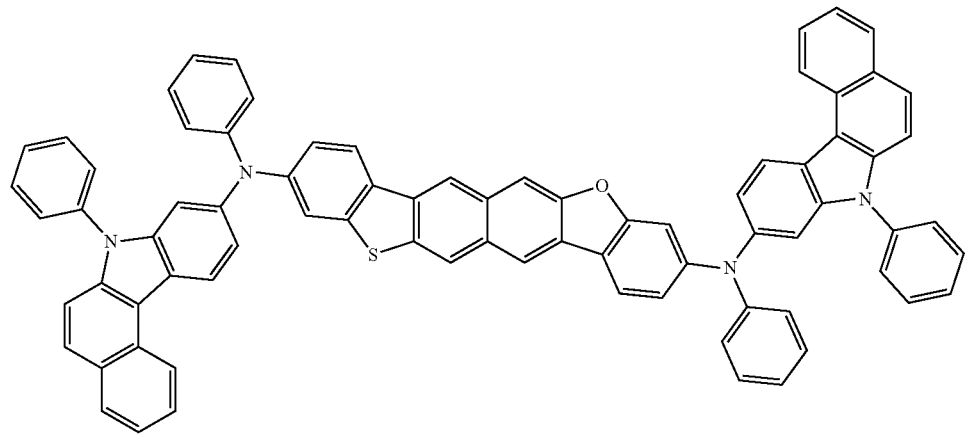
(166)
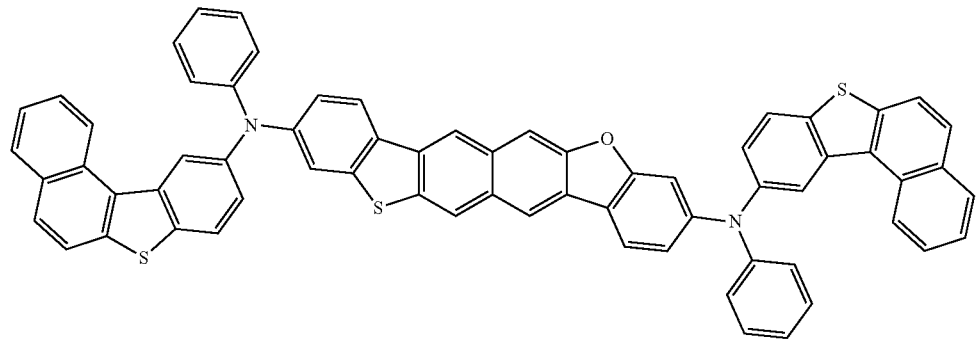
(167)
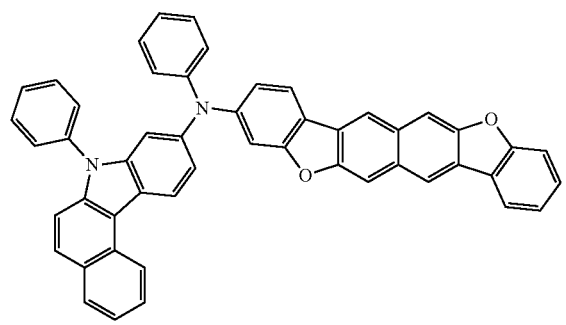
(168)
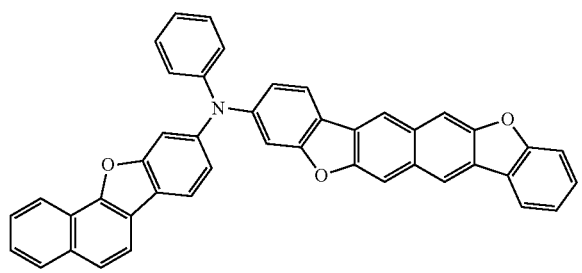

[Chemical Formulae 44]
(169)
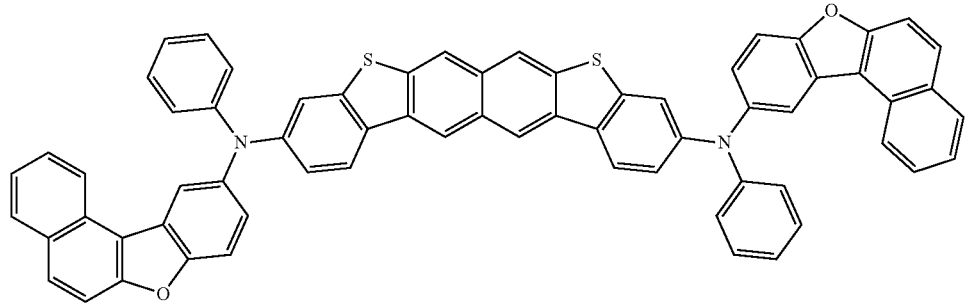
(170)
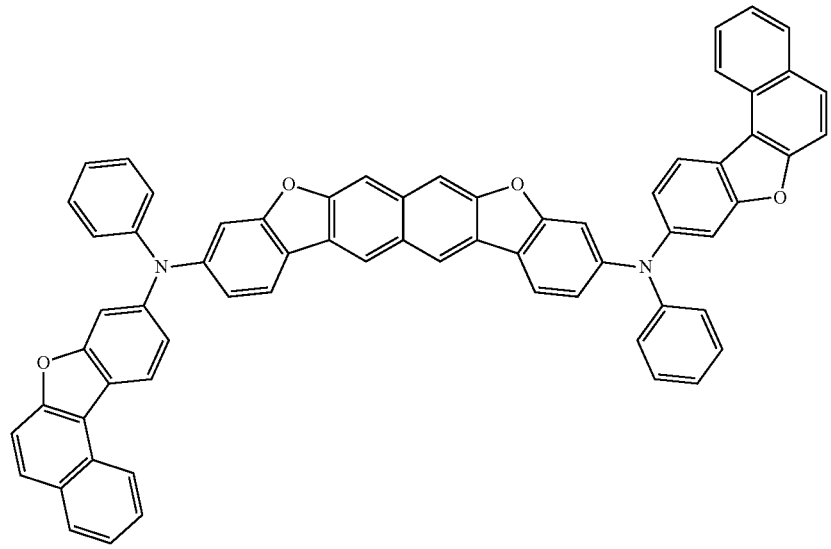
(171)
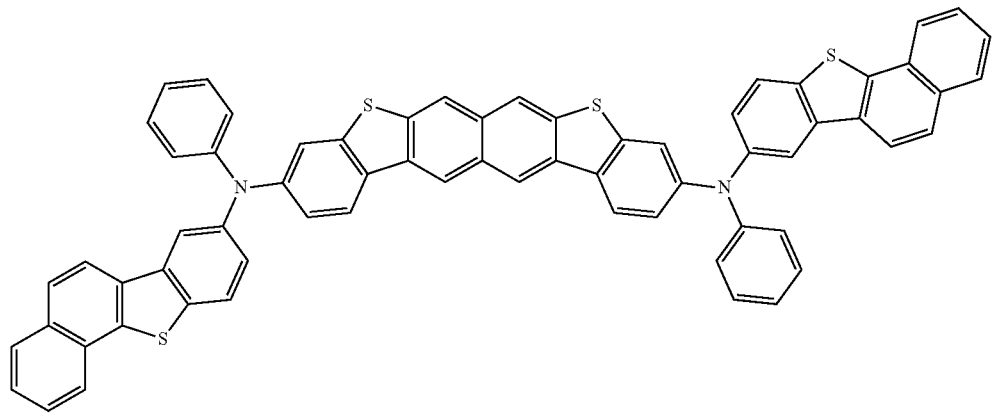

-continued
(172)
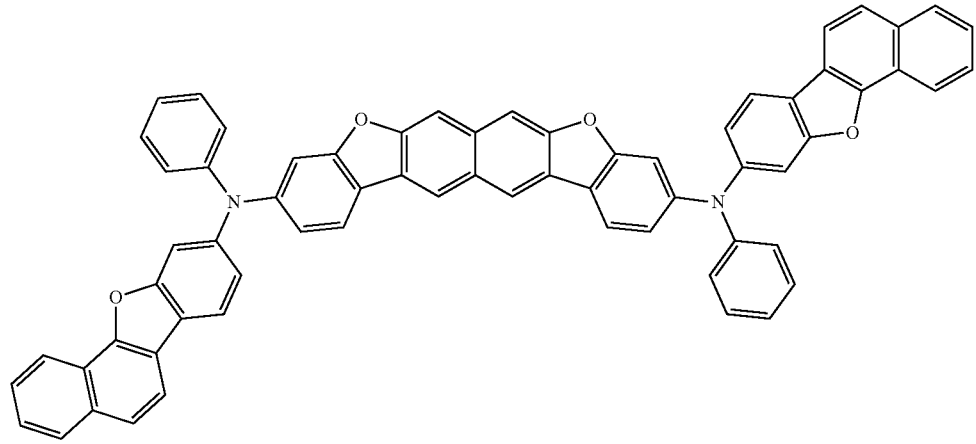
(173)
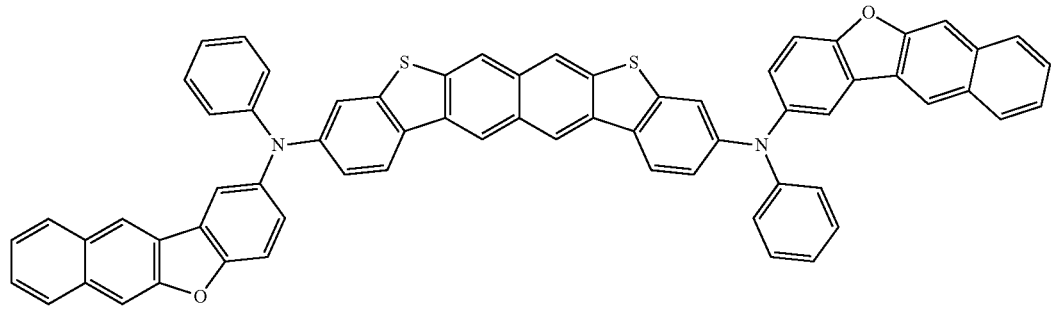
(174)
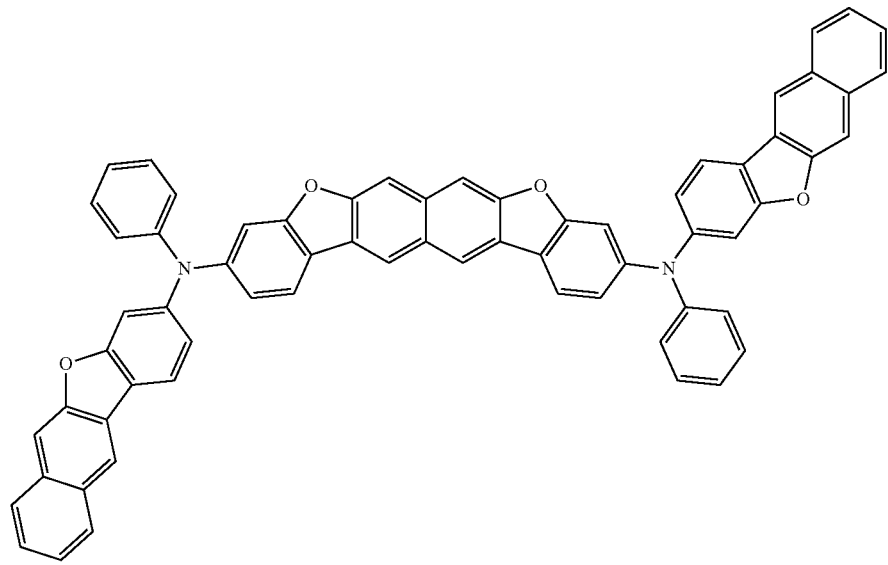

(175)
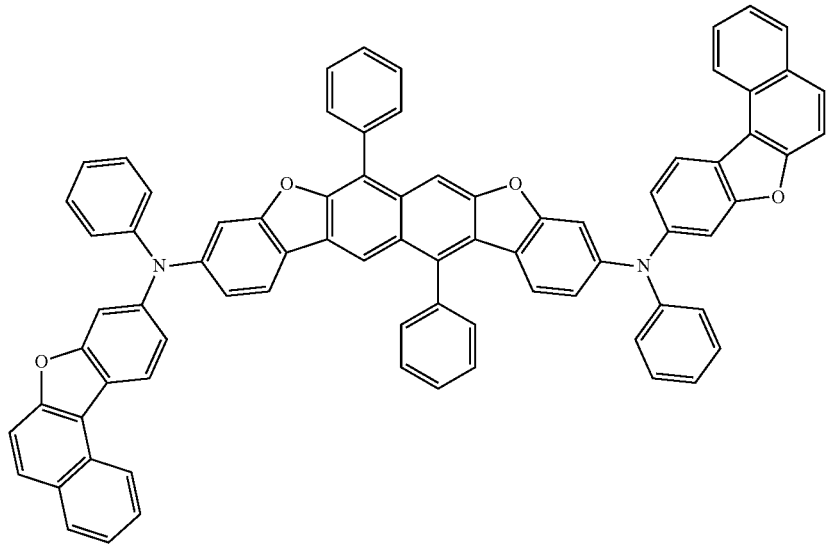
[Chemical formulae 45]
(176)
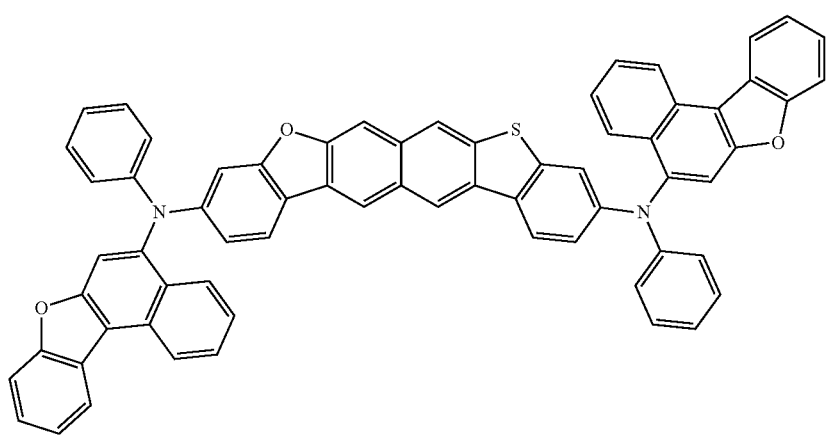
(177)
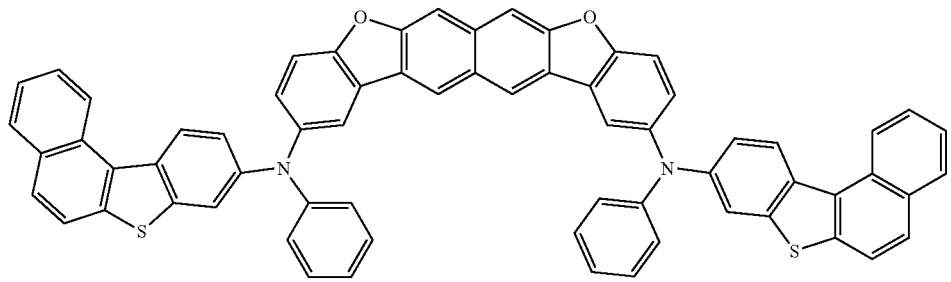

-continued
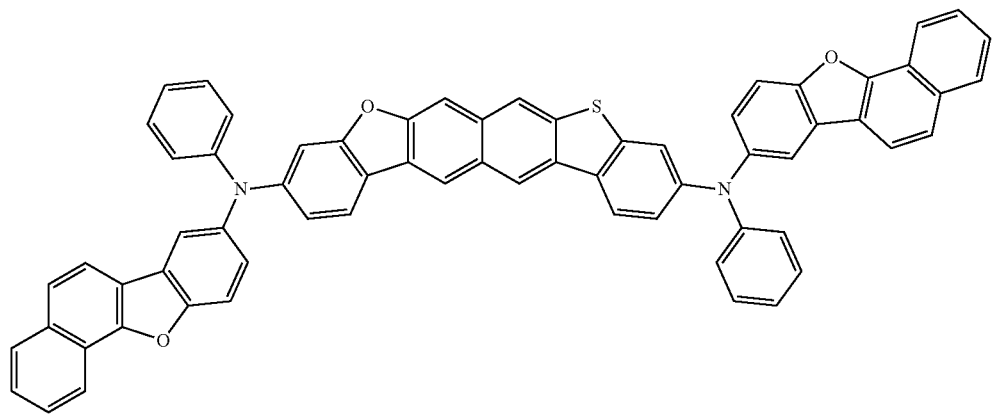
(178)
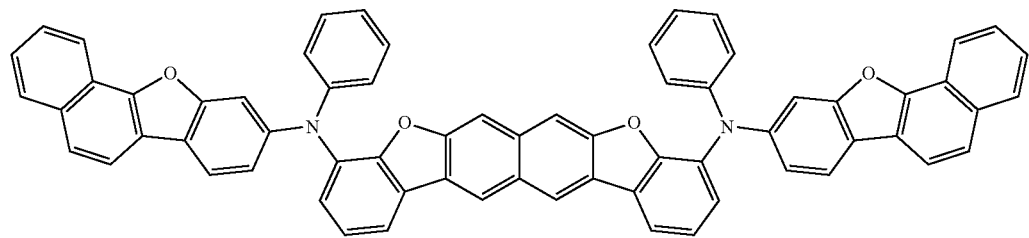
(179)
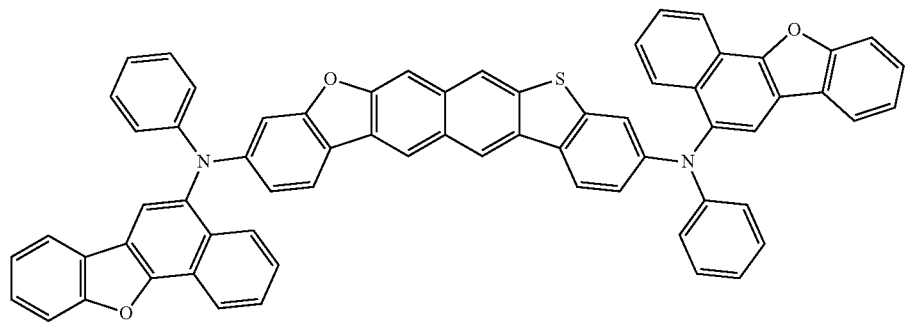
(180)
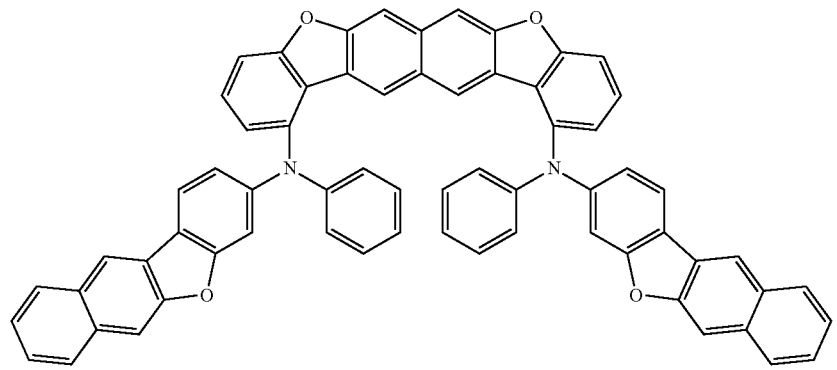
(181)

[Chemical Formulae 46]
(182)
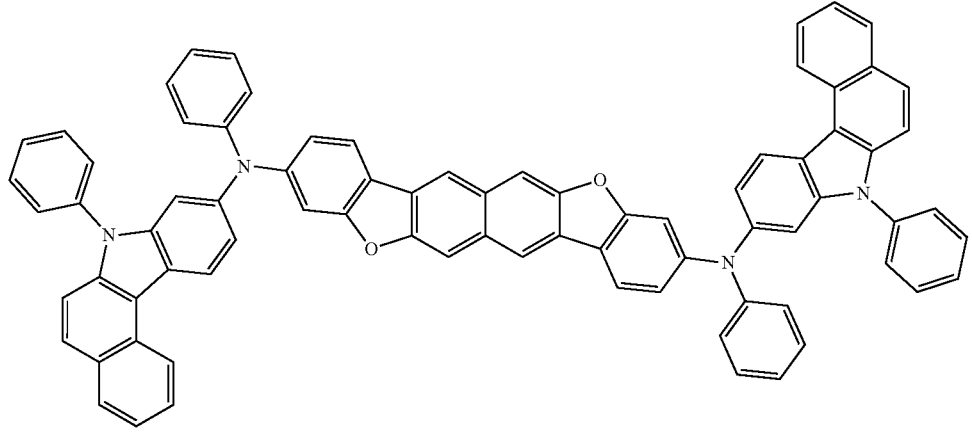
(183)
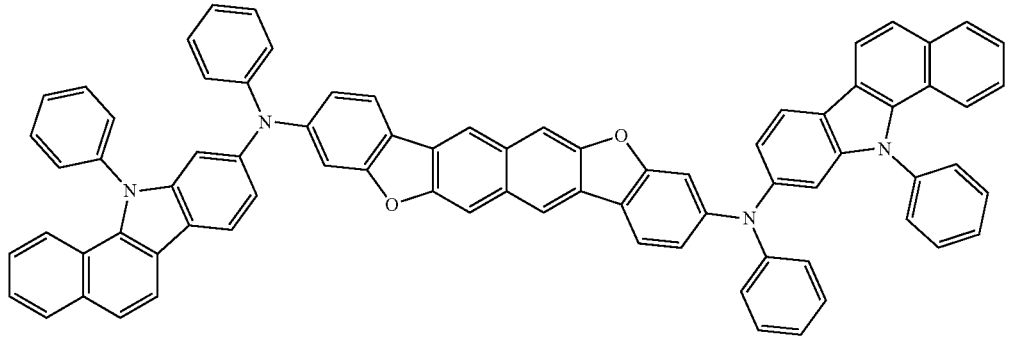
(184)
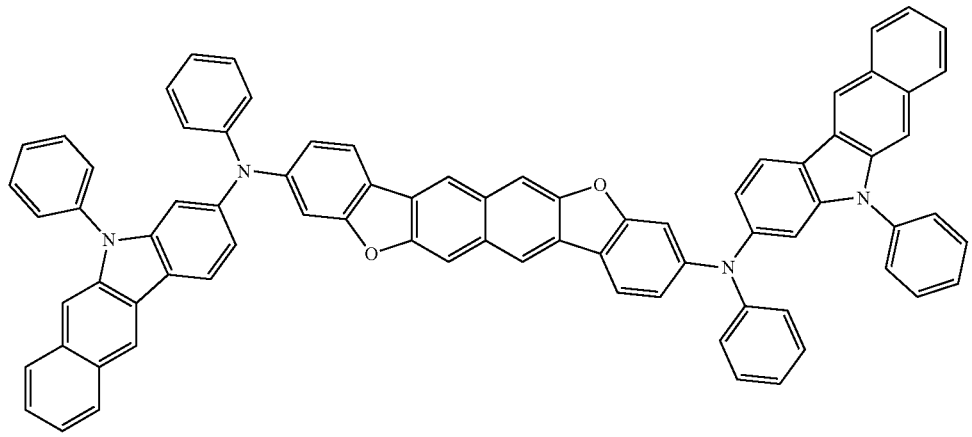

-continued
(185)
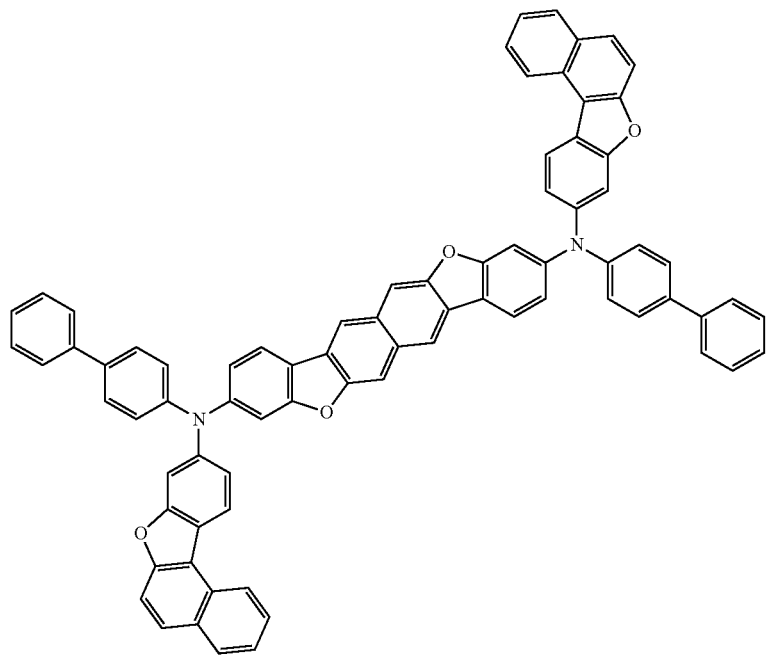
(186)
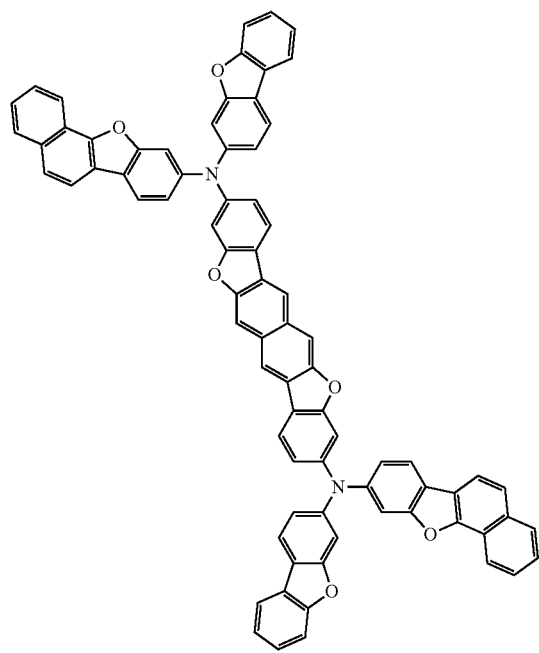
(187)
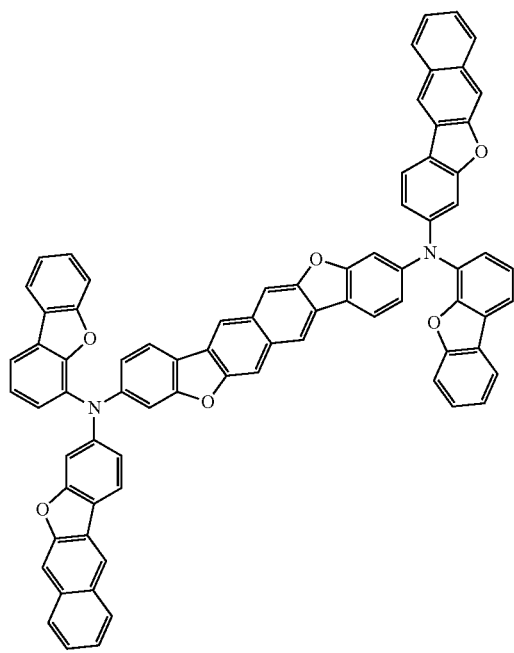

[Chemical Formulae 47]
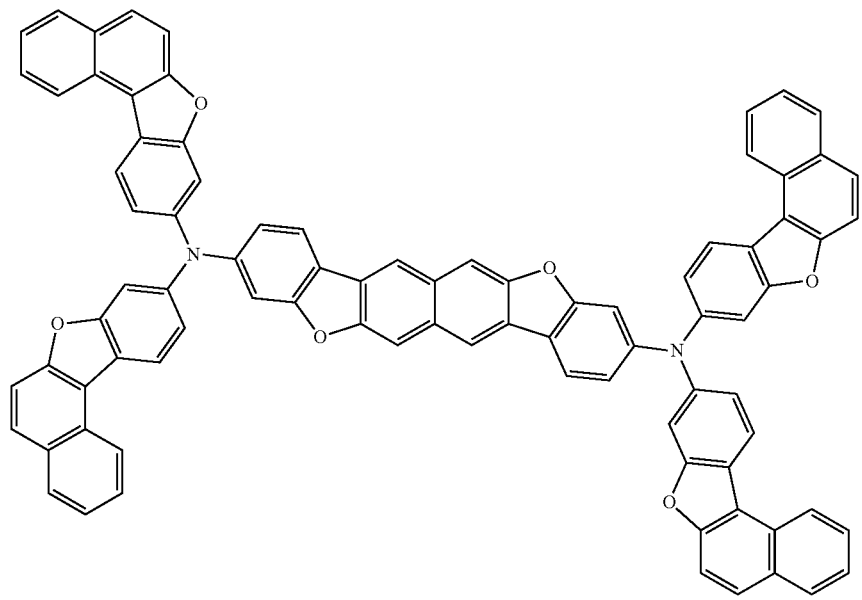
(188)
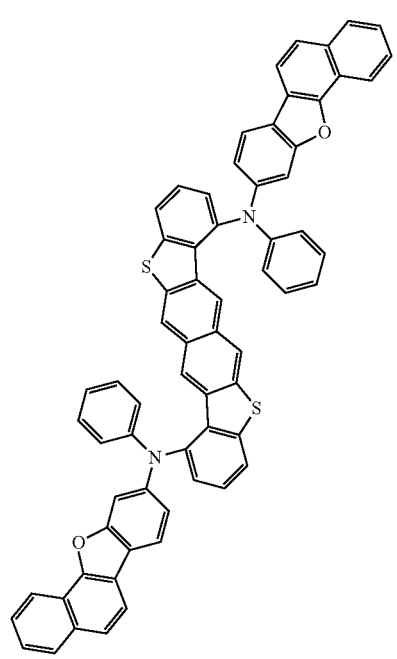
(189)

(190)
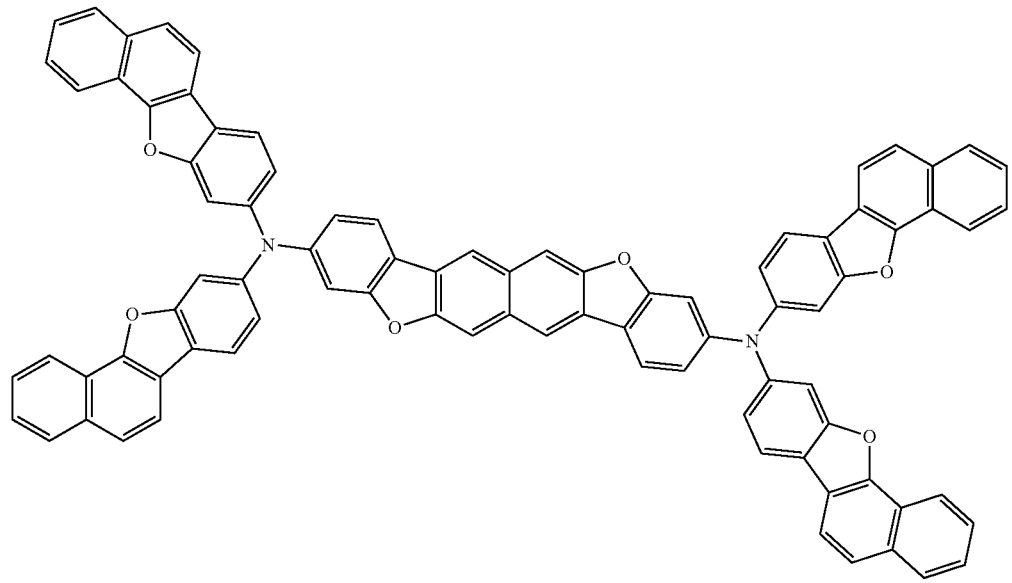
(191)
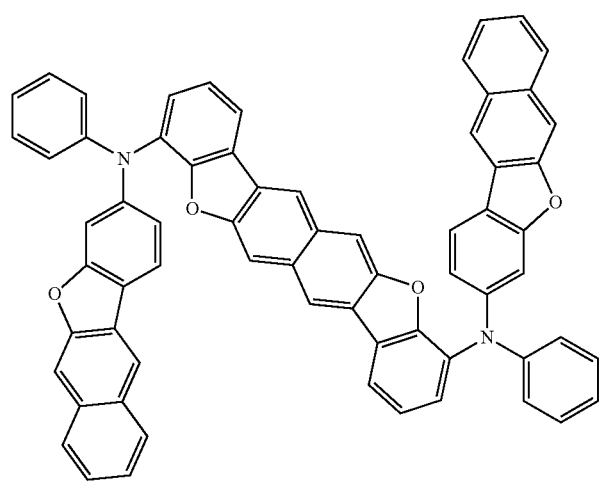

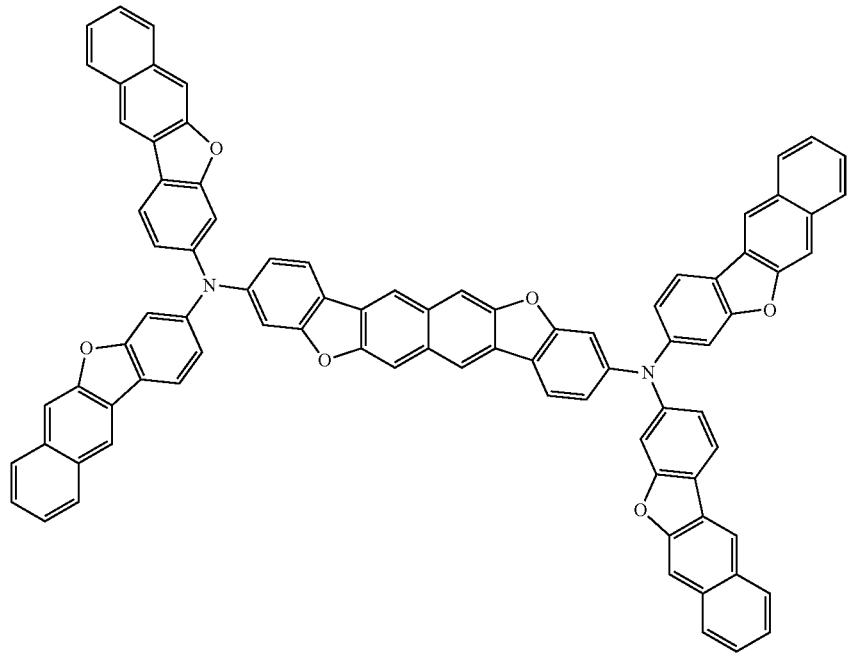
(192)
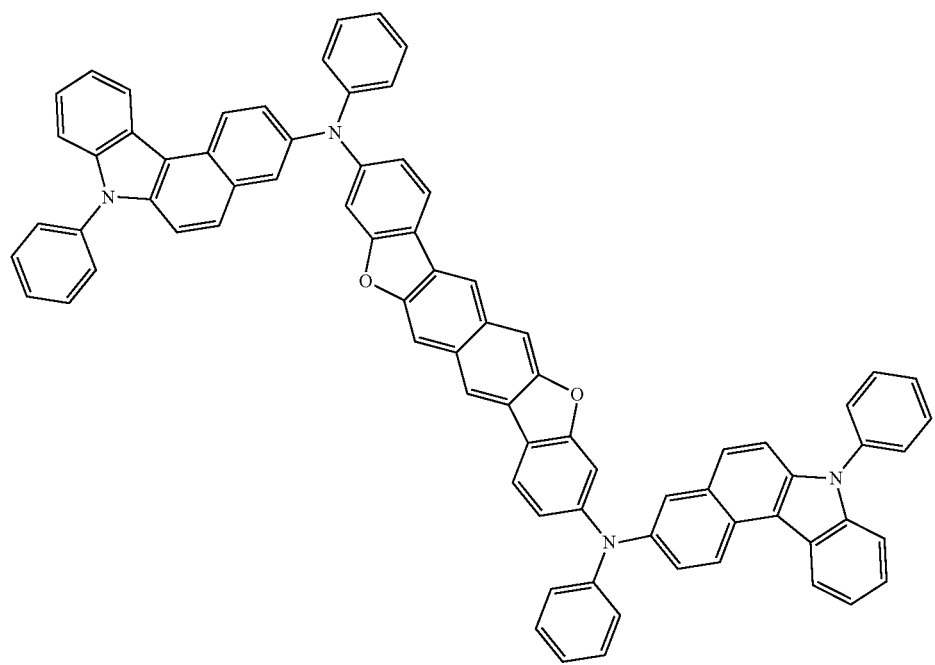
(193)

(194)
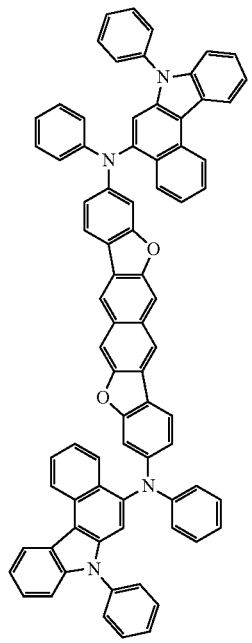
[Chemical Formulae 48]
(195)
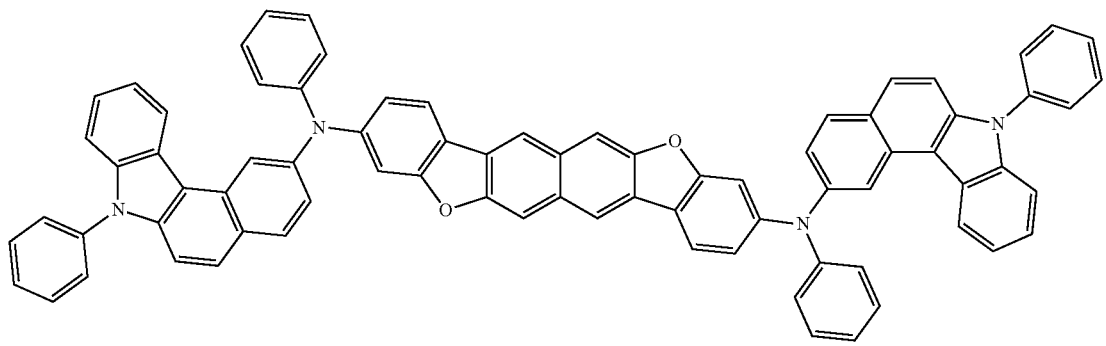
(196)
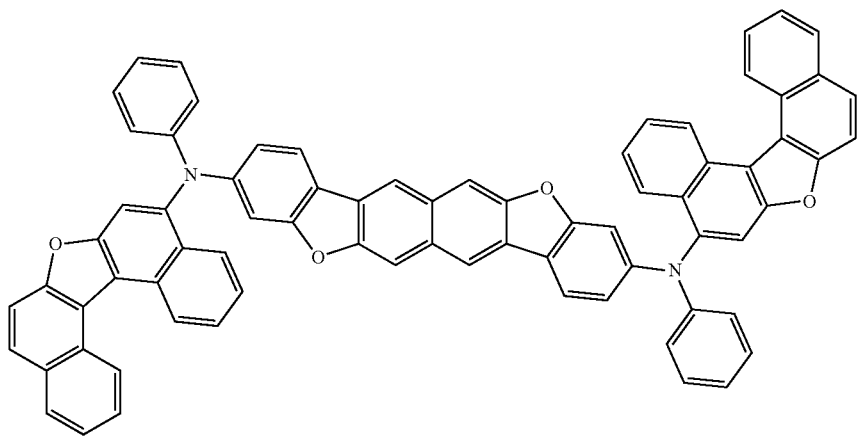

-continued
(197)
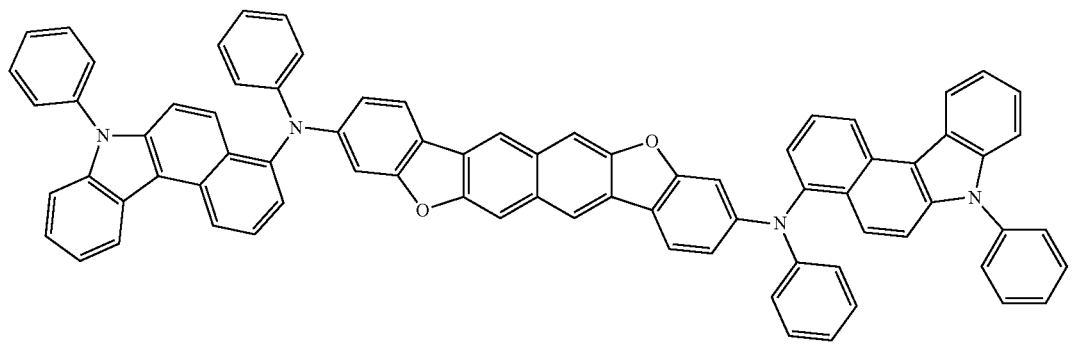
(198)
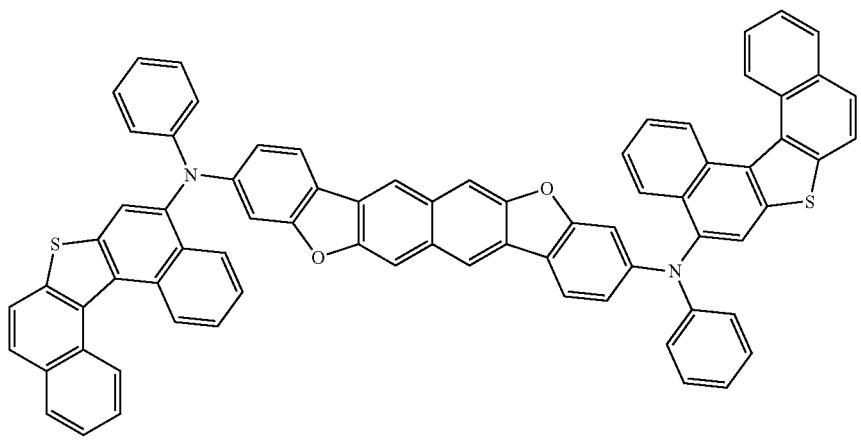
(199)
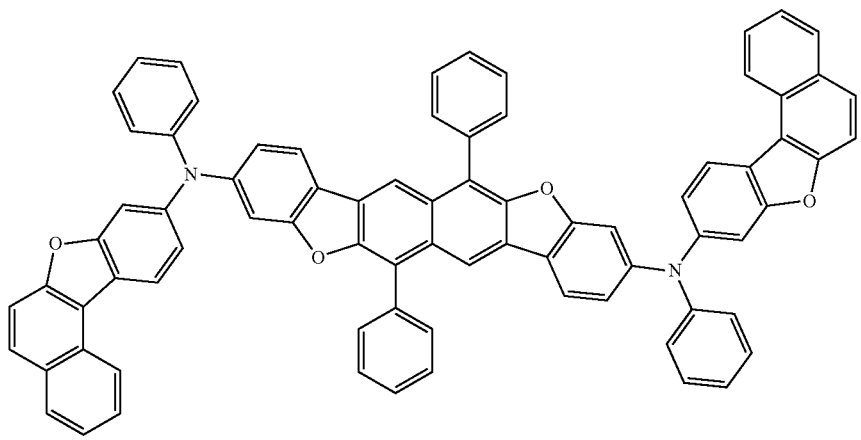
(200)
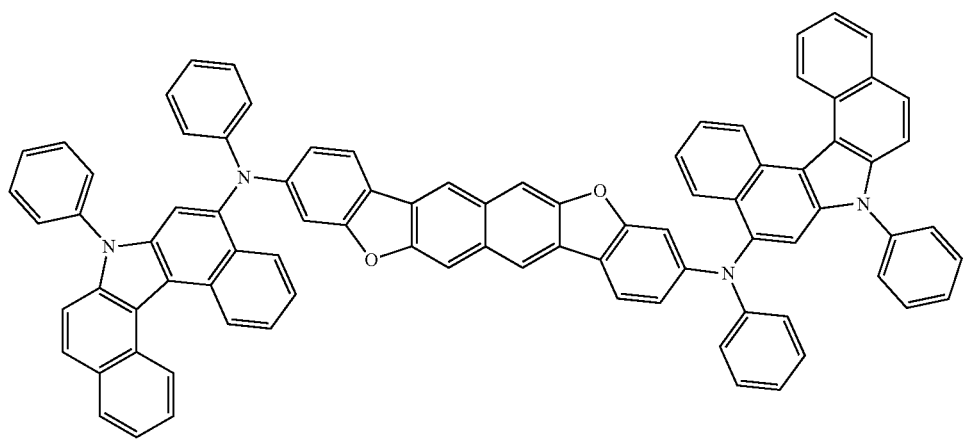

(201)
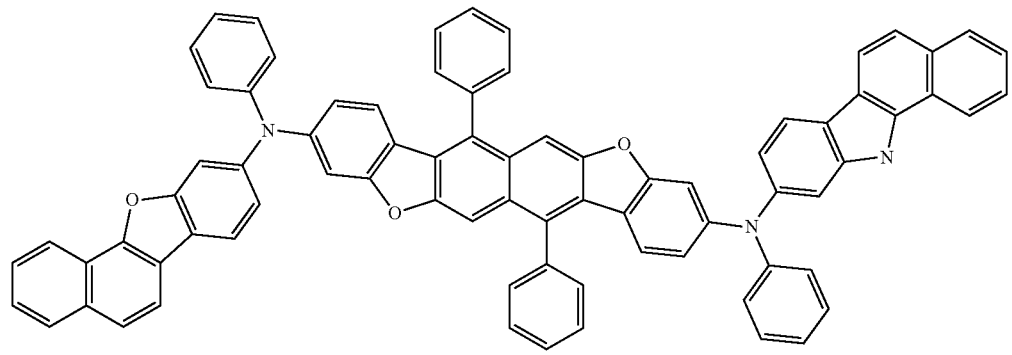
[Chemical Formulae 49]
(202)
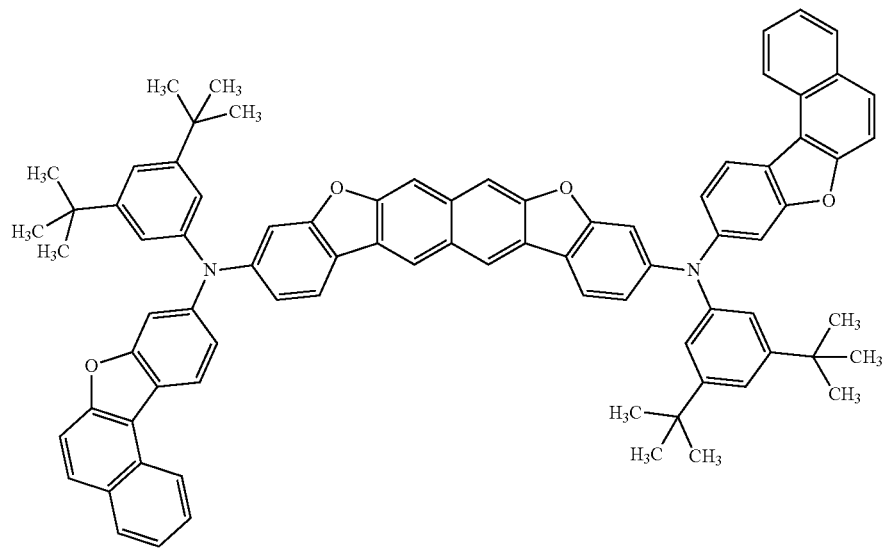
(203)
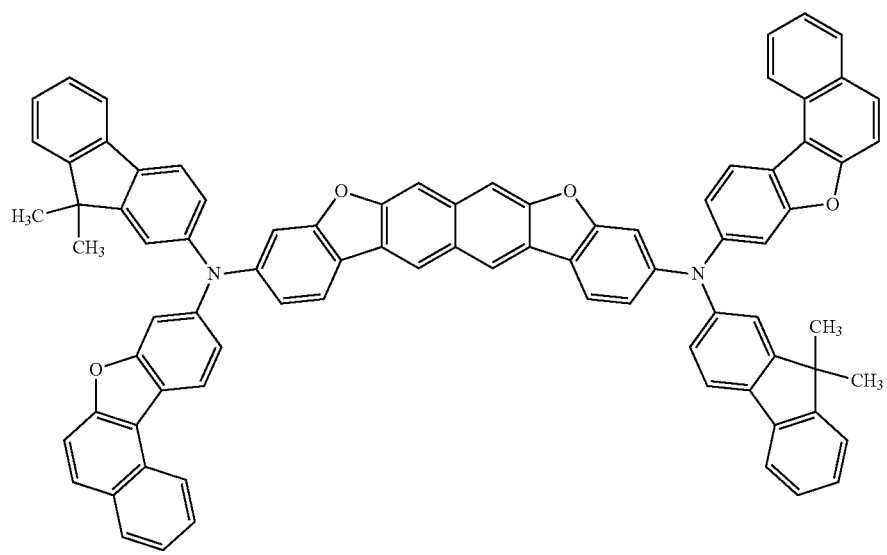

-continued
(204)
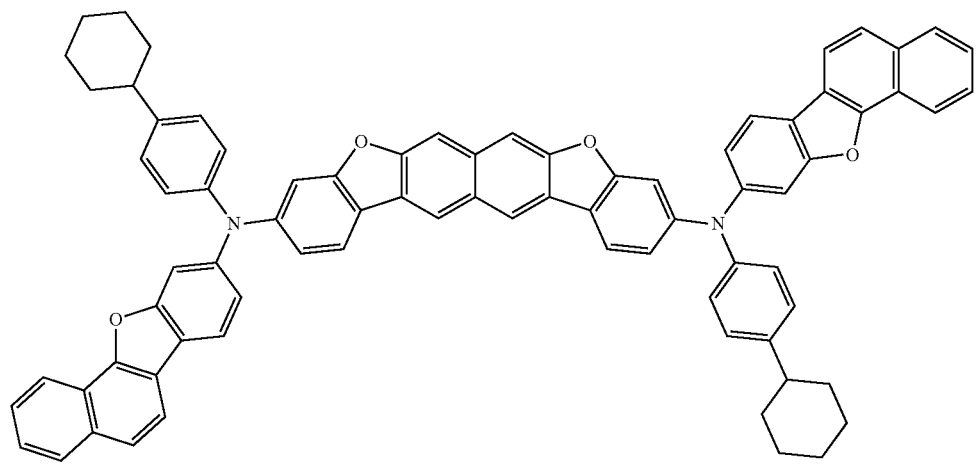
(205)
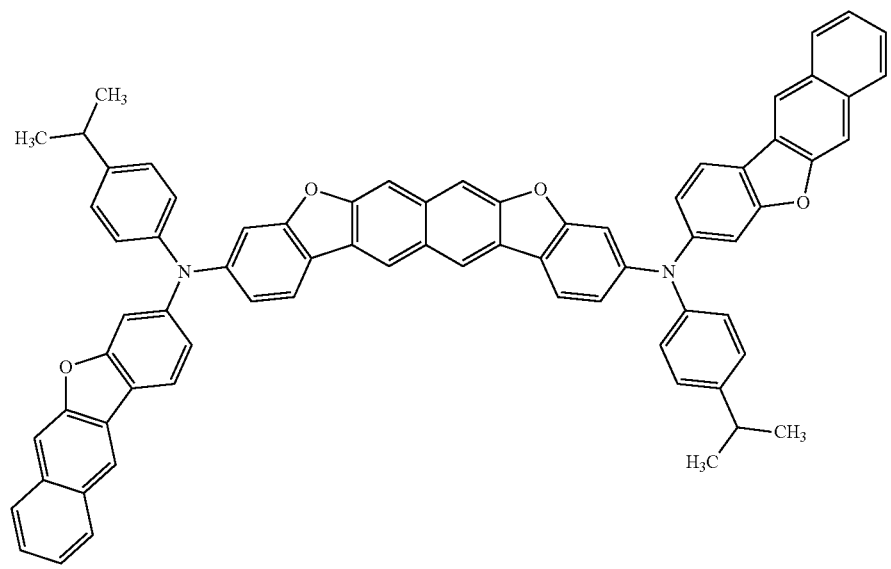
(206)
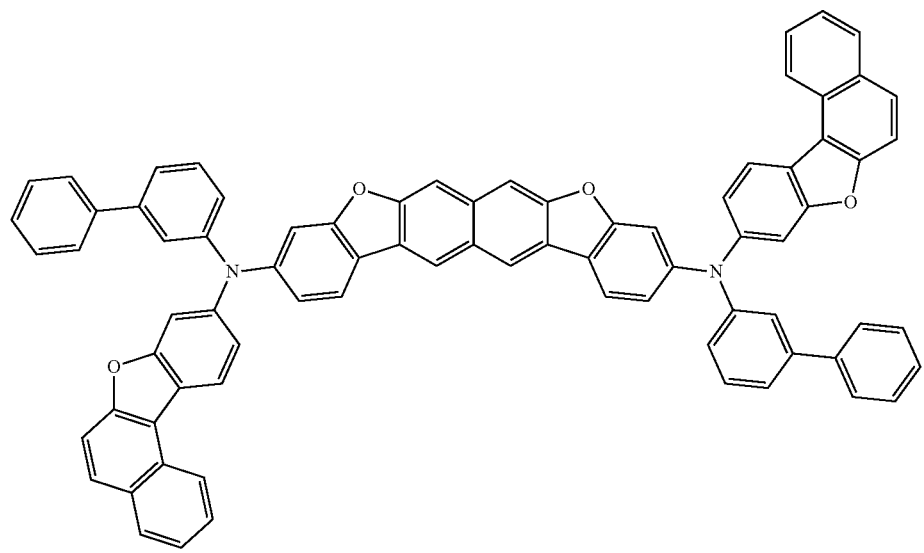

[Chemical Formulae 50]
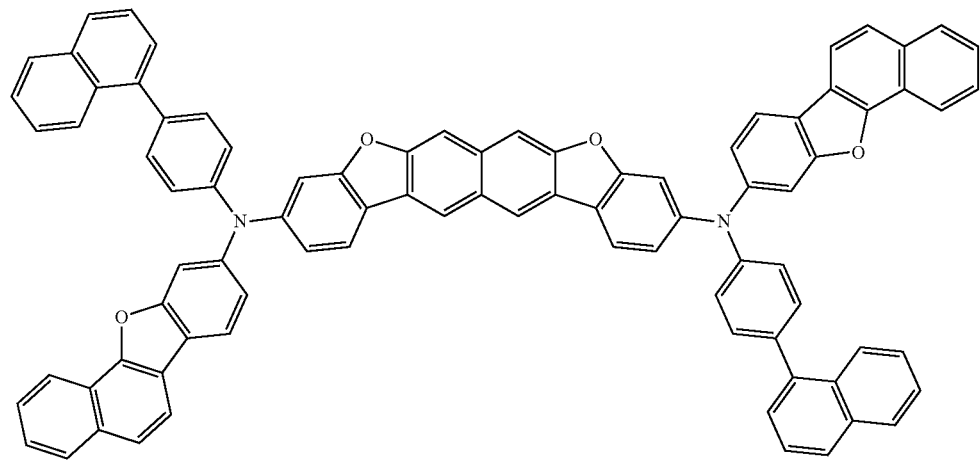
(207)
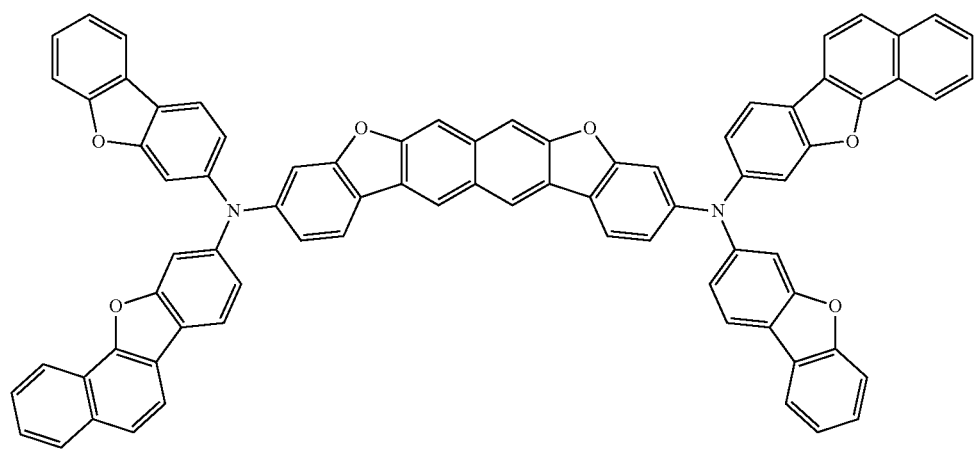
(208)
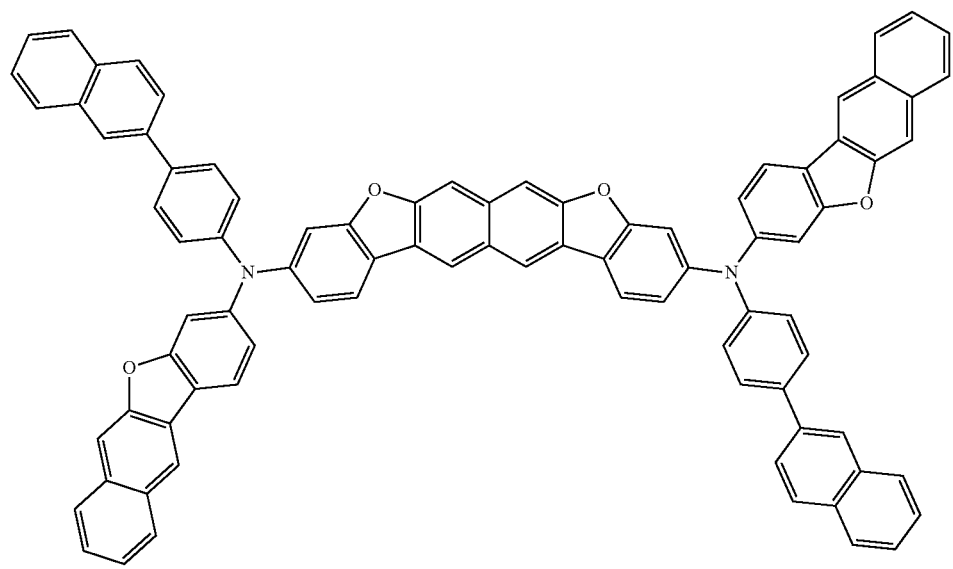
(209)

(210)
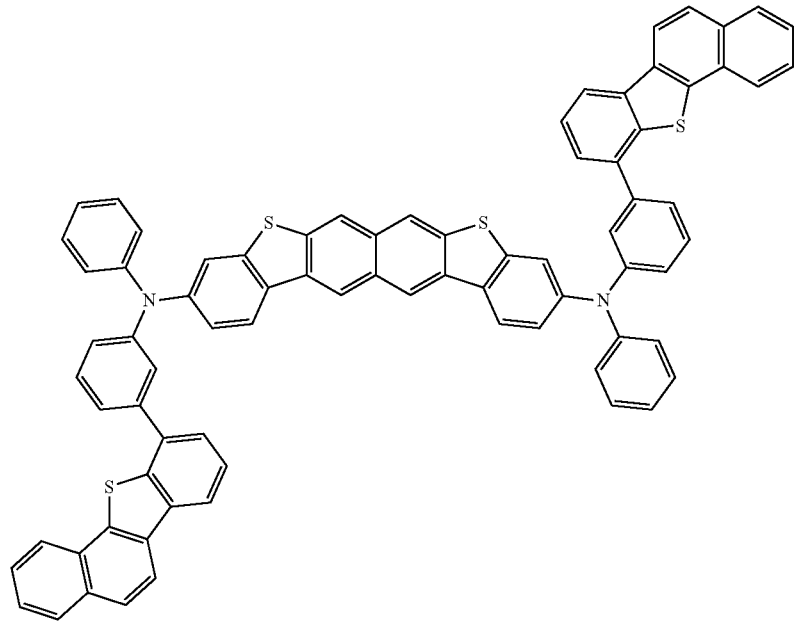
(211)
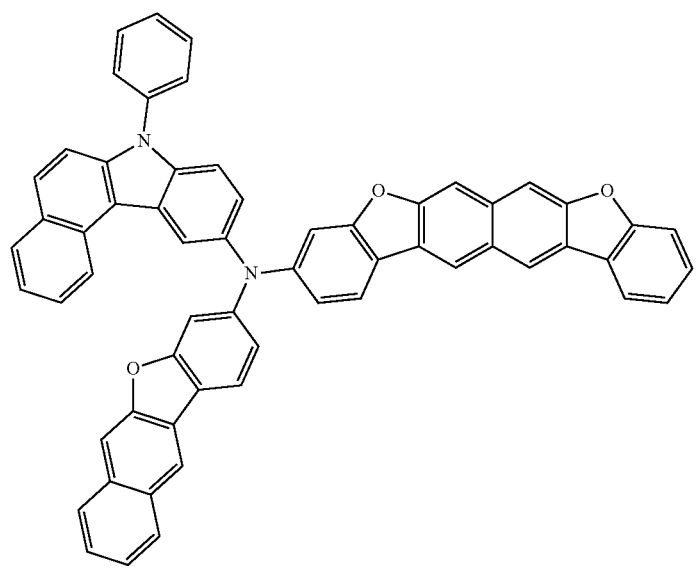
[Chemical Formulae 51]
(212)
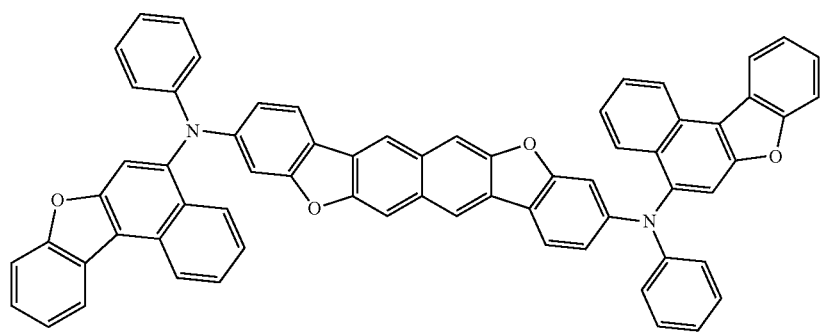

-continued
(213)
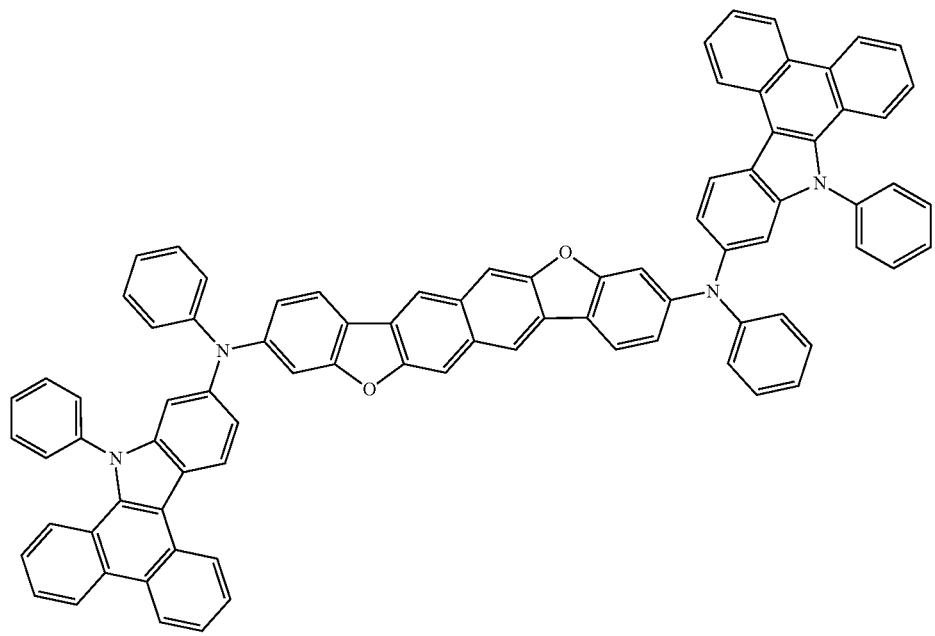
(214)
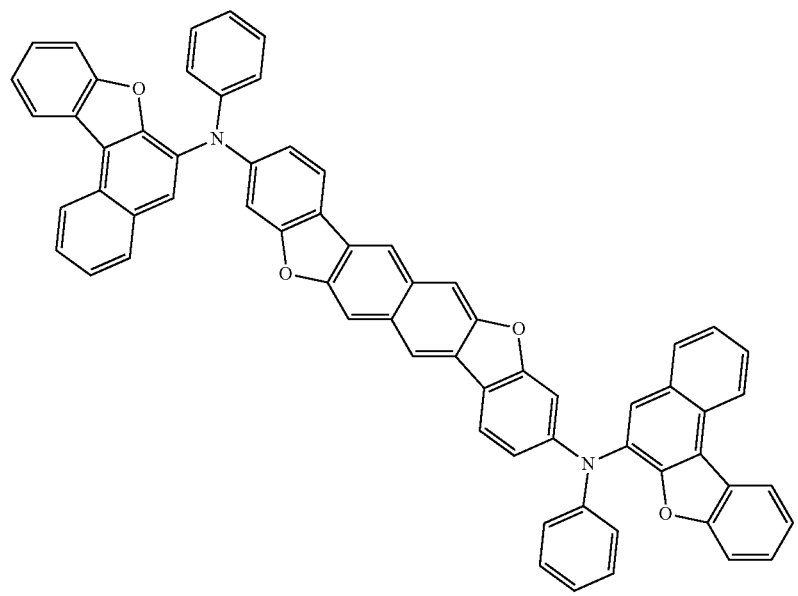
(215)
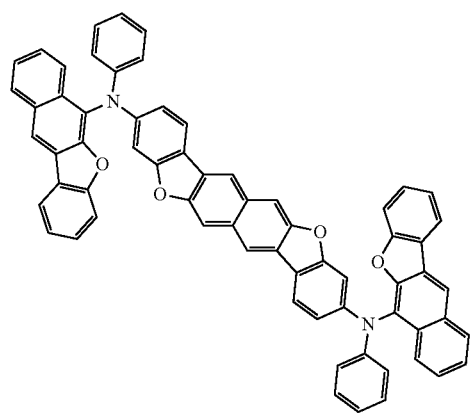
(216)
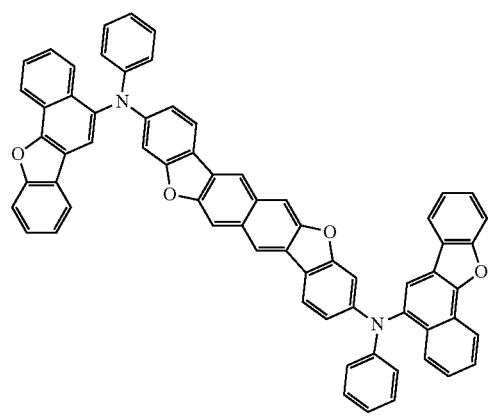

-continued
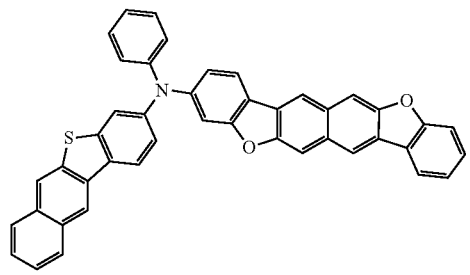
(217)
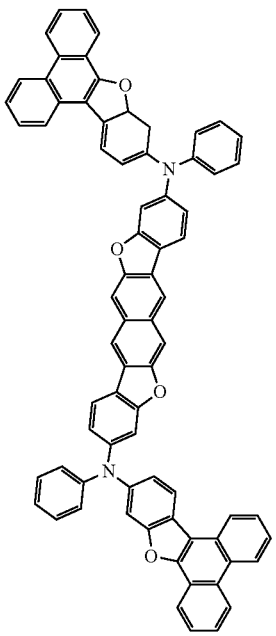
(218)
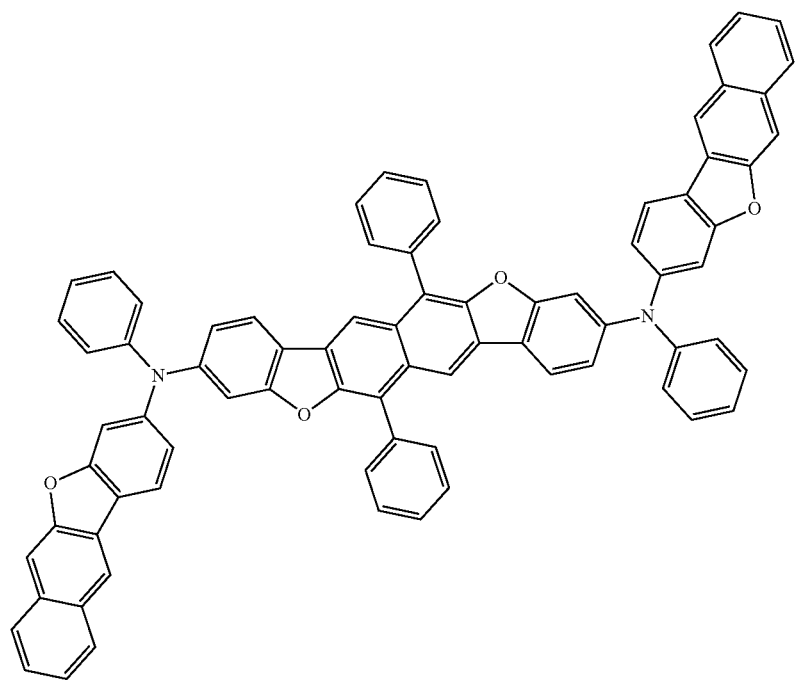
(219)

-continued
[Chemical Formulae 52]
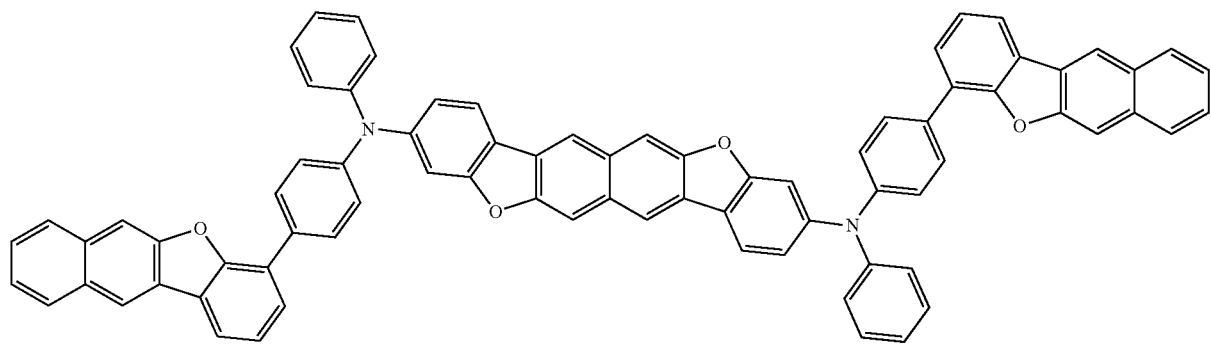
(220)
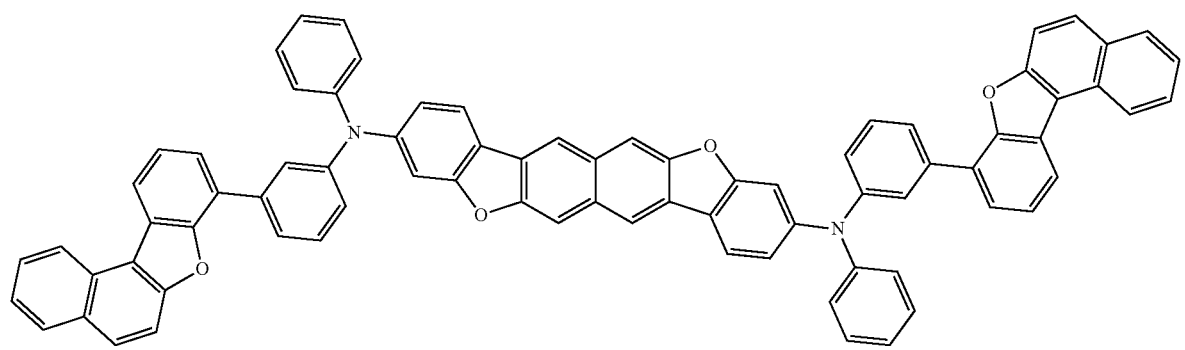
(221)
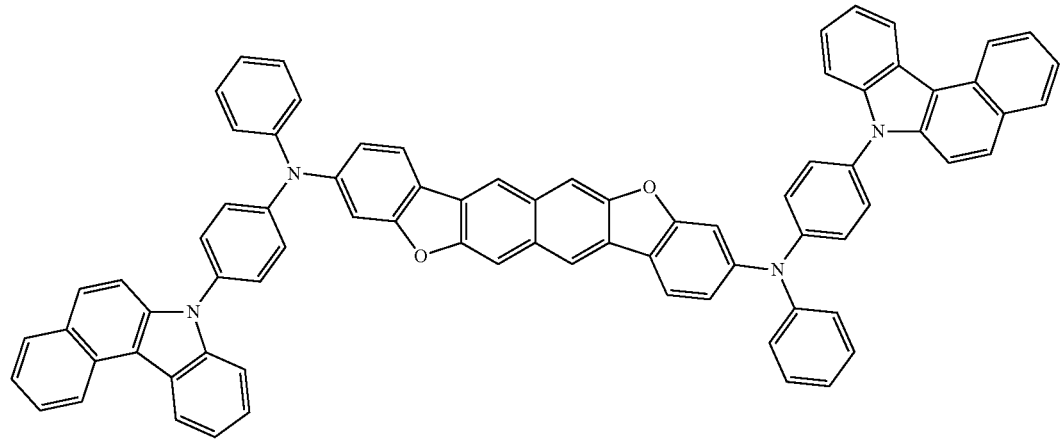
(222)
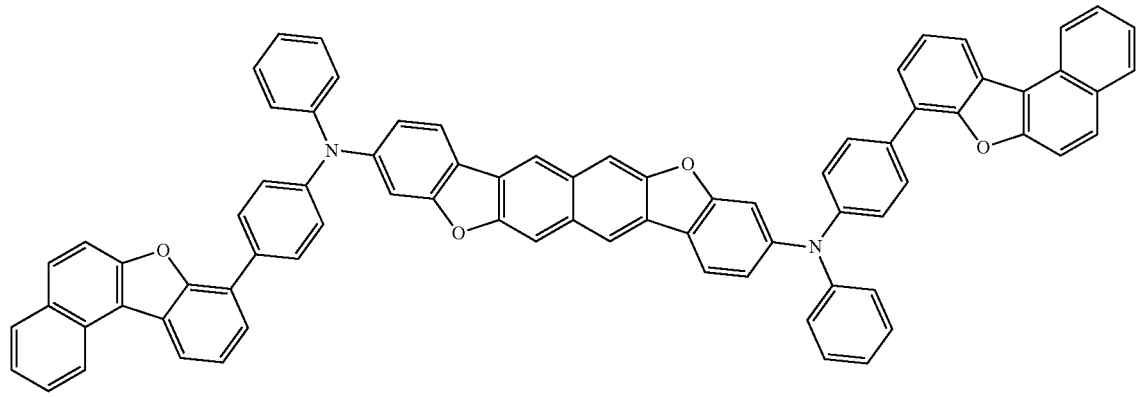
(223)

(224)
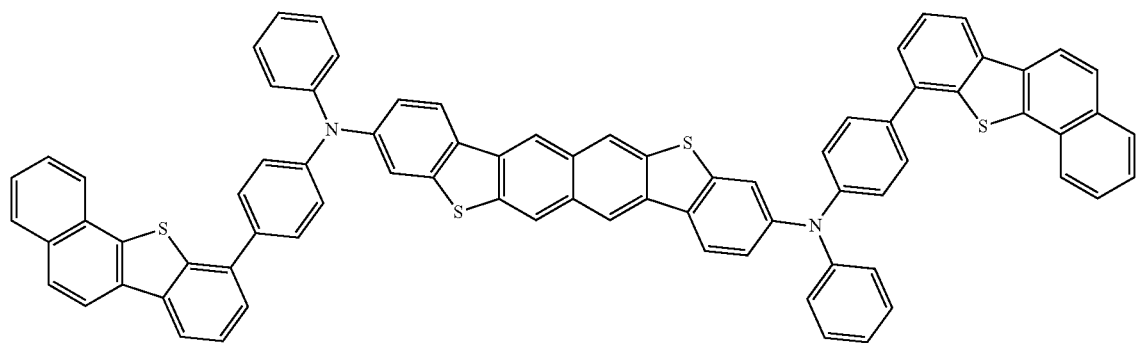
(225)
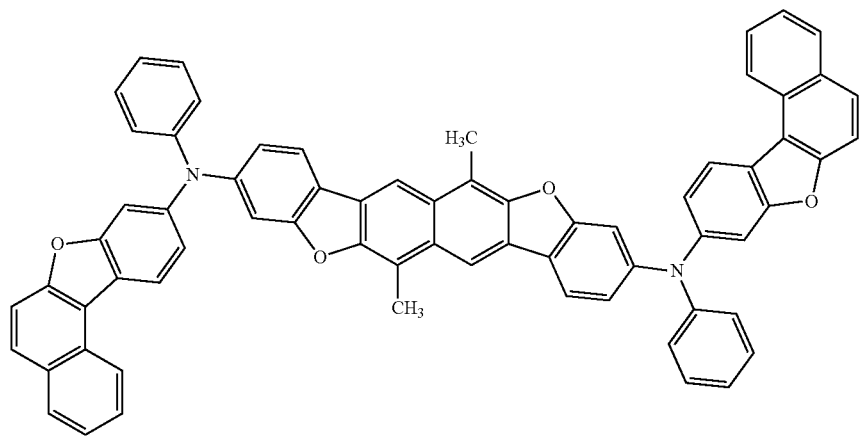
[Chemical Formulae 53]
(226)
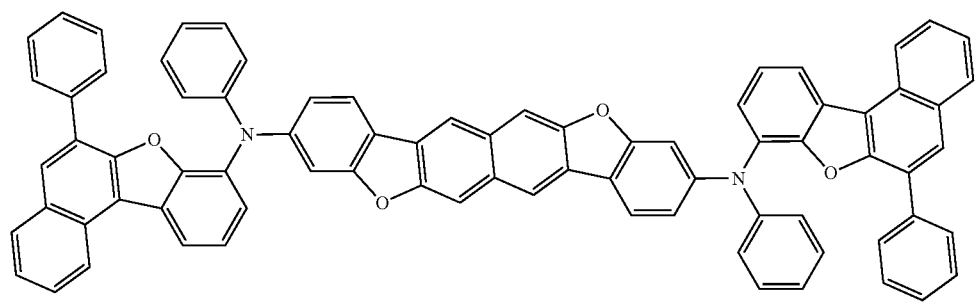
(227)
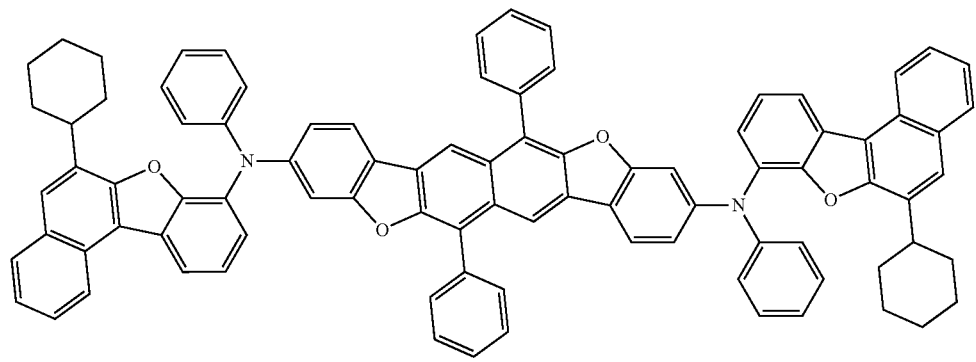

(228)
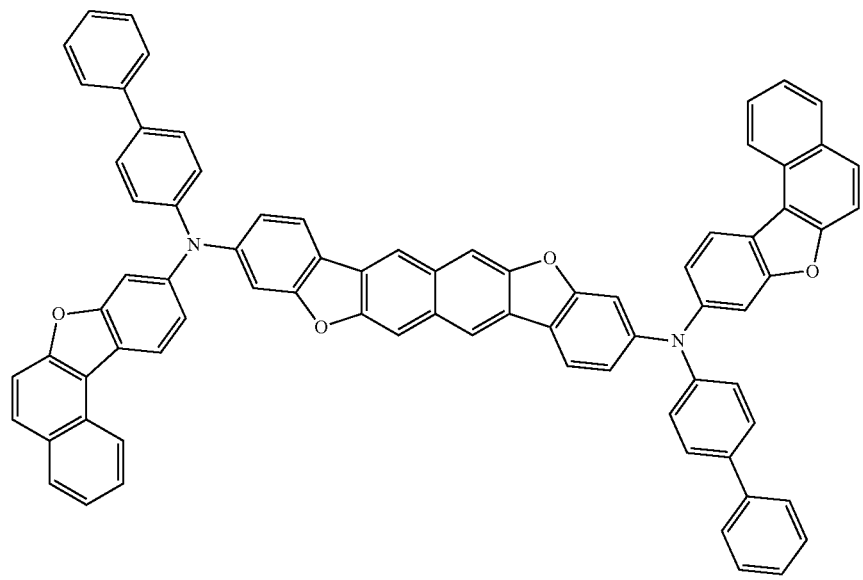
(229)
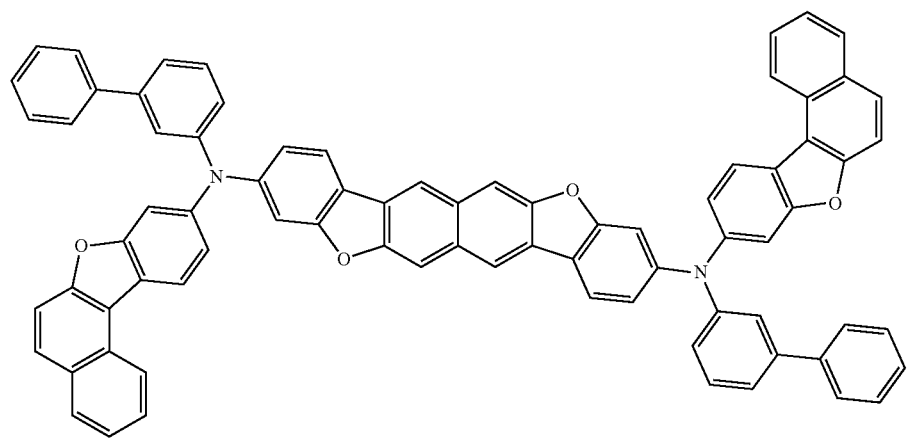
[Chemical Formulae 54]
(230)
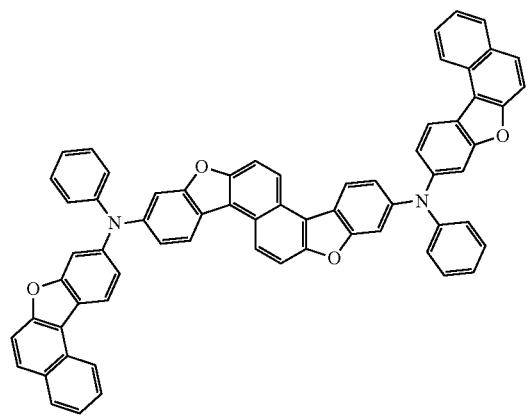
(231)
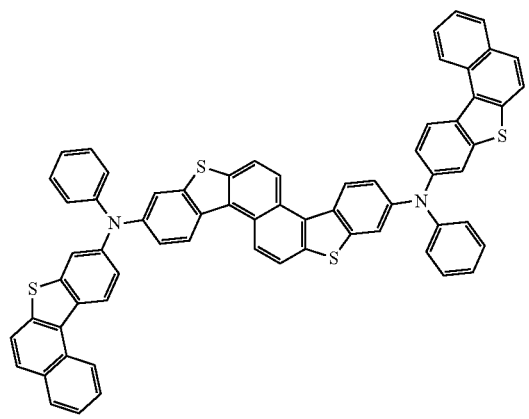

-continued
(232)
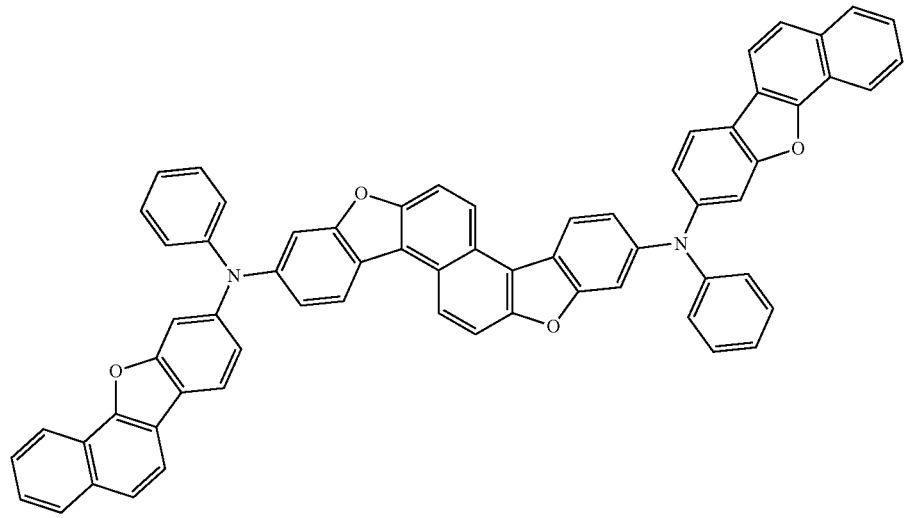
(233)
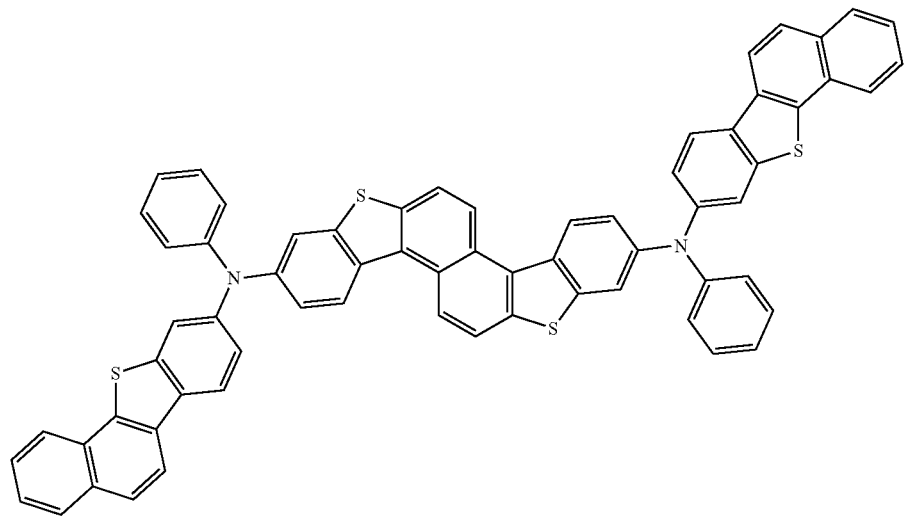
(234)
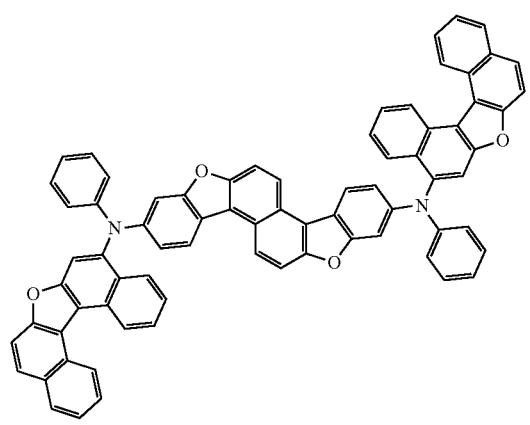
(235)
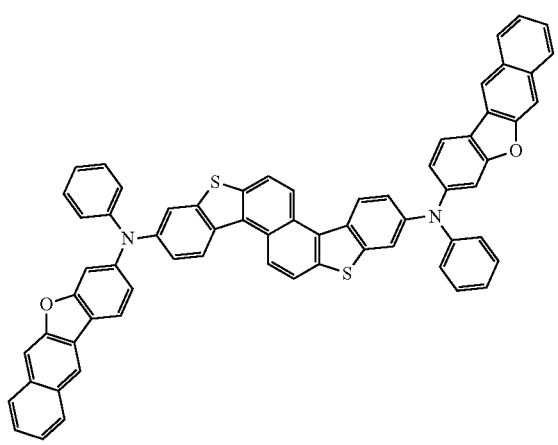

-continued
(236)
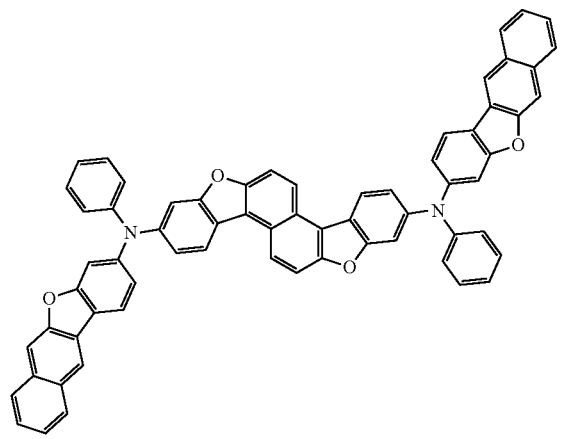
(237)
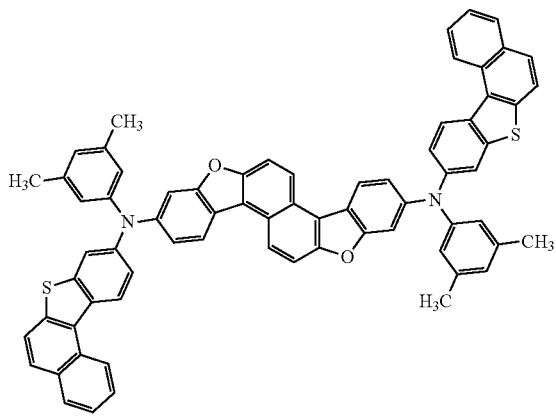
[Chemical Formulae 55]
(238)
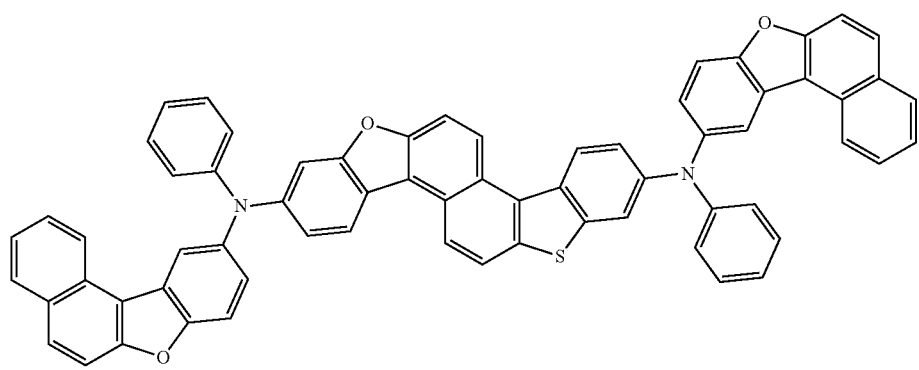
(239)
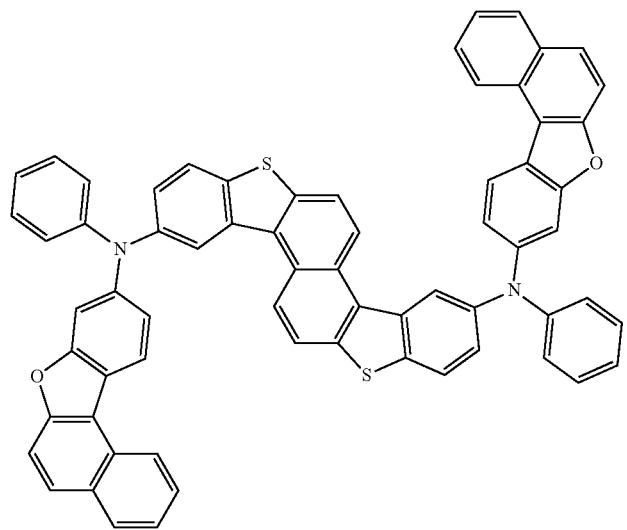

-continued
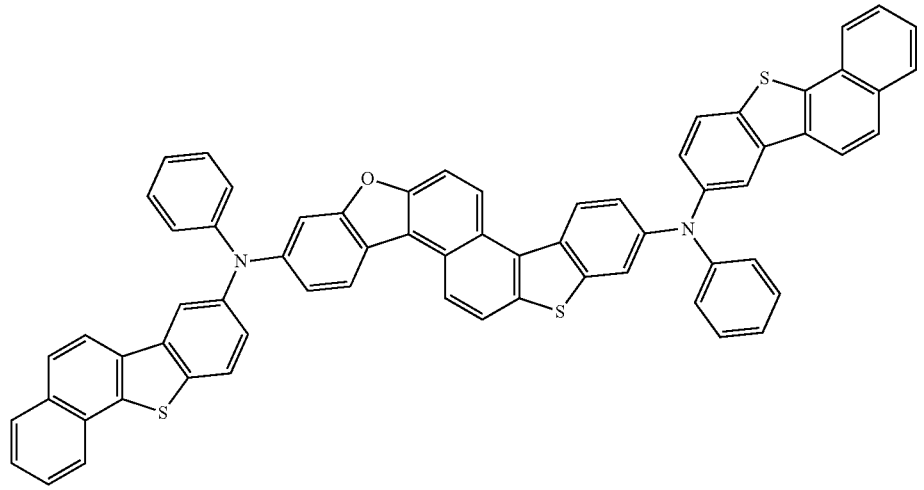
(240)
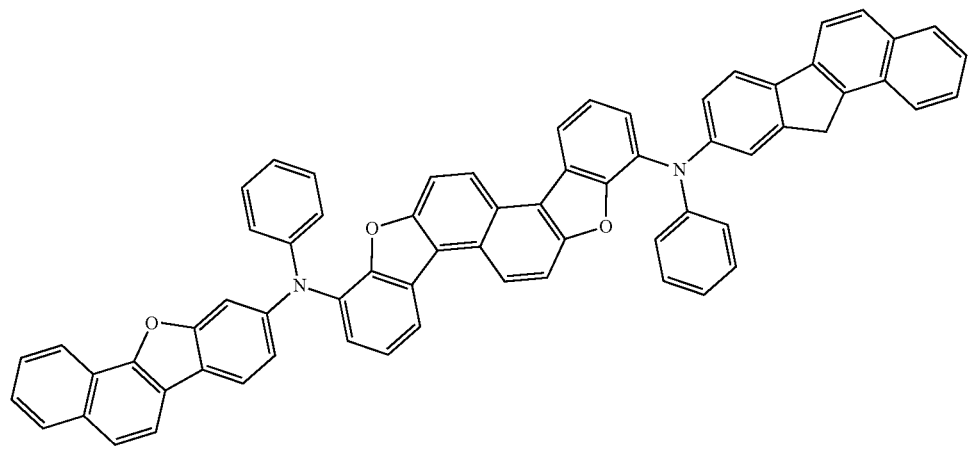
(241)
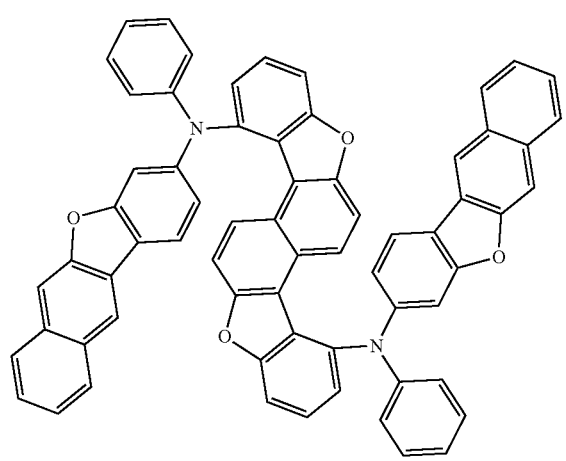
(242)

(243)
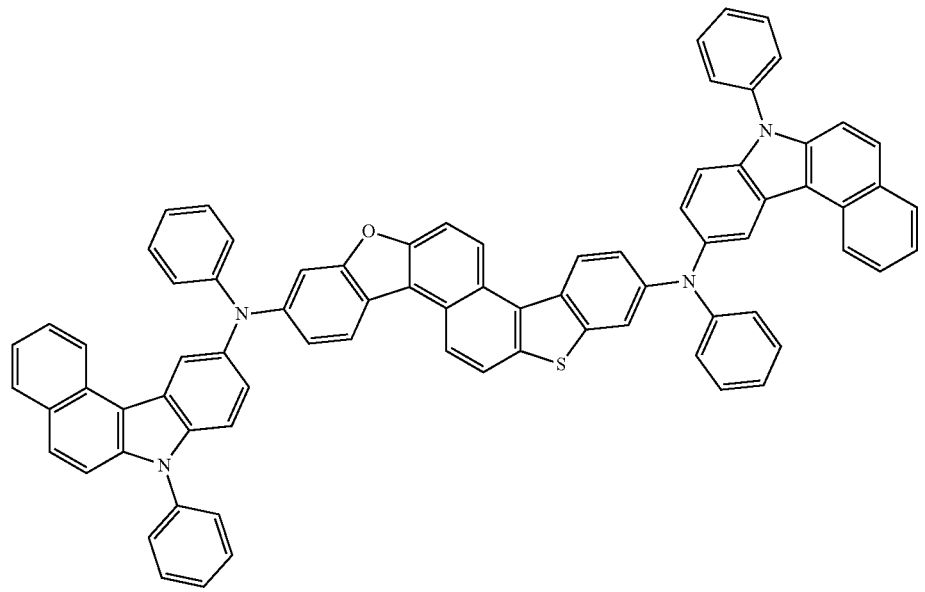
(244)
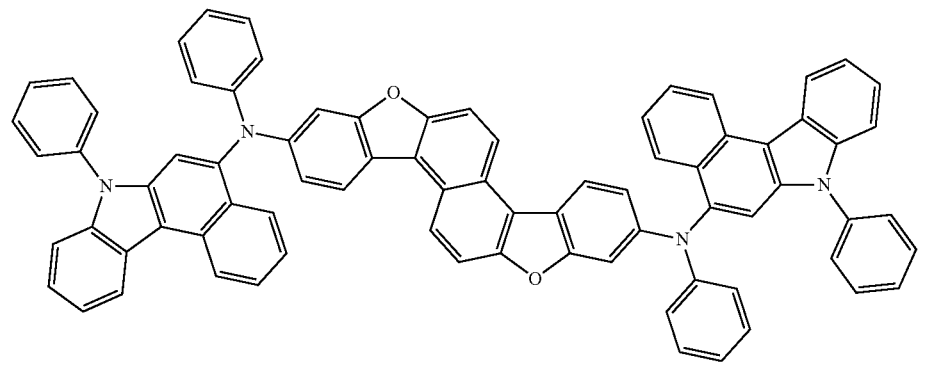
(245)
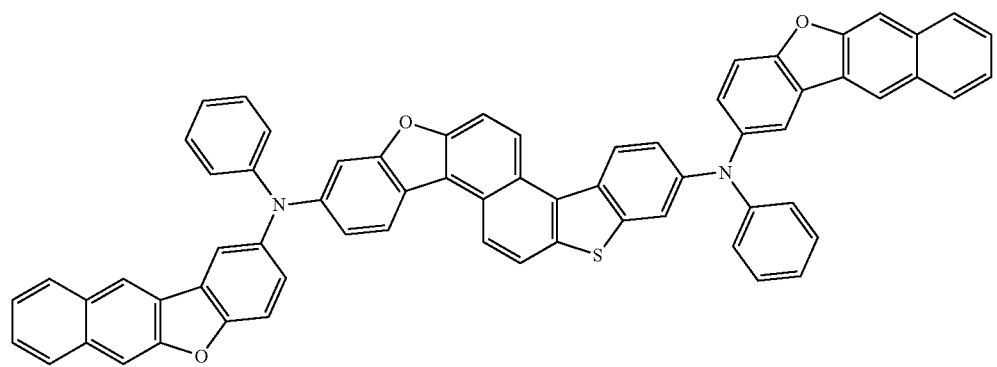

[Chemcial Formulae 56]
(246)
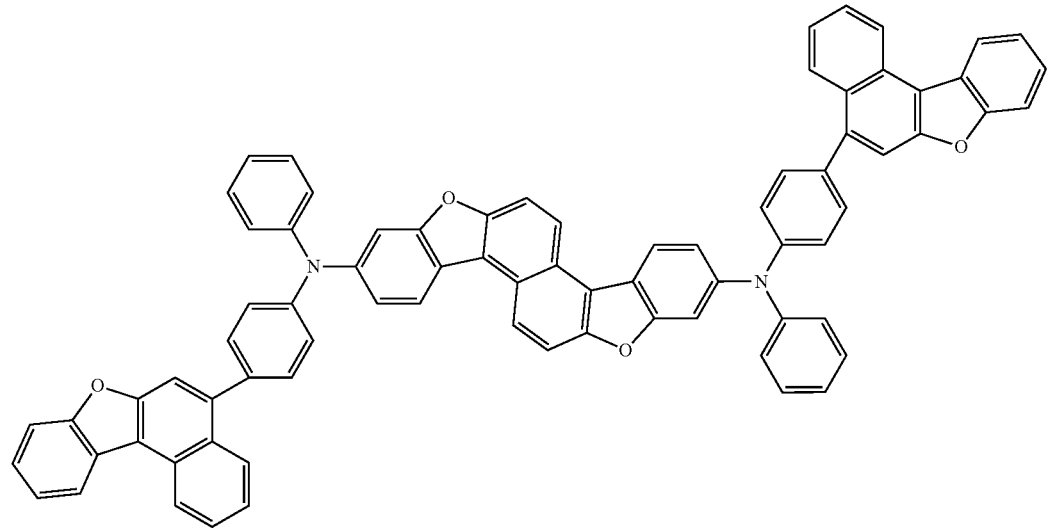
(247)
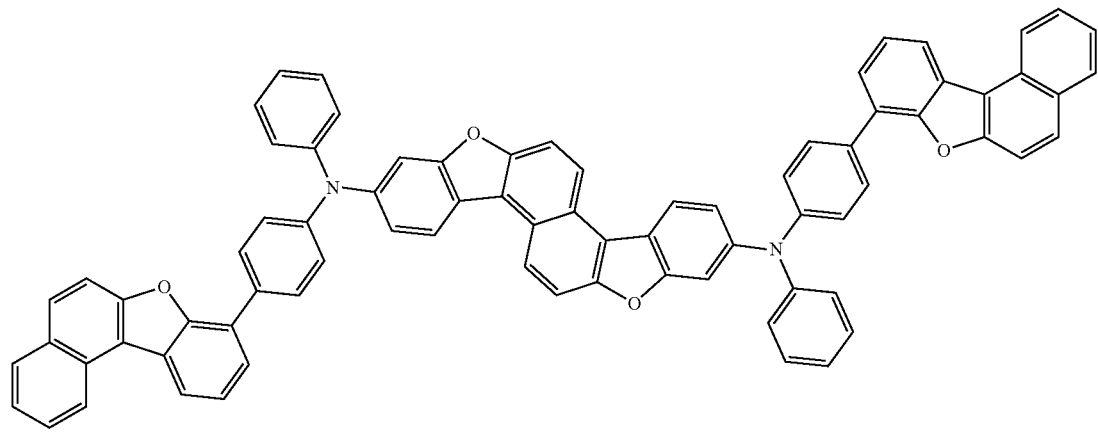
(248)
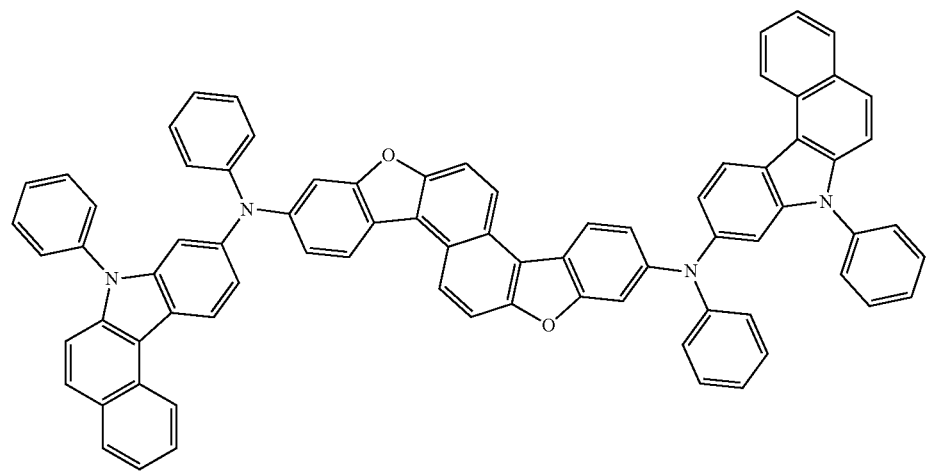

-continued
(249)
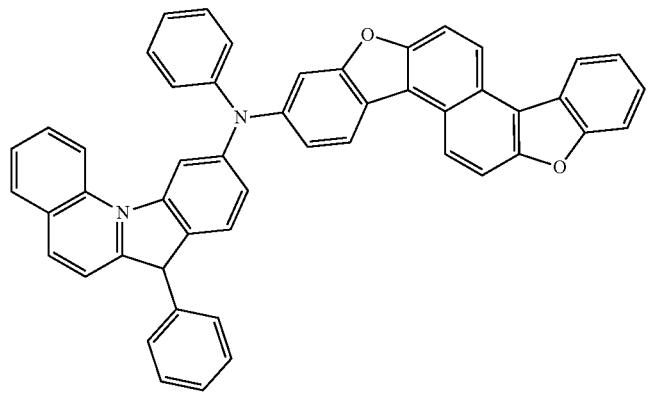
(250)
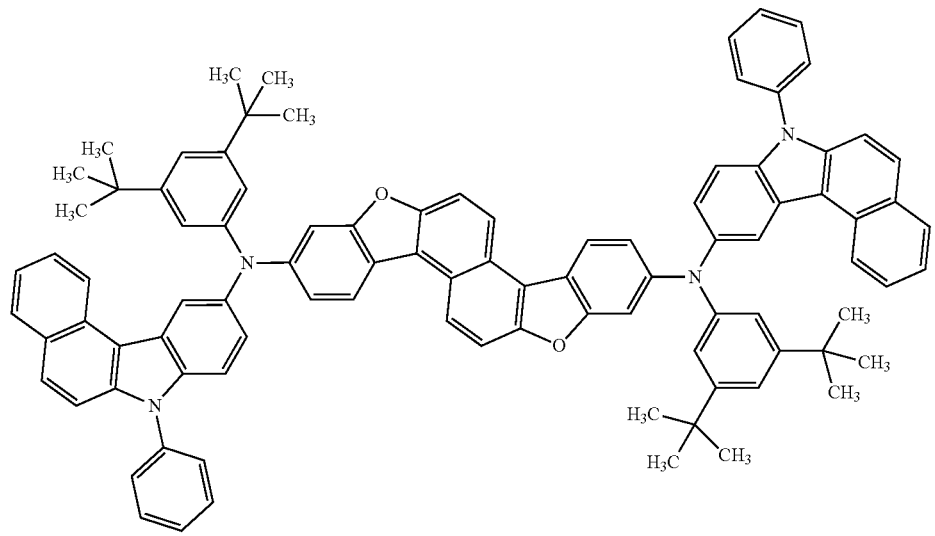
(251)
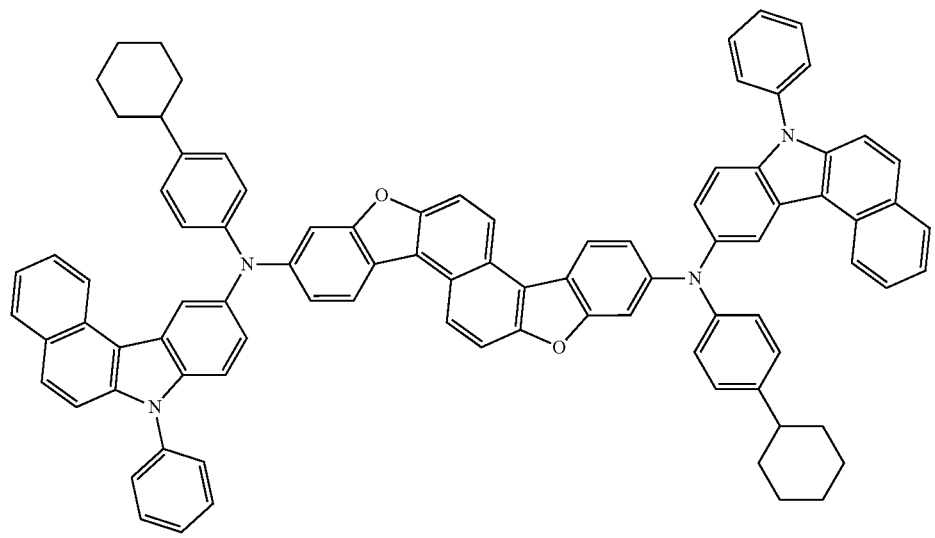

[Chemical Formulae 57]
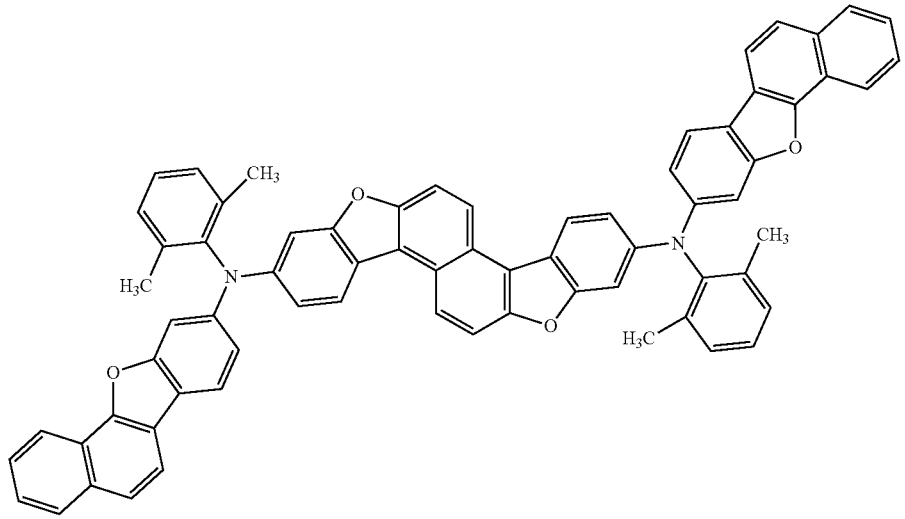
(252)
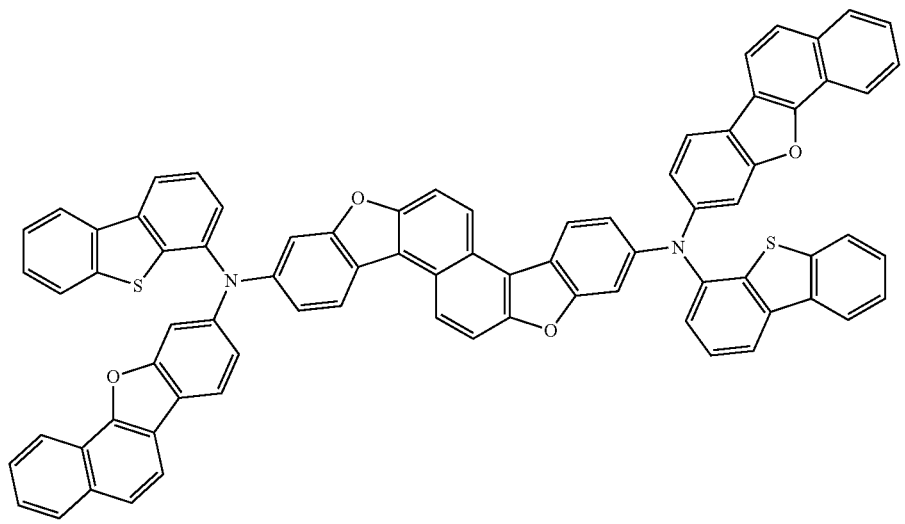
(253)

(254)
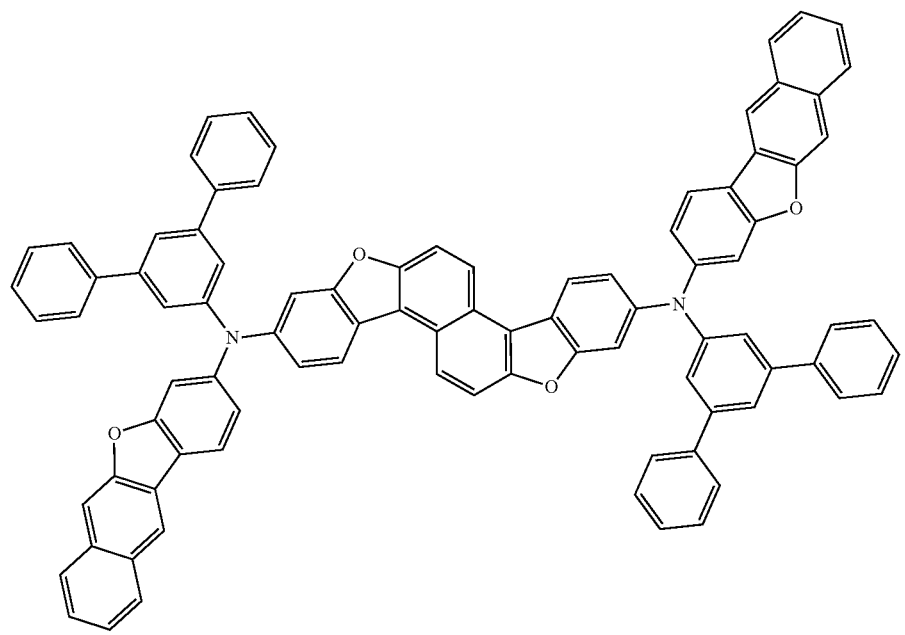
(255)
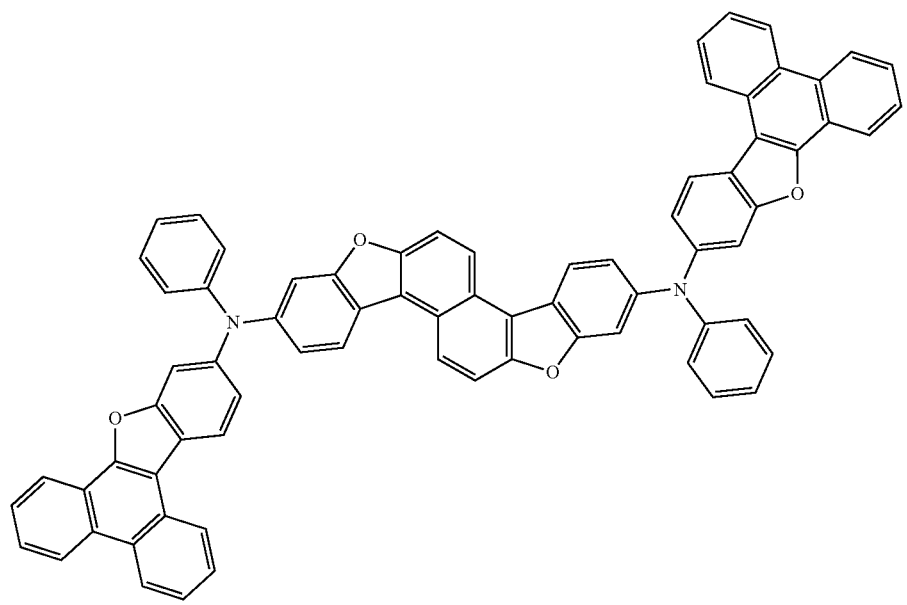

-continued
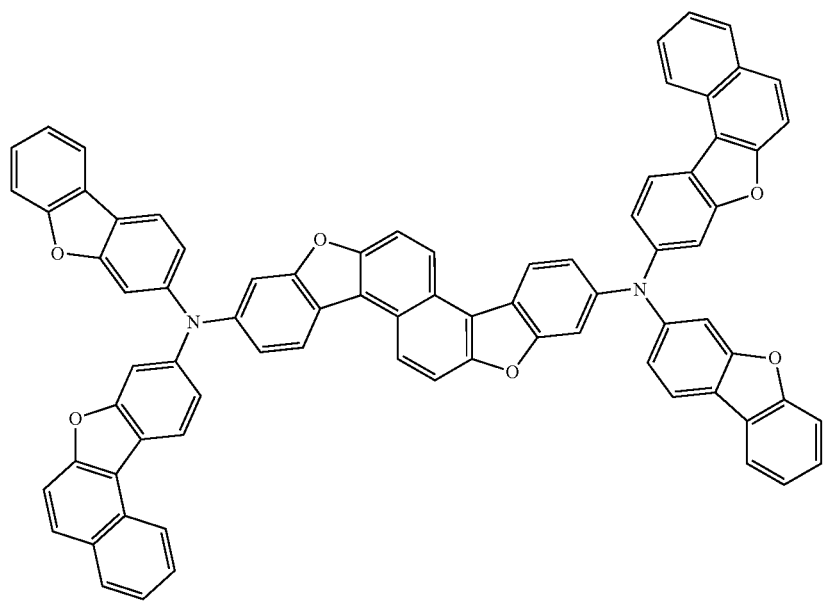
(256)
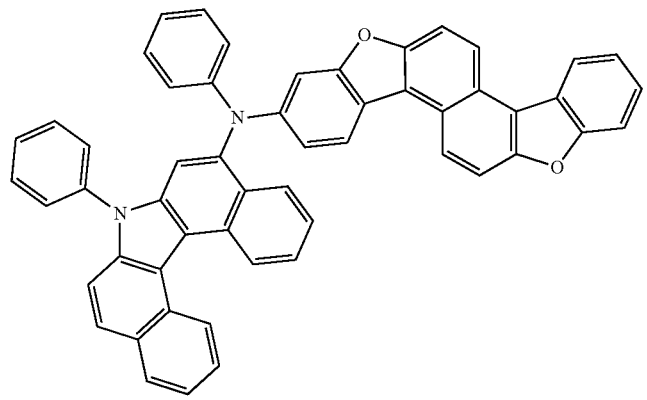
(257)
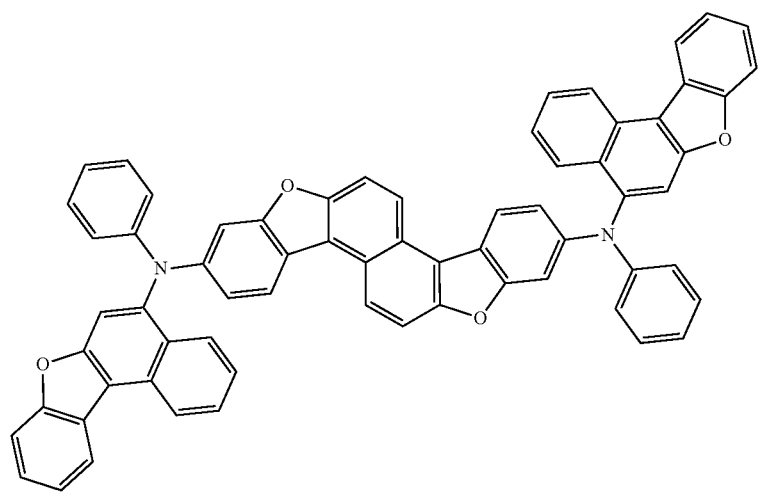
(258)

[Chemical Forulae 58]
(259)
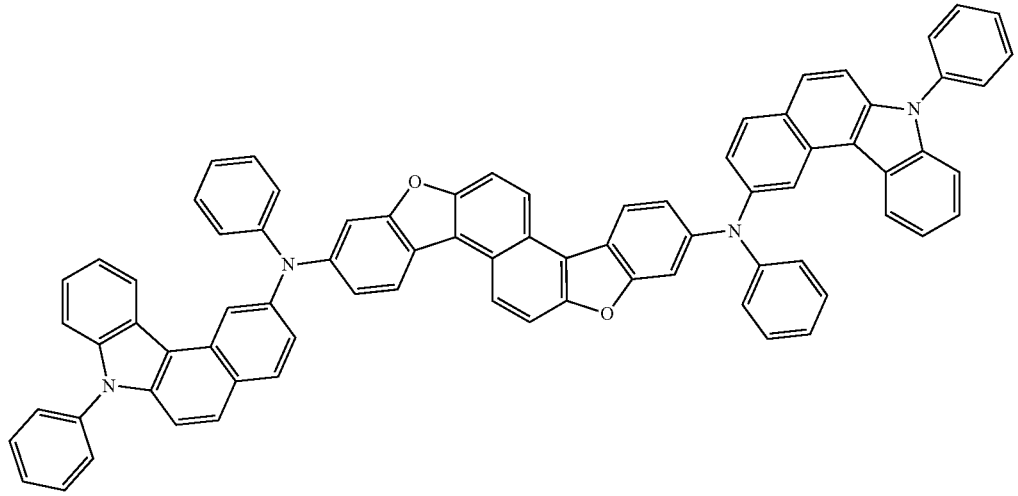
(260)
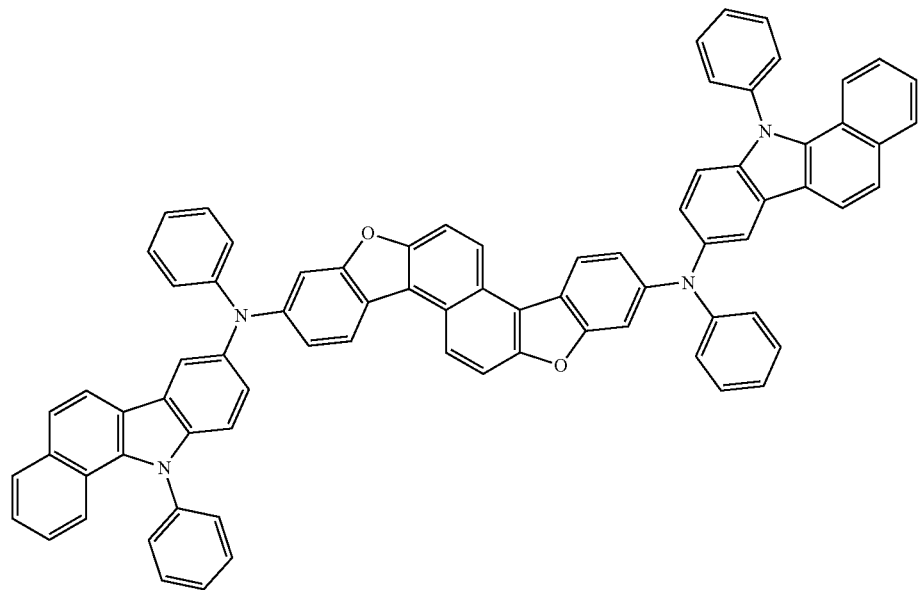

(261)
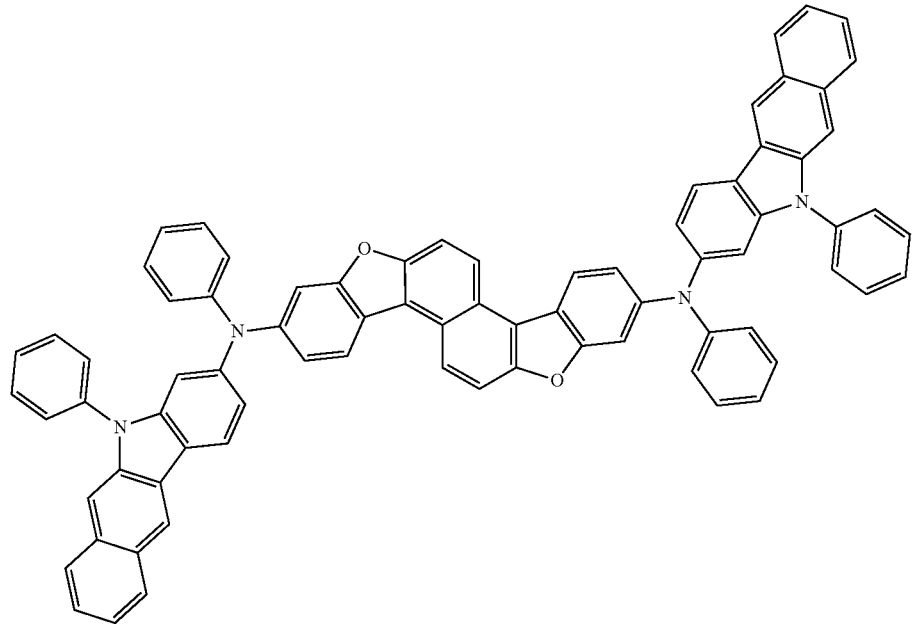
(262)
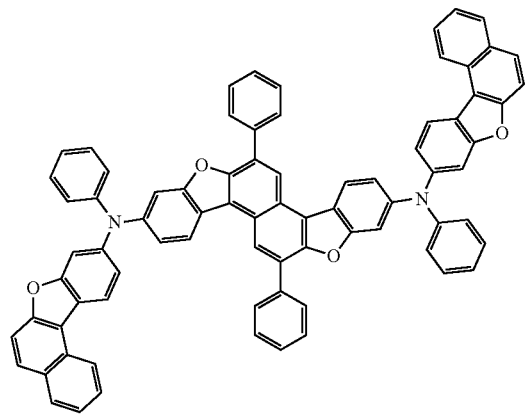
(263)
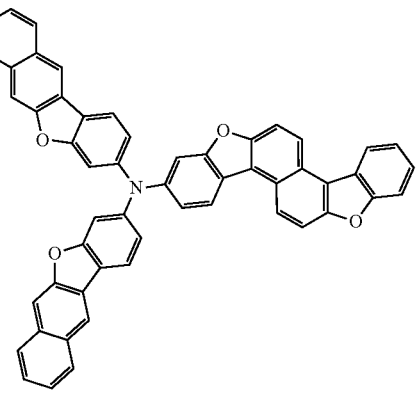
(264)
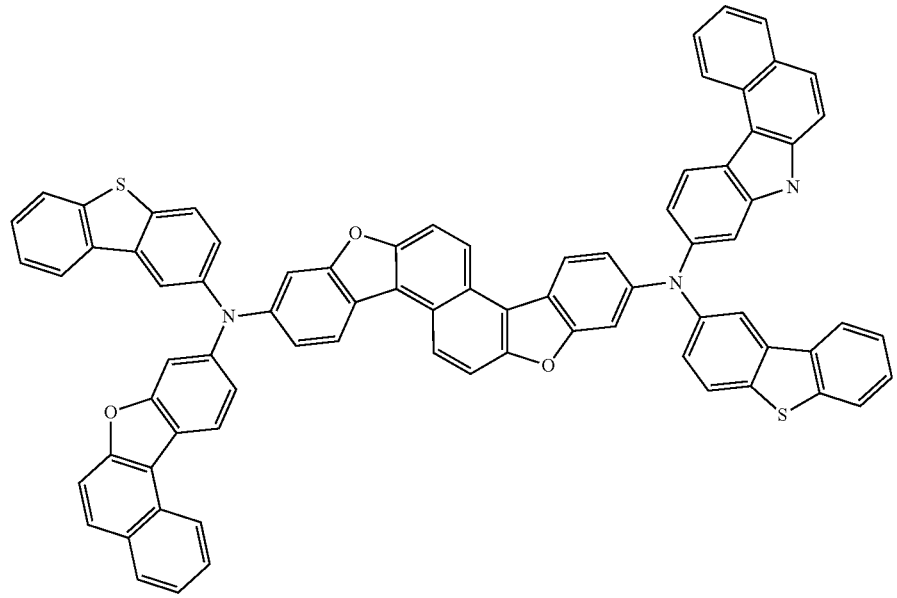

In the general formula (B1) to general formula (B4), $X^2$ and $X^3$ may be different as in a compound (238). However, $X^2$ and $X^3$ are preferably the same because the synthesis of the skeleton of B in the general formula (G1) is easier.

One embodiment of the present invention may have a structure in which one of the two arylamino groups is an arylamino group having any of a dibenzofuranyl group in which a benzene ring is condensed, a dibenzothiophenyl group in which a benzene ring is condensed, and a carbazolyl group in which a benzene ring is condensed and the other arylamino group is a diarylamino group. Note that an organic compound having the two arylamino groups being the same group is preferable for easy synthesis. Note that at least one of the two arylamino groups is preferably an arylamino group having any of a dibenzofuranyl group in which a benzene ring is condensed, a dibenzothiophenyl group in which a benzene ring is condensed, and a carbazolyl group in which a benzene ring is condensed because the reliability of a light-emitting device using the organic compound as a light-emitting material is high.

In the case where l in the general formula (G1) is 2, two $\alpha^1$ may be different skeletons or the same skeleton. Also in the case where m is 2, two $\alpha^2$ may be different skeletons or the same skeleton, and similarly in the case where n is 2, two $\alpha^3$ may be different skeletons or the same skeleton.

Then, one example of a method for synthesizing the above-described organic compound of the present invention will be described. The organic compound represented by the general formula (G1) is shown below.

[Chemical Formula 59]

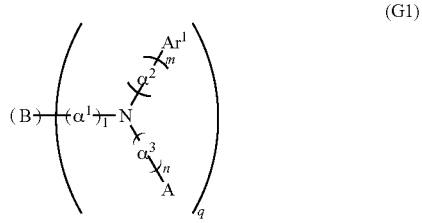

(G1)

Note that, in the formula, B represents a substituted or unsubstituted naphthobisbenzofuran skeleton, or a substituted or unsubstituted naphthobisbenzothiophene skeleton or naphthobenzothienobenzofuran skeleton. Furthermore, $Ar^1$ is any of a substituted or unsubstituted aromatic hydrocarbon group having 6 to 14 carbon atoms, a substituted or unsubstituted dibenzofuranyl group, a substituted or unsubstituted dibenzothiophenyl group, and a substituted or unsubstituted carbazolyl group, and a benzene ring may be condensed with these groups. A is any of a substituted or unsubstituted dibenzofuranyl group in which at least one benzene ring is condensed, a substituted or unsubstituted dibenzothiophenyl group in which at least one benzene ring is condensed, and a substituted or unsubstituted carbazolyl group in which at least one benzene ring is condensed, and $\alpha^1$ to $\alpha^3$ are each independently a substituted or unsubstituted divalent aromatic hydrocarbon group having 6 to 14 carbon atoms. Furthermore, l, m, and n each independently represent an integer of 0 to 2, and q is 1 or 2.

The organic compound represented by the general formula (G1) can be obtained by causing a cross coupling reaction of a compound (a1) and an arylamine compound (a2) as shown in the following synthesis scheme. Examples of $X_1$ include halogen such as chlorine, bromine, or iodine and a sulfonyl group. When l is 0 (that is, when the compound (a2) is a secondary amine), $D^1$ represents hydrogen; when l is 1 or larger (that is, when the compound (a2) is a tertiary amine), $D^1$ represents boronic acid, dialkoxyboronic acid, aryl aluminum, aryl zirconium, aryl zinc, aryl tin, or the like.

[Chemical Formula 60]

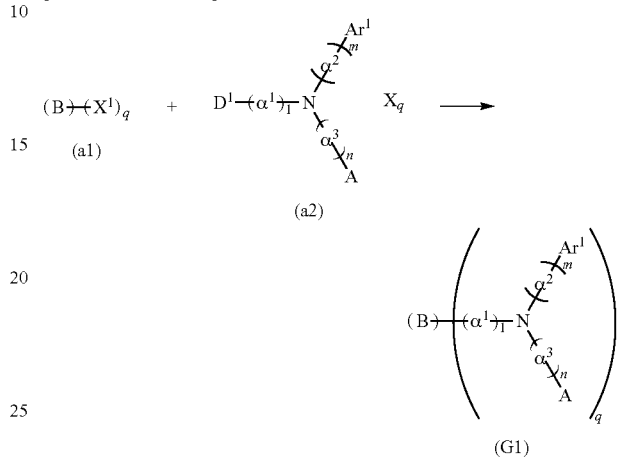

This reaction can proceed under various conditions; for example, a synthesis method in which a metal catalyst is used under the presence of a base can be employed. For example, Ullmann coupling or the Buchwald-Hartwig reaction can be used in the case where l is 0. In the case where l is 1 or larger, the Suzuki-Miyaura reaction can be used.

Here, q equivalents of the compound (a2) are reacted with the compound (a1); when q is two or more, i.e., the number of substituents represented in the parentheses for q with respect to B of the compound (G1) is two or more, and the substituents are not the same, the compounds (a2) may be reacted with the compound (a1) one kind by one kind.

The organic compound of one embodiment of the present invention can be synthesized in the above-described manner.

As a substance that can be used as the above compound (a1), compounds represented by a general formula (B1-a1) to a general formula (B4-a1) below can be given. These are compounds useful for the synthesis of the compound of one embodiment of the present invention. Raw materials thereof are also useful. As to the synthesis method, the synthesis can be performed similarly to that in Examples described later by changing the substitution position of halogen as appropriate.

[Chemical Formulae 61]

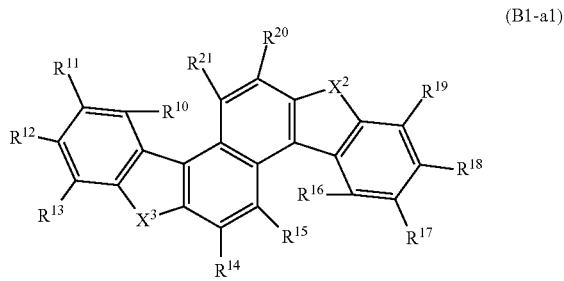

(B1-a1)

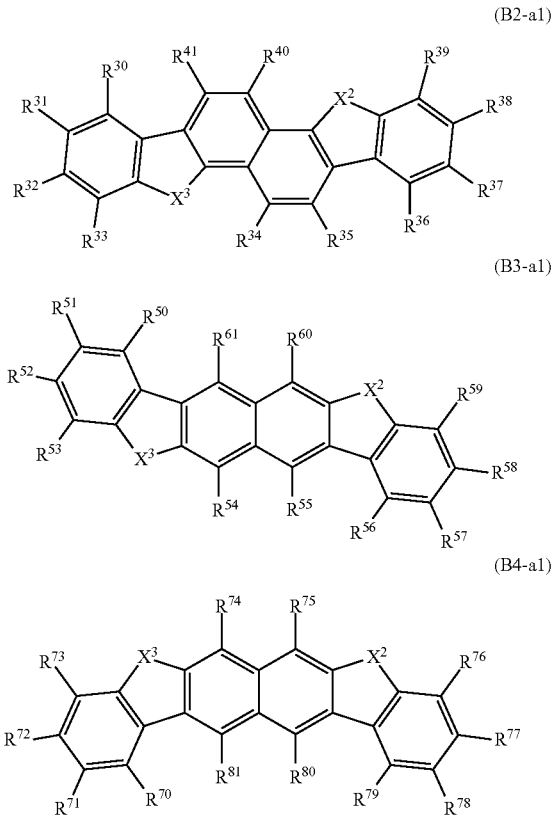
(B2-a1)
(B3-a1)
(B4-a1)

In the above general formula (B1-a1) to general formula (B4-a1), $X^2$ and $X^3$ each independently represent an oxygen atom or a sulfur atom.

In the above general formula (B1-a1), any one or two of $R^{10}$ to $R^{21}$ represent halogen, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{11}$, $R^{12}$, $R^{17}$, and $R^{18}$ of $R^{10}$ to $R^{21}$ are preferably halogen for easy synthesis.

In the case where any two of $R^{10}$ to $R^{21}$ in the general formula (B1-a1) are halogen, one of $R^{11}$ and $R^{12}$ and one of $R^{17}$ and $R^{18}$ are preferably halogen for easy synthesis. In that case, it is preferable that $R^{11}$ and $R^{17}$ be halogen or $R^{12}$ and $R^{18}$ be halogen.

In the above general formula (B2-a1), any one or two of $R^{30}$ to $R^{41}$ represent halogen, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{31}$, $R^{32}$, $R^{37}$, and $R^{38}$ of $R^{30}$ to $R^{41}$ are preferably halogen for easy synthesis.

In the case where any two of $R^{30}$ to $R^{41}$ in the general formula (B2-a1) are halogen, one of $R^{31}$ and $R^{32}$ and one of $R^{37}$ and $R^{38}$ are preferably halogen for easy synthesis. In that case, it is preferable that $R^{31}$ and $R^{37}$ be halogen or $R^{32}$ and $R^{38}$ be halogen.

In the above general formula (B3-a1), any one or two of $R^{50}$ to $R^{61}$ represent a single bond, and the others each independently represent any of hydrogen, a hydrocarbon group having 1 to 10 carbon atoms, a halogen hydrocarbon group having 3 to 10 carbon atoms, a substituted or unsubstituted aromatic hydrocarbon group having 6 to 14 carbon atoms, and substituted or unsubstituted diarylamino. Note that any one or two of $R^{51}$, $R^{52}$, $R^{57}$ and $R^{58}$ of $R^{50}$ to $R^{61}$ are preferably halogen.

In the case where any two of $R^{50}$ to $R^{61}$ in the general formula (B3-a1) are halogen, one of $R^{51}$ and $R^{52}$ and one of $R^{57}$ and $R^{58}$ are preferably halogen for easy synthesis. In that case, it is preferable that $R^{51}$ and $R^{57}$ be halogen or $R^{52}$ and $R^{58}$ be halogen.

In the above general formula (B4-a1), any one or two of $R^{70}$ to $R^{81}$ represent halogen, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{71}$, $R^{72}$, $R^{77}$, and $R^{78}$ of $R^{70}$ to $R^{81}$ are preferably halogen.

In the case where any two of $R^{70}$ to $R^{81}$ in the general formula (B4-a1) are halogen, one of $R^{71}$ and $R^{72}$ and one of $R^{77}$ and $R^{78}$ are preferably halogen for easy synthesis. In that case, it is preferable that $R^{71}$ and $R^{78}$ be halogen or $R^{72}$ and $R^{77}$ be halogen.

Embodiment 2

An example of a light-emitting device that is one embodiment of the present invention will be described in detail below with reference to FIG. 1(A).

In this embodiment, the light-emitting device includes a pair of electrodes composed of an anode 101 and a cathode 102, and an EL layer 103 provided between the anode 101 and the cathode 102. The EL layer 103 is formed by stacking at least some functional layers including a light-emitting layer 113. Typical examples of the functional layer include a hole-injection layer 111, a hole-transport layer 112, the light-emitting layer 113, an electron-transport layer 114, and an electron-injection layer 115; in addition, the functional layer may contain a carrier-blocking layer, an exciton-blocking layer, a charge-generation layer, or the like.

The anode 101 is preferably formed using a metal, an alloy, or a conductive compound with a high work function (specifically, 4.0 eV or more), a mixture thereof, or the like. Specific examples include indium oxide-tin oxide (ITO: Indium Tin Oxide), indium oxide-tin oxide containing silicon or silicon oxide, indium oxide-zinc oxide, and indium oxide containing tungsten oxide and zinc oxide (IWZO). Films of these conductive metal oxides are usually formed by a sputtering method but may be formed by application of a sol-gel method or the like. In an example of the formation method, indium oxide-zinc oxide is deposited by a sputtering method using a target in which zinc oxide is added to indium oxide at greater than or equal to 1 wt % and less than or equal to 20 wt %. Furthermore, indium oxide containing tungsten oxide and zinc oxide (IWZO) can also be deposited by a sputtering method using a target in which, with respect to indium oxide, tungsten oxide is contained at greater than or equal to 0.5 wt % and less than or equal to 5 wt % and zinc oxide is contained at greater than or equal to 0.1 wt % and less than or equal to 1 wt %. Other examples include gold (Au), platinum (Pt), nickel (Ni), tungsten (W), chromium (Cr), molybdenum (Mo), iron (Fe), cobalt (Co), copper (Cu), palladium (Pd), aluminum (Al), and nitrides of metal materials (e.g., titanium nitride). Graphene can also be used. In the case where a composite material including a first substance and a second substance is used for the hole-injection layer 111, an electrode material other than the above can be selected regardless of the work function.

The hole-injection layer 111 is formed using the first substance having a relatively high acceptor property. Preferably, the hole-injection layer 111 is formed using a composite material of the first substance having an acceptor property and the second substance having a hole-transport property. In the case where the composite material is used as a material of the hole-injection layer 111, a substance having an acceptor property with respect to the second substance is used as the first substance. The first substance draws electrons from the second substance, so that electrons are generated in the first substance. In the second substance from which electrons are drawn, holes are generated. By an electric field, the drawn electrons flow to the anode 101 and the generated holes are injected into the light-emitting layer 113 through the hole-transport layer 112. Thus, a light-emitting device having a low driving voltage can be obtained.

The first substance is preferably a transition metal oxide, an oxide of a metal belonging to any of Group 4 to Group 8 of the periodic table, an organic compound having an electron-withdrawing group (a halogen group or a cyano group), or the like.

As the transition metal oxide or the oxide of a metal belonging to any of Group 4 to Group 8 of the periodic table, vanadium oxide, niobium oxide, tantalum oxide, chromium oxide, molybdenum oxide, tungsten oxide, manganese oxide, rhenium oxide, titanium oxide, ruthenium oxide, zirconium oxide, hafnium oxide, or silver oxide is preferable because of its excellent acceptor property. Molybdenum oxide is particularly preferable because of its high stability in the air, low hygroscopicity, and high handiness.

Examples of the organic compound having an electron-withdrawing group (a halogen group or a cyano group) include 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). A compound in which electron-withdrawing groups are bonded to a condensed aromatic ring having a plurality of hetero atoms, such as HAT-CN, is particularly preferable because it is thermally stable.

The second substance has a hole-transport property and preferably has a hole mobility of $10^{-6}$ cm$^2$/Vs or higher. Examples of a material that can be used as the second substance include aromatic amines such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, pentacene, coronene, rubrene, perylene, and 2,5,8,11-tetra(tert-butyl)perylene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Alternatively, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); or a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be used. Among the above materials, the compound having an aromatic amine skeleton and the compound having a carbazole skeleton are preferred because these compounds have high reliability and high hole-transport properties and contribute to a reduction in driving voltage.

The organic compound of one embodiment of the present invention is also a substance having a hole-transport property and thus can be used as the second substance.

The hole-injection layer 111 can also be formed by a wet process. In this case, a conductive high molecular compound to which an acid, such as a poly(ethylenedioxythiophene)/ poly(styrenesulfonic acid) aqueous solution (PEDOT/PSS), a polyaniline/camphorsulfonic acid aqueous solution (PANI/CSA), PTPDES, Et-PTPDEK, PPBA, or polyaniline/poly(styrenesulfonic acid) (PANI/PSS), is added can be used, for example.

The hole-transport layer 112 is a layer containing a material having a hole-transport property. As the materials having a hole-transport property, the materials for the second substance, raised as a substance contained in the hole-injection layer 111, can be used. The hole-transport layer 112 may be formed of either a single layer or a plurality of layers. In the case where the hole-transport layer 112 is formed of a plurality of layers, to inject holes easily, the HOMO level of the hole-transport layer 112 preferably becomes deeper stepwise from a layer on the hole-injection layer 111 side to a layer on the light-emitting layer 113 side. Such a structure is highly suitable for a blue fluorescence-emitting element in which a host material in the light-emitting layer 113 has a deep HOMO level.

Note that the structure of the hole-transport layer 112 formed of a plurality of layers having a HOMO level which becomes deeper stepwise toward the light-emitting layer 113 is particularly suitable for an element having the hole-injection layer 111 formed with an organic acceptor (an organic compound having the above-mentioned electron-withdrawing group (a halogen group or a cyano group)), with which an element with an excellent carrier-injection property, a low driving voltage, and highly favorable characteristics can be obtained.

The organic compound of one embodiment of the present invention is also a substance having a hole-transport property and thus can be used as the material having a hole-transport property.

Note that the hole-transport layer 112 can also be formed by a wet process. In the case where the hole-transport layer 112 is formed by a wet process, a high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

The light-emitting layer 113 may be a layer containing any light-emitting substance, such as a layer containing a fluorescent substance, a layer containing a phosphorescent substance, a layer containing a substance that emits thermally activated delayed fluorescence (TADF), a layer containing quantum dots, or a layer containing a metal halide perovskite; however, the light-emitting layer 113 preferably contains the organic compound of one embodiment of the present invention described in Embodiment 1, as a light-emitting substance. The use of the organic compound of one embodiment of the present invention as a light-emitting substance facilitates formation of a light-emitting device having high efficiency and highly favorable chromaticity.

Furthermore, the light-emitting layer 113 may be a single layer or include a plurality of layers. In the case where a light-emitting layer including a plurality of layers is formed, a layer containing a phosphorescent substance and a layer containing a fluorescent substance may be stacked. In this case, an exciplex described later is preferably utilized in the layer containing a phosphorescent substance.

The organic compound of one embodiment of the present invention is also a substance having a favorable quantum yield and thus can be used as a light-emitting material.

Examples of an available fluorescent substance include, though other fluorescent substances can also be used, the following substances: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N, 9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: BisDCJTM). In particular, a condensed aromatic diamine compound typified by a pyrenediamine compound such as 1,6mMemFLPAPrn is preferable because of its high hole-trapping property, high emission efficiency, and high reliability.

Examples of a material that can be used as a phosphorescent substance in the light-emitting layer 113 are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5- methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptzl-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIracac). These compounds emit blue phosphorescence having an emission spectrum peak at 440 nm to 520 nm.

Other examples include an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetyl acetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). These compounds mainly emit green phosphorescence having an emission spectrum peak at 500 nm to 600 nm. Note that an organometallic iridium complex having a pyrimidine skeleton has distinctively high reliability and emission efficiency and thus is especially preferable.

Other examples include an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); an organometallic iridium complex having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); a platinum complex such as 2,3,7,8,12,13,17,18-octaethyl-21H,23H-porphyrin platinum (II) (abbreviation: PtOEP); and a rare earth metal complex such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These compounds emit red phosphorescence having an emission spectrum peak at 600 nm to 700 nm. Furthermore, an organometallic iridium complex having a pyrazine skeleton can emit red light with favorable chromaticity.

Besides the above phosphorescent compounds, a variety of phosphorescent materials may be selected and used.

A fullerene, a derivative thereof, an acridine, a derivative thereof, an eosin derivative, or the like can be used as the TADF material. Furthermore, porphyrin containing a metal such as magnesium (Mg), zinc (Zn), cadmium (Cd), tin (Sn), platinum (Pt), indium (In), or palladium (Pd) can be used. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formulae 62]

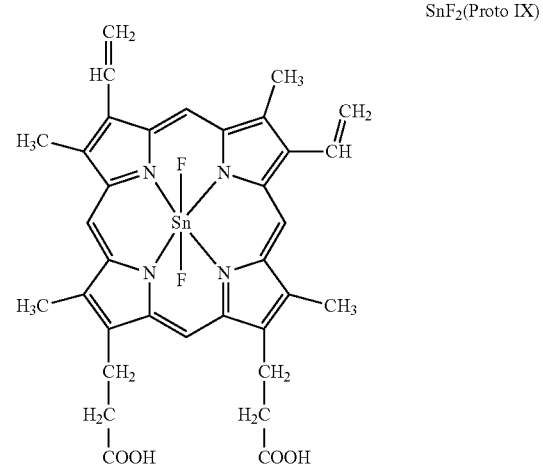

SnF$_2$(Proto IX)

SnF₂(Meso IX)

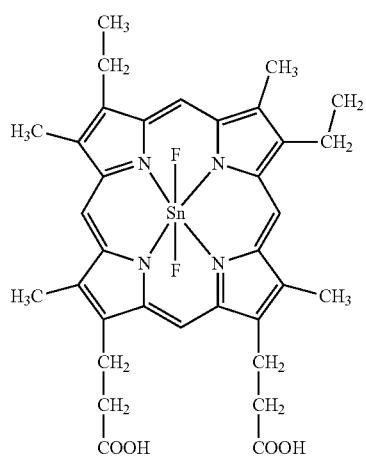

SnF₂(Hemato IX)

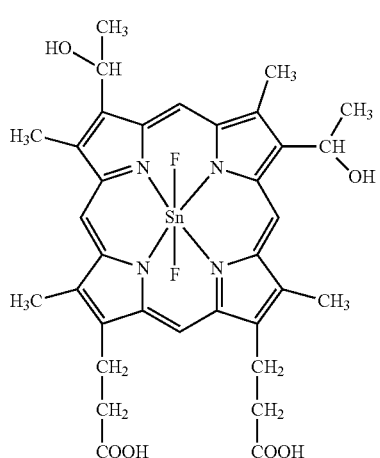

SnF₂(Copro III-4Me)

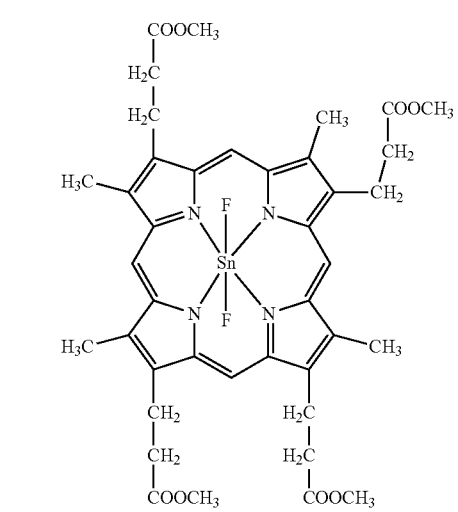

SnF₂(OEP)

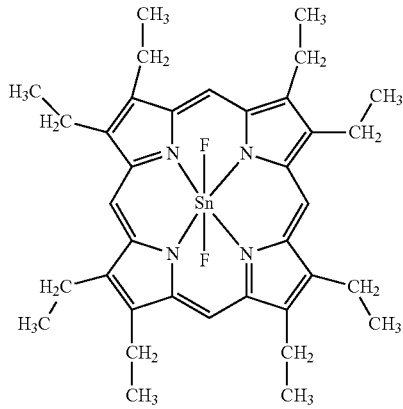

SnF₂(Etio I)

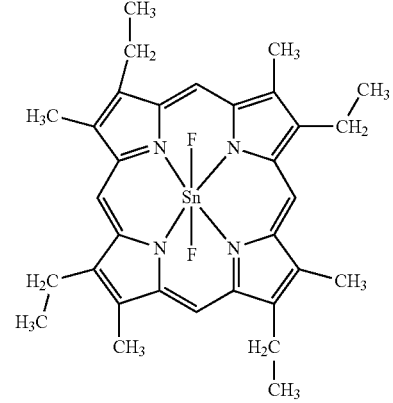

PtCl₂OEP

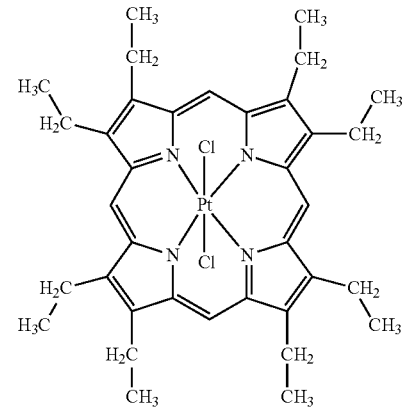

Alternatively, a heterocyclic compound having both a π-electron rich heteroaromatic ring and a π-electron deficient heteroaromatic ring, such as 2-(biphenyl4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3 TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation:

ACRSA), which are represented by the following structural formulae, can be used. Such a heterocyclic compound is preferable because of having both a high electron-transport property and a high hole-transport property owing to a π-electron rich heteroaromatic ring and a π-electron deficient heteroaromatic ring. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both improved and the energy difference between the S1 level and the T1 level becomes small, so that thermally activated delayed fluorescence can be obtained with high efficiency. Note that an aromatic ring to which an electron-withdrawing group such as a cyano group is bonded may be used instead of the π-electron deficient heteroaromatic ring.

[Chemical Formulae 63]

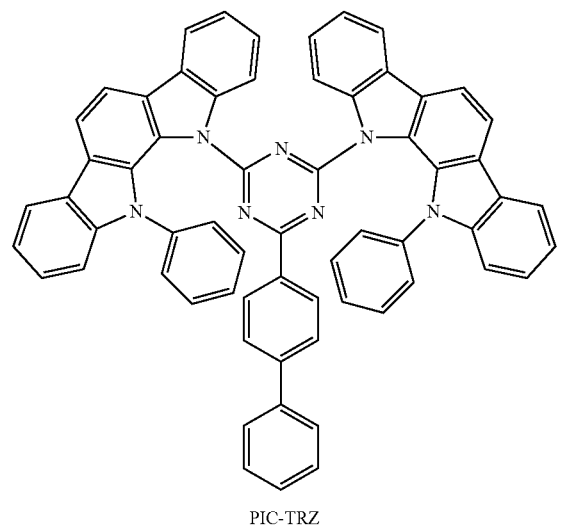

PIC-TRZ

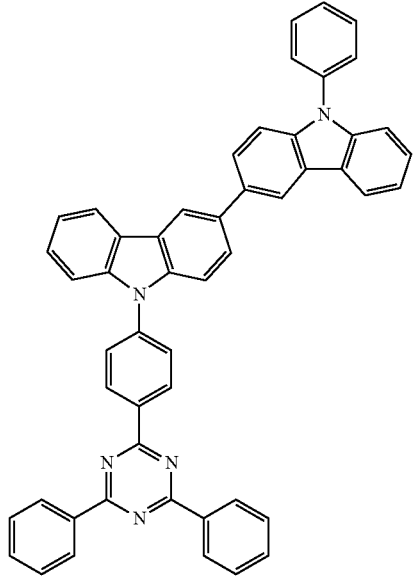

PCCzPTzn

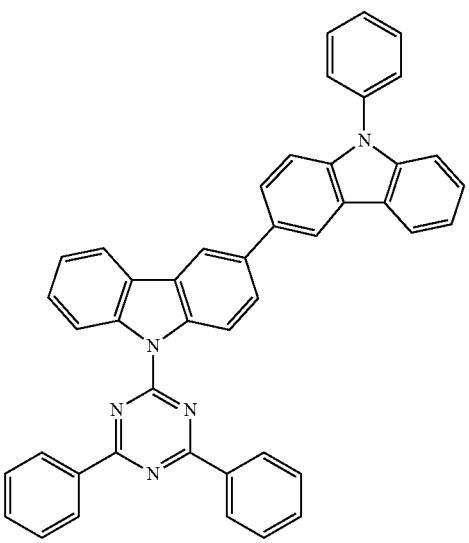

PCCzTzn

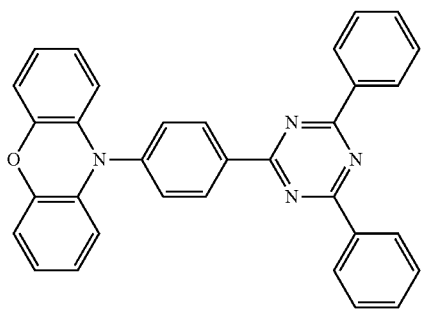

PXZ-TRZ

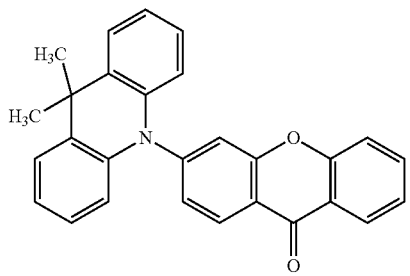

ACRXTN

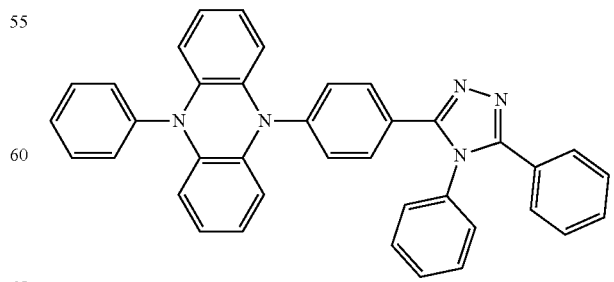

PPZ-3TPT

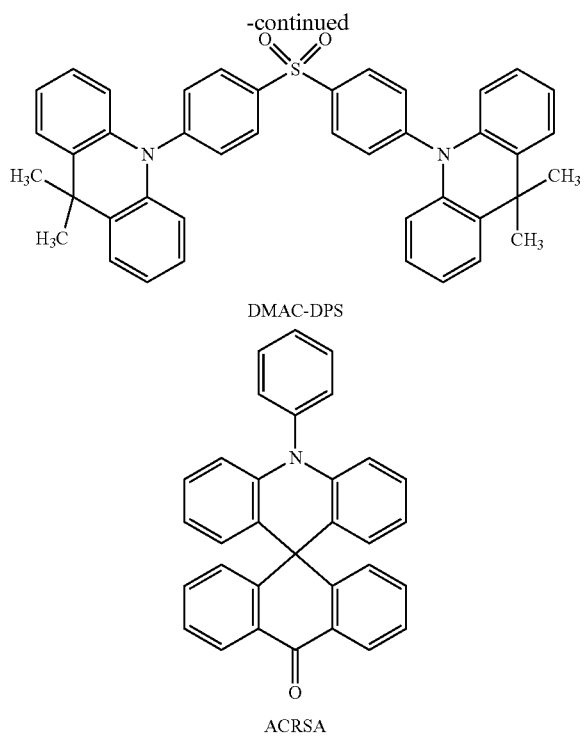

DMAC-DPS

ACRSA

Examples of the quantum dot include nano-sized particles of a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, semiconductor clusters, metal halide perovskites, and the like.

Specific examples include, but are not limited to, cadmium selenide (CdSe), cadmium sulfide (CdS), cadmium telluride (CdTe), zinc selenide (ZnSe), zinc oxide (ZnO), zinc sulfide (ZnS), zinc telluride (ZnTe), mercury sulfide (HgS), mercury selenide (HgSe), mercury telluride (HgTe), indium arsenide (InAs), indium phosphide (InP), gallium arsenide (GaAs), gallium phosphide (GaP), indium nitride (InN), gallium nitride (GaN), indium antimonide (InSb), gallium antimonide (GaSb), aluminum phosphide (AlP), aluminum arsenide (AlAs), aluminum antimonide (AlSb), lead(II) selenide (Pb Se), lead(II) telluride (PbTe), lead(II) sulfide (PbS), indium selenide ($In_2Se_3$), indium telluride ($In_2Te_3$), indium sulfide ($In_2S_3$), gallium selenide ($Ga_2Se_3$), arsenic(III) sulfide ($As_2S_3$), arsenic(III) selenide ($As_2Se_3$), arsenic(III) telluride ($As_2Te_3$), antimony(III) sulfide ($Sb_2S_3$), antimony(III) selenide ($Sb_2Se_3$), antimony(III) telluride ($Sb_2Te_3$), bismuth(III) sulfide ($Bi_2S_3$), bismuth(III) selenide ($Bi_2Se_3$), bismuth(III) telluride ($Bi_2Te_3$), silicon (Si), silicon carbide (SiC), germanium (Ge), tin (Sn), selenium (Se), tellurium (Te), boron (B), carbon (C), phosphorus (P), boron nitride (BN), boron phosphide (BP), boron arsenide (BAs), aluminum nitride (AlN), aluminum sulfide ($Al_2S_3$), barium sulfide (BaS), barium selenide (BaSe), barium telluride (BaTe), calcium sulfide (CaS), calcium selenide (CaSe), calcium telluride (CaTe), beryllium sulfide (BeS), beryllium selenide (BeSe), beryllium telluride (BeTe), magnesium sulfide (MgS), magnesium selenide (MgSe), germanium sulfide (GeS), germanium selenide (GeSe), germanium telluride (GeTe), tin(IV) sulfide ($SnS_2$), tin(II) sulfide (SnS), tin(II) selenide (SnSe), tin(II) telluride (SnTe), lead(II) oxide (PbO), copper(I) fluoride (CuF), copper(I) chloride (CuCl), copper(I) bromide (CuBr), copper(I) iodide (CuI), copper(I) oxide ($Cu_2O$), copper(I) selenide ($Cu_2Se$), nickel(II) oxide (NiO), cobalt(II) oxide (CoO), cobalt(II) sulfide (CoS), triiron tetraoxide ($Fe_3O_4$), iron(II) sulfide (FeS), manganese(II) oxide (MnO), molybdenum (IV) sulfide ($MoS_2$), vanadium(II) oxide (VO), vanadium (IV) oxide ($VO_2$), tungsten(IV) oxide ($WO_2$), tantalum(V) oxide ($Ta_2O_5$), titanium oxide ($TiO_2$, $Ti_2O_5$, $Ti_2O_3$, $Ti_5O_9$, or the like), zirconium oxide ($ZrO_2$), silicon nitride ($Si_3N_4$), germanium nitride ($Ge_3N_4$), aluminum oxide ($Al_2O_3$), barium titanate ($BaTiO_3$), a compound of selenium, zinc, and cadmium (CdZnSe), a compound of indium, arsenic, and phosphorus (InAsP), a compound of cadmium, selenium, and sulfur (CdSeS), a compound of cadmium, selenium, and tellurium (CdSeTe), a compound of indium, gallium, and arsenic (InGaAs), a compound of indium, gallium, and selenium (InGaSe), a compound of indium, selenium, and sulfur (InSeS), a compound of copper, indium, and sulfur (e.g., $CuInS_2$), and combinations thereof. What is called an alloyed quantum dot whose composition is represented by a given ratio may be used. For example, an alloyed quantum dot represented by $CdS_xSe_{1-x}$ (x is a given number between 0 and 1) is an effective means for obtaining blue light emission because its emission wavelength can be changed by changing x.

As the quantum dot structure, there are a core type, a core-shell type, a core-multishell type, and the like, and any of them may be used. When a core is covered with a shell formed of another inorganic material having a wider band gap, the influence of a defect or a dangling bond existing at the surface of a nanocrystal can be reduced. Since such a structure can significantly improve the quantum efficiency of light emission, it is preferable to use a core-shell or core-multishell quantum dot. Examples of the material of a shell include zinc sulfide (ZnS) and zinc oxide (ZnO).

Quantum dots have a high proportion of surface atoms and thus have high reactivity and easily cohere together. For this reason, it is preferable that a protective agent be attached to or a protective group be provided on the surfaces of the quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

The quantum dots may be quantum rods with rod-like shapes. A quantum rod emits directional light polarized in the c-axis direction; thus, by using quantum rods as a light-emitting material, a light-emitting device with higher external quantum efficiency can be obtained.

A light-emitting layer in which the quantum dots are dispersed as a light-emitting material in a host material may be formed by dispersing the quantum dots in the host material, or dissolving or dispersing the host material and the quantum dots in an appropriate liquid medium, then forming a layer by a wet process (a spin coating method, a casting method, a die coating method, a blade coating method, a roll coating method, an inkjet method, a printing method, a spray coating method, a curtain coating method, a Langmuir-Blodgett method, or the like), and subsequently removing the liquid medium or performing baking.

As the liquid medium used for the wet process, organic solvents, e.g., ketones such as methyl ethyl ketone and cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decalin, and dodecane, dimethylformamide (DMF), and dimethyl sulfoxide (DMSO) can be used In the case where a fluorescent substance is used, a host material suitable for the light-emitting layer is a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazol e (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}anthracene (abbreviation: FLPPA). The use of a substance having an anthracene skeleton as a host material for a fluorescent substance makes it possible to obtain a light-emitting layer with both high emission efficiency and high durability. In particular, CzPA, cgDBCzPA, 2mBnfPPA, and PCzPA exhibit excellent characteristics and thus are preferably selected.

In the case where a material other than the above materials is used as a host material, various carrier-transport materials, such as a material having an electron-transport property and a material having a hole-transport property, can be used.

Examples of the material with an electron-transport property include a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[fh]quinoxaline (abbreviation: 2mDBTBPDBq-II), 2-[3'-(9H-carbazol-9-yl)biphenyl-3-yl]dibenzo[f, h]quinoxaline (abbreviation: 2mCzBPDB q), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and a heterocyclic compound having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has an excellent electron-transport property and contributes to a reduction in driving voltage.

Examples of a material having a hole-transport property include a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and a compound having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds have high reliability and high hole-transport properties and contribute to a reduction in driving voltage. As well as the hole-transport materials given above, a hole-transport material among a variety of substances may be selected and used.

In the case where a fluorescent substance is used as a light-emitting substance, a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d] furan (abbreviation: 2mBnfPPA), and 9-phenyl-10-{4-(9-phenyl-9H-fluoren-9-yl)-biphenyl-4'-yl}-anthracene (abbreviation: FLPPA), is preferable. The use of a substance having an anthracene skeleton as a host material for a fluorescent substance makes it possible to achieve a light-emitting layer with both high emission efficiency and high durability. In particular, CzPA, cgDBCzPA, 2mBnfPPA, and PCzPA exhibit excellent characteristics and thus are preferably selected.

Note that a host material may be a mixture of a plurality of kinds of substances; in the case of using mixed host materials, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The content ratio of the material having a hole-transport property to the material having an electron-transport property may be 1:9 to 9:1 (weight ratio).

Mixed host materials may form an exciplex. When a combination of materials is selected so as to form an exciplex that exhibits light emission whose wavelength overlaps with the wavelength of the lowest-energy-side absorption band of a fluorescent substance, a phosphorescent substance, or a TADF material, energy can be transferred smoothly and light emission can be efficiently obtained. Such a structure is preferred because the driving voltage can also be reduced.

The light-emitting layer 113 having the above-described structure can be formed by co-evaporation by a vacuum evaporation method, or a gravure printing method, an offset printing method, an inkjet method, a spin coating method, a dip coating method, or the like as a method using a mixed solution.

The electron-transport layer 114 contains a substance having an electron-transport property. As the substance having an electron-transport property, the materials having electron-transport properties and the materials having anthracene skeletons, which can be used as a host material, can be used.

Between the electron-transport layer and the light-emitting layer, a layer that controls transport of electron carriers may be provided. This is a layer in which a small amount of a substance having a high electron-trapping property is added to the aforementioned material having a high electron-transport property and is capable of adjusting the carrier balance by retarding transport of electron carriers. Such a structure is very effective in preventing a problem (such as a reduction in element lifetime) caused when electrons pass through the light-emitting layer.

The electron-injection layer 115 may be provided between the electron-transport layer 114 and the cathode 102 and in contact with the cathode 102. For the electron-injection layer 115, an alkali metal, an alkaline earth metal, or a compound thereof, such as lithium fluoride (LiF), cesium fluoride (CsF), or calcium fluoride (CaF$_2$), can be used. For example, a layer that is formed of a substance having an electron-transport property and contains an alkali metal, an alkaline earth metal, or a compound thereof can be used. In addition, an electride may be used for the electron-injection layer 115. Examples of the electride include a substance in which electrons are added at high concentration to a mixed oxide of calcium and aluminum. Note that a layer that is formed of a substance having an electron-transport property and contains an alkali metal or an alkaline earth metal is preferably used as the electron-injection layer 115, in which case electron injection from the cathode 102 is efficiently performed.

Figure 1B:
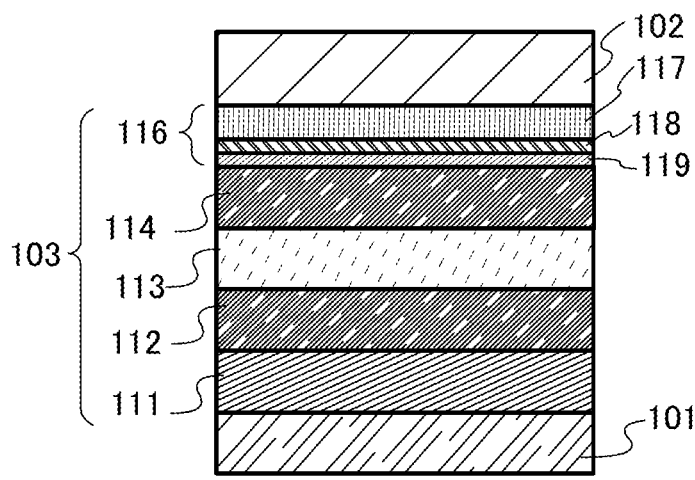

Instead of the electron-injection layer 115, a charge-generation layer 116 may be provided (FIG. 1(B)). The charge-generation layer 116 refers to a layer capable of injecting holes into a layer in contact with the cathode side of the charge-generation layer 116 and injecting electrons into a layer in contact with the anode side thereof when a potential is applied. The charge-generation layer 116 includes at least a P-type layer 117. The P-type layer 117 is preferably formed using any of the composite materials given above as examples of the material that can be used for the hole-injection layer 111. The P-type layer 117 may be formed by stacking a film containing the above acceptor material mentioned as a material included in the composite material and a film containing the above hole-transport material. When a potential is applied to the P-type layer 117, electrons are injected into the electron-transport layer 114 and holes are injected into the cathode 102; thus, the light-emitting device operates. When a layer containing the organic compound of one embodiment of the present invention exists in a portion of the electron-transport layer 114 that is in contact with the charge-generation layer 116, a luminance decrease over driving time of the light-emitting device can be suppressed, and thus, the light-emitting device with a long lifetime can be obtained.

Note that the charge-generation layer 116 preferably includes one or both of an electron-relay layer 118 and an electron-injection buffer layer 119 in addition to the P-type layer 117.

The electron-relay layer 118 contains at least a substance with an electron-transport property and has a function of preventing an interaction between the electron-injection buffer layer 119 and the P-type layer 117 to transfer electrons smoothly. The LUMO level of the substance with an electron-transport property contained in the electron-relay layer 118 is preferably between the LUMO level of an acceptor substance in the P-type layer 117 and the LUMO level of a substance contained in a layer of the electron-transport layer 114 in contact with the charge-generation layer 116. Specifically, the LUMO energy level of the substance with an electron-transport property used for the electron-relay layer 118 is higher than or equal to −5.0 eV, preferably higher than or equal to −5.0 eV and lower than or equal to −3.0 eV. As the substance with an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, for example, an alkali metal, an alkaline earth metal, a rare earth metal, or a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used.

In the case where the electron-injection buffer layer 119 contains the substance having an electron-transport property and a donor substance, an organic compound such as tetrathianaphthacene (abbreviation: TTN), nickelocene, or decamethylnickelocene, as well as an alkali metal, an alkaline earth metal, a rare earth metal, or a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used as the donor substance. As the substance having an electron-transport property, a material similar to the above-described material for the electron-transport layer 114 can be used.

As a substance contained in the cathode 102, a metal, an alloy, an electrically conductive compound, or a mixture thereof having a low work function (specifically, 3.8 eV or less) or the like can be used. Specific examples of such a cathode material include an element belonging to Group 1 or Group 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the cathode 102 and the electron-transport layer, a variety of conductive materials such as Al, Ag, ITO, or indium oxide-tin oxide containing silicon or silicon oxide can be used for the cathode 102 regardless of the value of the work function. These conductive materials can be deposited by a dry process such as a vacuum evaporation method or a sputtering method, an inkjet method, a spin coating method, or the like. Alternatively, these conductive materials may be formed by either a wet process using a sol-gel method or a wet process using a paste of a metal material.

A variety of methods, regardless of whether it is a dry process or a wet process, can be used as the formation method of the EL layer 103. For example, a vacuum evaporation method or a wet process (such as a spin coating method, a casting method, a die coating method, a blade coating method, a roll coating method, an inkjet method, a printing method (e.g., a gravure printing method, an offset printing method, and a screen printing method), a spray coating method, a curtain coating method, and a Langmuir-Blodgett method) may be used.

The electrodes or the layers described above may be formed by different deposition methods.

Here, a method for forming a layer 786 containing a light-emitting substance by a droplet discharge method will be described with reference to FIG. 2. FIG. 2(A) to FIG. 2(D) are cross-sectional views illustrating a method for forming the layer 786 containing a light-emitting sub stance.

Figure 2A:
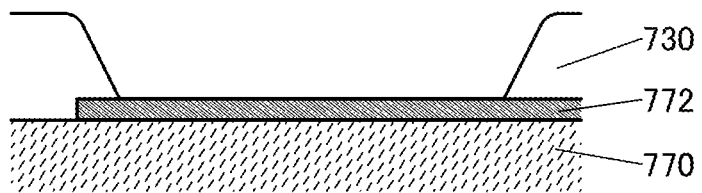
FIGS. 2A-2D are diagrams illustrating an example of a method for fabricating a light-emitting device.
Figure 2B:
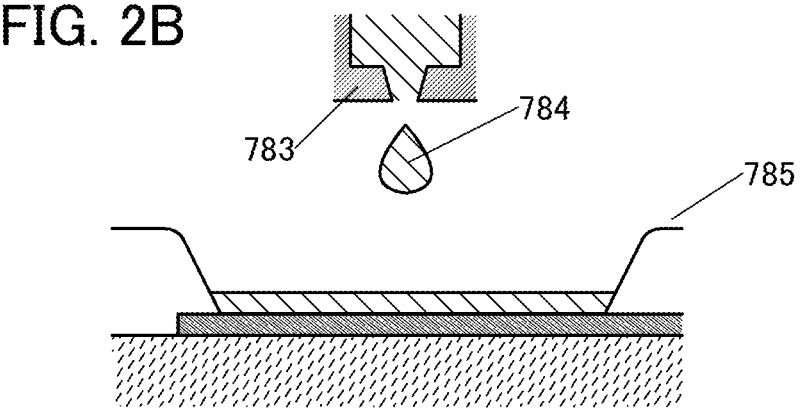

First, a conductive film 772 is formed over a planarization insulating film 770, and an insulating film 730 is formed to cover part of the conductive film 772 (see FIG. 2(A)).

Then, a droplet 784 is discharged from a droplet discharge apparatus 783 to the conductive film 772 exposed in an opening of the insulating film 730, so that a layer 785 containing a composition is formed. The droplet 784 is a composition containing a solvent and is attached onto the conductive film 772 (see FIG. 2(B)).

Note that the step of discharging the droplet 784 may be performed under reduced pressure.

Figure 2C:
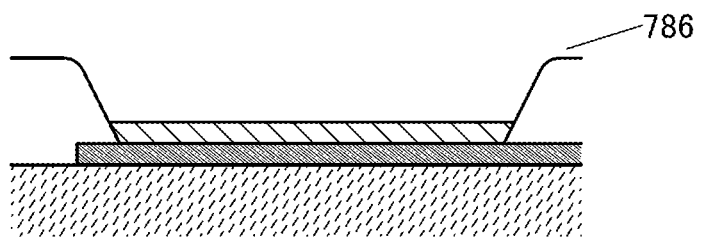

Next, the solvent is removed from the layer 785 containing a composition, and the layer is solidified to form the layer 786 containing a light-emitting substance (see FIG. 2(C)).

As the solvent removing method, a drying process or a heating process may be performed.

Figure 2D:
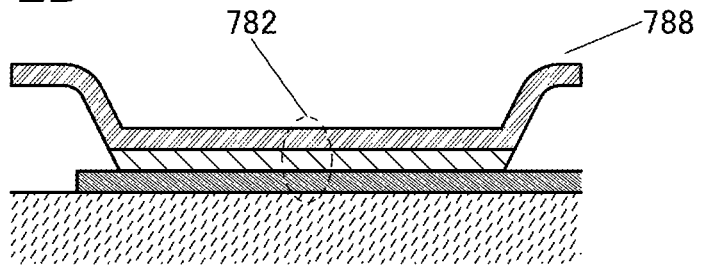

Next, a conductive film 788 is formed over the layer 786 containing a light-emitting substance; thus, a light-emitting device 782 is formed (see FIG. 2(D)).

When the layer 786 containing a light-emitting substance is formed by a droplet discharge method in this manner, the composition can be selectively discharged; accordingly, waste of the material can be reduced. Furthermore, a lithography process or the like for shaping is not needed, and thus, the process can be simplified and cost reduction can be achieved.

The droplet discharge method mentioned above is a general term for a method with a droplet discharge means such as a nozzle having a composition discharge outlet or a head having one or a plurality of nozzles.

Figure 3:
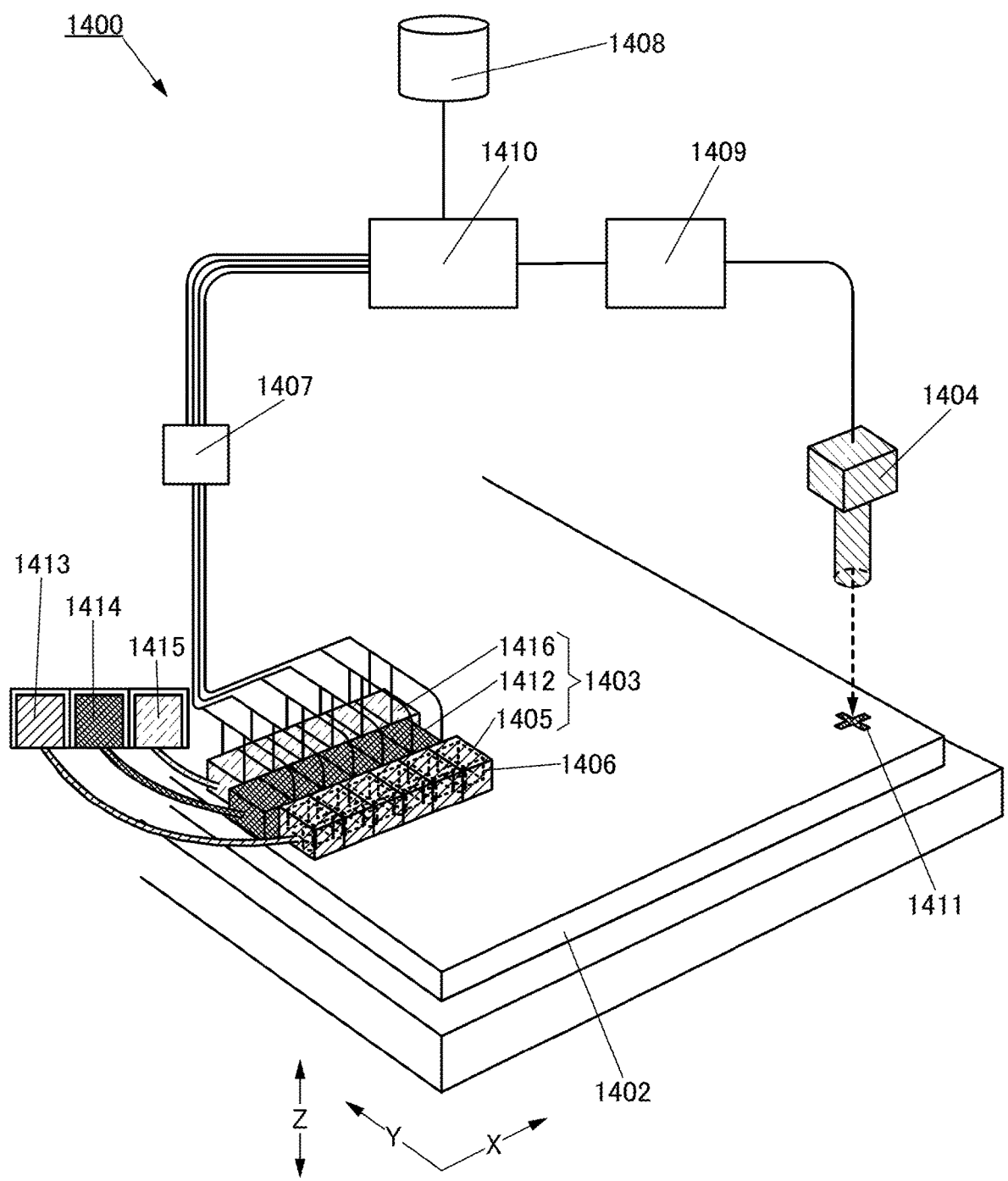
FIG. 3 is a conceptual diagram of a droplet discharge apparatus.

Next, a droplet discharge apparatus used for the droplet discharge method will be described with reference to FIG. 3. FIG. 3 is a conceptual diagram illustrating a droplet discharge apparatus 1400.

The droplet discharge apparatus 1400 includes a droplet discharge means 1403. The droplet discharge means 1403 further includes a head 1405, a head 1412, and a head 1416.

The head 1405, the head 1412, and the head 1416 are connected to a control means 1407 that is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits the control signal to the control means 1407.

An image sensor or the like utilizing a charge coupled device (CCD) or a complementary metal-oxide-semiconductor (CMOS) can be used as the imaging means 1404. Note that information on a pattern to be formed on the substrate 1402 is stored in a storage medium 1408, and a control signal is transmitted to the control means 1407 on the basis of the information, so that the head 1405, the head 1412, and the head 1416 of the droplet discharge means 1403 can be individually controlled. Materials to be discharged are supplied to the head 1405, the head 1412, and the head 1416 from a material supply source 1413, a material supply source 1414, and a material supply source 1415, respectively, through pipes.

Inside the head 1405, a space indicated by a dotted line 1406 to be filled with a liquid material and a nozzle serving as a discharge outlet are provided. Although not illustrated, the inside structures of the head 1412 and the head 1416 are similar to that of the head 1405. When the nozzle sizes of the head 1405, the head 1412, and the head 1416 are different from each other, different materials with different widths can be discharged simultaneously. Each head can discharge a plurality of kinds of light-emitting materials or the like to draw a pattern. In the case of drawing a pattern over a large area, the same material can be simultaneously discharged from a plurality of nozzles in order to improve throughput. When a large substrate is used, the head 1405, the head 1412, and the head 1416 can freely scan the substrate in the directions of arrows X, Y, and Z in FIG. 3, a region in which a pattern is drawn can be freely set, and the same patterns can be drawn on one substrate.

Furthermore, the step of discharging the composition may be performed under reduced pressure. The substrate may be heated at the time of discharging. The discharge of the composition is followed by one or both steps of drying and baking. Both the drying and baking steps are heat treatments but different in purpose, temperature, and time. The drying step and the baking step are performed under normal pressure or reduced pressure by laser irradiation, rapid thermal annealing, heating in a heating furnace, or the like. Note that there is no particular limitation on the timing of the heat treatment and the number of times of the heat treatment. The temperature for adequately performing the drying and baking steps depends on the material of the substrate and the properties of the composition.

In the above-described manner, the layer 786 containing a light-emitting substance can be formed with the droplet discharge apparatus.

When the layer 786 containing a light-emitting substance is formed with the droplet discharge apparatus by a wet process with a composition in which any of a variety of organic materials and organic-inorganic halide perovskites is dissolved or dispersed in a solvent, various organic solvents can be used to form a coating composition. As the organic solvents that can be used for the composition, a variety of organic solvents such as benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, and cyclohexane can be used. In particular, a low polarity benzene derivative such as benzene, toluene, xylene, or mesitylene is preferably used because a solution with a suitable concentration can be obtained and a material contained in ink can be prevented from deteriorating due to oxidation or the like. Furthermore, in light of the uniformity of a formed film or the uniformity of film thickness, the boiling point is preferably 100° C. or higher, and toluene, xylene, or mesitylene is further preferable.

Note that the above-described structure can be combined with another embodiment or another structure in this embodiment as appropriate.

Next, an embodiment of a light-emitting device in which a plurality of light-emitting units are stacked (also referred to as a stacked device) will be described with reference to FIG. 1(C). This light-emitting device includes a plurality of light-emitting units between an anode and a cathode. One light-emitting unit has a structure similar to that of the EL layer 103 illustrated in FIG. 1(A). In other words, it can be said that the light-emitting device illustrated in FIG. 1(A) or FIG. 1(B) is a light-emitting device that includes one light-emitting unit, and the light-emitting device illustrated in FIG. 1(C) is a light-emitting device that includes a plurality of light-emitting units.

Figure 1C:
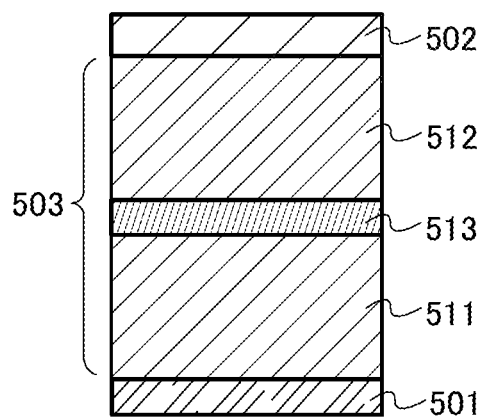

In FIG. 1(C), a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond to the anode 101 and the cathode 102, respectively, in FIG. 1(A), and the description of FIG. 1(A) can be applied thereto. Furthermore, the first light-emitting unit 511 and the second light-emitting unit 512 may have either the same structure or different structures.

The charge-generation layer 513 has a function of injecting electrons into one of the light-emitting units and injecting holes into the other light-emitting unit when a voltage is applied to the first electrode 501 and the second electrode 502. That is, in FIG. 1(C), the charge-generation layer 513 injects electrons into the first light-emitting unit 511 and injects holes into the second light-emitting unit 512 when a voltage is applied such that the potential of the first electrode is higher than the potential of the second electrode.

The charge-generation layer 513 preferably has a structure similar to that of the charge-generation layer 116 described with reference to FIG. 1(B). A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 serves as an electron-injection layer in the light-emitting unit on the anode side; therefore, the light-emitting unit is not necessarily provided with an additional electron-injection layer.

The light-emitting device having two light-emitting units is described with reference to FIG. 1(C); however, the above structure can also be used for a light-emitting device in which three or more light-emitting units are stacked. With a plurality of light-emitting units partitioned by the charge-generation layers 513 between a pair of electrodes as in the light-emitting device of this embodiment, it is possible to provide a long-life device that can emit light at high luminance with the current density kept low. A light-emitting apparatus that can be driven at a low voltage and has low power consumption can be achieved.

Furthermore, by varying emission colors of the light-emitting units, light emission of a desired color can be obtained from the light-emitting device as a whole.

Embodiment 3

In this embodiment, a light-emitting apparatus using the light-emitting device described in Embodiment 1 will be described.

Figure 4A:
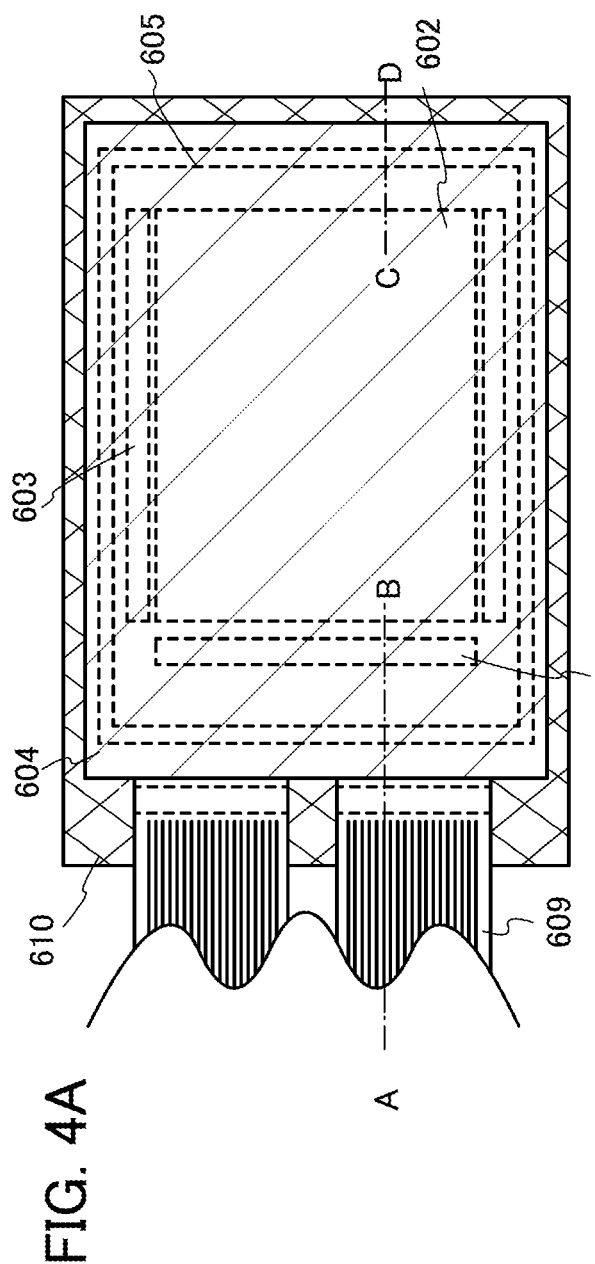
FIGS. 4A and 4B are schematic diagrams of an active matrix light-emitting apparatus.
Figure 4B:
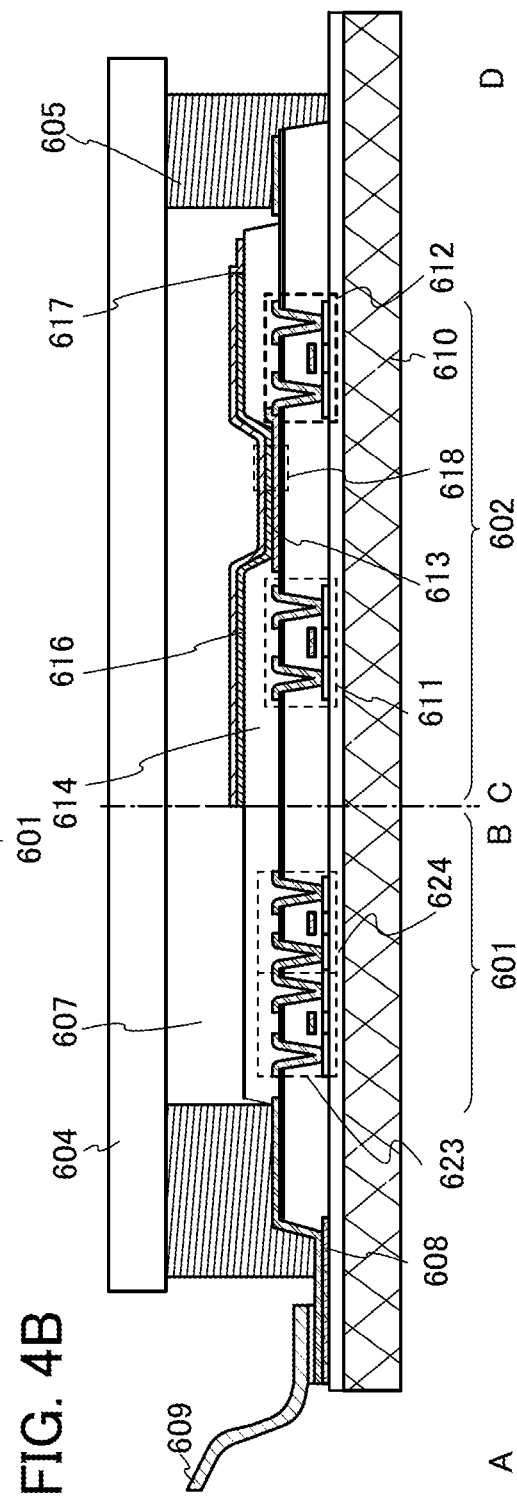

A light-emitting apparatus of one embodiment of the present invention will be described with reference to FIG. 4. Note that FIG. 4(A) is a top view illustrating the light-emitting apparatus, and FIG. 4(B) is a cross-sectional view taken along A-B and C-D in FIG. 4(A). The light-emitting apparatus includes a driver circuit portion (source line driver circuit) 601, a pixel portion 602, and a driver circuit portion (gate line driver circuit) 603, which control light emission of a light-emitting device and are illustrated with dotted lines. Furthermore, 604 denotes a sealing substrate and 605 denotes a sealant; the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting apparatus in this specification includes not only the light-emitting apparatus itself but also the state where the FPC or the PWB is attached thereto.

Next, a cross-sectional structure will be described with reference to FIG. 4(B). The driver circuit portion and the pixel portion are formed over an element substrate 610.

Here, the source line driver circuit 601, which is the driver circuit portion, and one pixel in the pixel portion 602 are illustrated.

In the source line driver circuit 601, a CMOS circuit in which an n-channel FET 623 and a p-channel FET 624 are combined is formed. The driver circuit may be formed using various circuits such as a CMOS circuit, a PMOS circuit, and an NMOS circuit. Although a driver-integrated type in which the driver circuit is formed over the substrate is described in this embodiment, the driver circuit is not necessarily integrated, and may be formed not over the substrate but outside the substrate.

The pixel portion 602 is composed of a plurality of pixels each including a switching FET 611, a current controlling FET 612, and a first electrode 613 electrically connected to a drain of the current controlling FET 612; not limited to that structure, the pixel portion may have the combination of three or more FETs and a capacitor.

There is no particular limitation on the kind and crystallinity of a semiconductor used for the FETs; either an amorphous semiconductor or a crystalline semiconductor may be used. Examples of the semiconductor used for the FETs include Group 13 semiconductors, Group 14 semiconductors, compound semiconductors, oxide semiconductors, and organic semiconductor materials. In particular, oxide semiconductors are preferably used. Examples of the oxide semiconductors include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, further preferably 3 eV or more is preferably used, in which case the off-state current of the transistors can be reduced.

Note that an insulator 614 is formed to cover an end portion of the first electrode 613. Here, the insulator 614 can be formed using a positive photosensitive acrylic resin film.

In order to improve the coverage, the insulator 614 is formed to have a curved surface with curvature at its upper end portion or lower end portion. For example, in the case where a positive photosensitive acrylic resin is used as a material of the insulator 614, only the upper end portion of the insulator 614 preferably has a curved surface with a curvature radius (0.2 µm to 3 µm). As the insulator 614, either a negative photosensitive resin or a positive photosensitive resin can be used.

An EL layer 616 and a second electrode 617 are both formed over the first electrode 613. The first electrode 613, the EL layer 616, and the second electrode 617 respectively correspond to the anode 101, the EL layer 103, and the cathode 102 in FIGS. 1(A) and 1(B), or to the first electrode 501, the EL layer 503, and the second electrode 502 in FIG. 1(C).

The EL layer 616 preferably contains an organometallic complex. The organometallic complex is preferably used as an emission center substance in the light-emitting layer.

The sealing substrate 604 is attached to the element substrate 610 with the sealant 605; thus, a light-emitting device 618 is provided in the space 607 surrounded by the element substrate 610, the sealing substrate 604, and the sealant 605. The space 607 is filled with a filler, and may be filled with an inert gas (nitrogen, argon, or the like) or the sealant 605. It is preferable that the sealing substrate have a recessed portion provided with a desiccant, in which case deterioration due to the influence of moisture can be suppressed.

An epoxy-based resin or a glass frit is preferably used as the sealant 605. These materials are desirably materials that transmit moisture or oxygen as little as possible. As the materials used for the element substrate 610 and the sealing substrate 604, a glass substrate, a quartz substrate, and a plastic substrate formed of FRP (Fiber Reinforced Plastics), PVF (polyvinyl fluoride), polyester, an acrylic resin, or the like can be used.

In this specification and the like, a transistor or a light-emitting device can be formed using a variety of substrates, for example. The type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of the glass substrate include barium borosilicate glass, aluminoborosilicate glass, and soda lime glass. Examples of the flexible substrate, the attachment film, the base material film, and the like are as follows: for example, plastic typified by polyethylene terephthalate (PET), polyethylene naphthalate (PEN), and polyether sulfone (PES). Another example is a synthetic resin such as an acrylic resin. Other examples include polytetrafluoroethylene (PTFE), polypropylene, polyester, polyvinyl fluoride, and polyvinyl chloride. Other examples include polyamide, polyimide, aramid, epoxy, an inorganic vapor deposition film, and paper. In particular, the use of a semiconductor substrate, a single crystal substrate, an SOI substrate, or the like for the manufacture of transistors enables the manufacture of small-sized transistors with a small variation in characteristics, size, shape, or the like and high current capability. A circuit including such transistors achieves lower power consumption or higher integration of the circuit.

Alternatively, a flexible substrate may be used as the substrate, and the transistor or the light-emitting device may be directly formed over the flexible substrate. Alternatively, a separation layer may be provided between the substrate and the transistor or between the substrate and the light-emitting device. After part or the whole of a semiconductor device is completed over the separation layer, the separation layer can be used for separation from the substrate and transfer to another substrate. At this time, the transistor can be transferred to even a substrate having low heat resistance or a flexible substrate. As the separation layer, a stacked structure of inorganic films of a tungsten film and a silicon oxide film, or a structure in which an organic resin film of polyimide or the like is formed over a substrate can be used, for example.

In other words, the transistor or the light-emitting device may be formed using one substrate and then transferred to and arranged over another substrate. Examples of the substrate to which the transistor or the light-emitting device is transferred include, in addition to the above-described substrates over which the transistor can be formed, a paper substrate, a cellophane substrate, an aramid film substrate, a polyimide film substrate, a stone substrate, a wood substrate, a cloth substrate (including a natural fiber (silk, cotton, and hemp), a synthetic fiber (nylon, polyurethane, and polyester), a regenerated fiber (acetate, cupro, rayon, or regenerated polyester), and the like), a leather substrate, and a rubber substrate. The use of such a substrate enables the formation of a transistor with excellent properties, the formation of a transistor with low power consumption, the manufacture of a device that is hard to break, the impartment of heat resistance, or a reduction in weight or thickness.

FIG. 5 illustrates an example of a light-emitting apparatus in which a light-emitting device exhibiting white light emission is formed and coloring layers (color filters) and the like are provided to achieve full-color display. FIG. 5(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a cathode 1029 of the light-emitting devices, a sealing substrate 1031, a sealant 1032, and the like.

In FIG. 5(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5(A), some light-emitting layers emit light that goes outside without passing through the coloring layers, while the other light-emitting layer emits light that passes through the respective coloring layers to go outside. Since light that does not pass through the coloring layers is white and light that passes through the coloring layers is red, blue, or green, an image can be represented using pixels of the four colors.

FIG. 5(B) illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 6:
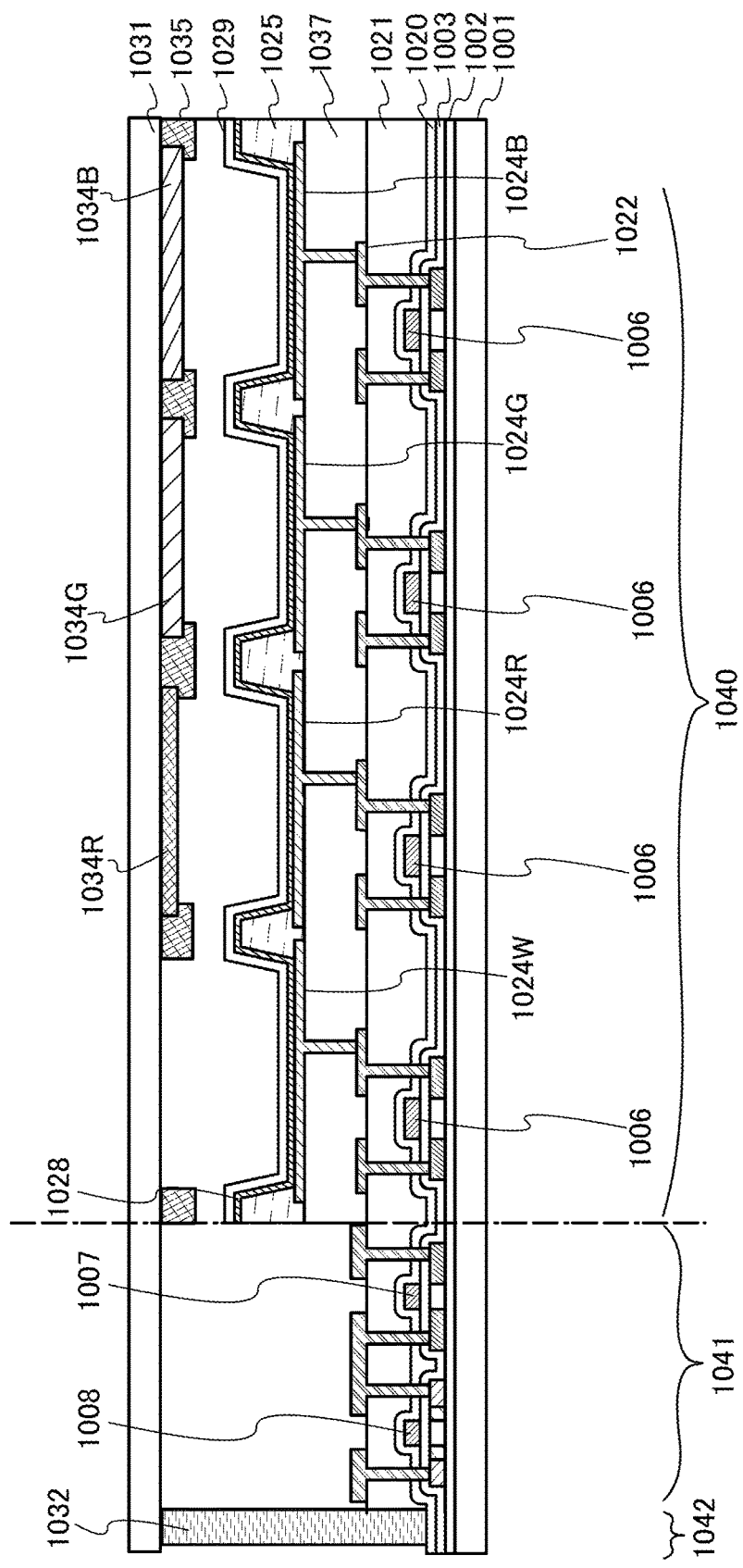
FIG. 6 is a schematic diagram of an active matrix light-emitting apparatus.

The above-described light-emitting apparatus has a structure in which light is extracted from the substrate 1001 side, over which the FETs are formed (a bottom emission structure), but may have a structure in which light is extracted from the sealing substrate 1031 side (a top emission structure). FIG. 6 is a cross-sectional view of a top-emission light-emitting apparatus. In this case, a substrate that does not transmit light can be used as the substrate 1001. The light-emitting apparatus is formed in a manner similar to that of the bottom-emission light-emitting apparatus, up to the step of forming a connection electrode that connects the FET to the anode of the light-emitting device. Then, a third interlayer insulating film 1037 is formed to cover an electrode 1022. This insulating film may have a planarization function. The third interlayer insulating film 1037 can be formed using a material similar to that of the second interlayer insulating film or using any of other various materials.

The first electrodes 1024W, 1024R, 1024G, and 1024B of the light-emitting devices serve as anodes here, but may serve as cathodes. Furthermore, in the case of the top-emission light-emitting apparatus illustrated in FIG. 6, the first electrodes are preferably reflective electrodes. The EL layer 1028 has an element structure similar to the structure of the EL layer 103 in FIGS. 1(A) and 1(B) or the EL layer 503 in FIG. 1(C), with which white light emission can be obtained.

In the case of a top emission structure as in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 that is positioned between pixels. The coloring layers (the red coloring layer 1034R, the green coloring layer 1034G, and the blue coloring layer 1034B) and the black layer may be covered with an overcoat layer. Note that a light-transmitting substrate is used as the sealing substrate 1031.

Although an example in which full-color display is performed using four colors of red, green, blue, and white is shown here, there is no particular limitation and full-color display may be performed using three colors of red, green, and blue or four colors of red, green, blue, and yellow.

Figure 7A:
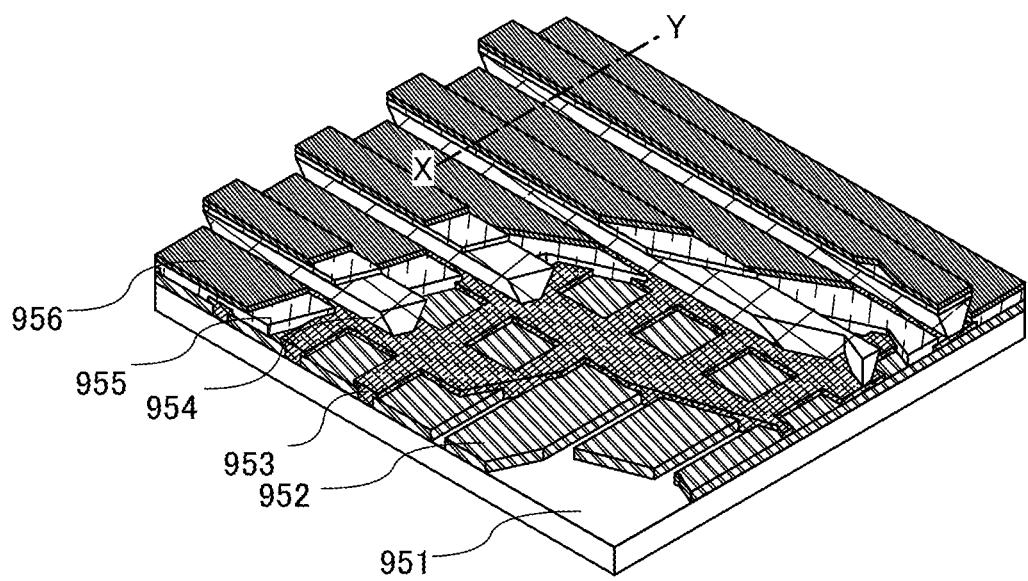
FIGS. 7A and 7B are schematic diagrams of a passive matrix light-emitting apparatus.
Figure 7B:
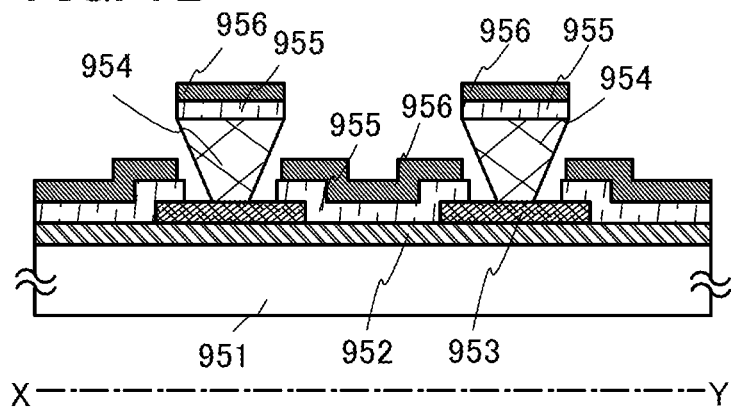

FIG. 7 illustrates a passive matrix light-emitting apparatus of one embodiment of the present invention. FIG. 7(A) is a perspective view of the light-emitting apparatus, and FIG. 7(B) is a cross-sectional view taken along X-Y in FIG. 7(A). In FIG. 7, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between one of the sidewalls and the other of the sidewalls is gradually narrowed toward the surface of the substrate. That is, a cross section in the short side direction of the partition layer 954 is a trapezoidal shape, and the lower side (the side that is in a direction similar to the plane direction of the insulating layer 953 and is in contact with the insulating layer 953) is shorter than the upper side (the side that is in a direction similar to the plane direction of the insulating layer 953 and is not in contact with the insulating layer 953). The partition layer 954 provided in this manner can prevent defects of the light-emitting device due to static electricity or the like.

Since many minute light-emitting devices arranged in a matrix can be independently controlled by the FETs formed in the pixel portion, the above-described light-emitting apparatus can be suitably used as a display device for representing an image.

<<Lighting Device>>

Figure 8A:
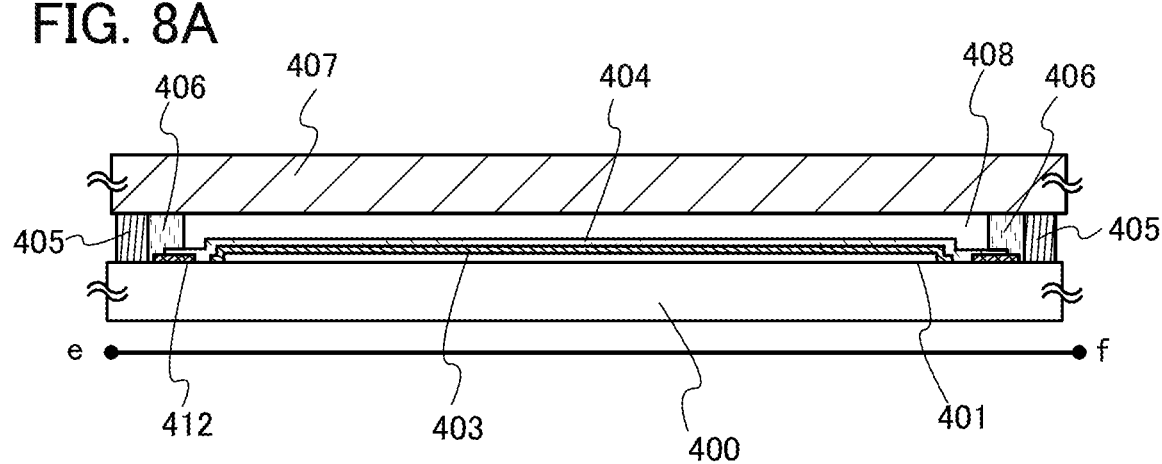
FIGS. 8A and 8B are diagrams illustrating a lighting device.
Figure 8B:
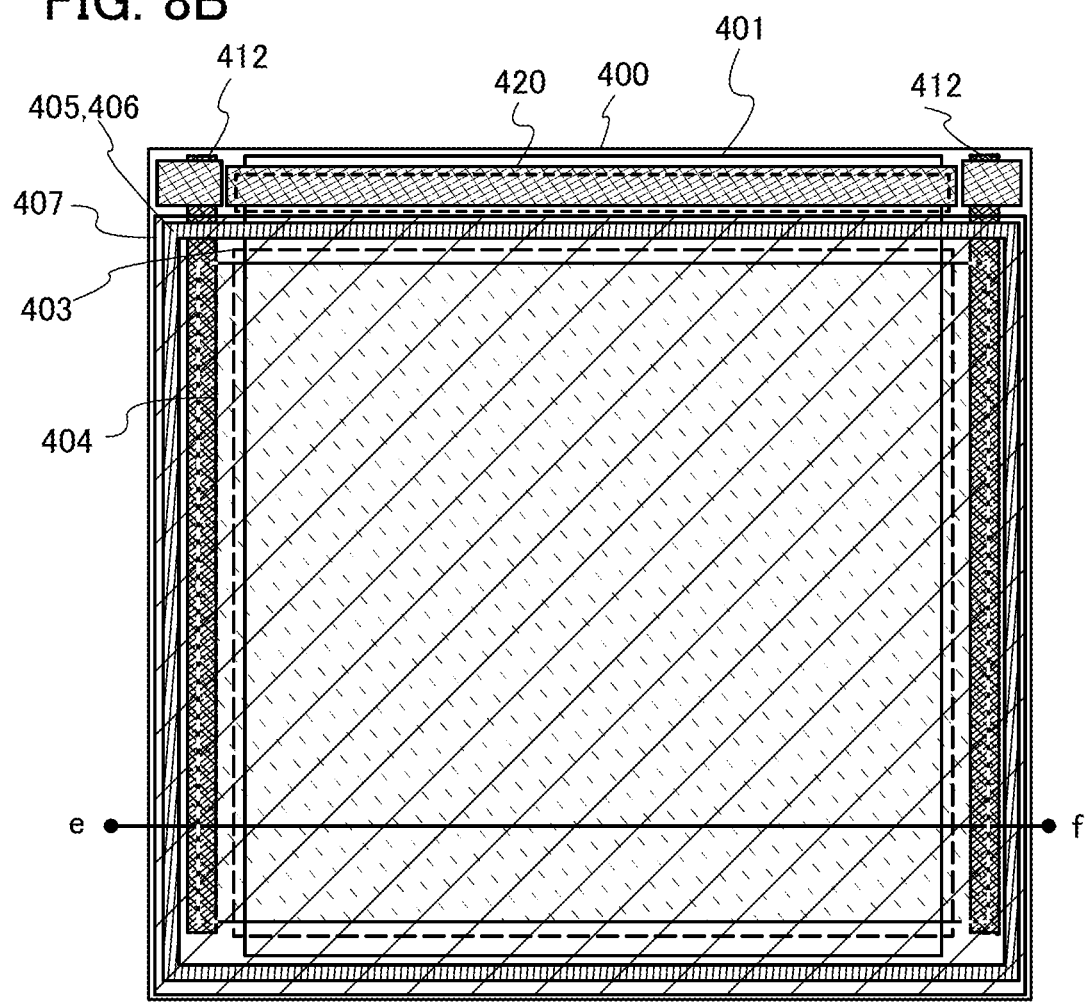

A lighting device of one embodiment of the present invention will be described with reference to FIG. 8. FIG. 8(B) is a top view of the lighting device, and FIG. 8(A) is a cross-sectional view taken along e-f in FIG. 8(B).

In the lighting device, a first electrode 401 is formed over a substrate 400 that is a support and has a light-transmitting property. The first electrode 401 corresponds to the anode 101 in FIGS. 1(A) and 1(B). When light emission is extracted from the first electrode 401 side, the first electrode 401 is formed using a material having a light-transmitting property.

A pad 412 for applying a voltage to a second electrode 404 is formed over the substrate 400.

An EL layer 403 is formed over the first electrode 401. The EL layer 403 corresponds to, for example, the EL layer 103 in FIGS. 1(A) and 1(B) or the EL layer 503 in FIG. 1(C). For these structures, refer to the corresponding description.

The second electrode 404 is formed to cover the EL layer 403. The second electrode 404 corresponds to the cathode 102 in FIGS. 1(A) and 1(B). The second electrode 404 contains a material having high reflectivity when light emission is extracted from the first electrode 401 side. The second electrode 404 is connected to the pad 412, whereby a voltage is applied.

A light-emitting device is formed with the first electrode 401, the EL layer 403, and the second electrode 404. The light-emitting device is sealed by being fixed to a sealing substrate 407 with sealants 405 and 406, whereby the lighting device is completed. Only either the sealant 405 or 406 may be provided. In addition, the inner sealant 406 (not illustrated in FIG. 8(B)) can be mixed with a desiccant, whereby moisture can be adsorbed and reliability can be improved.

When part of the pad 412 and part of the first electrode 401 are extended to the outside of the sealants 405 and 406, the extended parts can serve as external input terminals. An IC chip 420 or the like including a converter or the like may be provided over the external input terminals.

<<Electronic Device>>

Examples of an electronic device of one embodiment of the present invention will be described. Examples of the electronic device include a television device (also referred to as a television or a television receiver), a monitor for a computer or the like, a digital camera, a digital video camera, a digital photo frame, a mobile phone (also referred to as a cellular phone or a mobile phone device), a portable game machine, a portable information terminal, an audio reproducing device, and a large-sized game machine such as a pachinko machine. Specific examples of these electronic devices are shown below.

FIG. 9(A) illustrates an example of a television device. In the television device, a display portion 7103 is incorporated in a housing 7101. Here, a structure in which the housing 7101 is supported by a stand 7105 is shown. Images can be displayed by the display portion 7103, and the display portion 7103 is composed of light-emitting devices arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9(B1) is a computer, which includes a main body 7201, a housing 7202, a display portion 7203, a keyboard 7204, an external connection port 7205, a pointing device 7206, and the like. Note that this computer is manufactured by arranging light-emitting devices in a matrix and using them in the display portion 7203. The computer in FIG. 9(B1) may have a form shown in FIG. 9(B2). The computer in FIG. 9(B2) is provided with a second display portion 7210 instead of the keyboard 7204 and the pointing device 7206. The second display portion 7210 is a touch panel, and input can be performed by operating input display displayed on the second display portion 7210 with a finger or a dedicated pen. The second display portion 7210 can also display images other than the input display. The display portion 7203 may also be a touch panel. Connecting the two screens with a hinge can prevent the occurrence of troubles such as damage or breaks of the screens at the time of storing or carrying the computer.

FIGS. 9(C) and 9(D) illustrate examples of a portable information terminal. The portable information terminal is provided with a display portion 7402 incorporated in a housing 7401, operation buttons 7403, an external connection port 7404, a speaker 7405, a microphone 7406, and the like. Note that the portable information terminal includes the display portion 7402 in which light-emitting devices are arranged in a matrix.

The portable information terminals illustrated in FIGS. 9(C) and 9(D) can have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable information terminal, it is possible to determine the orientation of the portable information terminal (whether it is placed horizontally or vertically) and automatically change the screen display of the display portion 7402.

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is moving image data, the screen mode is switched to the display mode. When the signal is text data, the screen mode is switched to the input mode.

Moreover, in the input mode, when a signal detected by an optical sensor in the display portion 7402 is sensed and there is no input by touch operation of the display portion 7402 for a certain period, the screen mode may be controlled so as to be switched from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by providing a backlight that emits near-infrared light or a sensing light source that emits near-infrared light in the display portion, an image of a finger vein, a palm vein, or the like can also be taken.

Note that in the above electronic devices, the structures described in this specification can be combined and used as appropriate.

The light-emitting device of one embodiment of the present invention is preferably used for the display portion. The light-emitting device can be a light-emitting device that has high emission efficiency. In addition, the light-emitting device can be driven at low voltage. Thus, the electronic device including the light-emitting device of one embodiment of the present invention can be an electronic device that has low power consumption.

Figure 10:
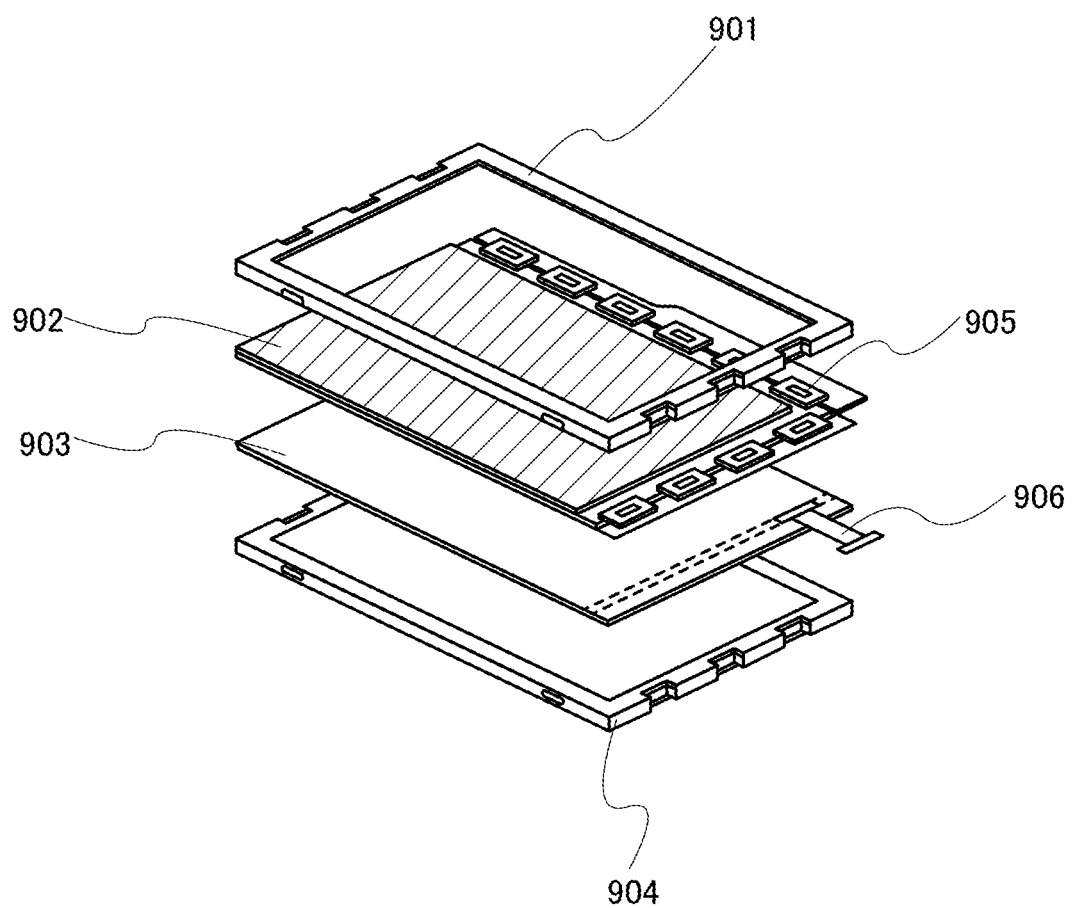
FIG. 10 is a diagram illustrating a light source device.

FIG. 10 illustrates an example of a liquid crystal display device in which a light-emitting device is used for a backlight. The liquid crystal display device illustrated in FIG. 10 includes a housing 901, a liquid crystal layer 902, a backlight unit 903, and a housing 904. The liquid crystal layer 902 is connected to a driver IC 905. The light-emitting device is used for the backlight unit 903, to which a current is supplied through a terminal 906.

As the light-emitting device, the light-emitting device of one embodiment of the present invention is preferably used. By using the light-emitting device in the backlight of the liquid crystal display device, the backlight with reduced power consumption can be obtained.

Figure 11:
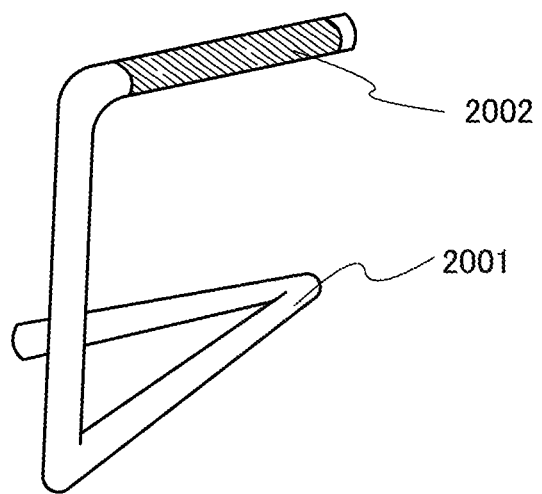
FIG. 11 is a diagram illustrating a lighting device.

FIG. 11 illustrates an example of a desk lamp of one embodiment of the present invention. The desk lamp illustrated in FIG. 11 includes a housing 2001 and a light source 2002, and a lighting device using a light-emitting device is used as the light source 2002.

Figure 12:
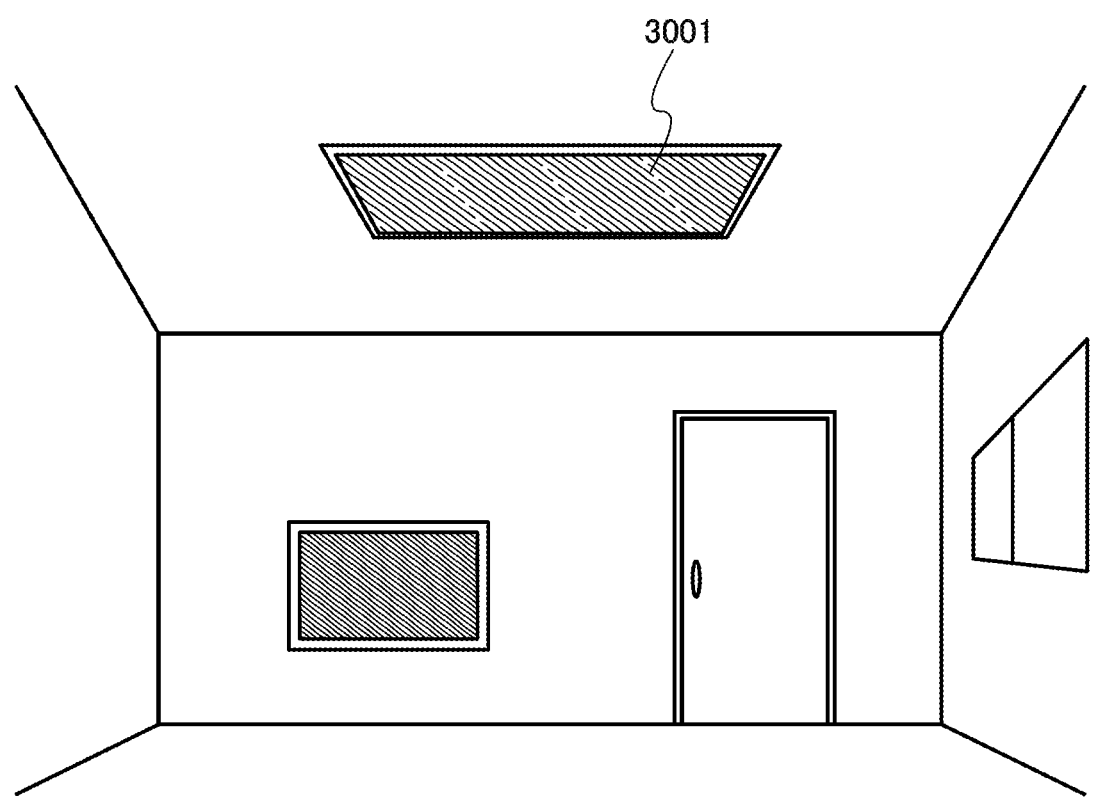
FIG. 12 is a diagram illustrating a lighting device.

FIG. 12 illustrates an example of an indoor lighting device 3001. The light-emitting device of one embodiment of the present invention is preferably used for the lighting device 3001.

Figure 13:
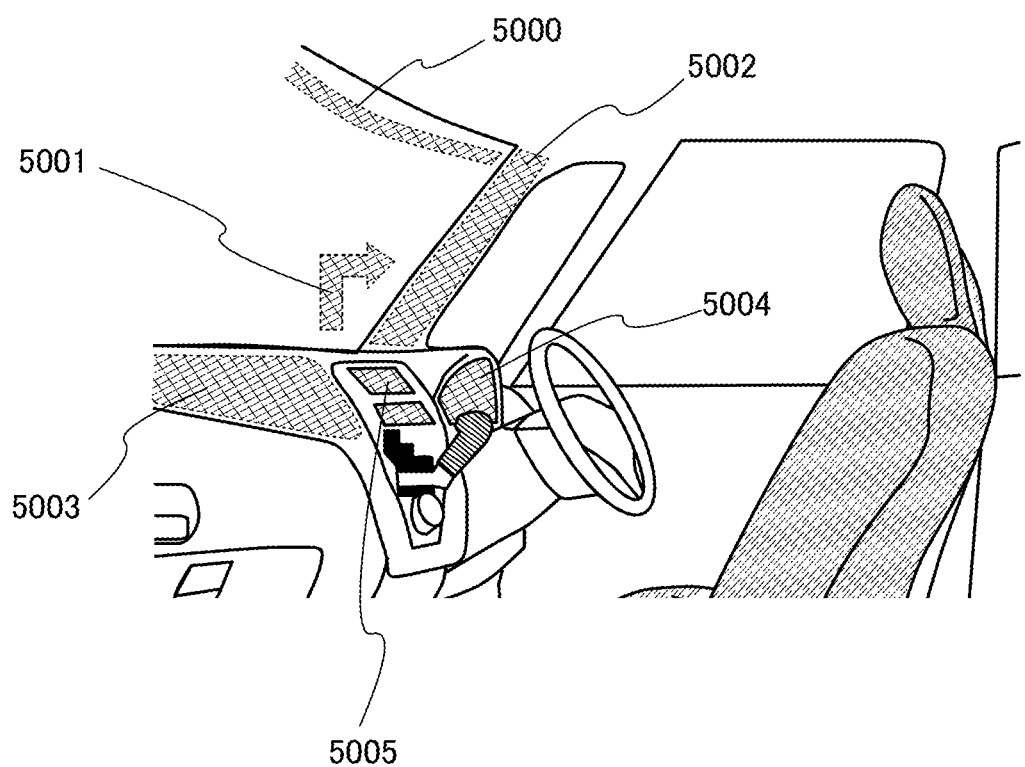
FIG. 13 is a diagram illustrating car-mounted display devices and lighting devices.

An automobile of one embodiment of the present invention is illustrated in FIG. 13. In the automobile, light-emitting devices are used for a windshield and a dashboard. A display region 5000 to a display region 5005 are display regions formed using light-emitting devices. The light-emitting devices of one embodiment of the present invention are preferably used, in which case the power consumption of the display region 5000 to the display region 5005 can be reduced; accordingly, they can be used in the automobile suitably.

The display region 5000 and the display region 5001 are display devices which are provided in the automobile windshield and use the light-emitting devices. When first electrodes and second electrodes of these light-emitting devices are formed of electrodes having light-transmitting properties, what is called see-through display devices, through which the opposite side can be seen, can be obtained. Such see-through display can be provided even in the automobile windshield without hindering the vision. In the case where a driving transistor or the like is provided, a transistor having a light-transmitting property, such as an organic transistor including an organic semiconductor material or a transistor including an oxide semiconductor, is preferably used.

The display region 5002 is a display device which is provided in a pillar portion and uses the light-emitting device. The display region 5002 can compensate for the view hindered by the pillar by displaying an image taken by an imaging unit provided in the car body. Similarly, the display region 5003 provided in the dashboard portion displays an image taken by an imaging unit provided on the outside of the automobile, so that blind areas, the view hindered by the car body, can be eliminated to improve the safety. Displaying images that compensate for the blind areas enables more natural, comfortable safety confirmation.

The display region 5004 and the display region 5005 can provide a variety of information by displaying navigation information, a speedometer, a rotation rate, a mileage, a fuel meter, a gearshift indicator, air-condition setting, and the like. The content or layout of the display can be changed based on a user's preference as appropriate. Such information can also be displayed on the display region 5000 to the display region 5003. The display region 5000 to the display region 5005 can also be used as lighting devices.

Figure 14A:
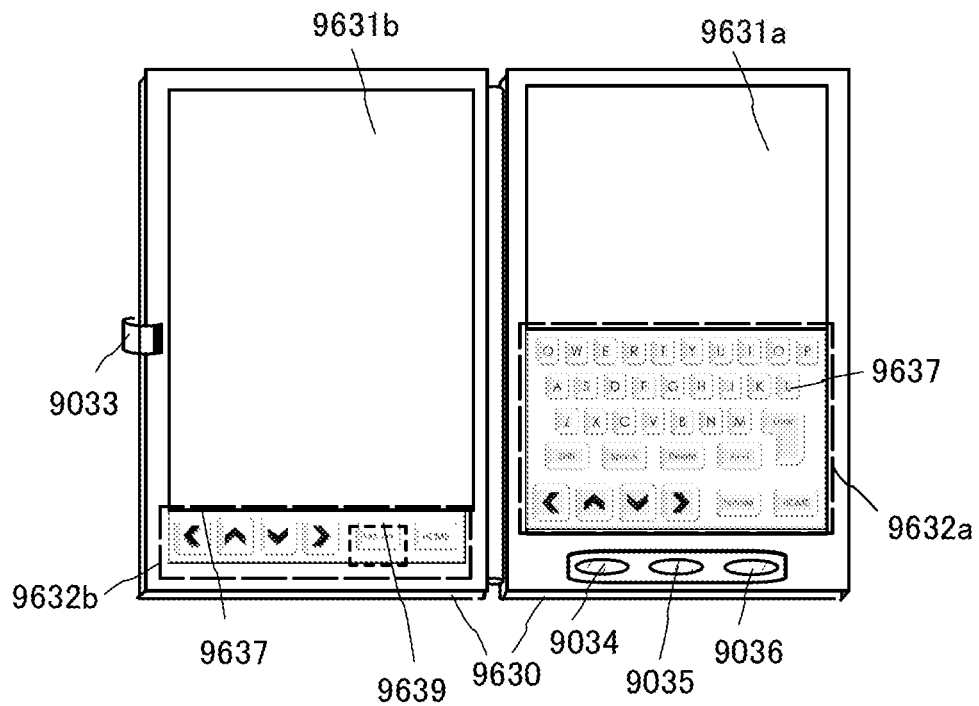
FIGS. 14A-14C are diagrams illustrating an electronic device. (C) A block diagram.
Figure 14B:
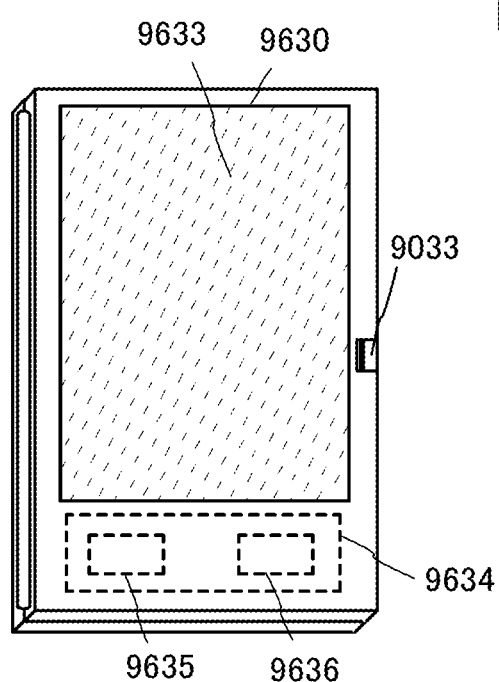

FIG. 14(A) and FIG. 14(B) illustrate an example of a double-foldable tablet terminal. FIG. 14(A) is the opened state and the tablet terminal includes a housing 9630, a display portion 9631a, a display portion 9631b, a display mode changing switch 9034, a power switch 9035, a power-saving-mode changing switch 9036, and a fastener 9033. The tablet terminal is fabricated by using a light-emitting apparatus which includes the light-emitting device of one embodiment of the present invention for one or both of the display portion 9631a and the display portion 9631b.

Part of the display portion 9631a can be a touch panel region 9632a and data can be input when a displayed operation key 9637 is touched. Note that a structure in which half of the area of the display portion 9631a has only a display function and the other half of the area has a touch panel function is illustrated as an example; however, the structure is not limited to this. The whole area in the display portion 9631a may have a touch panel function. For example, the display portion 9631a can display keyboard buttons in the whole area to be a touch panel, and the display portion 9631b can be used as a display screen.

In the display portion 9631b, as in the display portion 9631a, part of the display portion 9631b can be a touch panel region 9632b. When a finger, a stylus, or the like touches the place where a keyboard display switching button 9639 is displayed in the touch panel, keyboard buttons can be displayed on the display portion 9631b.

Touch input can also be performed on the touch panel region 9632a and the touch panel region 9632b at the same time.

The display mode changing switch 9034 can switch the display orientation between vertical display, horizontal display, and the like, and between monochrome display and color display, for example. With the power-saving-mode changing switch 9036, the luminance of display can be optimized depending on the amount of external light at the time when the tablet terminal is in use, which is detected with an optical sensor incorporated in the tablet terminal. The tablet terminal may include another detection device such as a sensor detecting inclination, e.g., a gyroscope sensor or an acceleration sensor, in addition to the optical sensor.

Although an example in which the display areas of the display portion 9631a and the display portion 9631b are the same is illustrated in FIG. 14(A), without particular limitation thereon, the size of one of the display areas may be different from the size of the other, and the display quality may also be different. For example, one may be a display panel that can display higher-definition images than the other.

FIG. 14(B) illustrates an example in the closed state in which the tablet terminal in this embodiment includes the housing 9630, a solar cell 9633, a charge and discharge control circuit 9634, a battery 9635, and a DCDC converter 9636. In FIG. 14(B), a structure including the battery 9635 and the DCDC converter 9636 is illustrated as an example of the charge and discharge control circuit 9634.

Since the tablet terminal can be folded in half, the housing 9630 can be in the closed state when the tablet terminal is not in use. Thus, the display portion 9631a and the display portion 9631b can be protected, whereby a tablet terminal with excellent durability and excellent reliability for long-term use can be provided.

The tablet terminal illustrated in FIG. 14(A) and FIG. 14(B) can also have a function of displaying various kinds of data (e.g., a still image, a moving image, and a text image), a function of displaying a calendar, a date, the time, or the like on the display portion, a touch-input function of operating or editing data displayed on the display portion by touch input, a function of controlling processing by various kinds of software (programs), and the like.

The solar cell 9633, which is attached on the surface of the tablet terminal, can supply electric power to the touch panel, the display portion, a video signal processing portion, or the like. Note that the solar cell 9633 is preferably provided on one surface or two surfaces of the housing 9630, in which case the battery 9635 can be charged efficiently.

Figure 14C:
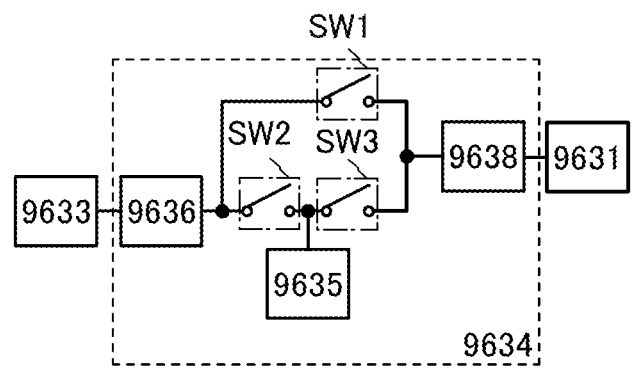

The structure and operation of the charge and discharge control circuit 9634 illustrated in FIG. 14(B) are described with reference to a block diagram illustrated in FIG. 14(C). The solar cell 9633, the battery 9635, the DCDC converter 9636, a converter 9638, switches SW1 to SW3, and the display portion 9631 are illustrated in FIG. 14(C), and the battery 9635, the DCDC converter 9636, the converter 9638, and the switches SW1 to SW3 correspond to the charge and discharge control circuit 9634 illustrated in FIG. 14(B).

First, an example of the operation in the case where electric power is generated by the solar cell 9633 with external light is described. The voltage of electric power generated by the solar cell is raised or lowered by the DCDC converter 9636 so as to be a voltage for charging the battery 9635. Then, when the electric power charged by the solar cell 9633 is used for the operation of the display portion 9631, the switch SW1 is turned on and the voltage is raised or lowered by the converter 9638 so as to be a voltage needed for the display portion 9631. When display on the display portion 9631 is not performed, SW1 may be turned off and SW2 may be turned on so that the battery 9635 is charged.

The solar cell 9633 is described as an example of a power generation means; however, the power generation means is not particularly limited, and the battery 9635 may be charged with another power generation means such as a piezoelectric element or a thermoelectric conversion element (Peltier element). A non-contact power transmission module that transmits and receives electric power wirelessly (without contact) to charge the battery or a combination with other charging means may be employed, and the power generation means is not necessarily provided.

One embodiment of the present invention is not limited to the tablet terminal having the shape illustrated in FIG. 14 as long as the above display portion 9631 is included.

Figure 15A:
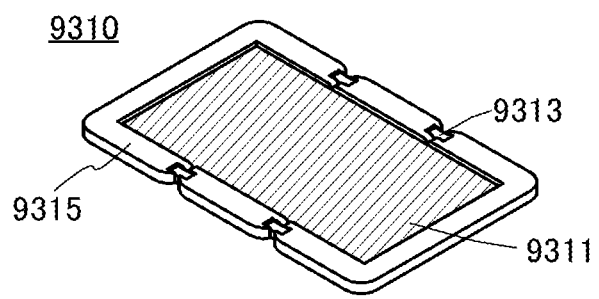
FIGS. 15A-15C are diagrams illustrating an electronic device.
Figure 15B:
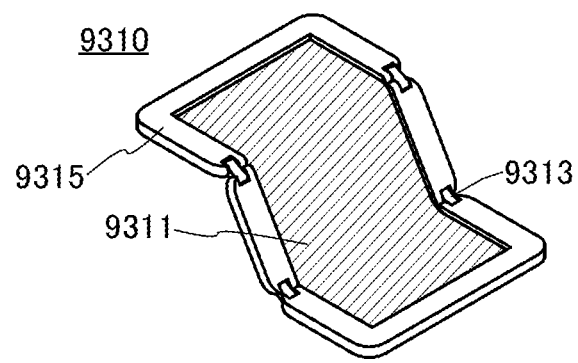
Figure 15C:
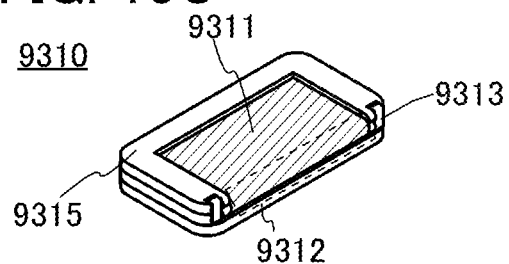

FIGS. 15(A) to 15(C) illustrate a foldable portable information terminal 9310. FIG. 15(A) illustrates the portable information terminal 9310 in an opened state. FIG. 15(B) illustrates the portable information terminal 9310 in a state in the middle of change from one of an opened state and a folded state to the other. FIG. 15(C) illustrates the portable information terminal 9310 in a folded state. The portable information terminal 9310 has excellent portability when in a folded state. The portable information terminal 9310 has excellent browsability when in an opened state because of its seamless large display region.

A display panel 9311 is supported by three housings 9315 joined together by hinges 9313. The display panel 9311 may be a touch panel (an input/output device) including a touch sensor (an input device). By bending the display panel 9311 at a portion between two housings 9315 with the use of the hinges 9313, the portable information terminal 9310 can be reversibly changed in shape from an opened state to a folded state. A light-emitting apparatus of one embodiment of the present invention can be used for the display panel 9311. A display region 9312 in the display panel 9311 is a display region that is positioned at a side surface of the portable information terminal 9310 in a folded state. In the display region 9312, information icons, file shortcuts of frequently used applications or programs, and the like can be displayed, and confirmation of information and start of application can be smoothly performed.

The organic compound of one embodiment of the present invention can be used for an electronic device such as an organic thin film solar cell. Specifically, the organic compound can be used in a carrier-transport layer or a carrier-injection layer because the organic compound has a carrier-transport property. In addition, a mixed film of the organic compound and an acceptor substance can be used as a charge-generation layer. The organic compound is photoexcited and hence can be used for a power generation layer.

Example 1

Synthesis Example 1

In this synthesis example, a method for synthesizing N,N'-bis(benzo[b]naphtho[1,2-d]furan-9-yl)-N,N'-diphenylnaphtho[2,3-b;6,7-b"]bisbenzofuran-3,10-diamine (abbreviation: 3,10BnfA2Nbf(IV)-02), which is an organic compound of one embodiment of the present invention, is described in detail. The structural formula of 3,10BnfA2Nbf(IV)-02 is shown below.

[Chemical Formula 64]

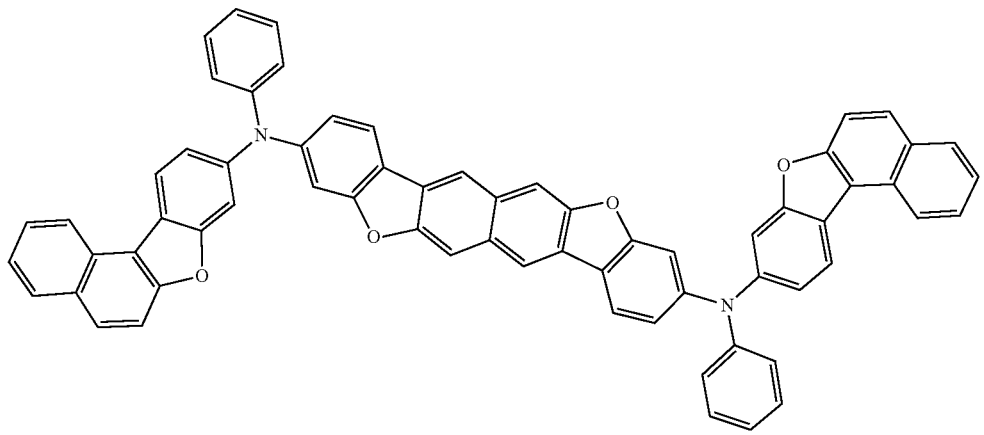

Step 1: Synthesis of 3,7-bis(4-chloro-2-fluorophenyl)-2,6-dimethoxynaphthalene Into a 500-mL three-neck flask were put 11 g (24 mmol) of 3,7-diiodo-2,6-dimethoxynaphthalene, 14 g (78 mmol) of 4-chloro-2-fluorophenylboronic acid, 22 g (0.16 mol) of potassium carbonate, and 0.74 g (2.4 mmol) of tris(2-methylphenyl)phosphine. To this mixture was added 120 mL of toluene. This mixture was degassed by being stirred while the pressure was reduced. To this mixture was added 0.11 g (0.49 mmol) of palladium(II) acetate, and the resulting mixture was stirred for 50.5 hours at 110° C. under a nitrogen stream.

After the stirring, toluene was added to the mixture, and the resulting mixture was suction-filtered through Florisil (Wako Pure Chemical Industries, Ltd., Catalog No. 540-00135), Celite (Wako Pure Chemical Industries, Ltd., Catalog No. 531-16855), and alumina to obtain a filtrate. The filtrate was concentrated to obtain a solid.

The obtained solid was purified by silica gel column chromatography (developing solvent: toluene:hexane=1:1). The obtained solid was recrystallized with ethyl acetate, and 5.7 g of a white solid was obtained in a yield of 53%. A synthesis scheme of Step 1 is shown below.

[Chemical Formula 65]

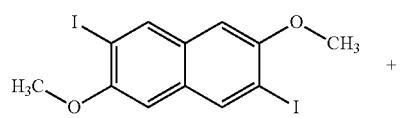

Step 2: Synthesis of 3,7-bis(4-chloro-2-fluorophenyl)-2,6-dihydroxynaphthalene Into a 200-mL three-neck flask was put 5.7 g (13 mmol) of 3,7-bis(4-chloro-2-fluorophenyl)-2,6-dimethoxynaphthalene, and the air in the flask was replaced with nitrogen. Into the flask was added 32 mL of dichloromethane. To the solution were dripped 28 mL (28 mmol) of boron tribromide (approximately 1.0 mol/L dichloromethane solution) and 20 mL of dichloromethane. After the dripping, the solution was stirred at room temperature all night under a nitrogen stream.

After the stirring, approximately 20 mL of water was added to this solution under cooling with ice, and the solution was stirred. After the stirring, an organic layer and an aqueous layer were separated from each other, and the aqueous layer was subjected to extraction with dichloromethane and ethyl acetate. The extracted solution and the organic layer were combined and washed with saturated saline and a saturated aqueous solution of sodium hydrogen carbonate. Moisture in the organic layer was adsorbed by magnesium sulfate, and after drying, the mixture was subjected to gravity filtration. The obtained filtrate was concentrated and 5.4 g of a white solid was obtained. A synthesis scheme of Step 2 is shown below.

[Chemical Formula 66]

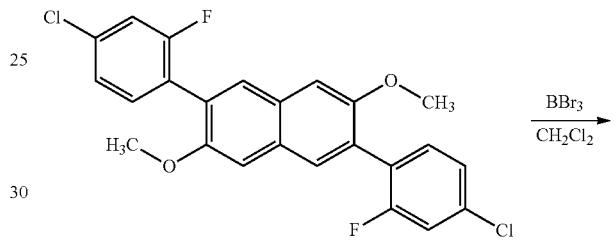

Step 3: Synthesis of 3,10-dichloronaphtho[2,3-b;6,7-b']bisbenzofuran

Into a 200-mL three-neck flask were put 5.4 g (13 mmol) of 3,7-bis(4-chloro-2-fluorophenyl)-2,6-dihydroxynaphthalene and 7.1 g (52 mmol) of potassium carbonate. To this mixture was added 130 mL of N-methyl-2-pyrrolidone, and the mixture was degassed by being stirred while the pressure was reduced. After the degassing, this mixture was stirred under a nitrogen stream at 120° C. for 7 hours. After the stirring, water was added to the mixture, and the precipitated solid was collected by filtration. This solid was washed with water and ethanol. Ethanol was added to the washed solid; after heating and stirring, filtration was performed and a solid was obtained. Ethyl acetate was added to the obtained solid; after heating and stirring, filtration was performed and 4.5 g of a pale yellow solid was obtained in a yield of 92%. A synthesis scheme of Step 3 is shown below.

[Chemical Formula 67]

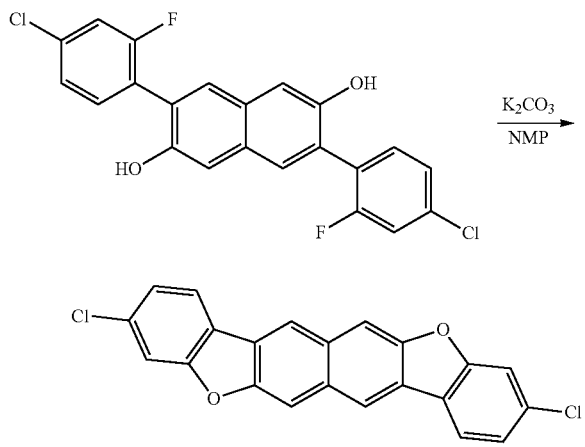

(54 µmol) of bis(dibenzylideneacetone)palladium(0), and the mixture was stirred under a nitrogen stream at 150° C. for 21 hours.

After the stirring, this mixture was filtered, and a solid was obtained. The obtained solid was washed with water and ethanol. This solid was purified by silica gel column chromatography (developing solvent: toluene) and a solid was obtained. The obtained solid was recrystallized with toluene twice, so that 1.9 g of a yellow solid was obtained in a yield of 74%.

By a train sublimation method, 1.2 g of the obtained solid was sublimated and purified. Heating was performed at 390° C. under conditions where the pressure was $2.4 \times 10^{-2}$ Pa and the flow rate of argon was 0 mL/min. After the sublimation purification, 0.6 g of a yellow solid was obtained in a collection rate of 45%. The synthesis scheme of Step 4 is shown below.

[Chemical Formula 68]

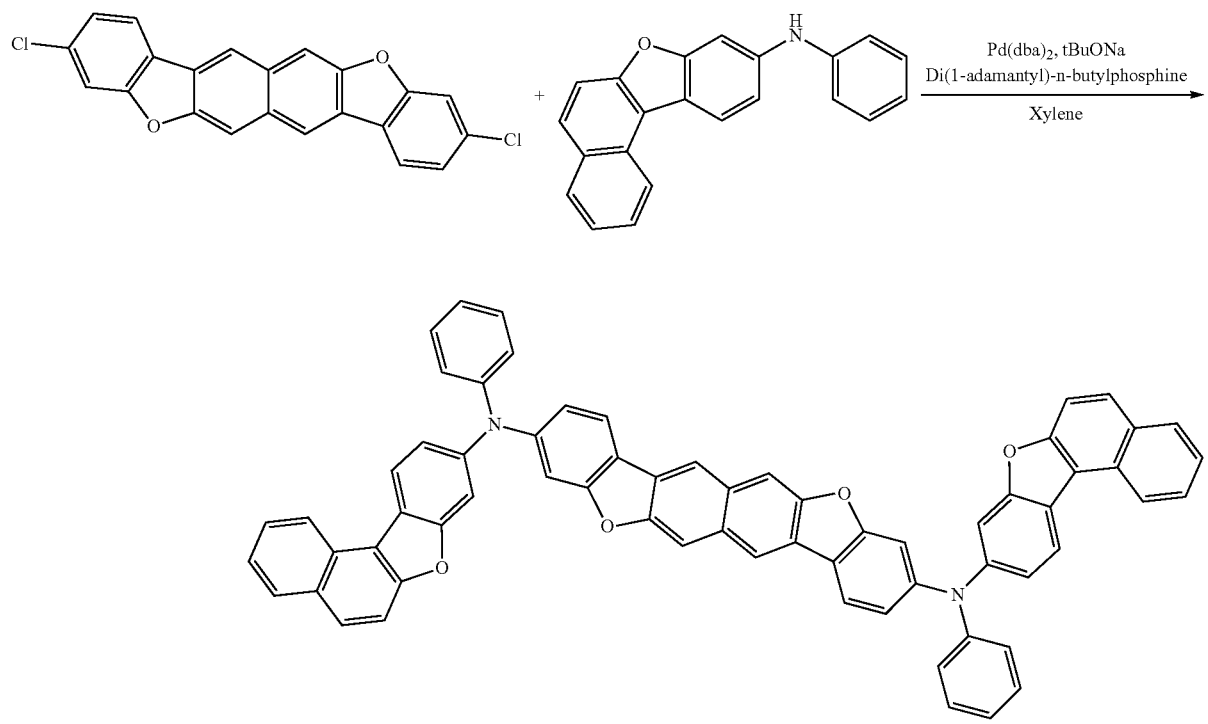

Step 4: Synthesis of N,N'-bis(benzo[b]naphtho[1,2-d]furan-9-yl)-N,N'-diphenylnaphtho[2,3-b; 6,7-b"]bisbenzofuran-3,10-diamine (abbreviation: 3,10BnfA2Nbf(IV)-02)

Figure 16A:
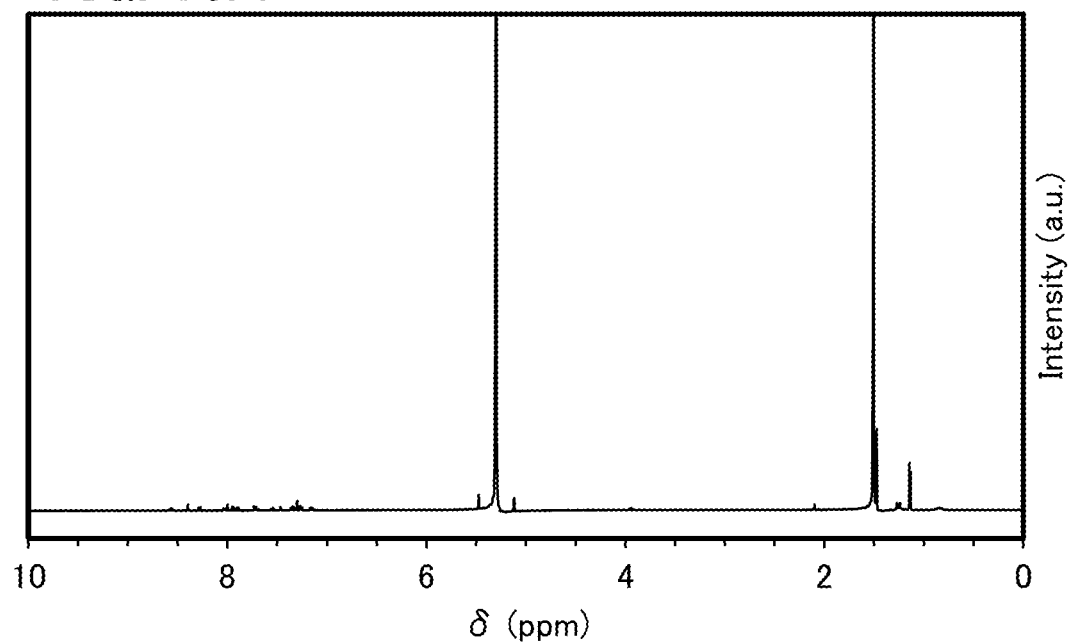
FIGS. 16A and 16B are $^1$H NMR spectra of 3,10BnfA2Nbf(IV)-02.
Figure 16B:
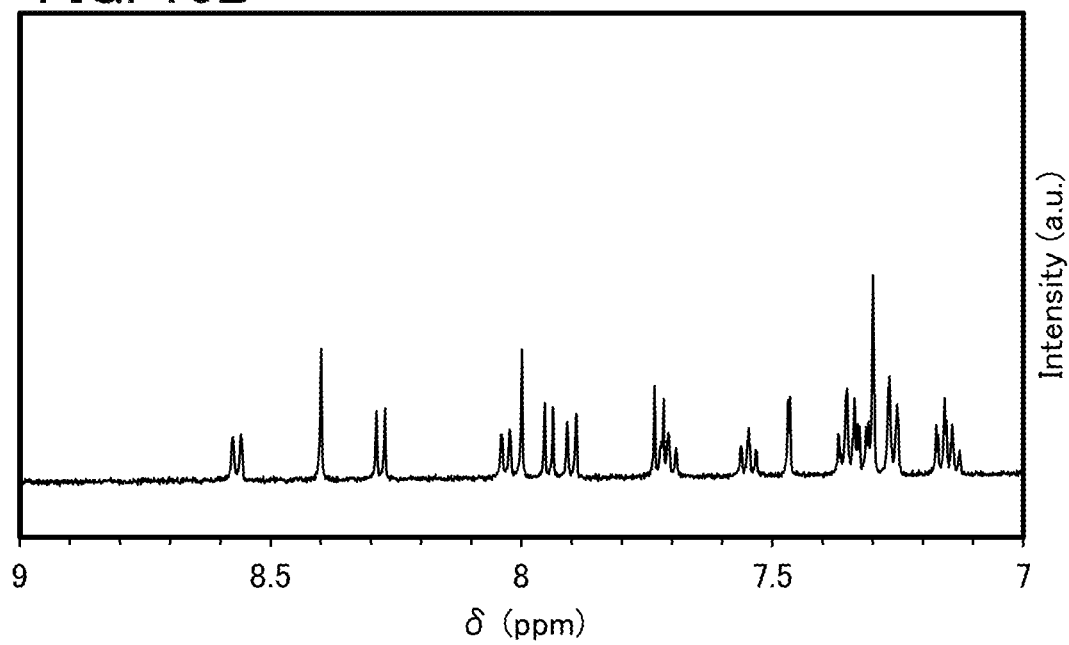

Into a 200-mL three-neck flask were put 1.0 g (2.7 mmol) of 3,10-dichloronaphtho[2,3-b;6,7-b']bisbenzofuran, 2.1 g (6.8 mmol) of N-phenylbenzo[b]naphtho[1,2-d]furan-9-amine, 97 mg (0.27 mmol) of di(1-adamantyl)-n-butylphosphine, 1.6 g (16 mmol) of sodium tert-butoxide, and 30 mL of xylene. This mixture was degassed by being stirred while the pressure was reduced. To this mixture was added 31 mg FIG. 16 shows $^1$H NMR data of the obtained solid, whose numerical data is given below. The data indicates that 3,10BnfA2Nbf(IV)-02, which is an organic compound of one embodiment of the present invention, was obtained in this synthesis example.

$^1$H NMR (CD$_2$Cl$_2$, 500 MHz): δ=7.13-7.18 (m, 4H), 7.25-7.37 (m, 12H), 7.47 (d, J1=1.5 Hz, 2H), 7.55 (t, J1=8.5 Hz, 2H), 7.69-7.74 (m, 4H), 7.90 (d, J1=9.0 Hz, 2H), 7.95 (d, J1=8.5 Hz, 2H), 8.00 (s, 2H), 8.04 (d, J1=8.0 Hz, 2H), 8.29 (d, J1=9.0 Hz, 2H), 8.40 (s, 2H), 8.57 (d, J1=8.0 Hz, 2H).

Figure 17:
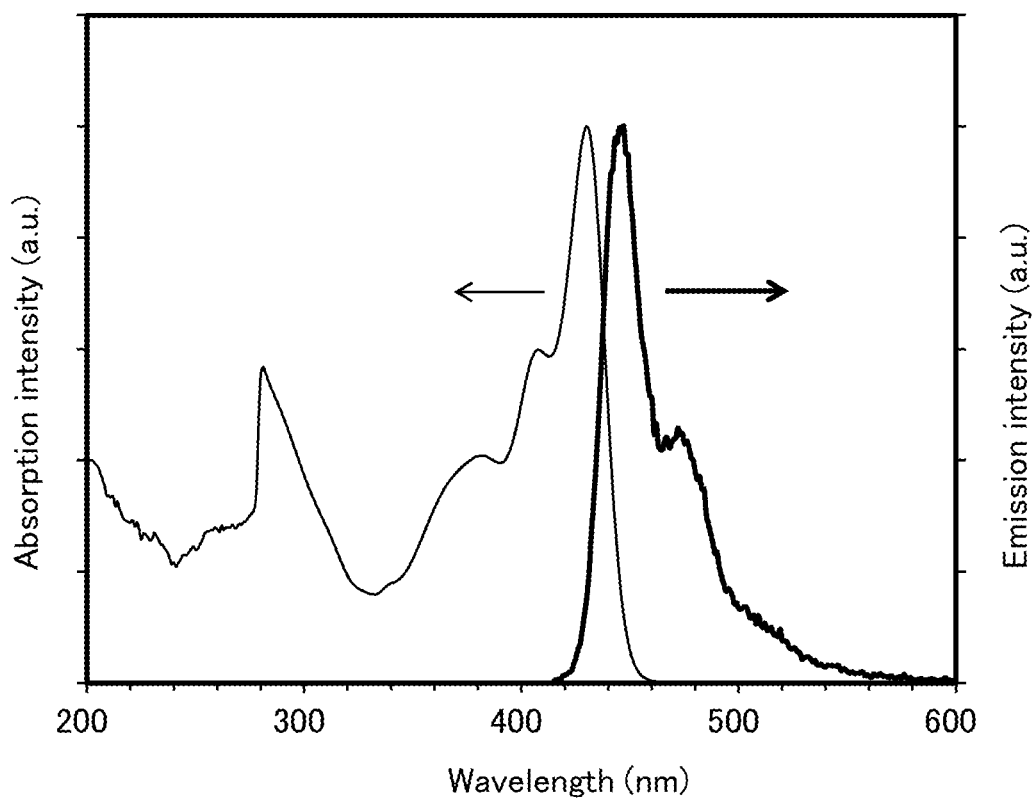
FIG. 17 is an absorption spectrum and an emission spectrum of 3,10BnfA2Nbf(IV)-02 in a toluene solution.
Figure 18:
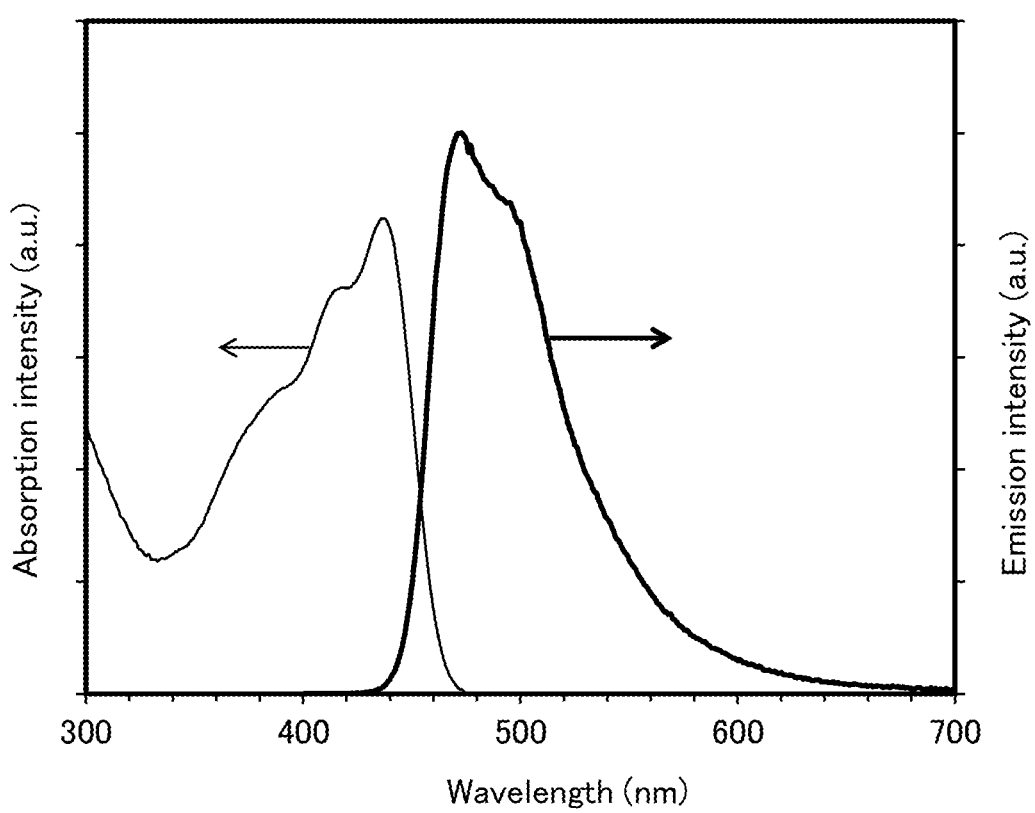
FIG. 18 is an absorption spectrum and an emission spectrum of 3,10BnfA2Nbf(IV)-02 in a thin film state.

Next, FIG. 17 shows the measurement results of the absorption spectrum and the emission spectrum of 3,10BnfA2Nbf(IV)-02 in a toluene solution. FIG. 18 shows the absorption spectrum and the emission spectrum of a thin film of 3,10BnfA2Nbf(IV)-02. The solid thin film was fabricated over a quartz substrate by a vacuum evaporation method. The absorption spectrum of the toluene solution was measured with an ultraviolet-visible light spectrophotometer (V550, manufactured by JASCO Corporation), and the spectrum from which the measured spectrum of toluene alone put in a quartz cell was subtracted was shown. The absorption spectrum of the thin film was measured with a spectrophotometer (U4100 Spectrophotometer, manufactured by Hitachi High-Technologies Corporation). The emission spectrum of the thin film was measured with a fluorescence spectrophotometer (FS920, manufactured by Hamamatsu Photonics K.K.). The emission spectrum and emission quantum yield in the solution were measured using an absolute PL quantum yield measurement system (Quantaurus-QY, manufactured by Hamamatsu Photonics K. K.).

As shown in FIG. 17, 3,10BnfA2Nbf(IV)-02 in the toluene solution has absorption peaks at 430 nm, 408 nm, and 382 nm, and emission wavelength peaks at 446 nm and 472 nm (excitation wavelength: 405 nm). As shown in FIG. 18, the thin film of 3,10BnfA2Nbf(IV)-02 has absorption peaks at 436 nm, 416 nm, 389 nm, 285 nm, and 257 nm, and emission wavelength peaks at 473 nm and 495 nm (excitation wavelength: 375 nm). These results indicate that 3,10BnfA2Nbf(IV)-02 emits blue light and can be used as a host for a light-emitting substance or a substance that emits fluorescence in the visible region.

Furthermore, the measured emission quantum yield in the toluene solution was as high as 96%, which indicates that 3,10BnfA2Nbf(IV)-02 is suitable as a light-emitting material.

Next, 3,10BnfA2Nbf(IV)-02 obtained in this example was analyzed by liquid chromatography mass spectrometry (abbreviation: LC/MS analysis).

In the LC/MS analysis, liquid chromatography (LC) separation was performed with Ultimate 3000 produced by Thermo Fisher Scientific K.K., and the mass analysis (MS analysis) was performed with Q Exactive produced by Thermo Fisher Scientific K.K.

In the LC separation, a given column was used at a column temperature of 40° C., and solution sending was performed under the conditions where an appropriate solvent was selected, the sample was prepared by dissolving 3,10BnfA2Nbf(IV)-02 in an organic solvent at a given concentration, and the injection amount was 5.0 µL.

$MS^2$ measurement of m/z=922.28, which is an ion derived from 3,10BnfA2Nbf(IV)-02, was performed by a parallel reaction monitoring (PRM) method. For setting of the PRM, the mass range of a target ion was set to m/z=922.28±2.0 (isolation window=4) and detection was performed in a positive mode. The measurement was performed with energy NCE (Normalized Collision Energy) for accelerating a target ion in a collision cell set to 60. The obtained MS spectrum is shown in FIG. 19.

Figure 19:
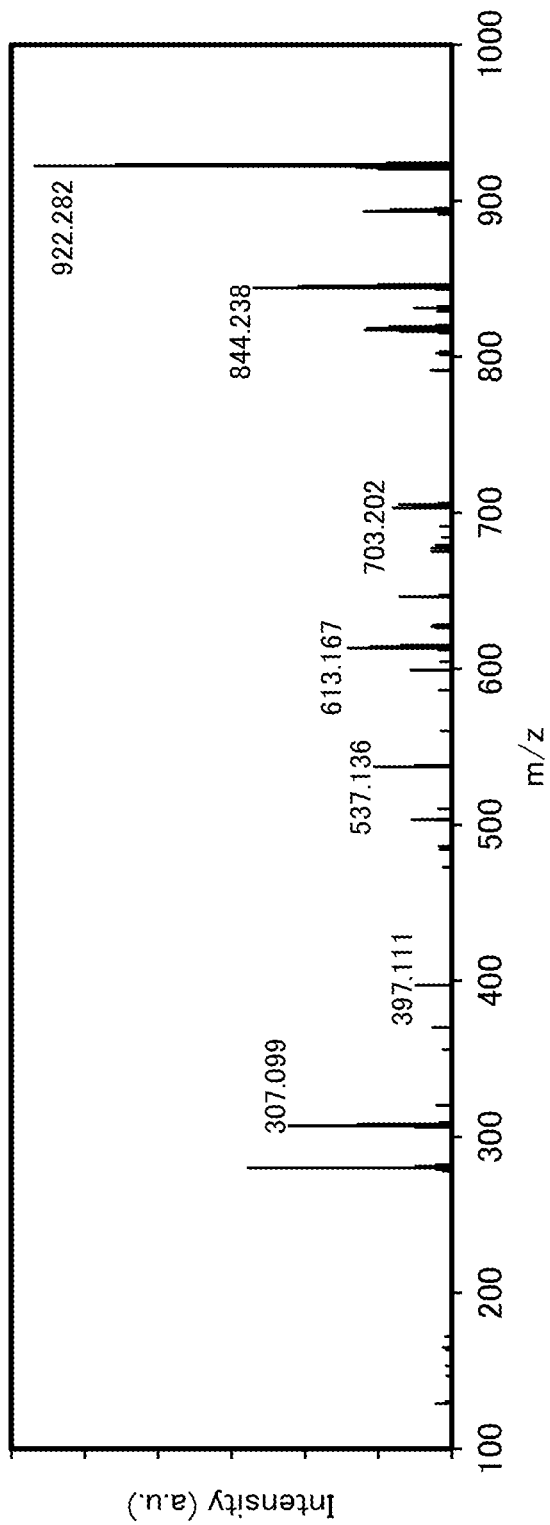
FIG. 19 is an MS spectrum of 3,10BnfA2Nbf(IV)-02.

The results in FIG. 19 show that product ions of 3,10BnfA2Nbf(IV)-02 are mainly detected around m/z=844, 703, 613, 537, 397, and 307. Note that the results in the figure are characteristic results derived from 3,10BnfA2Nbf(IV)-02 and therefore can be regarded as important data for identifying 3,10BnfA2Nbf(IV)-02 contained in a mixture.

Note that the product ion around m/z=844 is presumed to be a cation in the state where a phenyl group was eliminated from 3,10BnfA2Nbf(IV)-02, which suggests that 3,10BnfA2Nbf(IV)-02 includes a phenyl group.

Note that the product ion around m/z=703 is presumed to be a cation in the state where a benzo[b]naphtho[1,2-d]furanyl group was eliminated from 3,10BnfA2Nbf(IV)-02, which suggests that 3,10BnfA2Nbf(IV)-02 includes a benzo[b]naphtho[1,2-d]furanyl group.

Note that the product ion around m/z=613 is presumed to be a cation in the state where an N-(benzo[b]naphtho[1,2-d]furan-9-yl)-N-phenylamino group was eliminated from 3,10BnfA2Nbf(IV)-02, which suggests that 3,10BnfA2Nbf(IV)-02 includes an N-(benzo[b]naphtho[1,2-d]furan-9-yl)-N-phenylamino group.

Example 2

Synthesis Example 2

In this synthesis example, a method for synthesizing N,N'-bis(benzo[b]naphtho[2,1-d]furan-9-yl)-N,N'-(diphenyl)naphtho[2,3-b;6,7-b"]bisbenzofuran-3,10-diamine (abbreviation: 3,10aBnfA2Nbf(IV)-02), which is an organic compound of one embodiment of the present invention, is described in detail. The structural formula of 3,10aBnfA2Nbf(IV)-02 is shown below.

[Chemical Formula 69]

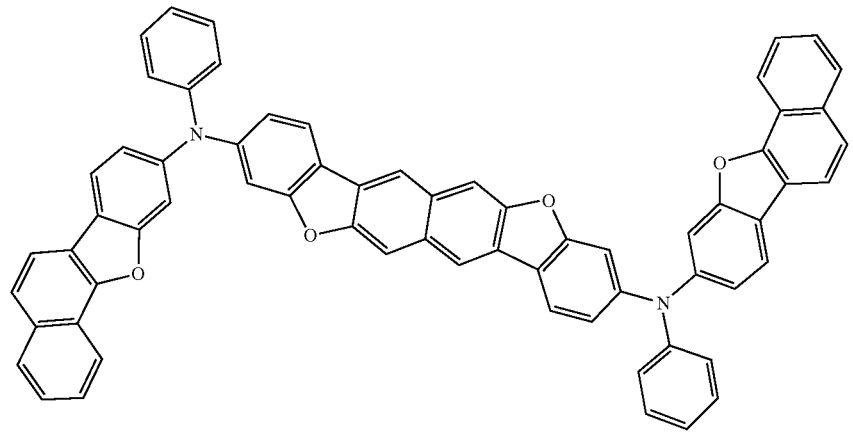

Step 1: Synthesis of 3,7-bis(4-chloro-2-fluorophenyl)-2,6-dimethoxynaphthalene The synthesis was performed in a manner similar to that of Step 1 in Synthesis example 1 of Example 1.

Step 2: Synthesis of 3,7-bis(4-chloro-2-fluorophenyl)-2,6-dihydroxynaphthalene The synthesis was performed in a manner similar to that of Step 2 in Synthesis example 1 of Example 1.

Step 3: Synthesis of 3,10-dichloronaphtho[2,3-b;6,7-b']bisbenzofuran

The synthesis was performed in a manner similar to that of Step 3 in Synthesis example 1 of Example 1.

Step 4: Synthesis of N,N'-bis(benzo[b]naphtho[2,1-d]furan-9-yl)-N,N'-diphenylnaphtho[2,3-b;6,7-b"]bisbenzofuran-3,10-diamine (abbreviation: 3,10aBnfA2Nbf(IV)-02)

Into a 200-mL three-neck flask were put 0.84 g (2.2 mmol) of 3,10-dichloronaphtho[2,3-b;6,7-b']bisbenzofuran, 1.7 g (5.3 mmol) of N-phenylbenzo[b]naphtho[2,1-d]furan-9-amine, 80 mg (0.22 mmol) of di(1-adamantyl)-n-butylphosphine, and 1.3 g (13 mmol) of sodium tert-butoxide. To this mixture was added 25 mL of xylene. This mixture was degassed by being stirred while the pressure was reduced. To this mixture was added 25 mg (44 µmol) of bis(dibenzylideneacetone)palladium(0), and stirring was performed under a nitrogen stream at 150° C. for 15 hours.

After the stirring, the mixture was filtered, whereby a solid was collected. The collected solid was washed with ethanol and water. The obtained solid was purified by silica gel column chromatography (developing solvent: toluene) and a solid was obtained.

The obtained solid was recrystallized with toluene twice, so that 1.6 g of a yellow solid was obtained in a yield of 79%. By a train sublimation method, 1.2 g of the obtained solid was sublimated and purified. The heating was performed at 400° C. under the conditions where the pressure was $2.4\times10^{-2}$ Pa and the flow rate of argon was 0 mL/min. After the sublimation purification, 0.95 g of a yellow solid was obtained in a collection rate of 81%. The synthesis scheme of Step 4 is shown below.

[Chemical Formula 70]

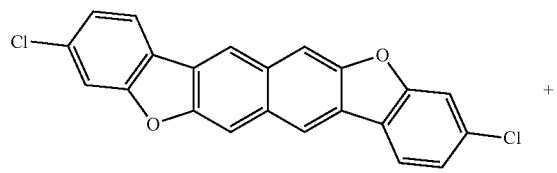

+

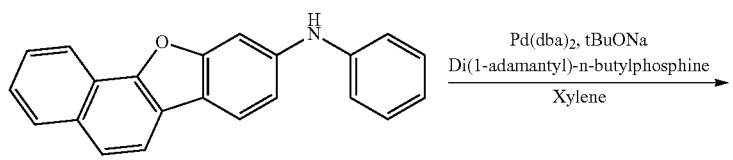

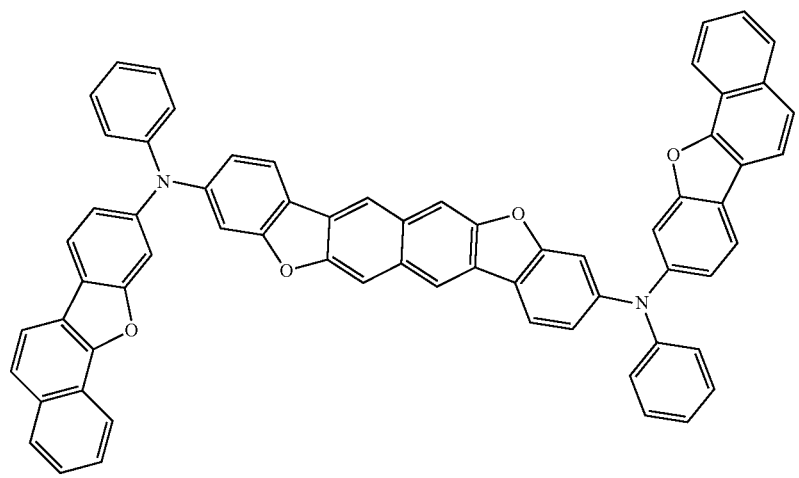

Figure 20A:
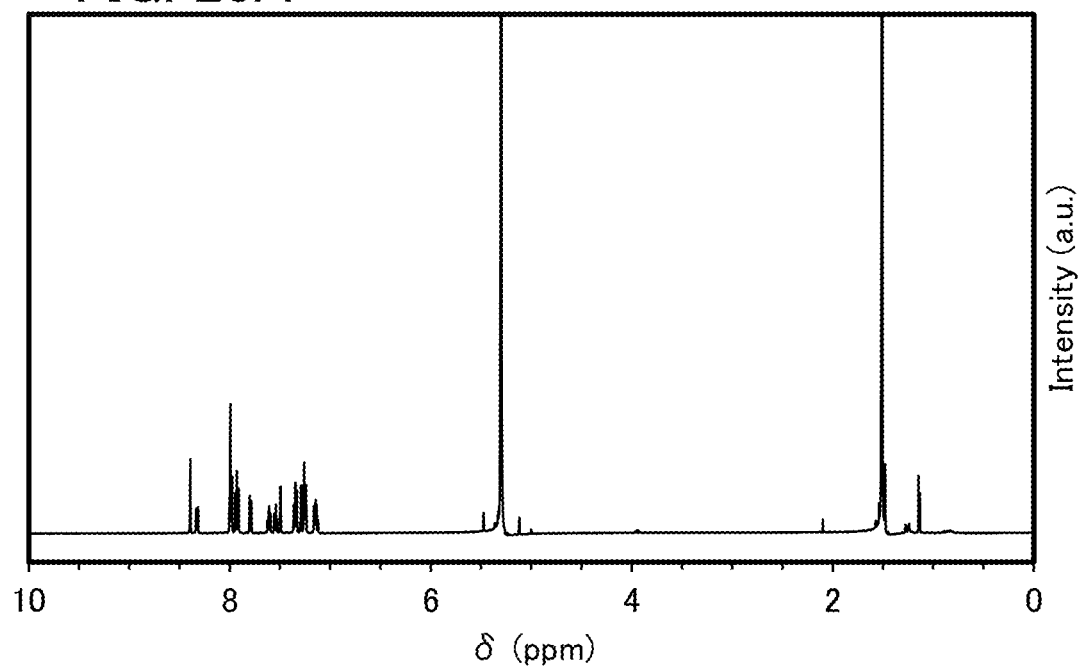
FIGS. 20A and 20B are 1H NMR spectra of 3,10aBnfA2Nbf(IV)-02.
Figure 20B:
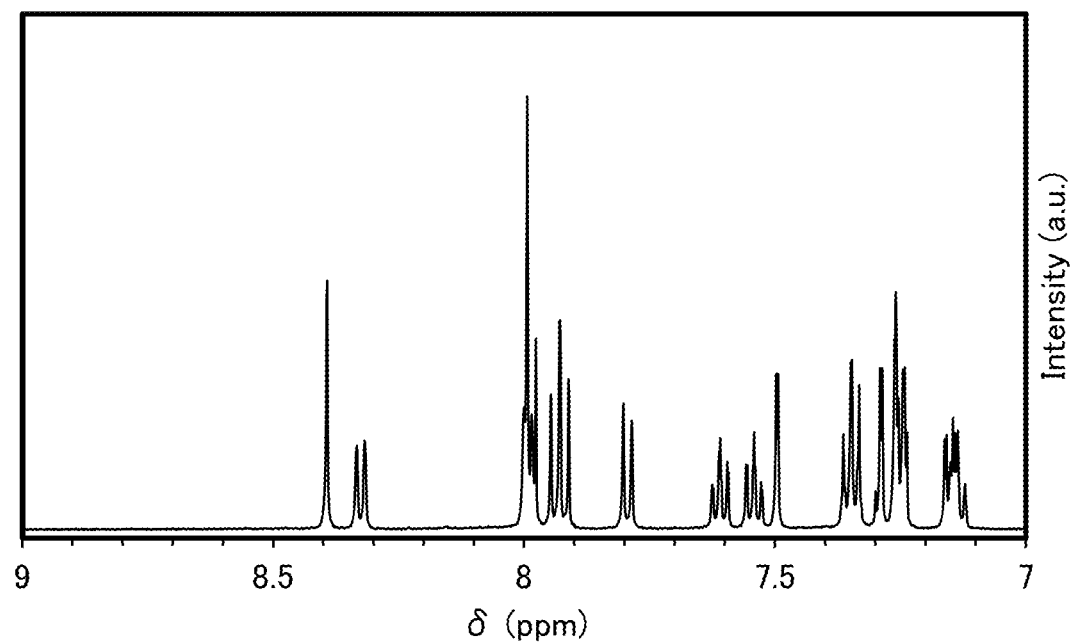

FIG. 20 shows ¹H NMR data of the obtained solid, whose numerical data is given below. The data indicates that 3,10aBnfA2Nbf(IV)-02, which is an organic compound of one embodiment of the present invention, was obtained in this synthesis example.

¹H NMR (CD$_2$Cl$_2$, 500 MHz): δ=7.14-7.19 (m, 4H), 7.26-7.39 (m, 12H), 7.52 (d, J1=1.5 Hz, 2H), 7.57 (t, J1=8.0 Hz, 2H), 7.63 (t, J1=8.0 Hz, 2H), 7.82 (d, J1=8.5 Hz, 2H), 7.93-8.03 (m, 10H), 8.35 (d, J1=8.0 Hz, 2H), 8.42 (s, 2H).

Figure 21:
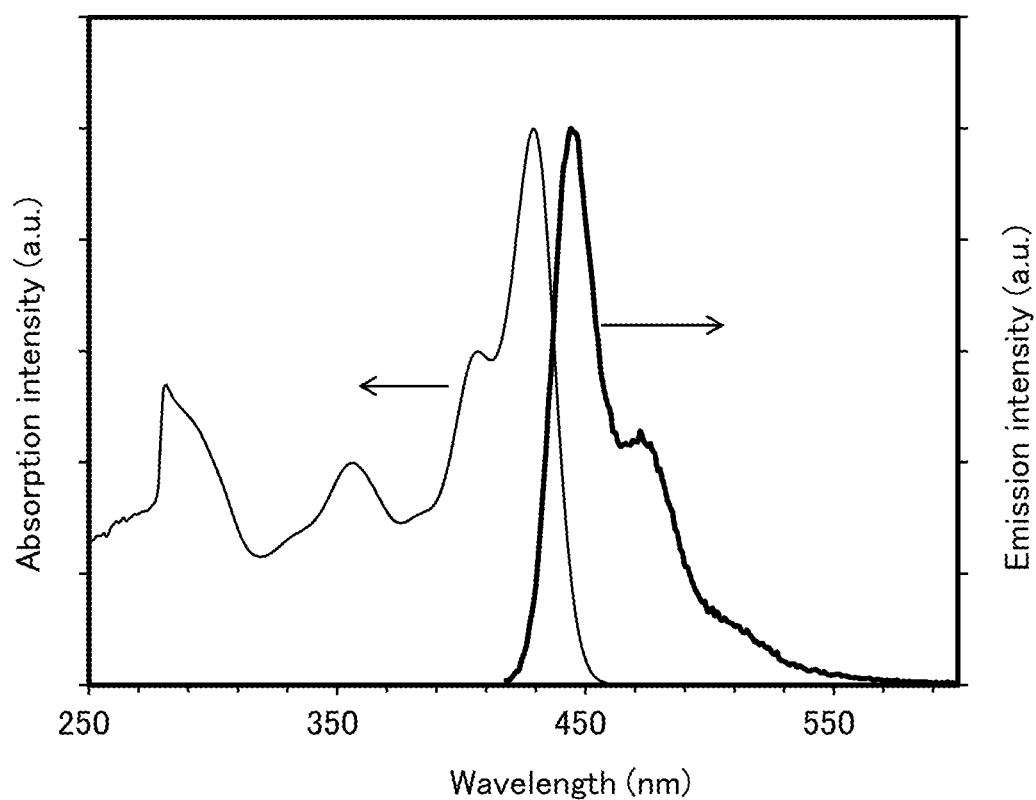
FIG. 21 is an absorption spectrum and an emission spectrum of 3,10aBnfA2Nbf(IV)-02 in a toluene solution.
Figure 22:
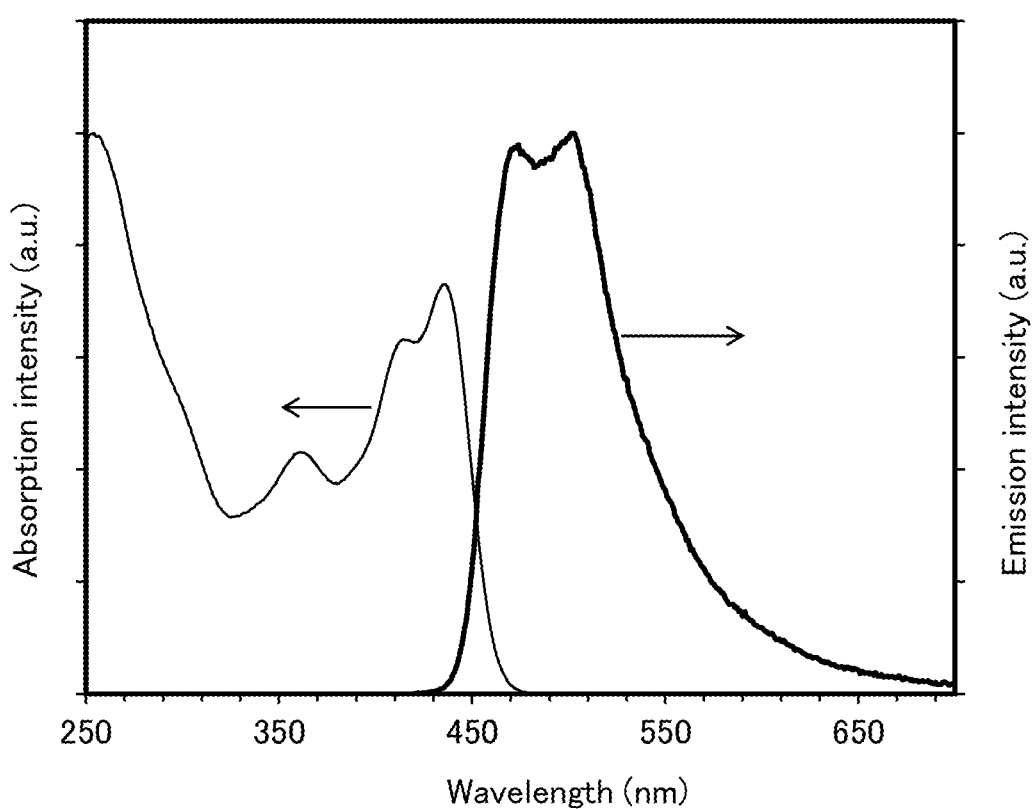
FIG. 22 is an absorption spectrum and an emission spectrum of 3,10aBnfA2Nbf(IV)-02 in a thin film state.

Next, FIG. 21 shows the measurement results of the absorption spectrum and the emission spectrum of 3,10aBnfA2Nbf(IV)-02 in a toluene solution, and FIG. 22 shows the absorption spectrum and the emission spectrum thereof in a thin film state. Since the apparatuses and the measurement methods are similar to those in Example 1, the description thereof is omitted.

As shown in FIG. 21, 3,10aBnfA2Nbf(IV)-02 in the toluene solution has absorption peaks at 429 nm, 407 nm, and 356 nm, and emission wavelength peaks at 445 nm and 472 nm (excitation wavelength: 408 nm). As shown in FIG. 22, the thin film of 3,10aBnfA2Nbf(IV)-02 has absorption peaks at 435 nm, 414 nm, 361 nm, and 254 nm, and emission wavelength peaks at 474 nm and 502 nm (excitation wavelength: 410 nm). These results indicate that 3,10aBnfA2Nbf(IV)-02 emits blue light and can be used as a host for a light-emitting substance or a substance that emits fluorescence in the visible region.

Furthermore, the measured emission quantum yield in the toluene solution was as high as 96%, which indicates that 3,10aBnfA2Nbf(IV)-02 is suitable as a light-emitting material.

Next, 3,10aBnfA2Nbf(IV)-02 obtained in this example was subjected to LC/MS analysis. Since the apparatuses and the measurement method are similar to those in Example 1, the description thereof is omitted. The obtained MS spectrum is shown in FIG. 23.

Figure 23:
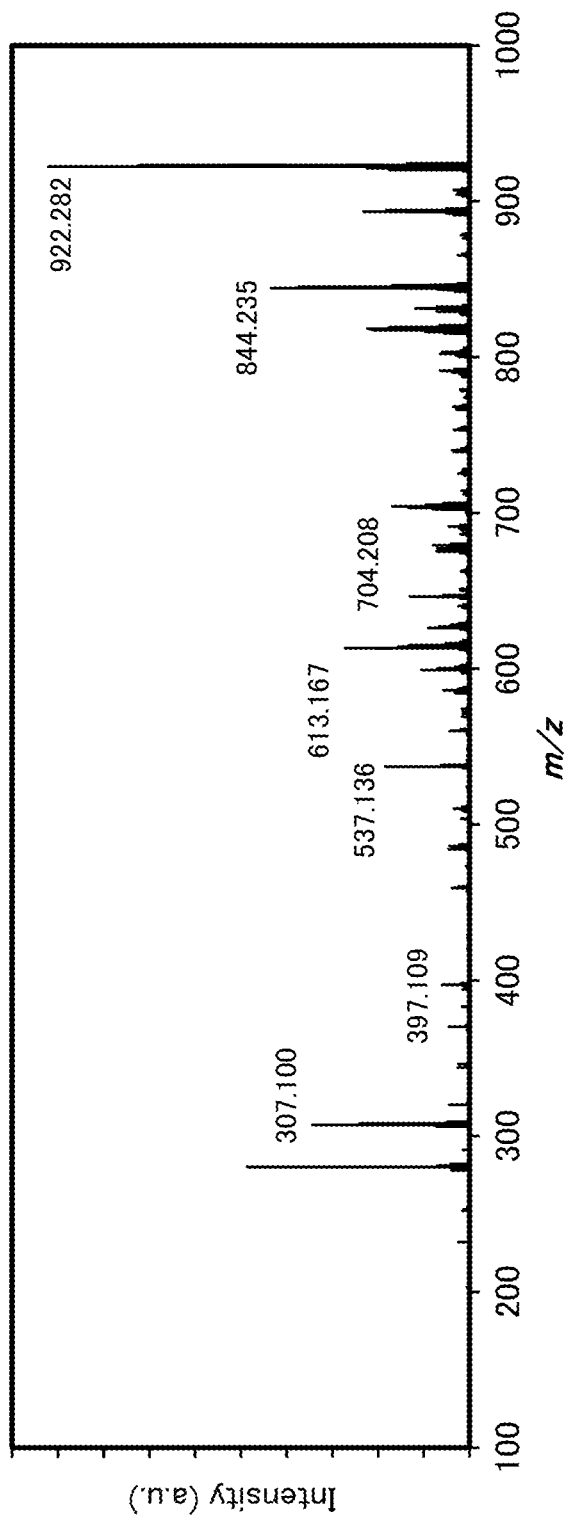
FIG. 23 is an MS spectrum of 3,10aBnfA2Nbf(IV)-02.

The results in FIG. 23 show that product ions of 3,10aBnfA2Nbf(IV)-02 are mainly detected around m/z=844, 704, 613, 537, 397, and 307. Note that the results in the figure are characteristic results derived from 3,10aBnfA2Nbf(IV)-02 and therefore can be regarded as important data for identifying 3,10aBnfA2Nbf(IV)-02 contained in a mixture.

Note that the product ion around m/z=844 is presumed to be a cation in the state where a phenyl group was eliminated from 3,10aBnfA2Nbf(IV)-02, which suggests that 3,10aBnfA2Nbf(IV)-02 includes a phenyl group.

Note that the product ion around m/z=704 is presumed to be a cation in the state where a benzo[b]naphtho[2,1-d]furanyl group was eliminated from 3,10aBnfA2Nbf(IV)-02, which suggests that 3,10aBnfA2Nbf(IV)-02 includes a benzo[b]naphtho[2,1-d]furanyl group.

Note that the product ion around m/z=613 is presumed to be a cation in the state where an N-(benzo[b]naphtho[2,1-d]furan-9-yl)-N-phenylamino group was eliminated from 3,10aBnfA2Nbf(IV)-02, which suggests that 3,10aBnfA2Nbf(IV)-02 includes an N-(benzo[b]naphtho[2,1-d]furan-9-yl)-N-phenylamino group.

Example 3

Synthesis Example 3

In this synthesis example, a method for synthesizing N,N'-bis(benzo[b]naphtho[2,3-d]furan-3-yl)-N,N'-diphenylnaphtho[2,3-b;6,7-b"]bisbenzofuran-3,10-diamine (abbreviation: 3,10Bnf(II)A2Nbf(IV)-02), which is an organic compound of one embodiment of the present invention, is described in detail. The structural formula of 3,10Bnf(II)A2Nbf(IV)-02 is shown below.

[Chemical Formula 71]

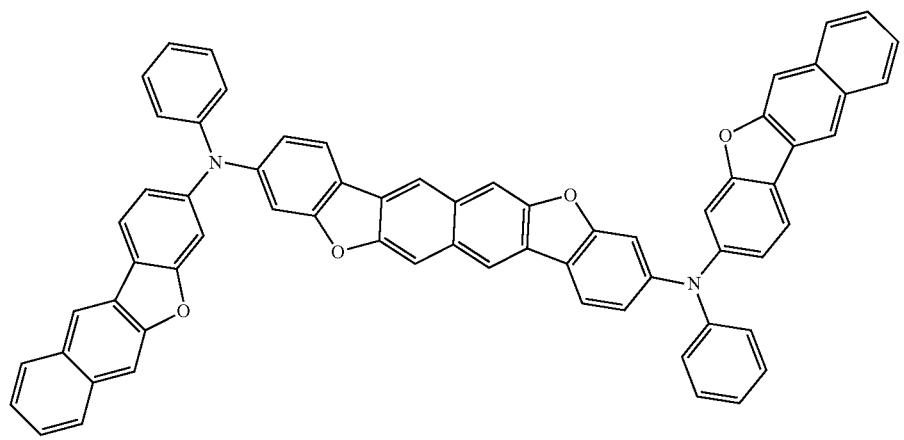

Step 1: Synthesis of 3,7-bis(4-chloro-2-fluorophenyl)-2,6-dimethoxynaphthalene

The synthesis was performed in a manner similar to that of Step 1 in Synthesis example 1 of Example 1.

Step 2: Synthesis of 3,7-bis(4-chloro-2-fluorophenyl)-2,6-dihydroxynaphthalene

The synthesis was performed in a manner similar to that of Step 2 in Synthesis example 1 of Example 1.

Step 3: Synthesis of 3,10-dichloronaphtho[2,3-b;6,7-b']bisbenzofuran

The synthesis was performed in a manner similar to that of Step 3 in Synthesis example 1 of Example 1.

Step 4: Synthesis of N,N'-bis(benzo[b]naphtho[2,3-d]furan-3-yl)-N,N'-diphenylnaphtho[2,3-b;6,7-b'']bisbenzofuran-3,10-diamine (abbreviation: 3,10Bnf(II)A2Nbf(IV)-02)

Into a 200-mL three-neck flask were put 1.0 g (2.7 mmol) of 3,10-dichloronaphtho[2,3-b;6,7-b']bisbenzofuran, 2.0 g (6.5 mmol) of N-phenyl-benzo[b]naphtho[2,3-d]furan-3-amine, 97 mg (0.27 mmol) of di(1-adamantyl)-n-butylphosphine, and 1.6 g (16 mmol) of sodium tert-butoxide. To this mixture was added 30 mL of xylene, and the resulting mixture was degassed by being stirred while the pressure was reduced. To this mixture was added 31 mg (54 μmol) of bis(dibenzylideneacetone)palladium(0), and the mixture was stirred under a nitrogen stream at 150° C. for 22 hours.

After the stirring, the mixture was filtered, whereby a solid was collected. The collected solid was washed with ethanol and water. Toluene was added to the obtained solid, and after heating and stirring, a solid was collected. This process was performed again to obtain 1.9 g of a yellow solid in a yield of 77%. The synthesis scheme of Step 4 is shown below.

[Chemical Formula 72]

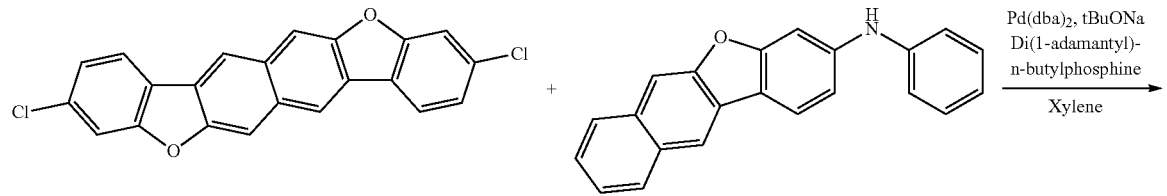

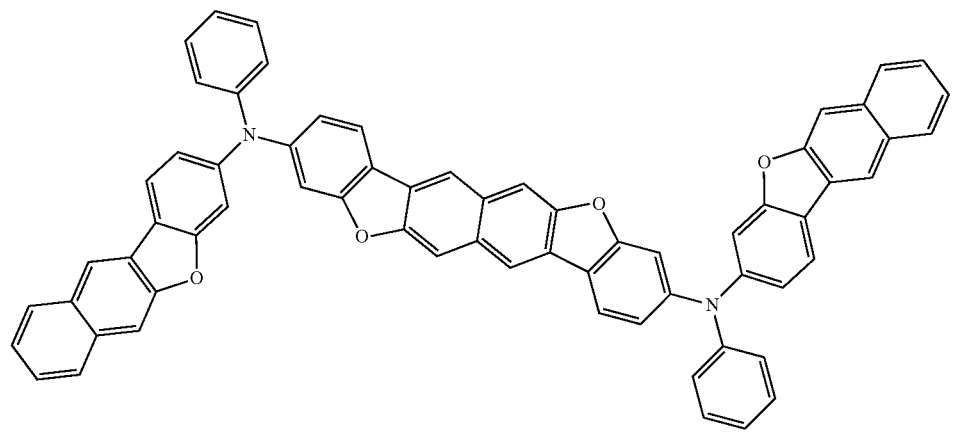

Figure 38:
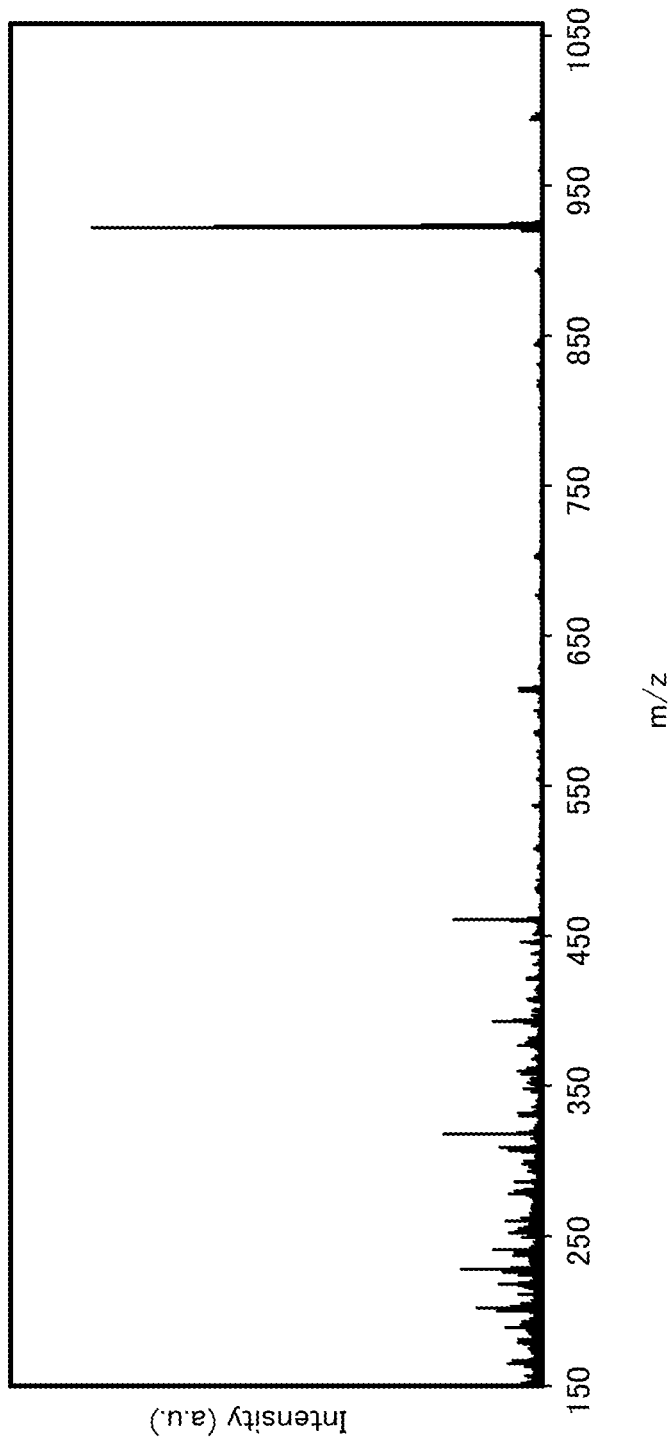
FIG. 38 is a diagram showing a mass spectrum of 3,10Bnf(II)A2Nbf(IV)-02.

The obtained yellow solid was subjected to ELMS measurement (Electron Impact-Mass Spectrometry). Accelerated electrons with 70 eV were used for the ionization. FIG. 38 shows the mass spectrum. In FIG. 38, the horizontal axis represents m/z (mass-to-charge ratio) and the vertical axis represents intensity (arbitrary unit). In the spectrum shown in FIG. 38, m/z=922 is derived from molecular ions. These indicate that 3,10Bnf(II)A2Nbf(IV)-02, which is an organic compound of one embodiment of the present invention, was obtained in this synthesis example.

Example 4

Synthesis Example 4

In this synthesis example, a method for synthesizing N,N'-diphenyl-N,N'-(7-phenylbenzo[c]carbazol-10-yl)naphtho[2,1-b; 6,5-b']bisbenzofuran-2,9-diamine (abbreviation: 2,9PcBCA2Nbf(III)), which is an organic compound of one embodiment of the present invention, is described in detail. The structural formula of 2,9PcBCA2Nbf(III) is shown below.

[Chemical Formula 73]

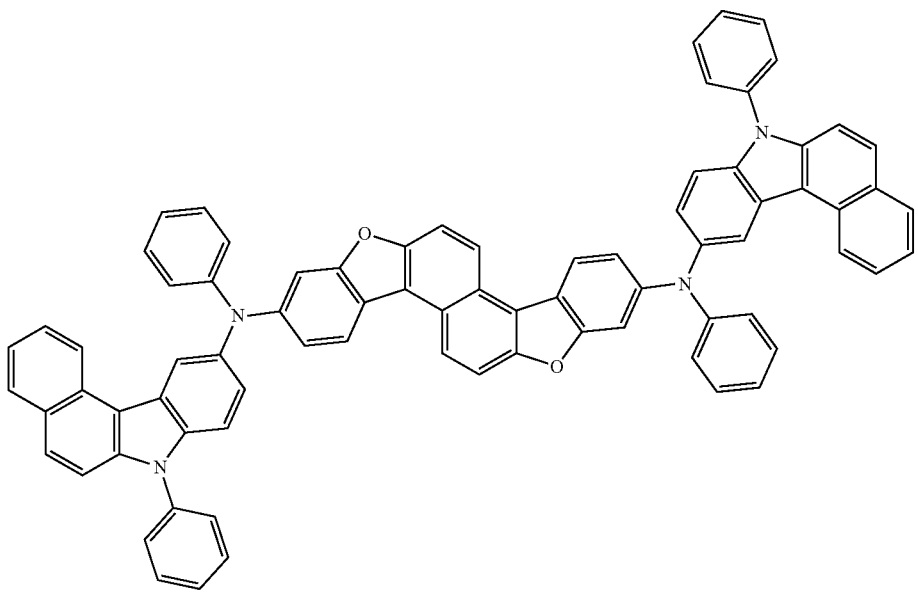

Step 1: Synthesis of 1,5-bis(4-chloro-2-fluorophenyl)-2,6-dihydroxynaphthalene

Into a 500-mL three-neck flask were put 6.2 g (19 mmol) of 1,5-dibromo-2,6-dihydroxynaphthalene, 7.5 g (43 mmol) of 5-chloro-2-fluorophenylboronic acid, 25 g (78 mmol) of cesium carbonate, and 0.80 g (1.9 mmol) of 2-dicyclohexylphosphino-2'-6'-dimethoxy-1,1'-biphenyl (abbreviation: SPhos). To this mixture was added 195 mL of toluene. This mixture was degassed by being stirred while the pressure was reduced. To this mixture was added 0.17 g (0.78 mmol) of palladium(II) acetate, and the mixture was stirred under a nitrogen stream at 110° C. for 7 hours. After the stirring, toluene was added to the mixture, and the resulting mixture was suction-filtered through Celite (Wako Pure Chemical Industries, Ltd., Catalog No. 531-16855) to obtain a filtrate. The obtained filtrate was concentrated to obtain a solid. The obtained solid was purified by silica gel column chromatography (neutral silica gel, developing solvent: toluene) to obtain a solid.

The obtained solid was recrystallized with toluene, so that 2.9 g of a white solid was obtained in a yield of 35%. The synthesis scheme of Step 1 is shown below.

[Chemical Formula 74]

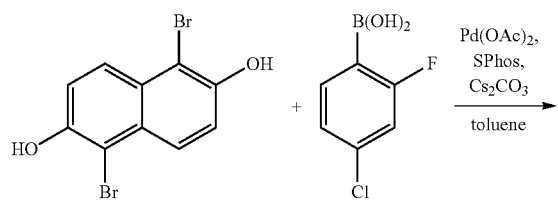

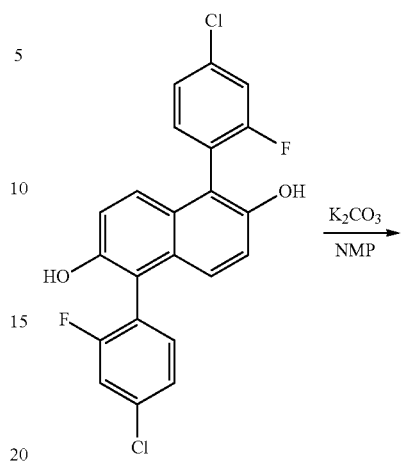

[Chemical Formula 75]

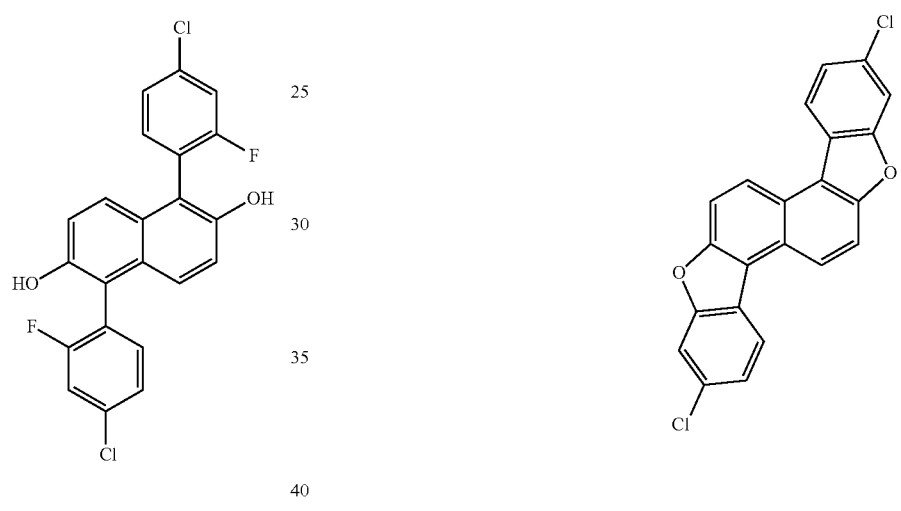

Step 2: Synthesis of 2,9-dichloronaphtho[2,1-b;6,5-b']bisbenzofuran

Into a 200-mL three-neck flask were put 2.8 g (6.8 mmol) of 1,5-bis(4-chloro-2-fluorophenyl)-2,6-dihydroxynaphthalene and 3.7 g (27 mmol) of potassium carbonate. To this mixture was added 70 mL of N-methyl-2-pyrrolidone, and this mixture was degassed by being stirred while the pressure was reduced. After the degassing, this mixture was stirred under a nitrogen stream at 120° C. for 7.5 hours. After the stirring, water was added to this mixture, and a precipitated solid was collected by filtration. This solid was washed with water and ethanol. Ethanol was added to the obtained solid, and after heating and stirring, a solid was collected. Toluene was added to the obtained solid, and after heating and stirring, a precipitated solid was collected, so that 2.3 g of a white solid was obtained in a yield of 91%. The synthesis scheme of Step 2 is shown below.

Step 3: Synthesis of N,N'-diphenyl-N,N'-(7-phenyl-benzo[c]carbazol-10-yl)naphtho[2,1-b; 6,5-b']bis-benzofuran-2,9-diamine (abbreviation: 2,9PcBCA2Nbf(III)

Into a 200-mL three-neck flask were put 0.88 g (2.3 mmol) of 2,9-dichloronaphtho[2,1-b;6,5-b']bisbenzofuran, 2.2 g (5.8 mmol) of N-phenyl-N-(7-phenyl-7H-benzo[c] carbazol-10-yl)amine, 83 mg (0.23 mmol) of di(1-adamantyl)-n-butylphosphine, and 1.3 g (14 mmol) of sodium tert-butoxide. To this mixture was added 25 mL of xylene. This mixture was degassed by being stirred while the pressure was reduced. To this mixture was added 27 mg (46 μmol) of bis(dibenzylideneacetone)palladium(0), and the mixture was stirred under a nitrogen stream at 150° C. for 10 hours. After the stirring, toluene was added to this mixture, and the resulting mixture was suction-filtered through Florisil, Celite, and alumina to obtain a filtrate. The obtained filtrate was concentrated to obtain an oily substance. This oily substance was purified by silica gel column chromatography (developing solvent: toluene:hexane=1:2 and then toluene:hexane=2:3) to obtain a solid. The obtained solid was recrystallized with toluene, so that 1.7 g of a yellow solid was obtained in a yield of 68%. The synthesis scheme of Step 3 is shown below.

[Chemical Formula 76]

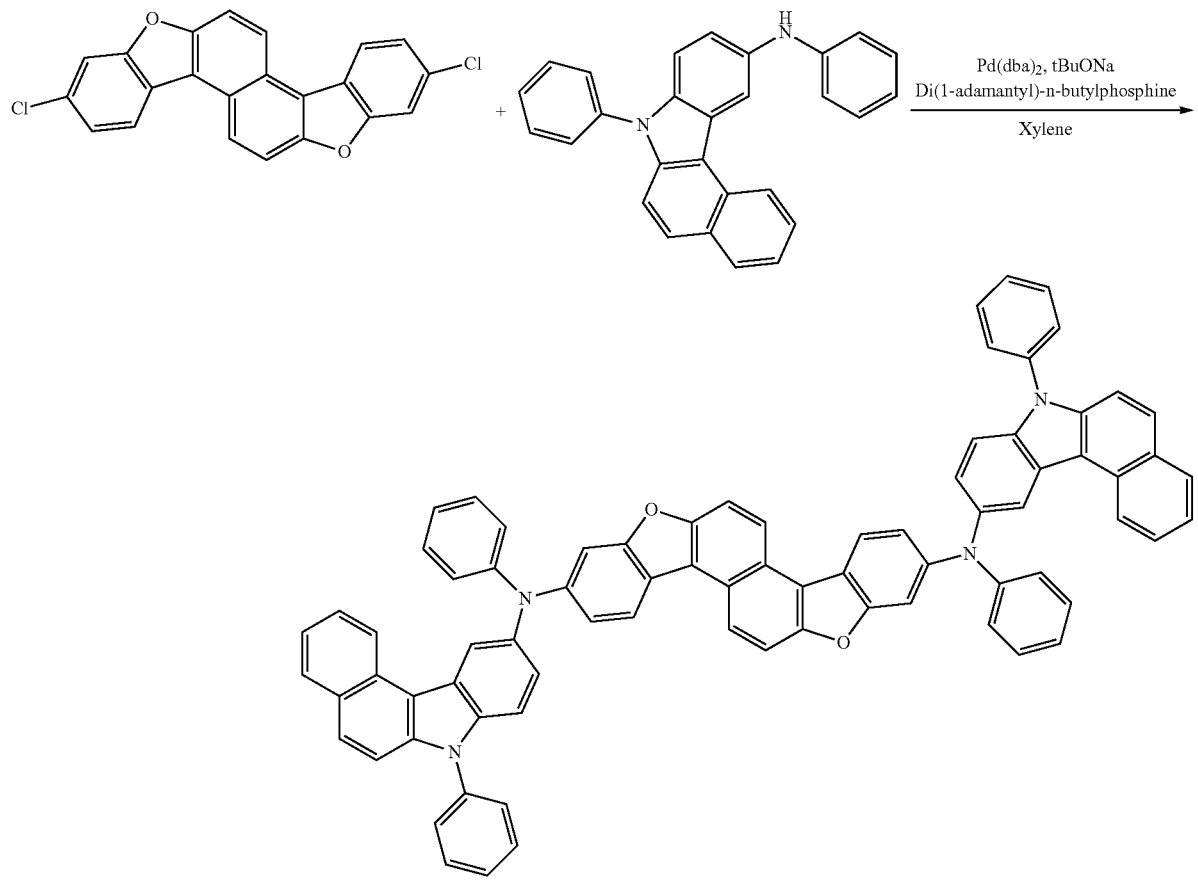

By a train sublimation method, 1.1 g of the obtained solid was sublimated and purified. The heating was performed at 420° C. under the conditions where the pressure was 2.7× $10^{-2}$ Pa and the flow rate of argon was 0 mL/min. After the sublimation purification, 0.74 g of a yellow solid was obtained in a collection rate of 67%.

Figure 39A:
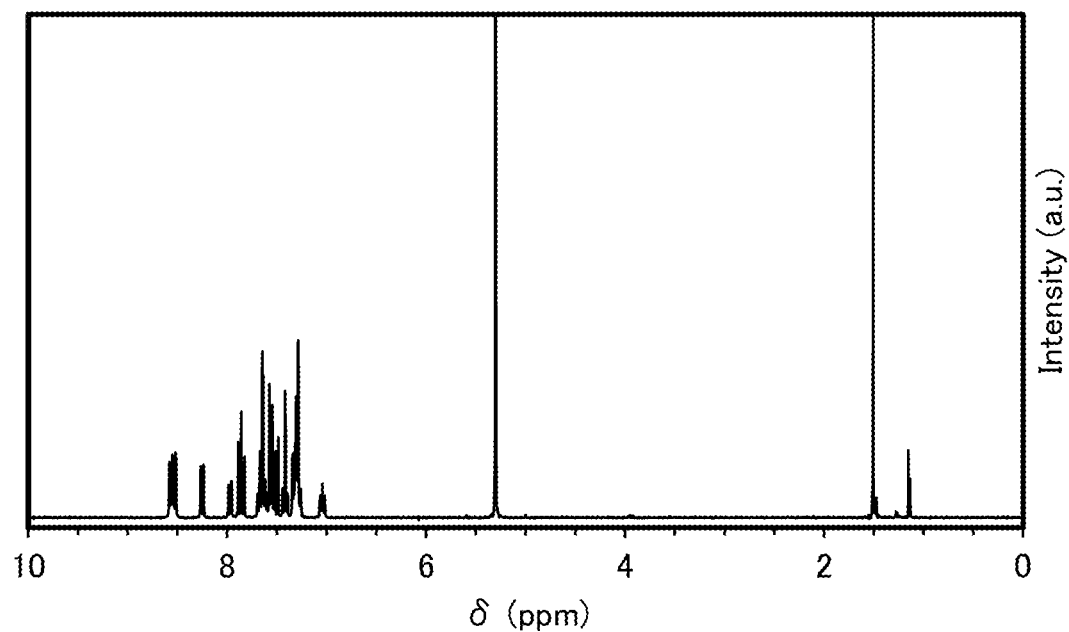
FIGS. 39A and 39B are 1H NMR spectra of 2,9PcBCA2Nbf(III).
Figure 39B:
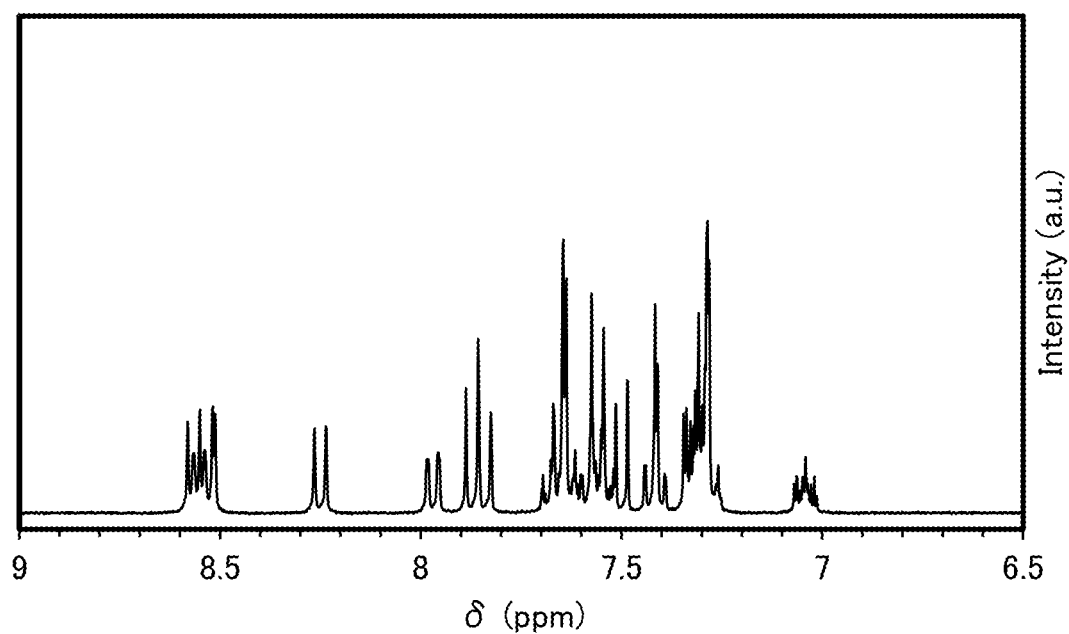

FIG. 39 shows $^1$H NMR data of the obtained solid, whose numerical data is given below. The data indicates that 2,9PcBCA2Nbf(III), which is an organic compound of one embodiment of the present invention, was obtained in this synthesis example.

$^1$H NMR (CD$_2$Cl$_2$, 300 MHz): δ=7.01-7.07 (m, 2H), 7.25-7.35 (m, 12H), 7.39-7.44 (m, 4H), 7.49-7.70 (m, 16H), 7.83-7.89 (m, 4H), 7.97 (d, J1=8.4 Hz, 2H), 8.25 (d, J1=8.4 Hz, 2H), 8.51-8.58 (m, 6H).

Figure 40:
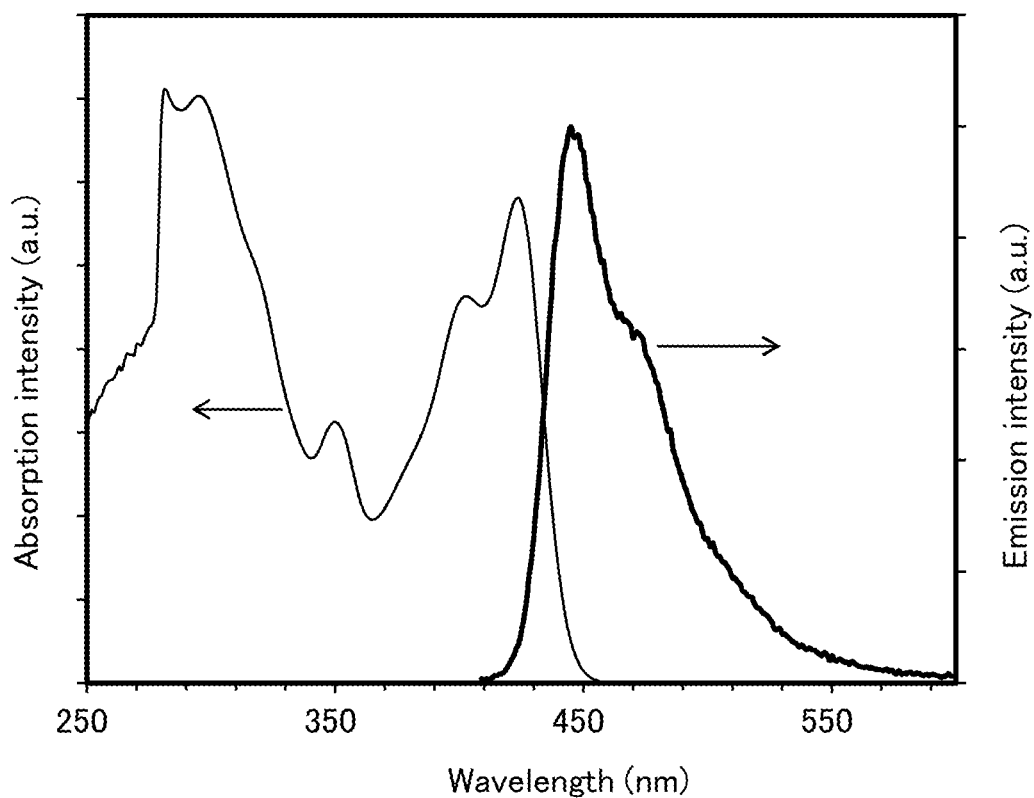
FIG. 40 is an absorption spectrum and an emission spectrum of 2,9PcBCA2Nbf(III) in a toluene solution.
Figure 41:
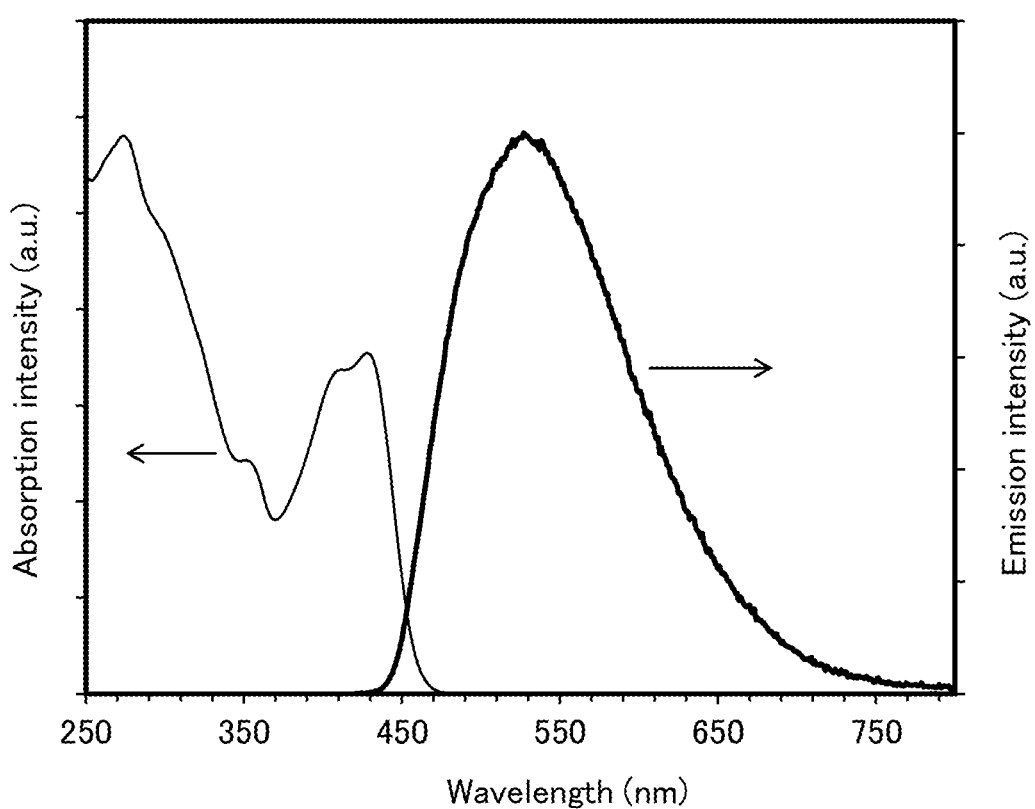
FIG. 41 is an absorption spectrum and an emission spectrum of 2,9PcBCA2Nbf(III) in a thin film state.

Next, FIG. 40 shows the measurement results of the absorption spectrum and the emission spectrum of 2,9PcBCA2Nbf(III) in a toluene solution, and FIG. 41 shows the absorption spectrum and the emission spectrum thereof in a thin film state. Since the apparatuses and the measurement methods are similar to those in Example 1, the description thereof is omitted.

The measurement results reveal that 2,9PcBCA2Nbf(III) in the toluene solution has absorption peaks at 422 nm, 402 nm, 350 nm, and 295 nm, and emission wavelength peaks at 445 nm and 473 nm (excitation wavelength: 399 nm). As shown in the figure, the thin film of 2,9PcBCA2Nbf(III) has absorption peaks at 428 nm, 411 nm, 356 nm, 300 nm, and 274 nm, and an emission wavelength peak at 527 nm (excitation wavelength: 415 nm). These results indicate that 2,9PcBCA2Nbf(III) emits blue light and can be used as a host for a light-emitting substance or a substance that emits fluorescence in the visible region.

Furthermore, the measured quantum yield in the toluene solution was as high as 91%, which indicates that 2,9PcBCA2Nbf(III) is suitable as a light-emitting material.

Figure 42:
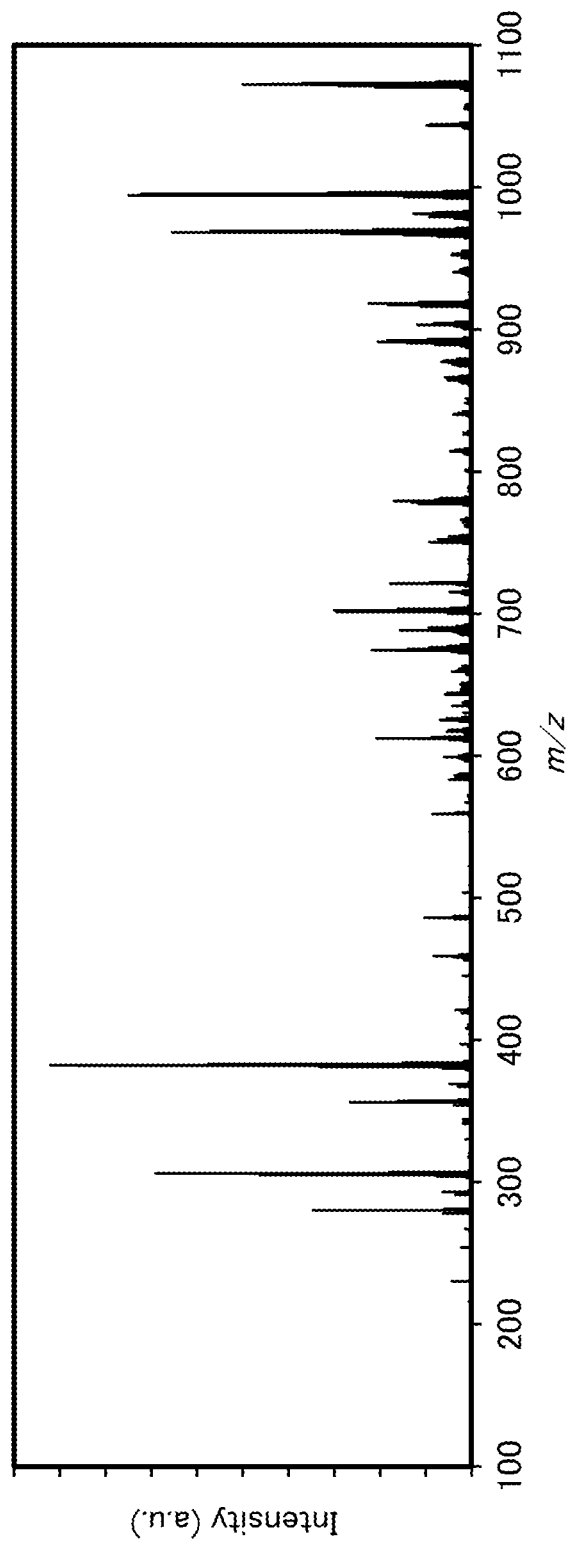
FIG. 42 is an MS spectrum of 2,9PcBCA2Nbf(III).

Next, 2,9PcBCA2Nbf(III) obtained in this example was subjected to LC/MS analysis. The description of the apparatuses and the measurement method similar to those in Example 1 is omitted. For setting of the PRM, the mass range of a target ion was set to m/z=1072.38±2.0 (isolation window=4), and the measurement was performed with NCE set to 60. The obtained MS spectrum is shown in FIG. 42.

The results in the figure show that product ions of 2,9PcBCA2Nbf(III) are mainly detected around m/z=994, 918, 779, 702, 382, and 306. Note that the results in the figure are characteristic results derived from 2,9PcBCA2Nbf (III) and therefore can be regarded as important data for identifying 2,9PcBCA2Nbf(III) contained in a mixture.

Note that the product ion around m/z=994 is presumed to be a cation in the state where a phenyl group was eliminated from 2,9PcBCA2Nbf(III), which suggests that 2,9PcBCA2Nbf(III) includes a phenyl group.

Note that the product ion around m/z=918 is presumed to be a cation in the state where two phenyl groups were eliminated from 2,9PcBCA2Nbf(III), which suggests that 2,9PcBCA2Nbf(III) includes phenyl groups.

239

Note that the product ion around m/z=779 is presumed to be a cation in the state where 7-phenyl-7H-benzo[c]carbazole was eliminated from 2,9PcBCA2Nbf(III), which suggests that 2,9PcBCA2Nbf(III) includes 7-phenyl-7H-benzo[c]carbazole.

Note that the product ion around m/z=382 is presumed to be a cation in the state where N-(7-phenyl-7H-benzo[c]carbazol-10-yl)-N-phenylnaphtho[2,1-b;6,5-b']bisbenzofuran-2-amine was eliminated from 2,9PcBCA2Nbf(III), which suggests that 2,9PcBCA2Nbf(III) includes N-(7-phenyl-7H-benzo[c]carbazol-10-yl)-N-phenylnaphtho[2,1-b;6,5-b']bisbenzofuran-2-amine.

240

Example 5

In this example, a light-emitting device 1 that is the light-emitting device of one embodiment of the present invention described in Embodiments and a comparative light-emitting device 1 that is a light-emitting device for a comparative example are described in detail. Structural formulae of organic compounds used in the light-emitting device 1 and the comparative light-emitting device 1 are shown below.

[Chemical Formulae 77]

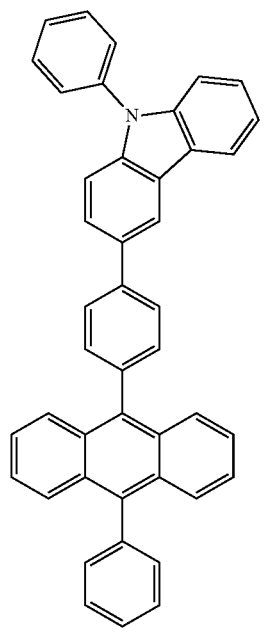

PCzPA (i)

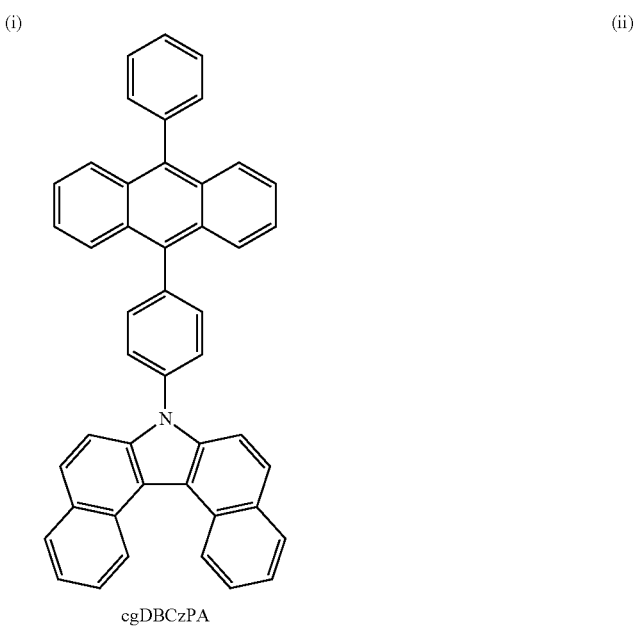

cgDBCzPA (ii)

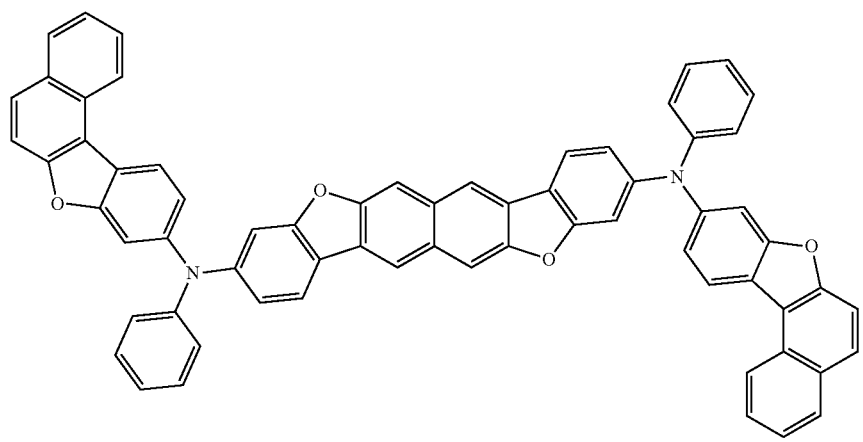

3,10BnfA2Nbf(IV)-02 (iii)

(iv)

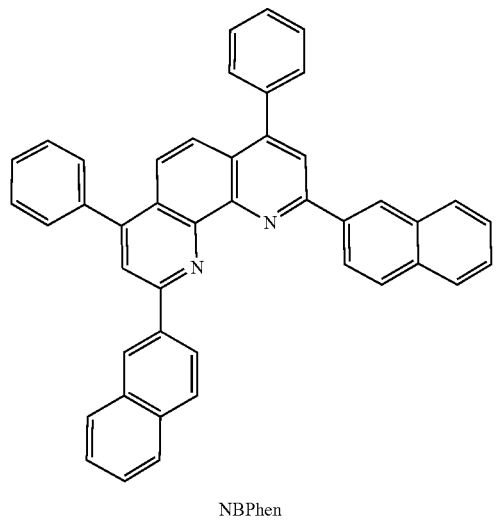

NBPhen (v)

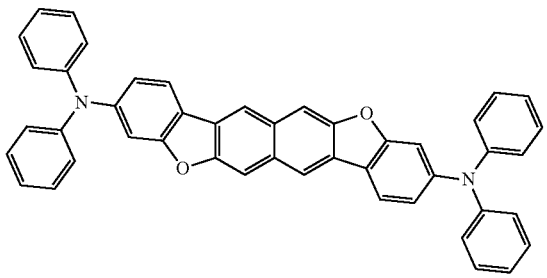

3,10DPhA2Nbf(IV)

(vi)

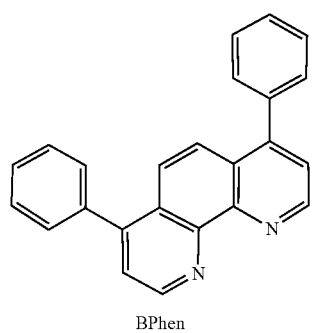

BPhen (Method for Fabricating Light-Emitting Device 1)

First, indium tin oxide containing silicon oxide (ITSO) was deposited on a glass substrate by a sputtering method to form the anode 101. The thickness was 70 nm, and the electrode area was 4 mm$^2$ (2 mm×2 mm).

Next, as pretreatment for forming a light-emitting device over the substrate, a surface of the substrate was washed with water, baking was performed at 200° C. for one hour, and then UV ozone treatment was performed for 370 seconds.

After that, the substrate was introduced into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 9-phenyl-3-[4-(10-phenyl-9-anthryl)phenyl]-9H-carbazole (abbreviation: PCzPA) represented by the above structural formula (i) and molybdenum(VI) oxide were deposited by co-evaporation on the anode 101 to have a weight ratio of 4:2 (=PCzPA: molybdenum oxide) to a thickness of 10 nm by an evaporation method using resistance heating, whereby the hole-injection layer 111 was formed.

Next, over the hole-injection layer 111, PCzPA was deposited by evaporation to a thickness of 30 nm to form the hole-transport layer 112.

Next, 7-[4-(10-phenyl-9-anthryl)phenyl]-7H-dibenzo[c,g]carbazole (abbreviation: cgDBCzPA) represented by the above structural formula (ii) and N,N'-bis(benzo[b]naphtho[1,2-d]furan-9-yl)-N,N'-(diphenyl)naphtho[2,3-b;6,7-b']bis-benzofuran-3,10-diamine (abbreviation: 3,10BnfA2Nbf (IV)-02) represented by the above structural formula (iii) were deposited by co-evaporation to have a weight ratio of 1:0.01 (=cgDBCzPA: 3,10BnfA2Nbf(IV)-02) to a thickness of 25 nm, whereby the light-emitting layer 113 was formed.

After that, over the light-emitting layer 113, cgDBCzPA was deposited by evaporation to a thickness of 15 nm, and 2,9-di(2-naphthyl)-4,7-diphenyl-1,10-phenanthroline (abbreviation: NBPhen) represented by the above structural formula (iv) was deposited by evaporation to a thickness of 10 nm, whereby the electron-transport layer 114 was formed.

After the formation of the electron-transport layer 114, lithium fluoride (LiF) was deposited to a thickness of 1 nm by evaporation to form the electron-injection layer 115 and then aluminum was deposited to a thickness of 200 nm by evaporation to form the cathode 102. Thus, the light-emitting device 1 was fabricated.

(Method for Fabricating Comparative Light-Emitting Device 1)

The comparative light-emitting device 1 was fabricated in such a manner that the light-emitting layer 113 was formed using 3,10-bis(diphenylamino)naphtho[2,3-b;6,7-b']bisbenzofuran (abbreviation: 3,10DPhA2Nbf(IV)) represented by the above structural formula (v) instead of 3,10BnfA2Nbf(IV)-02 used for the light-emitting layer 113 in the light-emitting device 1, and the electron-transport layer 114 was formed by depositing cgDBCzPA by evaporation to a thickness of 10 nm and then depositing bathophenanthroline (abbreviation: BPhen) represented by the above structural formula (vi) by evaporation to a thickness of 15 nm. Although 3,10DPhA2Nbf(IV) used in the comparative light-emitting device 1 and 3,10BnfA2Nbf(IV)-02 used in the light-emitting device 1 have the same structure of naphthobisbenzofuran, which is a main skeleton, they are different in the structure of amine bonded thereto.

The device structures of the light-emitting device 1 and the comparative light-emitting device 1 are listed in the following table.

TABLE 1

| | Hole-injection layer 10 nm | Hole-transport 30 nm | Light-emitting layer 25 nm | Electron-transport layer | | Electron-injection layer 1 nm |
|---|---|---|---|---|---|---|
| Light-emitting device 1 | PCzPA: MoOx (4:2) | PCzPA | cgDBCzPA: 3,10BnfA2Nbf(IV)-02 (1:0.01) | cgDBCzPA 15 nm | NBPhen 10 nm | LiF |
| Comparative light-emitting device 1 | | | cgDBCzPA: 3,10DPhA2Nbf(IV) (1:0.01) | cgDBCzPA 10 nm | BPhen 15 nm | |

The light-emitting device 1 and the comparative light-emitting device 1 were sealed using glass substrates in a glove box containing a nitrogen atmosphere so as not to be exposed to the air (a sealant was applied to surround the device, and UV treatment and 1-hour heat treatment at 80° C. were performed in sealing). Then, initial characteristics of these light-emitting devices were measured. The measurement was performed at room temperature.

Figure 24:
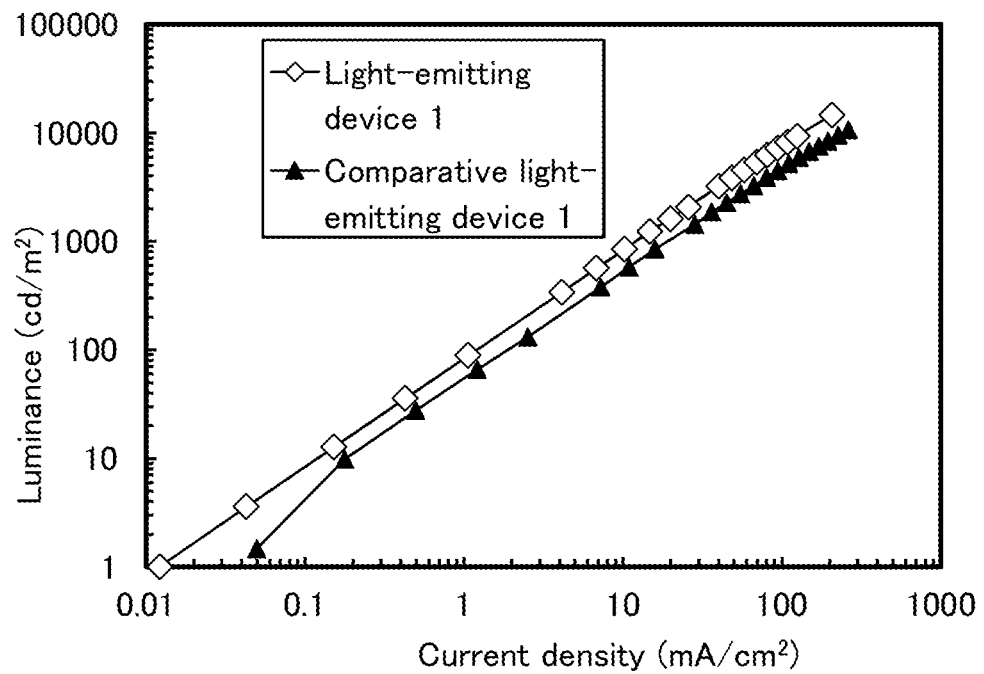
FIG. 24 is a diagram showing luminance-current density characteristics of a light-emitting device 1 and a comparative light-emitting device 1.
Figure 25:
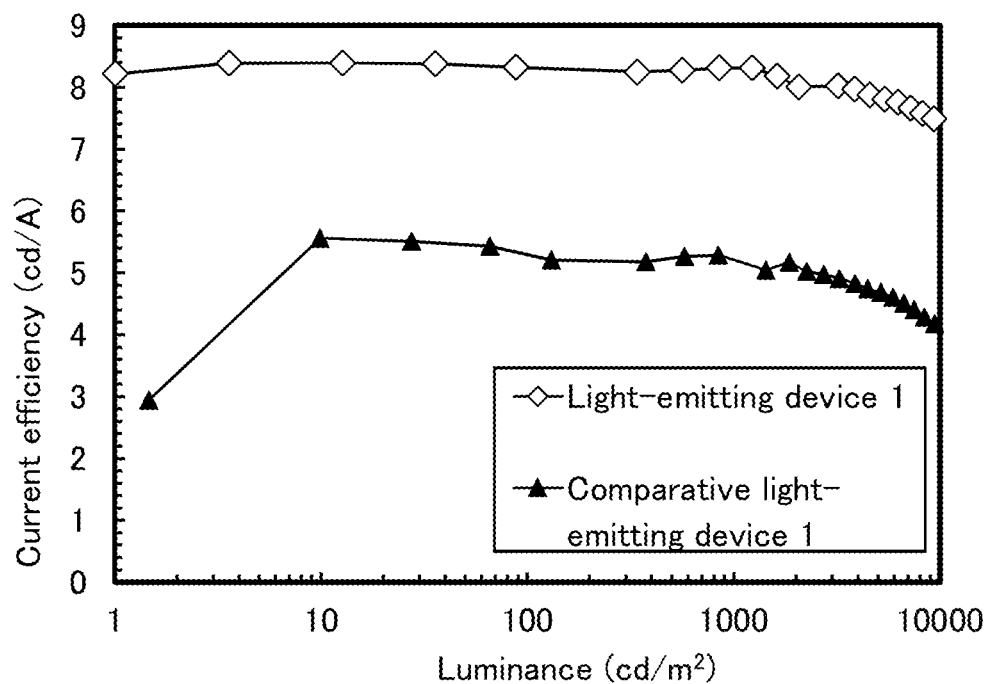
FIG. 25 is a diagram showing current efficiency-luminance characteristics of the light-emitting device 1 and the comparative light-emitting device 1.
Figure 26:
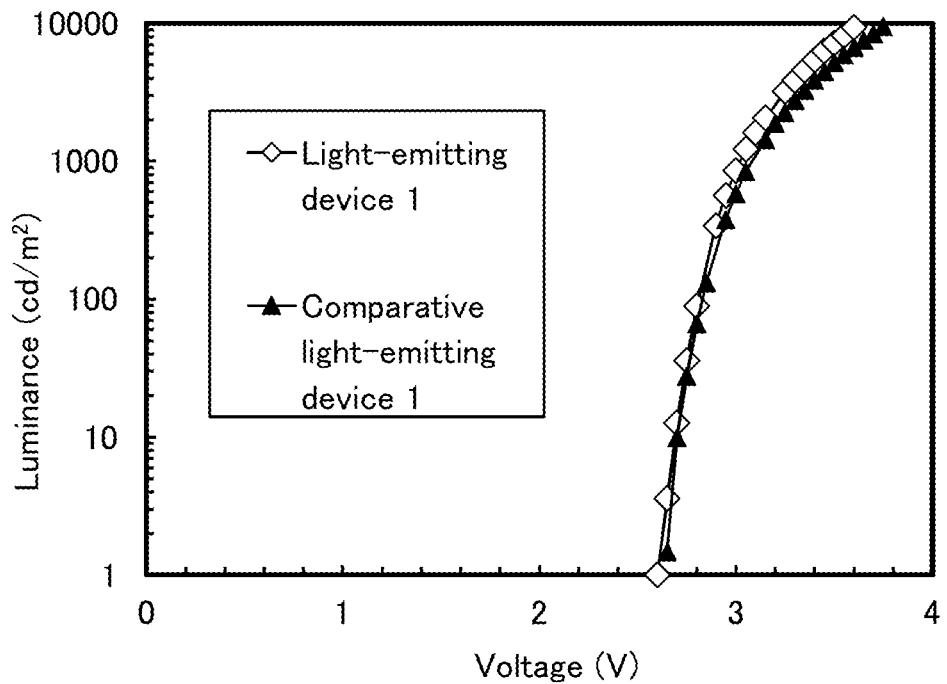
FIG. 26 is a diagram showing luminance-voltage characteristics of the light-emitting device 1 and the comparative light-emitting device 1.
Figure 27:
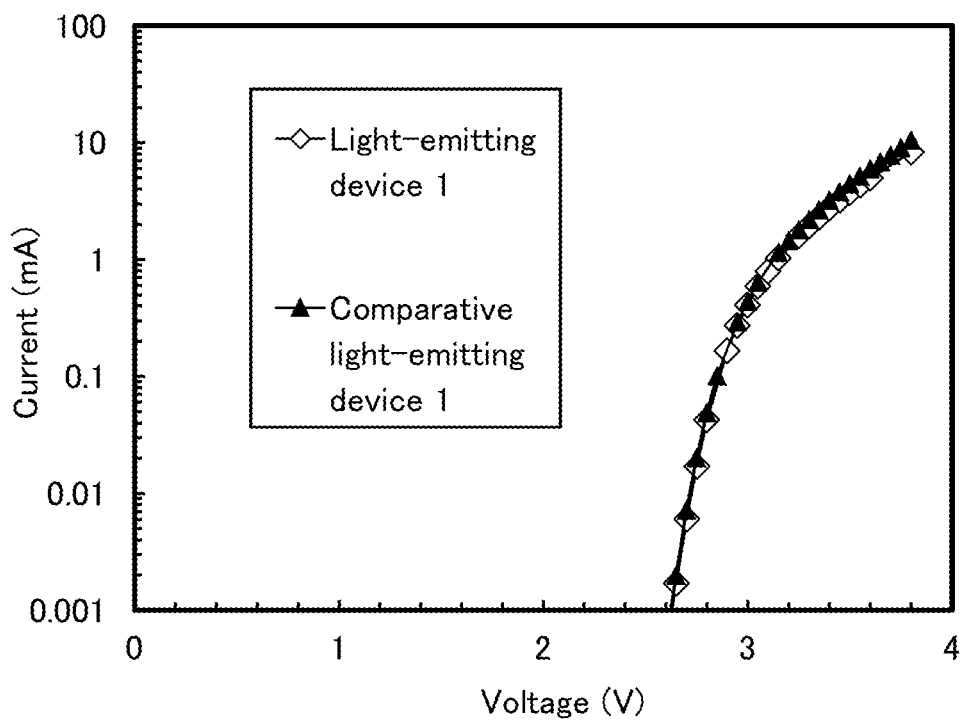
FIG. 27 is a diagram showing current-voltage characteristics of the light-emitting device 1 and the comparative light-emitting device 1.
Figure 28:
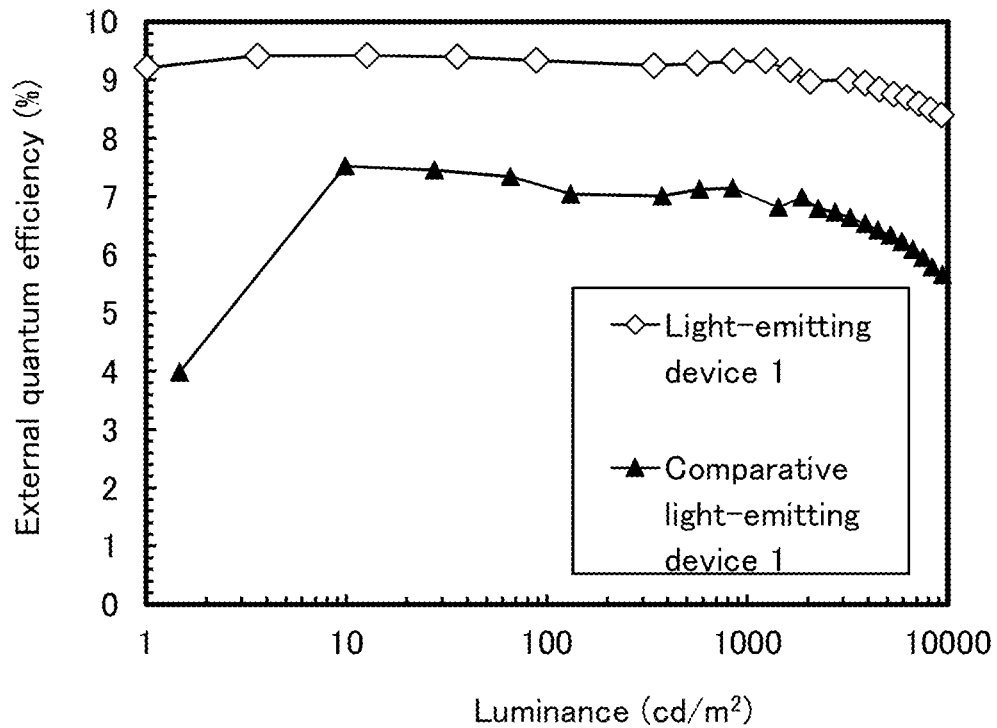
FIG. 28 is a diagram showing external quantum efficiency-luminance characteristics of the light-emitting device 1 and the comparative light-emitting device 1.
Figure 29:
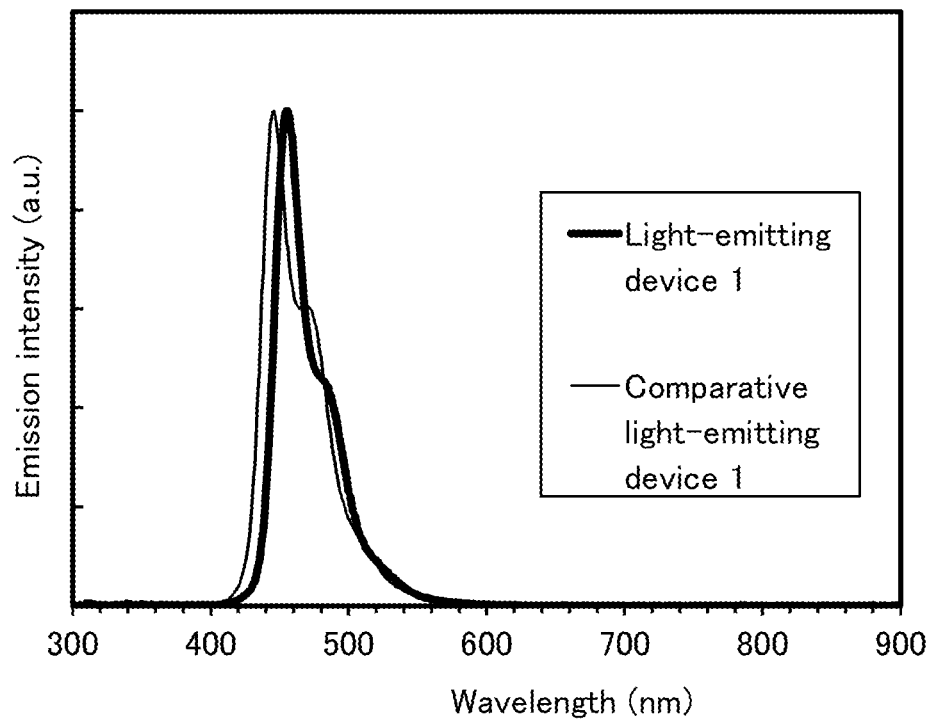
FIG. 29 is emission spectra of the light-emitting device 1 and the comparative light-emitting device 1.

FIG. 24 shows the luminance-current density characteristics of the light-emitting device 1 and the comparative light-emitting device 1; FIG. 25 shows the current efficiency-luminance characteristics thereof; FIG. 26 shows the luminance-voltage characteristics thereof; FIG. 27 shows the current-voltage characteristics thereof; FIG. 28 shows the external quantum efficiency-luminance characteristics thereof; and FIG. 29 shows the emission spectra thereof. In addition, their device characteristics at around a luminance of 1000 cd/m$^2$ are listed in Table 2.

TABLE 2

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 1 | 3.0 | 0.41 | 10.2 | 0.14 | 0.11 | 8.3 | 9.3 |
| Comparative light-emitting device 1 | 3.1 | 0.64 | 15.9 | 0.14 | 0.08 | 5.3 | 7.1 |

According to FIG. 24 to FIG. 29 and Table 2, the light-emitting device 1 shows a favorable result, an external quantum efficiency of 9.3% at 1000 cd/m². It is also found that the light-emitting device 1 has higher efficiency than the comparative light-emitting device 1.

Figure 30:
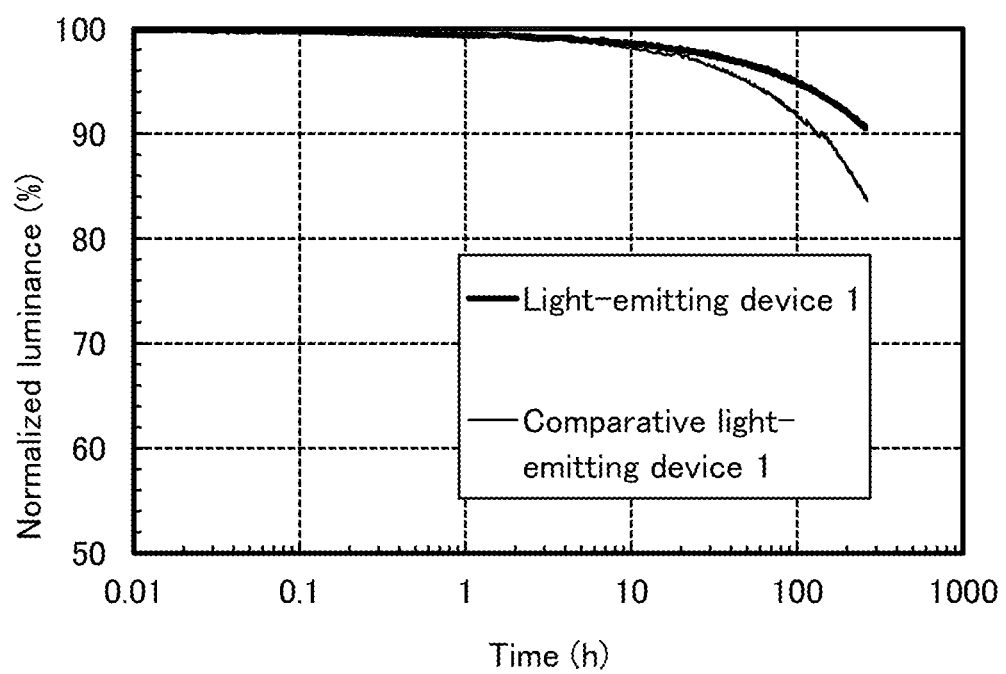
FIG. 30 is a diagram showing normalized luminance-time change characteristics of the light-emitting device 1 and the comparative light-emitting device 1.

FIG. 30 is a graph showing a change in luminance over driving time under the conditions where the current value was 2 mA and the current density was constant. As shown in FIG. 30, the light-emitting device 1 maintains 90% or more of the initial luminance even after 250-hour driving, which indicates that the light-emitting device 1 has a favorable lifetime. Furthermore, the light-emitting device 1 was found to be a light-emitting device with a more favorable lifetime than the comparative light-emitting device 1.

Example 6

In this example, a light-emitting device 2 that is the light-emitting device of one embodiment of the present invention described in Embodiments and a comparative light-emitting device 2 that is a light-emitting device for a comparative example are described in detail. Structural formulae of organic compounds used in the light-emitting device 2 and the comparative light-emitting device 2 are shown below.

[Chemical Formulae 78]

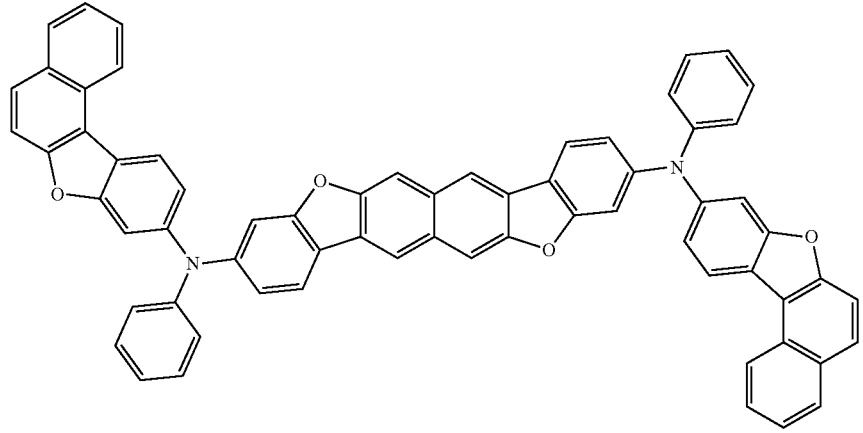

3,10BnfA2Nbf(IV)-02

(iii)

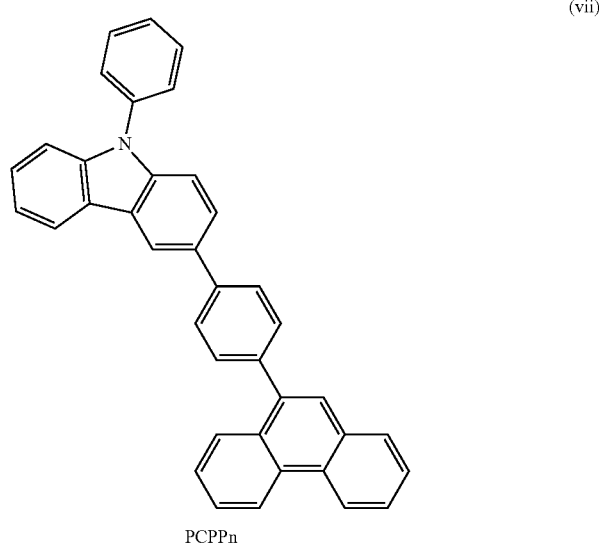

PCPPn (vii)

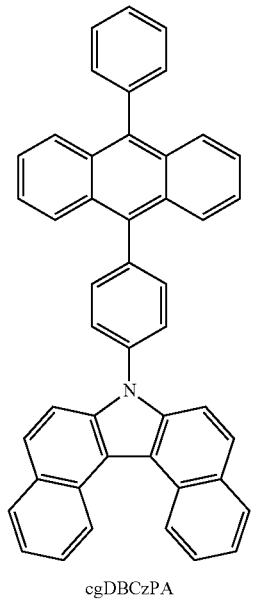

cgDBCzPA (ii)

(iv)

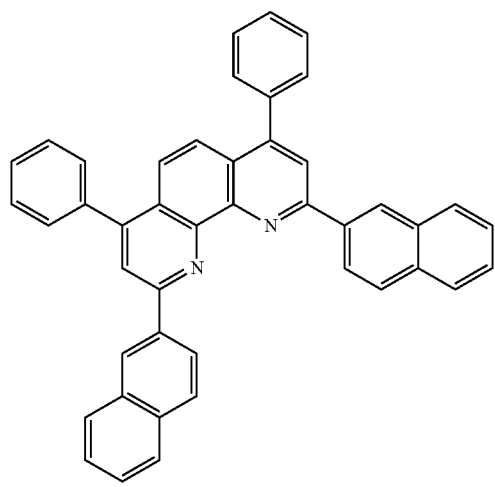

NBPhen

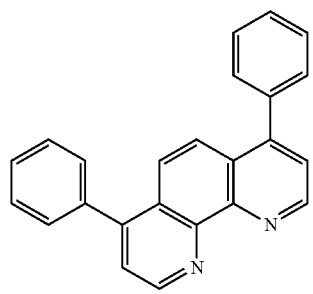

BPhen (v)

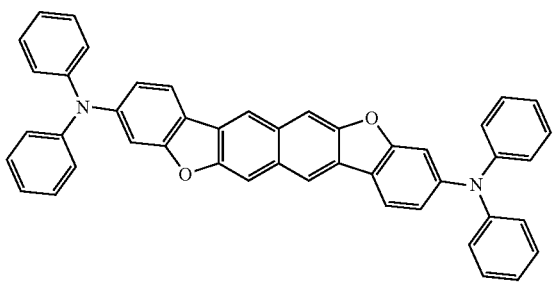

3,10DPhA2Nbf(IV)

(vi)

(Method for Fabricating Light-Emitting Device 2)

First, indium tin oxide containing silicon oxide (ITSO) was deposited on a glass substrate by a sputtering method to form the anode 101. The thickness was 70 nm, and the electrode area was 4 mm$^2$ (2 mm×2 mm).

Next, as pretreatment for forming a light-emitting device over the substrate, a surface of the substrate was washed with water, baking was performed at 200° C. for one hour, and then UV ozone treatment was performed for 370 seconds.

After that, the substrate was introduced into a vacuum evaporation apparatus where the pressure had been reduced to approximately 10$^{-4}$ Pa, and was subjected to vacuum baking at 170° C. for 30 minutes in a heating chamber of the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented by the above structural formula (vi) and molybdenum(VI) oxide were deposited by co-evaporation on the anode 101 to have a weight ratio of 4:2 (=PCPPn: molybdenum oxide) to a thickness of 10 nm by an evaporation method using resistance heating, whereby the hole-injection layer 111 was formed.

Next, over the hole-injection layer 111, PCPPn was deposited by evaporation to a thickness of 30 nm to form the hole-transport layer 112.

Next, 7-[4-(10-phenyl-9-anthryl)phenyl]-7H-dibenzo[c,g]carbazole (abbreviation: cgDBCzPA) represented by the above structural formula (ii) and N,N'-bis(benzo[b]naphtho[1,2-d]furan-9-yl)-N,N'-(diphenyl)naphtho[2,3-b;6,7-b']bis-benzofuran-3,10-diamine (abbreviation: 3,10BnfA2Nbf(IV)-02) represented by the above structural formula (iii) were deposited by co-evaporation to have a weight ratio of 1:0.01 (=cgDBCzPA: 3,10BnfA2Nbf(IV)-02) to a thickness of 25 nm, whereby the light-emitting layer 113 was formed.

After that, over the light-emitting layer 113, cgDBCzPA was deposited by evaporation to a thickness of 15 nm, and 2,9-di(2-naphthyl)-4,7-diphenyl-1,10-phenanthroline (abbreviation: NBPhen) represented by the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting device 2 of this example was fabricated.

(Method for Fabricating Comparative Light-Emitting Device 2)

The comparative light-emitting device 2 was fabricated in such a manner that the light-emitting layer 113 was formed using 3,10-bis(diphenylamino)naphtho[2,3-b;6,7-b']bisbenzofuran (abbreviation: 3,10DPhA2Nbf(IV)) represented by the above structural formula (v) instead of 3,10BnfA2Nbf(IV)-02 used for the light-emitting layer 113 in the light-emitting device 2, and the electron-transport layer 114 was formed by depositing cgDBCzPA by evaporation to a thickness of 10 nm and then depositing bathophenanthroline (abbreviation: BPhen) represented by the above structural formula (vi) by evaporation to a thickness of 15 nm. Although 3,10DPhA2Nbf(IV) used in the comparative light-emitting device 2 and 3,10BnfA2Nbf(IV)-02 used in the light-emitting device 2 have the same structure of naphthobisbenzofuran, which is a main skeleton, they are different in the structure of amine bonded thereto.

The device structures of the light-emitting device 2 and the comparative light-emitting device 2 are listed in the following table.

According to FIG. 31 to FIG. 36 and Table 4, the light-emitting device 2 exhibits favorable characteristics, an external quantum efficiency of 11.9% at 1000 $cd/m^2$. It is also found that the light-emitting device 2 emits light with higher efficiency than the comparative light-emitting device 2.

Figure 37:
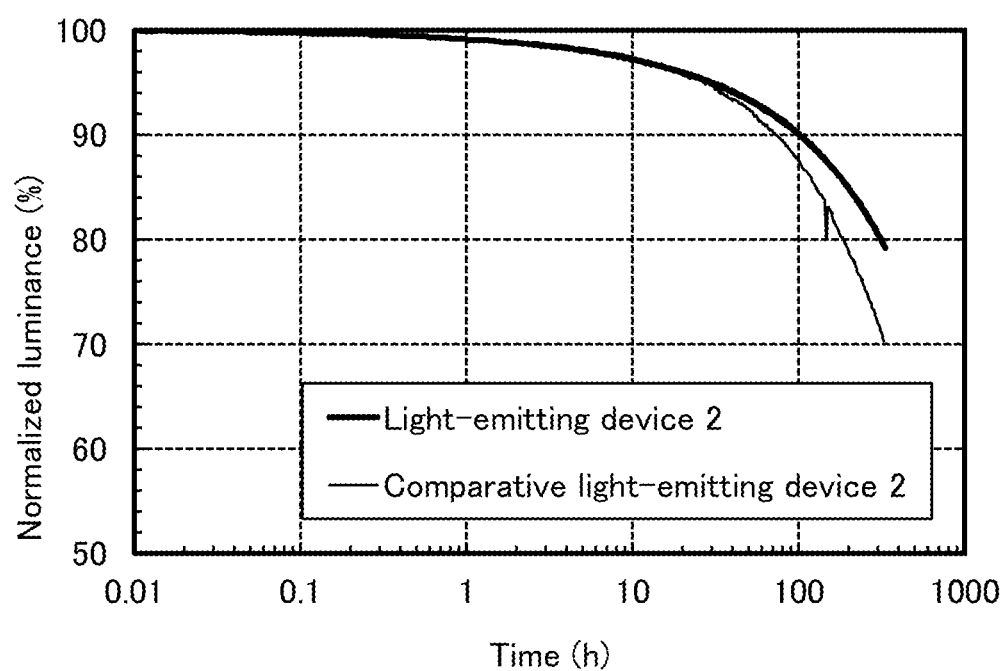
FIG. 37 is a diagram showing normalized luminance-time change characteristics of the light-emitting device 2 and the comparative light-emitting device 2.

FIG. 37 is a graph showing a change in luminance over driving time under the conditions where the current value was 2 mA and the current density was constant. As shown in FIG. 37, the light-emitting device 2 maintains 90% or more of the initial luminance even after 100-hour driving, which indicates that the light-emitting device 2 has an extremely favorable lifetime. Furthermore, the light-emit-

TABLE 3

|  | Hole-injection layer 10 nm | Hole-transport layer 30 nm | Light-emitting layer 25 nm | Electron-transport layer | Electron-injection layer 1 nm |
|---|---|---|---|---|---|
| Light-emitting device 2 | PCPPn: MoOx (4:2) | PCPPn | cgDBCzPA: 3,10BnfA2Nbf(IV)-02 (1:0.01) | cgDBCzPA 15 nm  NBPhen 10 nm | LiF |
| Comparative light-emitting device 2 |  |  | cgDBCzPA: 3,10DPhA2Nbf(IV) (1:0.01) | cgDBCzPA 10 nm  BPhen 15 nm |  |

The light-emitting device 2 and the comparative light-emitting device 2 were sealed using glass substrates in a glove box containing a nitrogen atmosphere so as not to be exposed to the air (a sealant was applied to surround the device, and UV treatment and 1-hour heat treatment at 80° C. were performed in sealing). Then, initial characteristics of these light-emitting devices were measured. The measurement was performed at room temperature.

Figure 31:
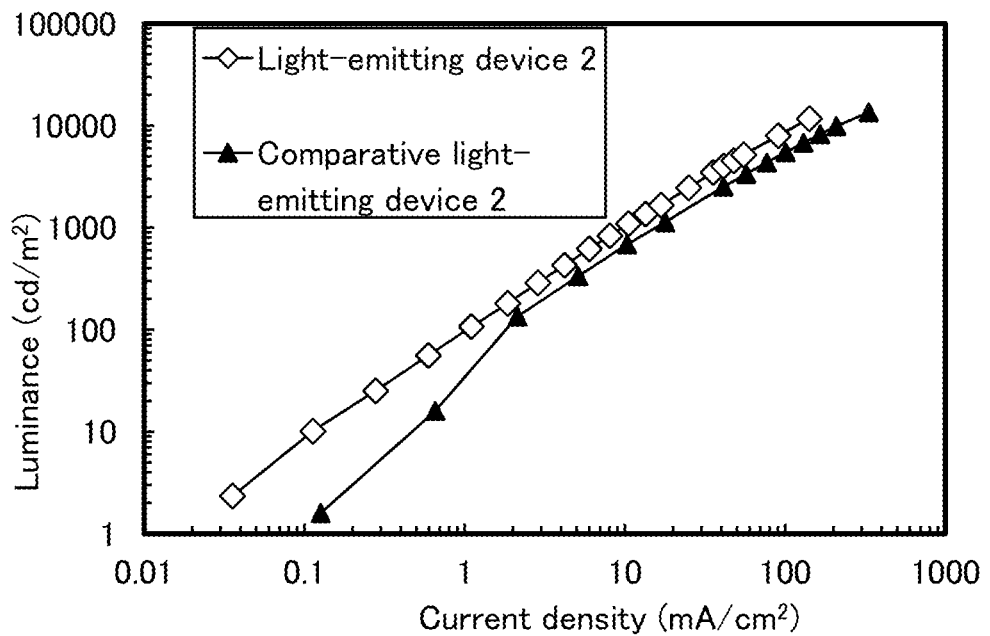
FIG. 31 is a diagram showing luminance-current density characteristics of a light-emitting device 2 and a comparative light-emitting device 2.
Figure 32:
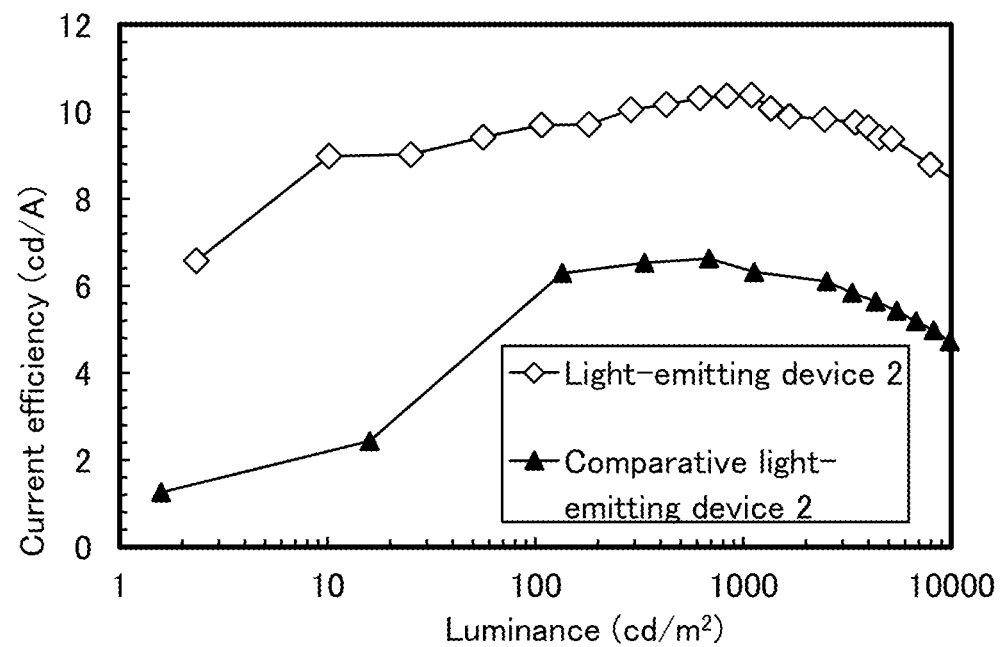
FIG. 32 is a diagram showing current efficiency-luminance characteristics of the light-emitting device 2 and the comparative light-emitting device 2.
Figure 33:
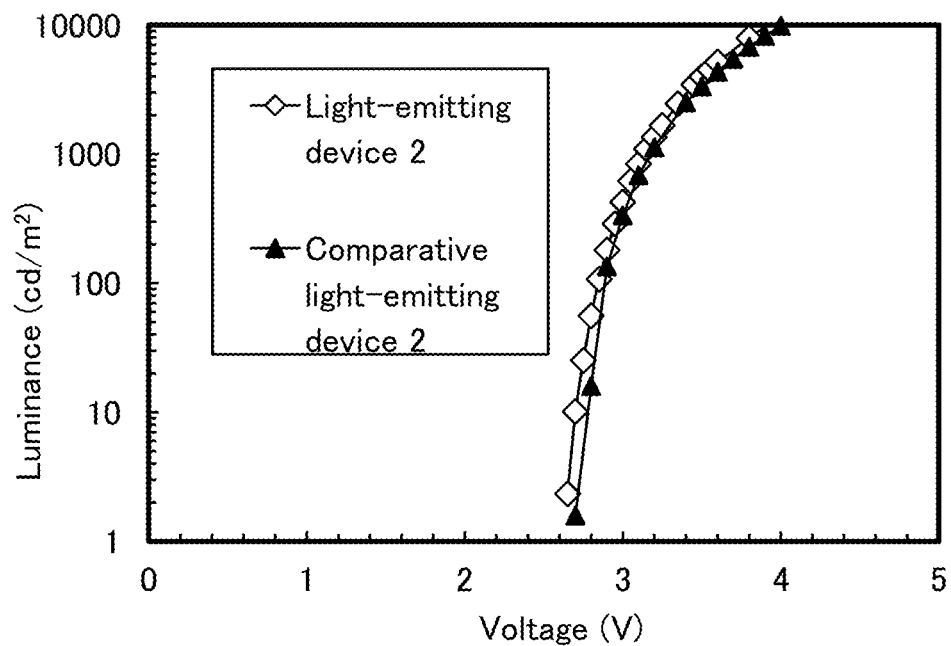
FIG. 33 is a diagram showing luminance-voltage characteristics of the light-emitting device 2 and the comparative light-emitting device 2.
Figure 34:
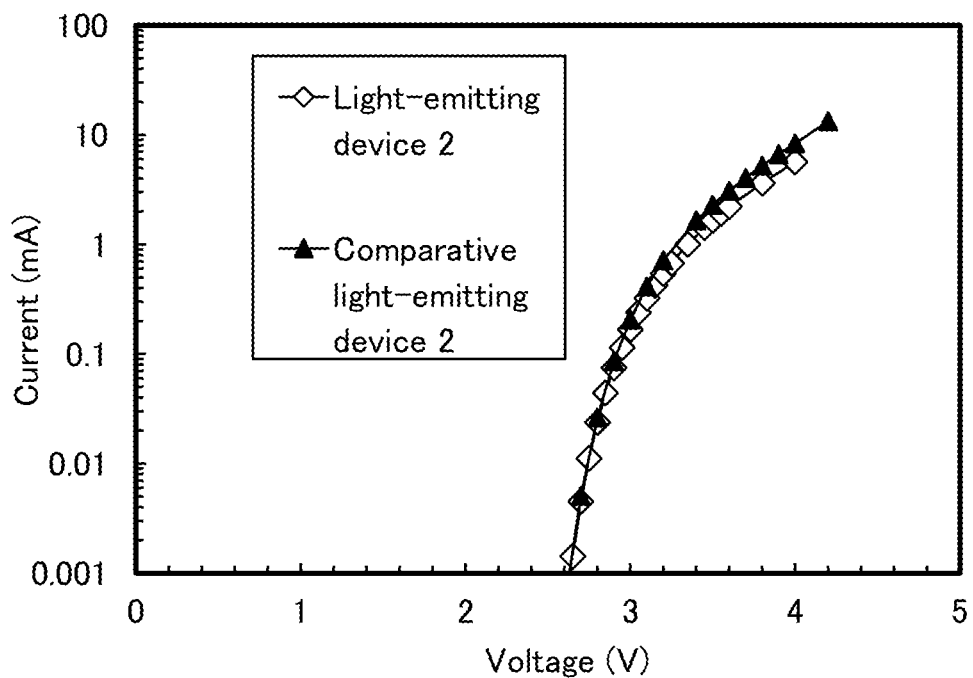
FIG. 34 is a diagram showing current-voltage characteristics of the light-emitting device 2 and the comparative light-emitting device 2.
Figure 35:
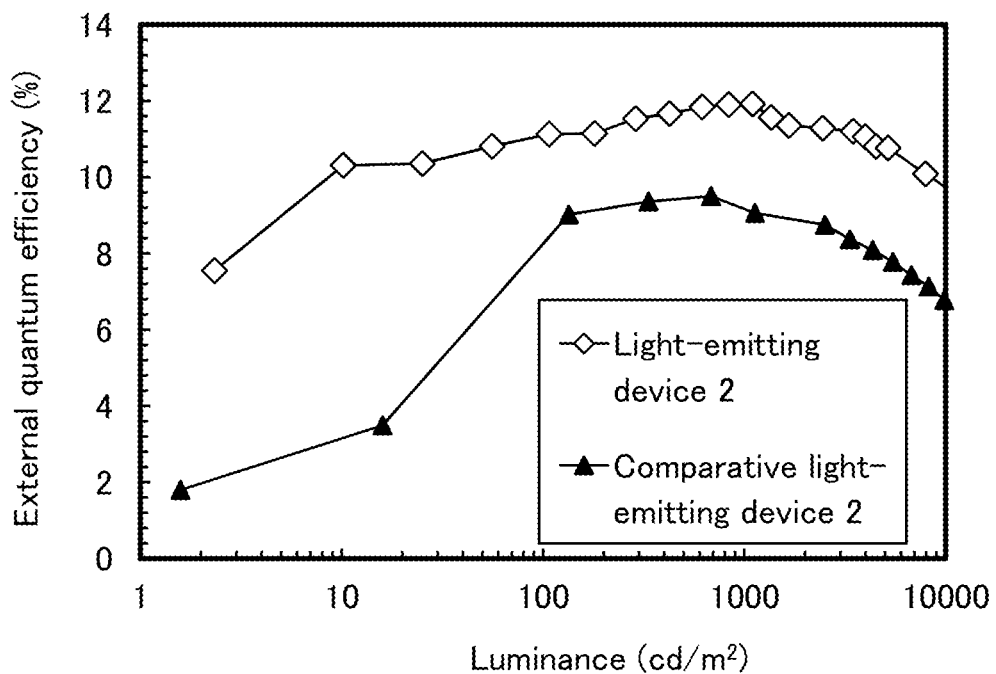
FIG. 35 is a diagram showing external quantum efficiency-luminance characteristics of the light-emitting device 2 and the comparative light-emitting device 2.
Figure 36:
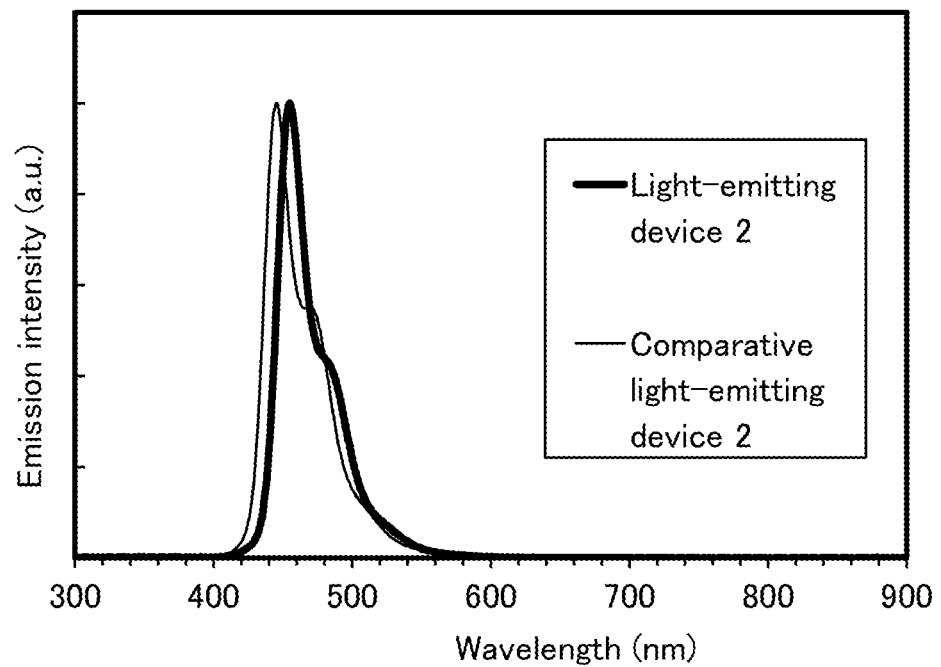
FIG. 36 is emission spectra of the light-emitting device 2 and the comparative light-emitting device 2.

FIG. 31 shows the luminance-current density characteristics of the light-emitting device 2 and the comparative light-emitting device 2; FIG. 32 shows the current efficiency-luminance characteristics thereof; FIG. 33 shows the luminance-voltage characteristics thereof; FIG. 34 shows the current-voltage characteristics thereof; FIG. 35 shows the external quantum efficiency-luminance characteristics thereof; and FIG. 36 shows the emission spectra thereof. In addition, their device characteristics at around a luminance of 1000 $cd/m^2$ are listed in Table 4.

ting device 2 was found to be a light-emitting device with a more favorable lifetime than the comparative light-emitting device 2.

The above results demonstrate that the naphthobisbenzofuran compound of one embodiment of the present invention, which has, as a substituent, an amino group including a benzonaphthofuranyl group, is a material with a favorable lifetime.

Example 7

In this example, a light-emitting device 3 that is the light-emitting device of one embodiment of the present invention described in Embodiments and a comparative light-emitting device 3 that is a light-emitting device for a comparative example are described in detail. Structural formulae of organic compounds used in the light-emitting device 3 and the comparative light-emitting device 3 are shown below.

TABLE 4

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 2 | 3.2 | 0.42 | 10.6 | 0.14 | 0.10 | 10.4 | 11.9 |
| Comparative light-emitting device 2 | 3.2 | 0.71 | 17.9 | 0.14 | 0.07 | 6.3 | 9.1 |

[Chemical Formulae 79]
(vii)
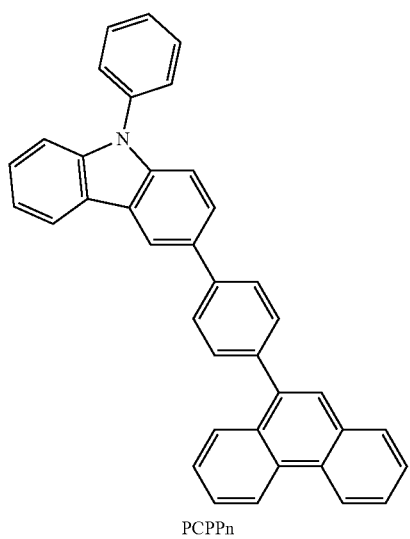
PCPPn
(viii)
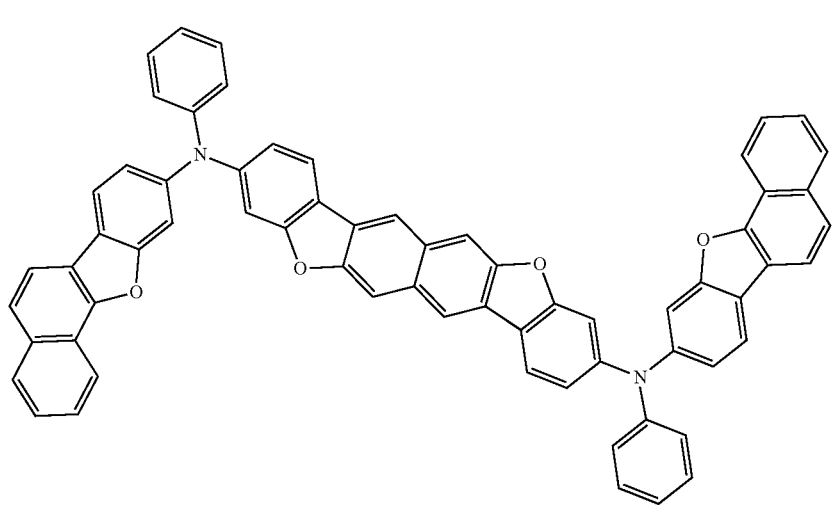
3,10aBnfA2Nbf(IV)-02

-continued
(ii)
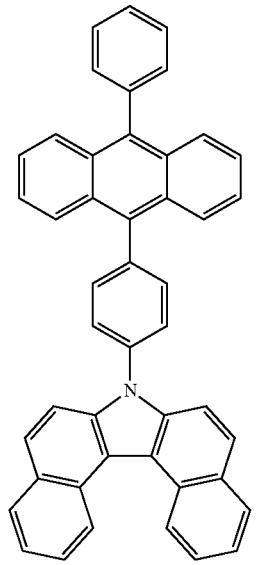
cgDBCzPA
(iv)
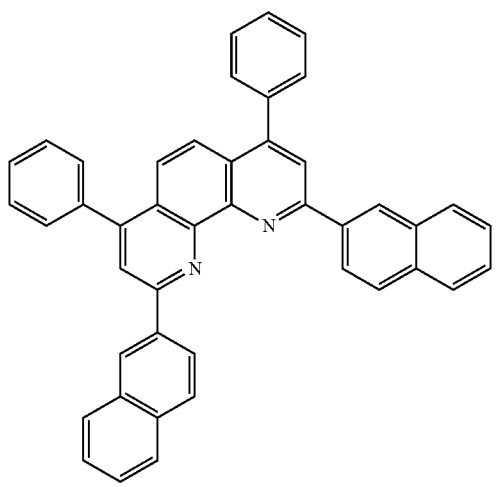
NBPhen
(v)
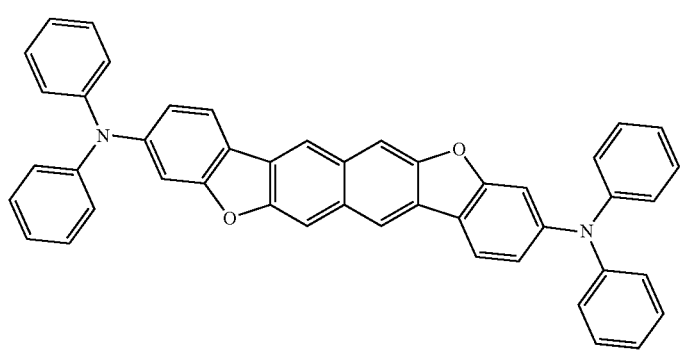
3,10DPhA2Nbf(IV)

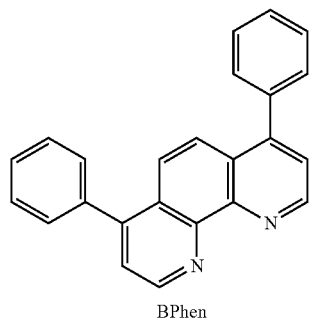

BPhen (Method for Fabricating Light-Emitting Device 3)

First, indium tin oxide containing silicon oxide (ITSO) was deposited on a glass substrate by a sputtering method to form the anode 101. The thickness was 70 nm, and the electrode area was 4 mm² (2 mm×2 mm).

Next, as pretreatment for forming a light-emitting device over the substrate, a surface of the substrate was washed with water, baking was performed at 200° C. for one hour, and then UV ozone treatment was performed for 370 seconds.

After that, the substrate was introduced into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)phenyl]-9-phenyl-9H-carbazole (abbreviation: PCPPn) represented by the above structural formula (vi) and molybdenum(VI) oxide were deposited by co-evaporation on the anode 101 to have a weight ratio of 4:2 (=PCPPn: molybdenum oxide) to a thickness of 10 nm by an evaporation method using resistance heating, whereby the hole-injection layer 111 was formed.

Next, over the hole-injection layer 111, PCPPn was deposited by evaporation to a thickness of 30 nm to form the hole-transport layer 112.

Next, 7-[4-(10-phenyl-9-anthryl)phenyl]-7H-dibenzo[c,g]carbazole (abbreviation: cgDBCzPA) represented by the above structural formula (ii) and N,N'-bis(benzo[b]naphtho[2,1-d]furan-9-yl)-N,N'-(diphenyl)naphtho[2,3-b;6,7-b"]bisbenzofuran-3,10-diamine (abbreviation: 3,10aBnfA2Nbf(IV)-02) represented by the above structural formula were deposited by co-evaporation to have a weight ratio of 1:0.01 (=cgDBCzPA: 3,10aBnfA2Nbf(IV)-02) to a thickness of 25 nm, whereby the light-emitting layer 113 was formed.

After that, over the light-emitting layer 113, cgDBCzPA was deposited by evaporation to a thickness of 15 nm, and 2,9-di(2-naphthyl)-4,7-diphenyl-1,10-phenanthroline (abbreviation: NBPhen) represented by the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting device 3 of this example was fabricated.

(Method for Fabricating Comparative Light-Emitting Device 3)

The comparative light-emitting device 3 was fabricated in such a manner that the light-emitting layer 113 was formed using 3,10-bis(diphenylamino)naphtho[2,3-b;6,7-b']bisbenzofuran (abbreviation: 3,10DPhA2Nbf(IV)) represented by the above structural formula (v) instead of 3,10aBnfA2Nbf(IV)-02 used for the light-emitting layer 113 in the light-emitting device 3, and the electron-transport layer 114 was formed by depositing cgDBCzPA by evaporation to a thickness of 10 nm and then depositing bathophenanthroline (abbreviation: BPhen) represented by the above structural formula (vi) by evaporation to a thickness of 15 nm. Although 3,10DPhA2Nbf(IV) used in the comparative light-emitting device 3 and 3,10aBnfA2Nbf(IV)-02 used in the light-emitting device 3 have the same structure of naphthobisbenzofuran, which is a main skeleton, they are different in the structure of amine bonded thereto.

The device structures of the light-emitting device 3 and the comparative light-emitting device 3 are listed in the following table.

TABLE 5

| | Hole-injection layer 10 nm | Hole-transport layer 30 nm | Light-emitting layer 25 nm | Electron-transport layer | | Electron-injection layer 1 nm |
|---|---|---|---|---|---|---|
| Light-emitting device 3 | PCPPn: MoOx (4:2) | PCPPn | cgDBCzPA: 3,10aBnfA2Nbf(IV)-02 (1:0.01) | cgDBCzPA 15 nm | NBPhen 10 nm | LiF |
| Comparative light-emitting device 3 | | | cgDBCzPA: 3,10DPhA2Nbf(IV) (1:0.01) | cgDBCzPA 10 nm | BPhen 15 nm | |

The light-emitting device 3 and the comparative light-emitting device 3 were sealed using glass substrates in a glove box containing a nitrogen atmosphere so as not to be exposed to the air (a sealant was applied to surround the device, and UV treatment and 1-hour heat treatment at 80° C. were performed in sealing). Then, initial characteristics of these light-emitting devices were measured. The measurement was performed at room temperature.

Figure 43:
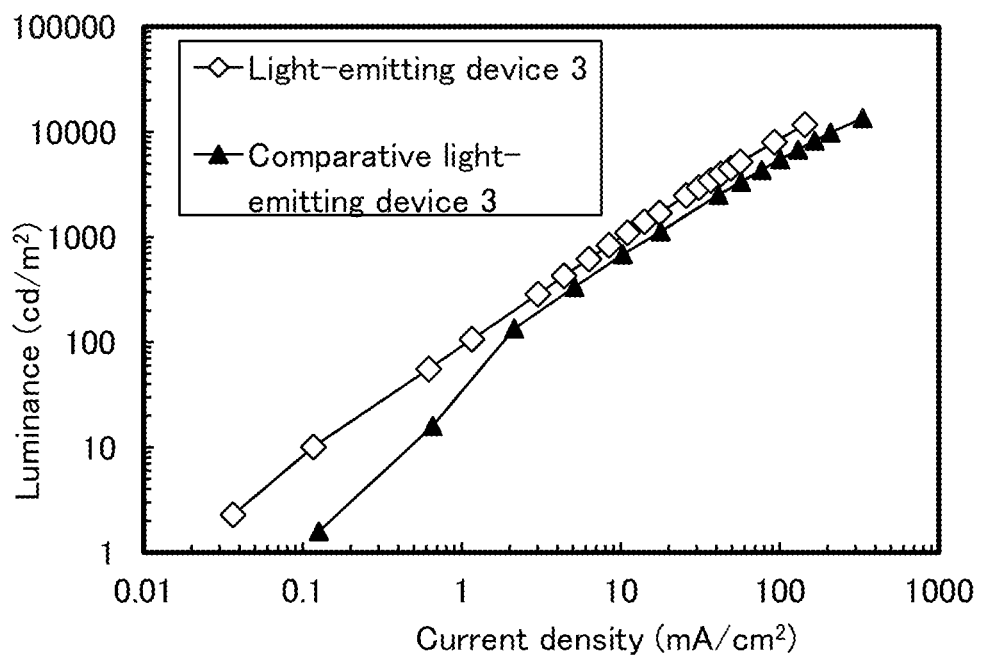
FIG. 43 is a diagram showing luminance-current density characteristics of a light-emitting device 3 and the comparative light-emitting device 2.
Figure 44:
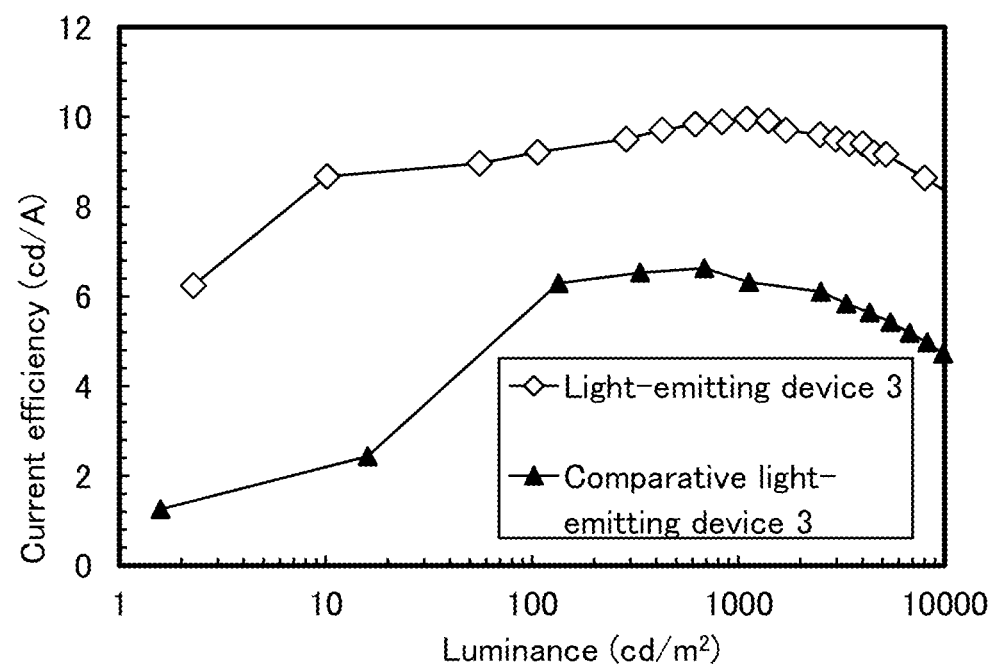
FIG. 44 is a diagram showing current efficiency-luminance characteristics of the light-emitting device 3 and the comparative light-emitting device 2.
Figure 45:
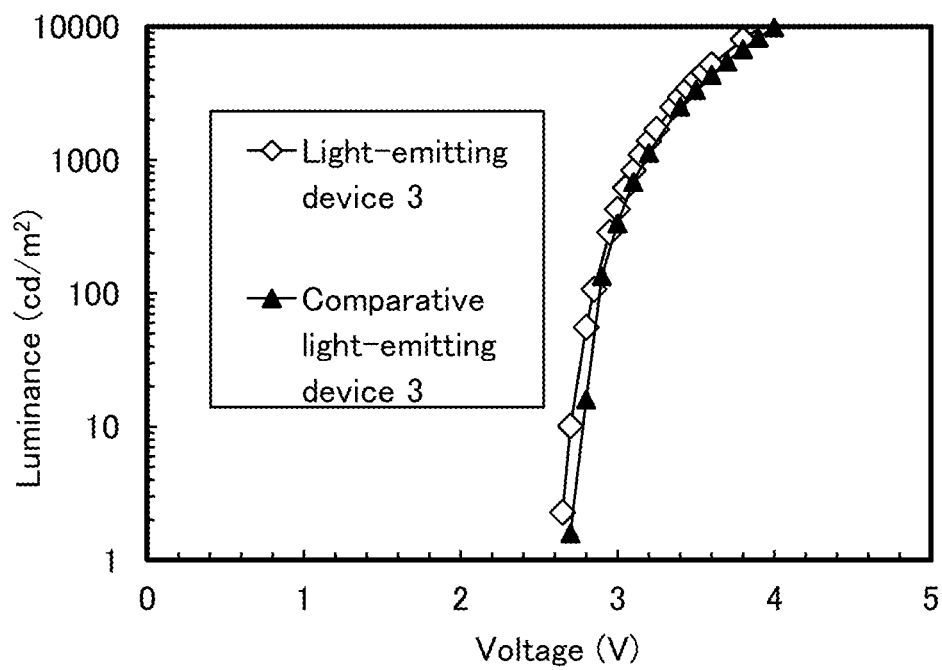
FIG. 45 is a diagram showing luminance-voltage characteristics of the light-emitting device 3 and the comparative light-emitting device 2.
Figure 46:
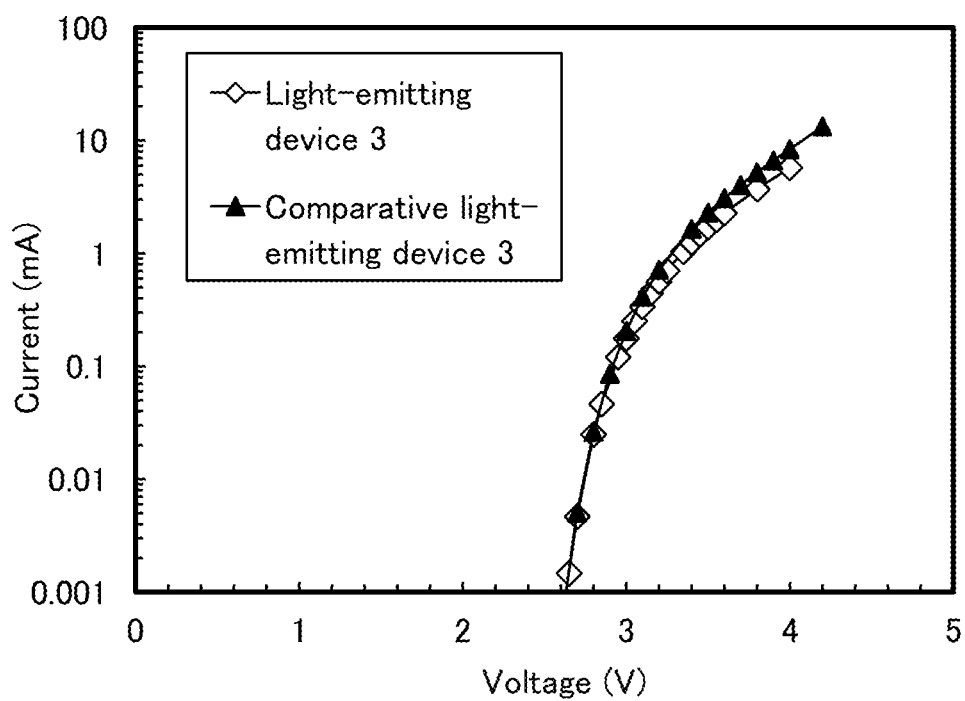
FIG. 46 is a diagram showing current-voltage characteristics of the light-emitting device 3 and the comparative light-emitting device 2.
Figure 47:
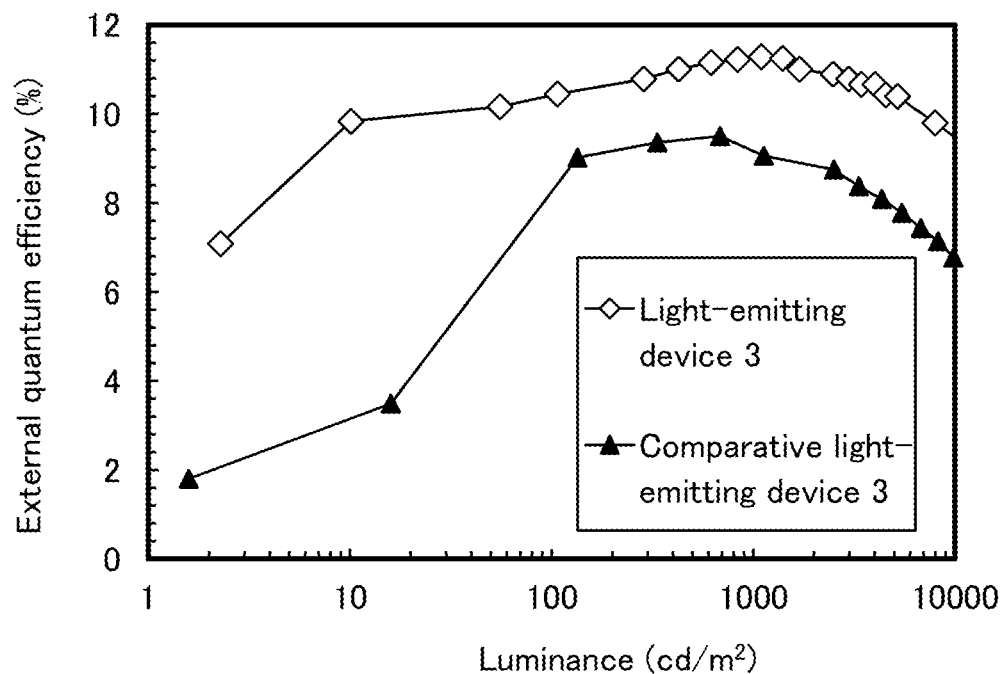
FIG. 47 is a diagram showing external quantum efficiency-luminance characteristics of the light-emitting device 3 and the comparative light-emitting device 2.
Figure 48:
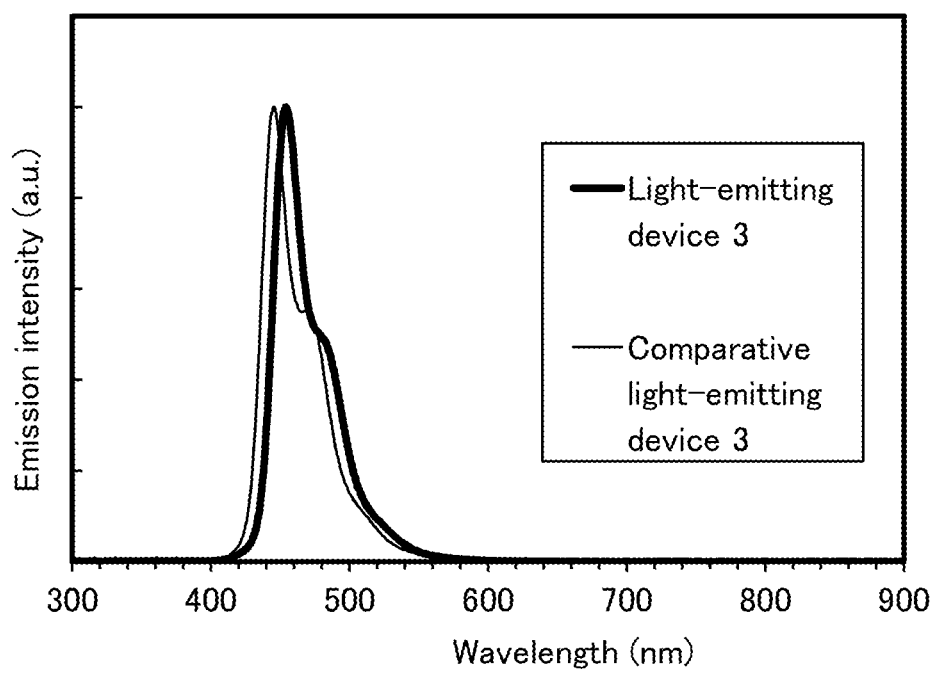
FIG. 48 is emission spectra of the light-emitting device 3 and the comparative light-emitting device 2.

FIG. 43 shows the luminance-current density characteristics of the light-emitting device 3 and the comparative light-emitting device 3; FIG. 44 shows the current efficiency-luminance characteristics thereof; FIG. 45 shows the luminance-voltage characteristics thereof; FIG. 46 shows the current-voltage characteristics thereof; FIG. 47 shows the external quantum efficiency-luminance characteristics thereof; and FIG. 48 shows the emission spectra thereof. In addition, their device characteristics at around a luminance of 1000 cd/m² are listed in Table 6.

TABLE 6

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 3 | 3.2 | 0.44 | 11.0 | 0.14 | 0.10 | 9.9 | 11.3 |
| Comparative light-emitting device 3 | 3.2 | 0.71 | 17.9 | 0.14 | 0.07 | 6.3 | 9.1 |

According to FIG. 43 to FIG. 48 and Table 6, the light-emitting device 3 exhibits favorable characteristics, an external quantum efficiency of 11.3% at a practical luminance of approximately 1000 cd/m², which reveals that the light-emitting device 3 emits light with higher efficiency than the comparative light-emitting device 3.

Figure 49:
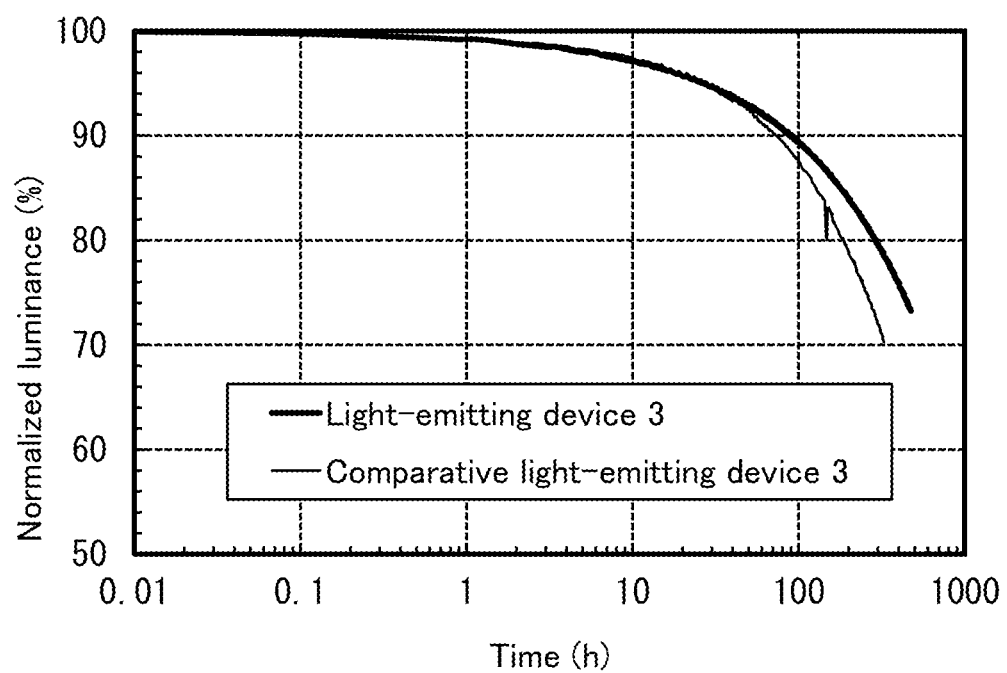
FIG. 49 is a diagram showing normalized luminance-time change characteristics of the light-emitting device 3 and the comparative light-emitting device 2.

FIG. 49 is a graph showing a change in luminance over driving time under the conditions where the current value was 2 mA and the current density was constant. As shown in FIG. 49, the light-emitting device 3 maintains approximately 90% of the initial luminance even after 100-hour driving, which indicates that the light-emitting device 3 has an extremely favorable lifetime. The light-emitting device 3 was also found to be a light-emitting device with a more favorable lifetime than the comparative light-emitting device.

The above results demonstrate that a light-emitting device using the naphthobisbenzofuran compound of one embodiment of the present invention, which has, as a substituent, an amino group including a benzonaphthofuranyl group, can be a light-emitting device emitting light efficiently and is a light-emitting device with a favorable lifetime.

Example 8

In this example, a light-emitting device 4 that is the light-emitting device of one embodiment of the present invention described in Embodiments and a comparative light-emitting device 4 that is a light-emitting device for a comparative example are described in detail. Structural formulae of organic compounds used in the light-emitting device 4 and the comparative light-emitting device 4 are shown below.

[Chemical Formulae 80]

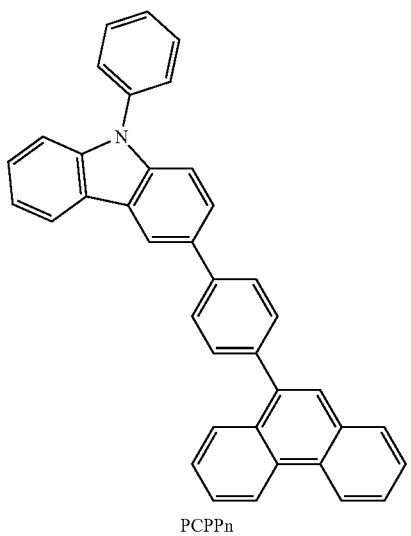

PCPPn (ix)
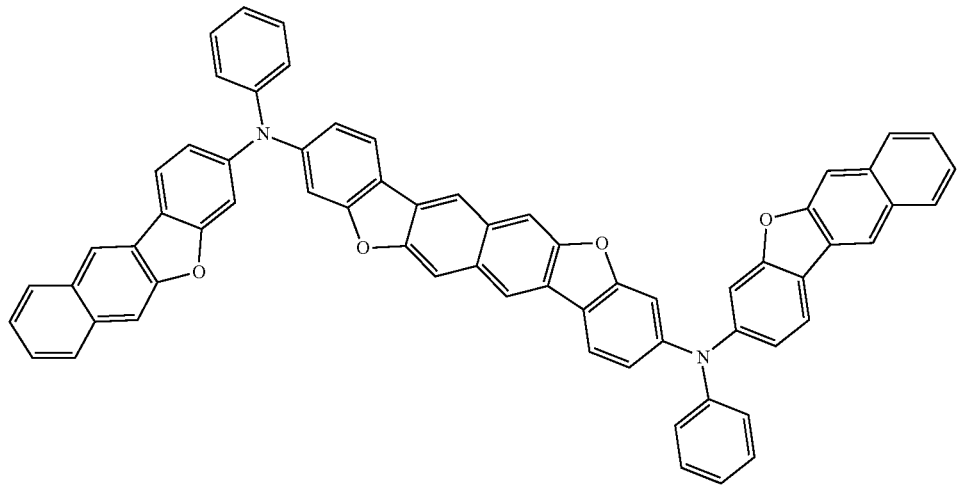
3,10Bnf(II)A2Nbf(IV)-02
(ii)
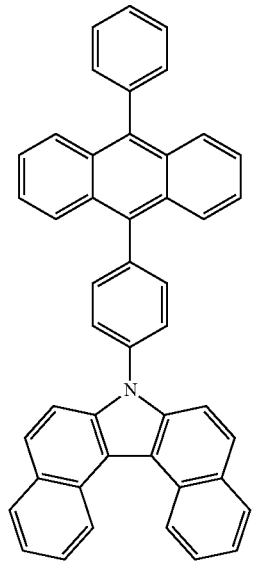
cgDBCzPA
(iv)
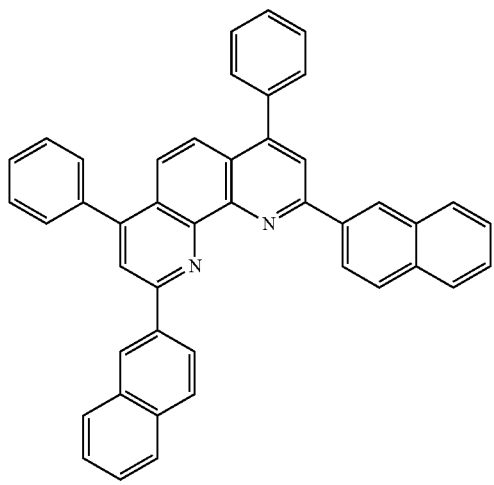
NBPhen

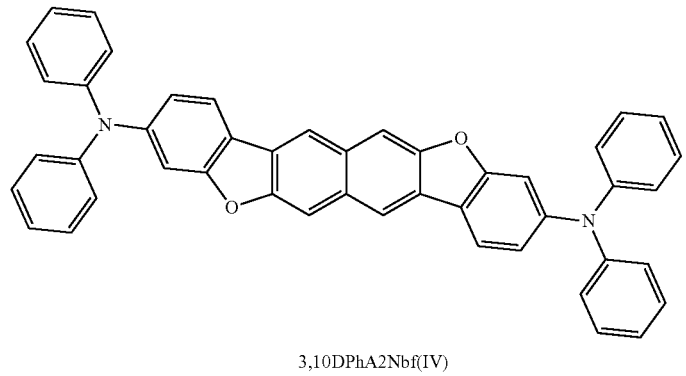

3,10DPhA2Nbf(IV)

BPhen (Method for Fabricating Light-Emitting Device 4)

First, indium tin oxide containing silicon oxide (ITSO) was deposited on a glass substrate by a sputtering method to form the anode 101. The thickness was 70 nm, and the electrode area was 4 mm² (2 mm×2 mm).

Next, as pretreatment for forming a light-emitting device over the substrate, a surface of the substrate was washed with water, baking was performed at 200° C. for one hour, and then UV ozone treatment was performed for 370 seconds.

After that, the substrate was introduced into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)phenyl]-9-phenyl-9H-carbazole (abbreviation: PCPPn) represented by the above structural formula (vi) and molybdenum(VI) oxide were deposited by co-evaporation on the anode 101 to have a weight ratio of 4:2 (=PCPPn: molybdenum oxide) to a thickness of 10 nm by an evaporation method using resistance heating, whereby the hole-injection layer 111 was formed.

Next, over the hole-injection layer 111, PCPPn was deposited by evaporation to a thickness of 30 nm to form the hole-transport layer 112.

Next, 7-[4-(10-phenyl-9-anthryl)phenyl]-7H-dibenzo[c,g]carbazole (abbreviation: cgDBCzPA) represented by the above structural formula (ii) and N,N'-bis(benzo[b]naphtho[2,3-d]furan-3-yl)-N,N'-diphenylnaphtho[2,3-b;6,7-b"]bis-benzofuran-3,10-diamine (abbreviation: 3,10Bnf(II)A2Nbf(IV)-02) represented by the above structural formula (ix) were deposited by co-evaporation to have a weight ratio of 1:0.015 (=cgDBCzPA: 3,10Bnf(II)A2Nbf(IV)-02) to a thickness of 25 nm, whereby the light-emitting layer 113 was formed.

After that, over the light-emitting layer 113, cgDBCzPA was deposited by evaporation to a thickness of 15 nm, and 2,9-di(2-naphthyl)-4,7-diphenyl-1,10-phenanthroline (abbreviation: NBPhen) represented by the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting device 4 of this example was fabricated.

(Method for Fabricating Comparative Light-Emitting Device 4)

The comparative light-emitting device 4 was fabricated in such a manner that the light-emitting layer 113 was formed using 3,10-bis(diphenylamino)naphtho[2,3-b;6,7-b']bisbenzofuran (abbreviation: 3,10DPhA2Nbf(IV)) represented by the above structural formula (v) instead of 3,10Bnf(II)A2Nbf(IV)-02 used for the light-emitting layer 113 in the light-emitting device 4, and the electron-transport layer 114 was formed by depositing cgDBCzPA by evaporation to a thickness of 10 nm and then depositing bathophenanthroline (abbreviation: BPhen) represented by the above structural formula (vi) by evaporation to a thickness of 15 nm. Although 3,10DPhA2Nbf(IV) used in the comparative light-emitting device 4 and 3,10Bnf(II)A2Nbf(IV)-02 used in the light-emitting device 4 have the same structure of naphthobisbenzofuran, which is a main skeleton, they are different in the structure of amine bonded thereto.

The device structures of the light-emitting device 4 and the comparative light-emitting device 4 are listed in the following table.

TABLE 7

|  | Hole-injection layer 10 nm | Hole-transport layer 30 nm | Light-emitting layer 25 nm | Electron-transport layer | | Electron-injection layer 1 nm |
|---|---|---|---|---|---|---|
| Light-emitting device 4 | PCPPn: MoOx (4:2) | PCPPn | cgDBCzPA: 3,10Bnf(II)A2Nbf(IV)-02 (1:0.015) | cgDBCzPA 15 nm | NBPhen 10 nm | LiF |
| Comparative light-emitting device 4 | | | cgDBCzPA: 3,10DPhA2Nbf(IV) (1:0.01) | cgDBCzPA 10 nm | BPhen 15 nm | |

The light-emitting device 4 and the comparative light-emitting device 4 were sealed using glass substrates in a glove box containing a nitrogen atmosphere so as not to be exposed to the air (a sealant was applied to surround the device, and UV treatment and 1-hour heat treatment at 80° C. were performed in sealing). Then, initial characteristics of these light-emitting devices were measured. The measurement was performed at room temperature.

Figure 50:
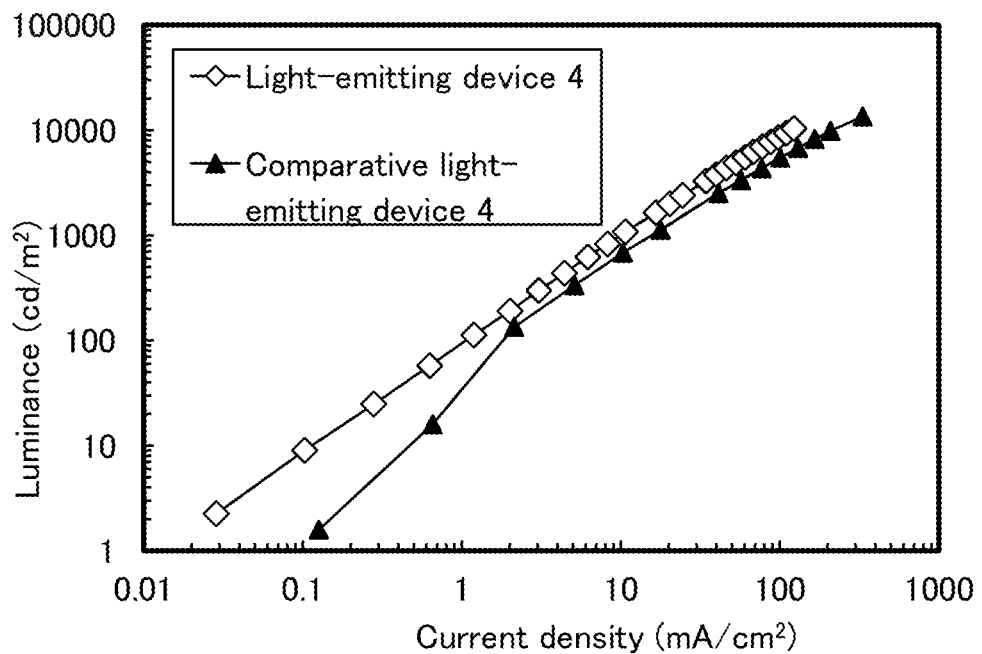
FIG. 50 is a diagram showing luminance-current density characteristics of a light-emitting device 4 and the comparative light-emitting device 2.
Figure 51:
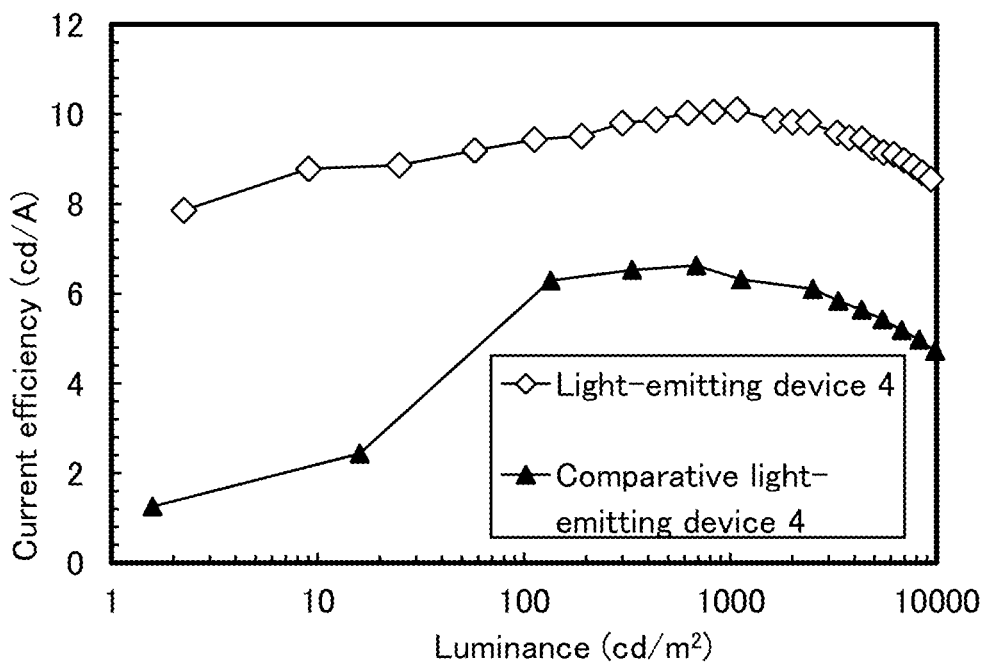
FIG. 51 is a diagram showing current efficiency-luminance characteristics of the light-emitting device 4 and the comparative light-emitting device 2.
Figure 52:
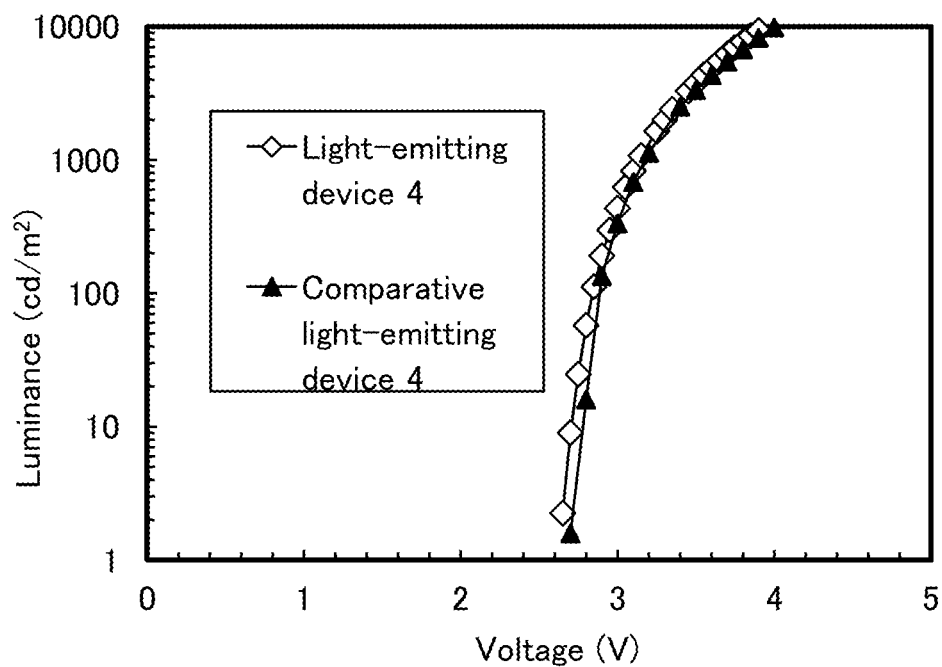
FIG. 52 is a diagram showing luminance-voltage characteristics of the light-emitting device 4 and the comparative light-emitting device 2.
Figure 53:
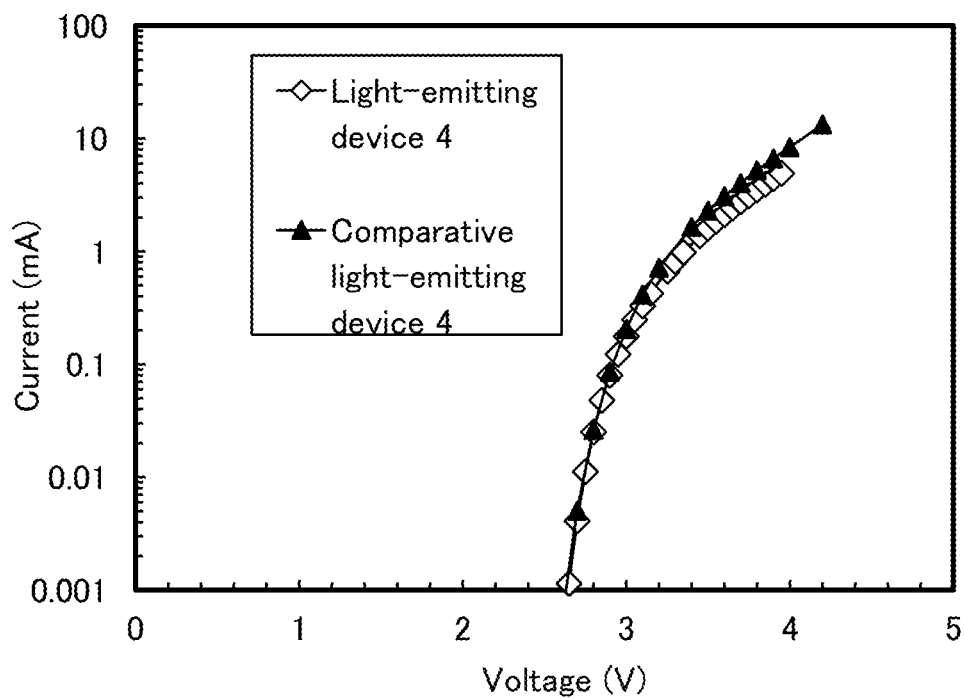
FIG. 53 is a diagram showing current-voltage characteristics of the light-emitting device 4 and the comparative light-emitting device 2.
Figure 54:
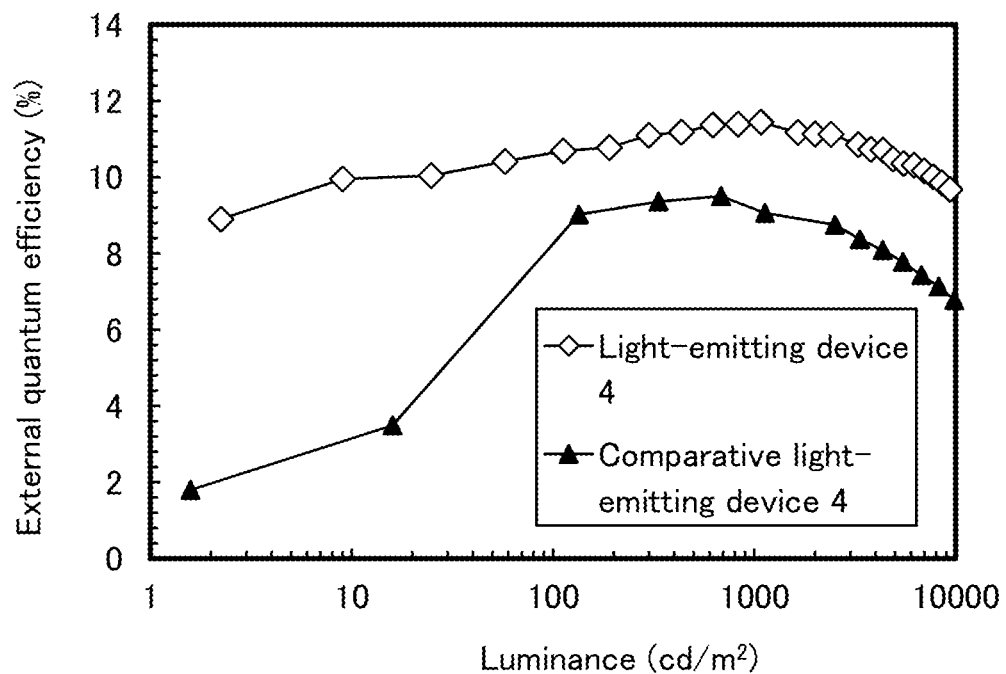
FIG. 54 is a diagram showing external quantum efficiency-luminance characteristics of the light-emitting device 4 and the comparative light-emitting device 2.
Figure 55:
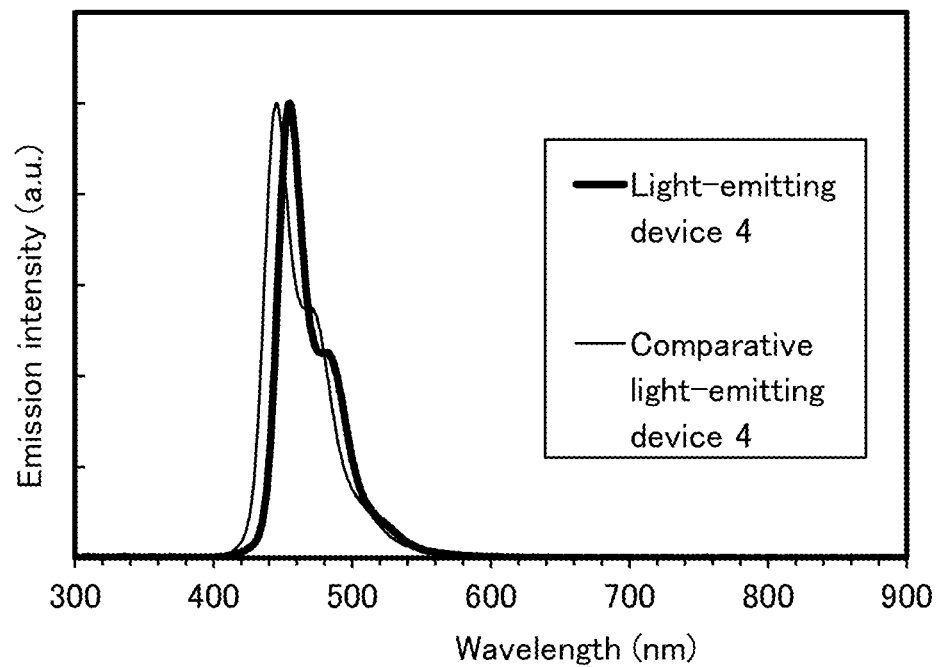
FIG. 55 is emission spectra of the light-emitting device 4 and the comparative light-emitting device 2.

FIG. 50 shows the luminance-current density characteristics of the light-emitting device 4 and the comparative light-emitting device 4; FIG. 51 shows the current efficiency-luminance characteristics thereof; FIG. 52 shows the luminance-voltage characteristics thereof; FIG. 53 shows the current-voltage characteristics thereof; FIG. 54 shows the external quantum efficiency-luminance characteristics thereof; and FIG. 55 shows the emission spectra thereof. In addition, their device characteristics at around a luminance of 1000 cd/m$^2$ are listed in Table 8.

TABLE 8

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 4 | 3.2 | 0.43 | 10.7 | 0.14 | 0.10 | 10.1 | 11.4 |
| Comparative light-emitting device 4 | 3.2 | 0.71 | 17.9 | 0.14 | 0.07 | 6.3 | 9.1 |

According to FIG. 50 to FIG. 55 and Table 8, the light-emitting device 4 exhibits favorable characteristics, an external quantum efficiency of 11.4% at a practical luminance of approximately 1000 cd/m², which reveals that the light-emitting device 4 emits light with higher efficiency than the comparative light-emitting device 4.

Example 9

In this example, a light-emitting device 5 that is the light-emitting device of one embodiment of the present invention described in Embodiments is described in detail. Structural formulae of organic compounds used in the light-emitting device 5 are shown below.

[Chemical Formulae 81]

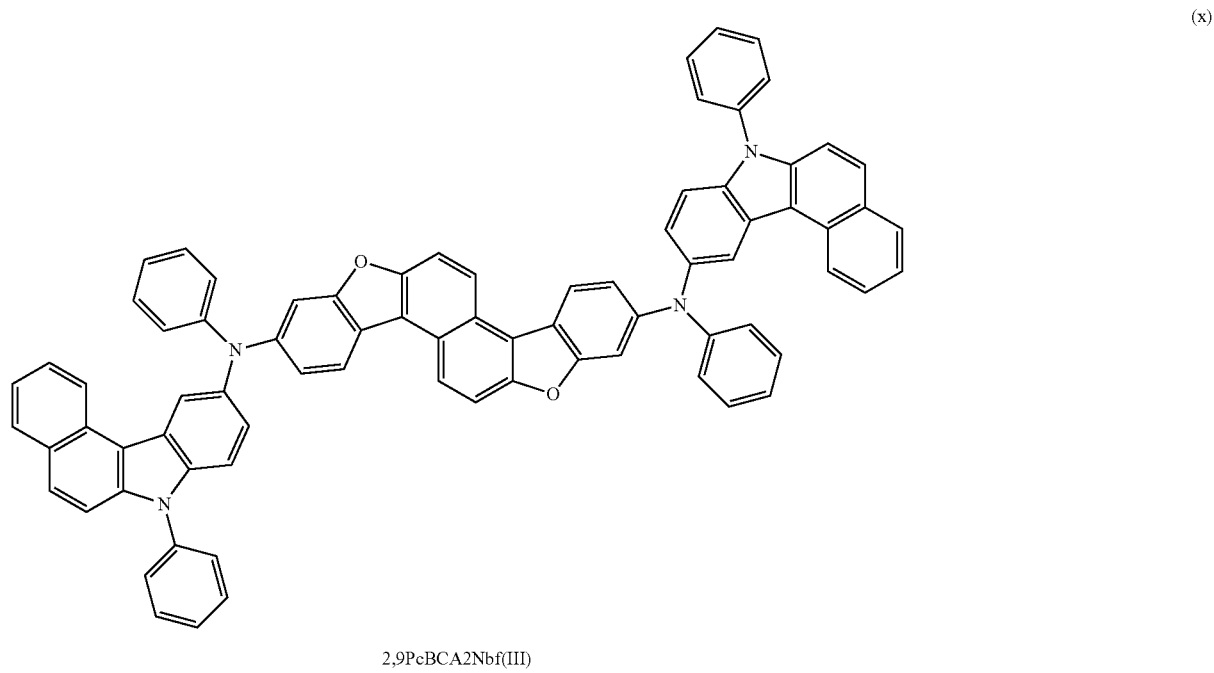

2,9PcBCA2Nbf(III)

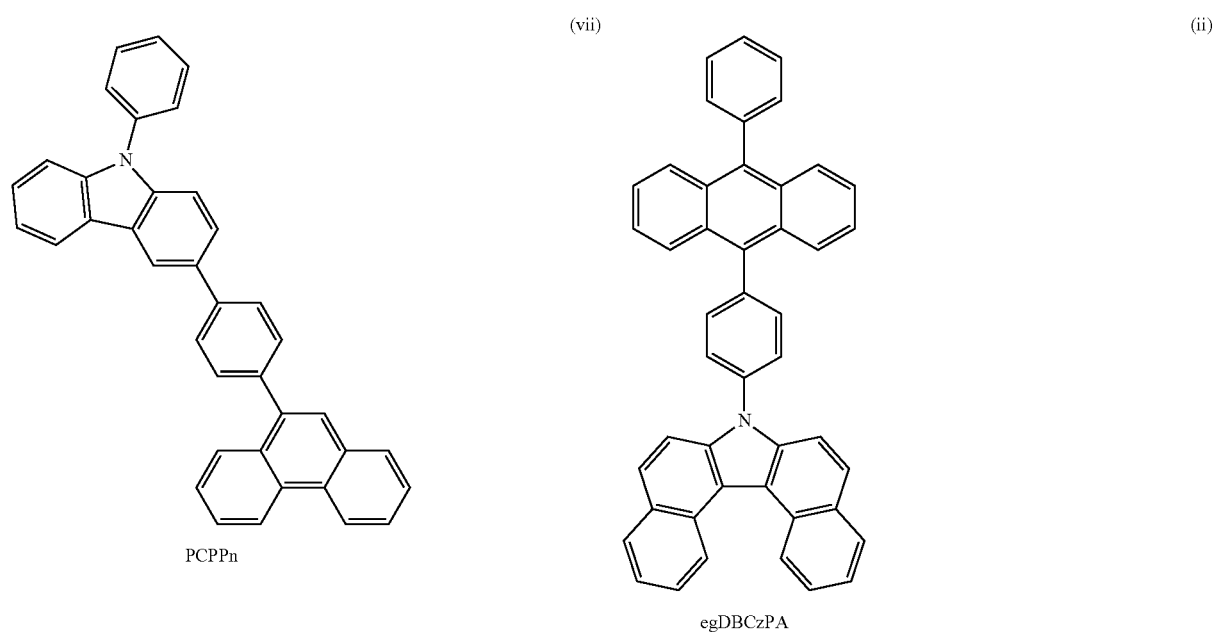

PCPPn egDBCzPA

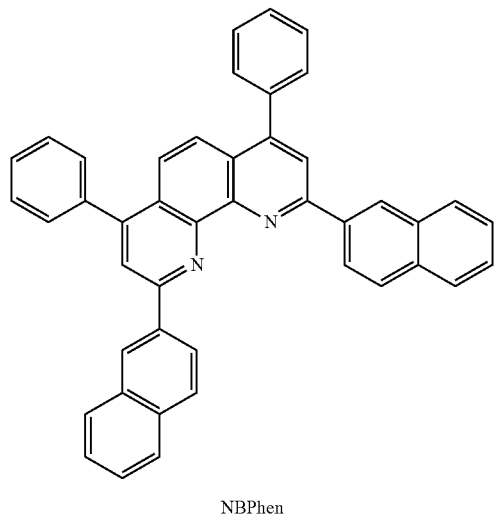

NBPhen (iv)

(Method for Fabricating Light-Emitting Device 5)

First, indium tin oxide containing silicon oxide (ITSO) was deposited on a glass substrate by a sputtering method to form the anode 101. The thickness was 70 nm, and the electrode area was 4 mm² (2 mm×2 mm).

Next, as pretreatment for forming a light-emitting device over the substrate, a surface of the substrate was washed with water, baking was performed at 200° C. for one hour, and then UV ozone treatment was performed for 370 seconds.

After that, the substrate was introduced into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)phenyl]-9-phenyl-9H-carbazole (abbreviation: PCPPn) represented by the above structural formula (vi) and molybdenum(VI) oxide were deposited by co-evaporation on the anode 101 to have a weight ratio of 4:2 (=PCPPn: molybdenum oxide) to a thickness of 10 nm by an evaporation method using resistance heating, whereby the hole-injection layer 111 was formed.

Next, over the hole-injection layer 111, PCPPn was deposited by evaporation to a thickness of 30 nm to form the hole-transport layer 112.

Next, 7-[4-(10-phenyl-9-anthryl)phenyl]-7H-dibenzo[c,g]carbazole (abbreviation: cgDBCzPA) represented by the above structural formula (ii) and N,N'-diphenyl-N,N'-(7-phenylbenzo[c]carbazol-10-yl)naphtho[2,1-b; 6,5-b']bisbenzofuran-2,9-diamine (abbreviation: 2,9PcBCA2Nbf(III)) represented by the above structural formula (x) were deposited by co-evaporation to have a weight ratio of 1:0.03 (=cgDBCzPA: 2,9PcBCA2Nbf(III)) to a thickness of 25 nm, whereby the light-emitting layer 113 was formed.

After that, over the light-emitting layer 113, cgDBCzPA was deposited by evaporation to a thickness of 15 nm, and 2,9-di(2-naphthyl)-4,7-diphenyl-1,10-phenanthroline (abbreviation: NBPhen) represented by the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting device 5 of this example was fabricated.

The device structure of the light-emitting device 5 is listed in the following table.

TABLE 9

| | Hole-injection layer 10 nm | Hole-transport layer 30 nm | Light-emitting layer 25 nm | Electron-transport layer | | Electron-injection layer 1 nm |
|---|---|---|---|---|---|---|
| Light-emitting device 5 | PCPPn: MoOx (4:2) | PCPPn | cgDBCzPA: 2,9PcBCA2Nbf(III) (1:0.03) | cgDBCzPA 15 nm | NBPhen 10 nm | LiF |

The light-emitting device 5 was sealed using glass substrates in a glove box containing a nitrogen atmosphere so as not to be exposed to the air (a sealant was applied to surround the device, and UV treatment and 1-hour heat treatment at 80° C. were performed in sealing). Then, initial characteristics of the light-emitting device were measured. The measurement was performed at room temperature.

Figure 56:
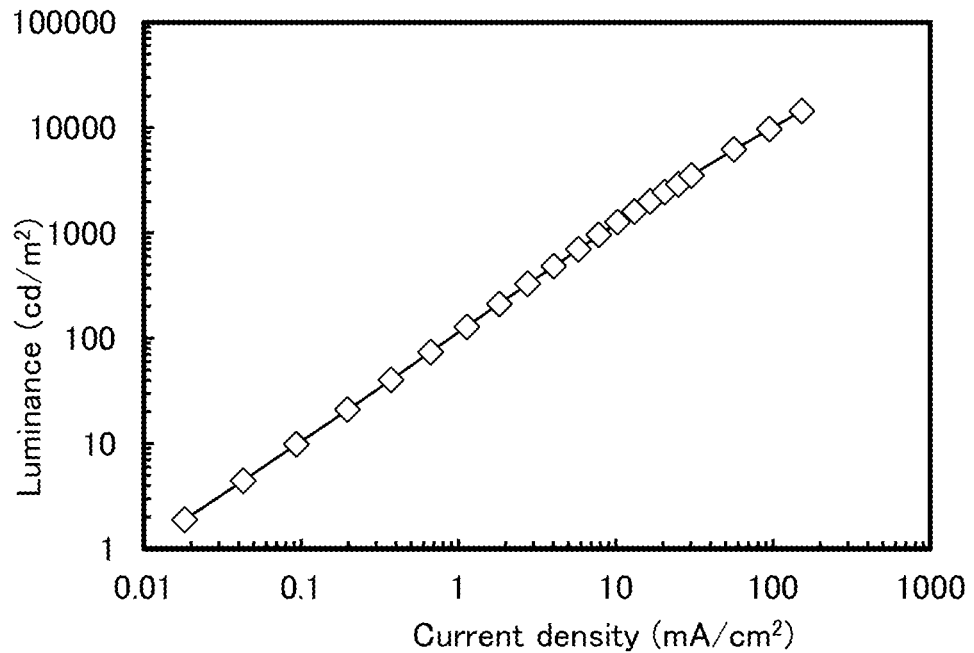
FIG. 56 is a diagram showing luminance-current density characteristics of a light-emitting device 5.
Figure 57:
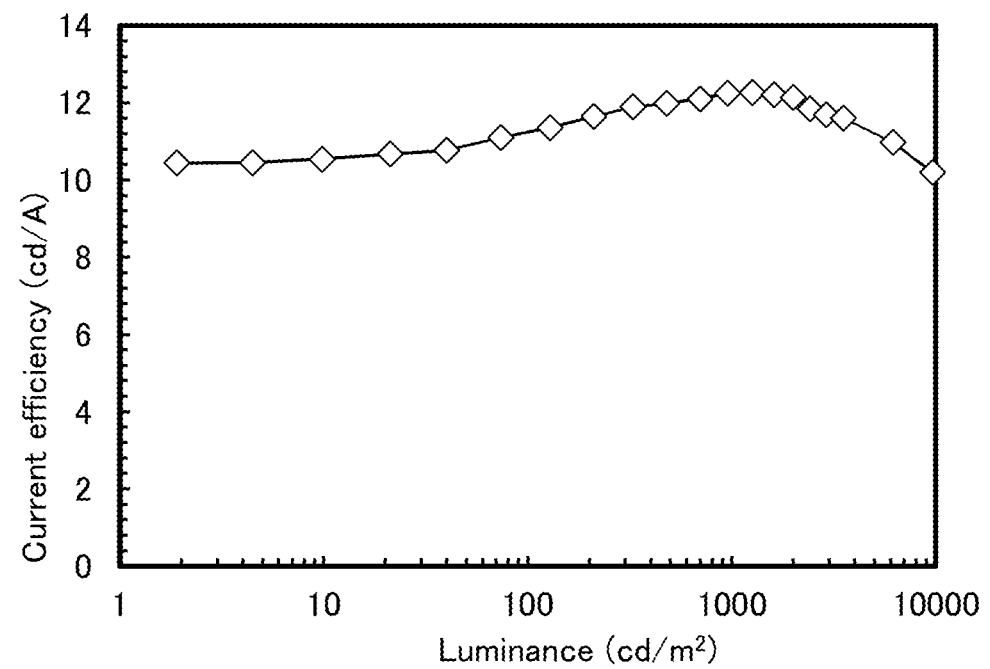
FIG. 57 is a diagram showing current efficiency-luminance characteristics of the light-emitting device 5.
Figure 58:
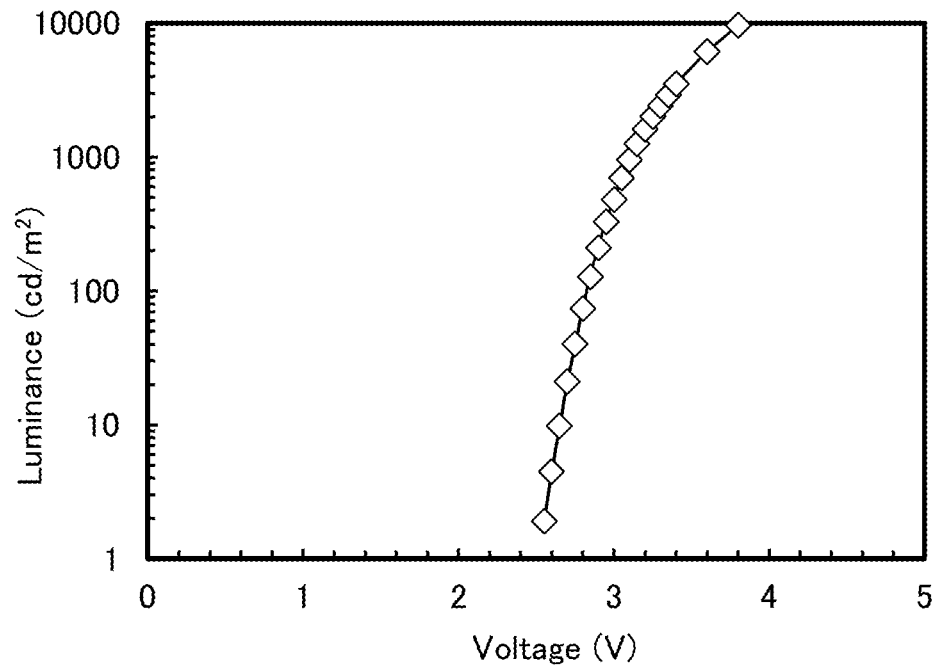
FIG. 58 is a diagram showing luminance-voltage characteristics of the light-emitting device 5.
Figure 59:
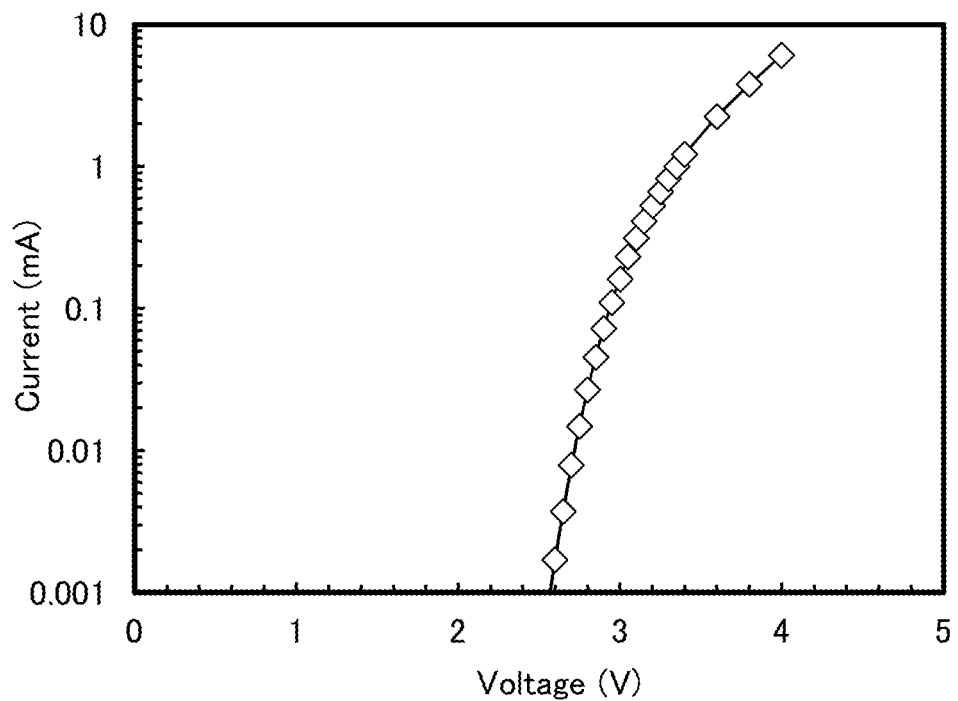
FIG. 59 is a diagram showing current-voltage characteristics of the light-emitting device 5.

FIG. 56 shows the luminance-current density characteristics of the light-emitting device 5; FIG. 57 shows the current efficiency-luminance characteristics thereof; FIG. 58 shows the luminance-voltage characteristics thereof; FIG.

Figure 60:
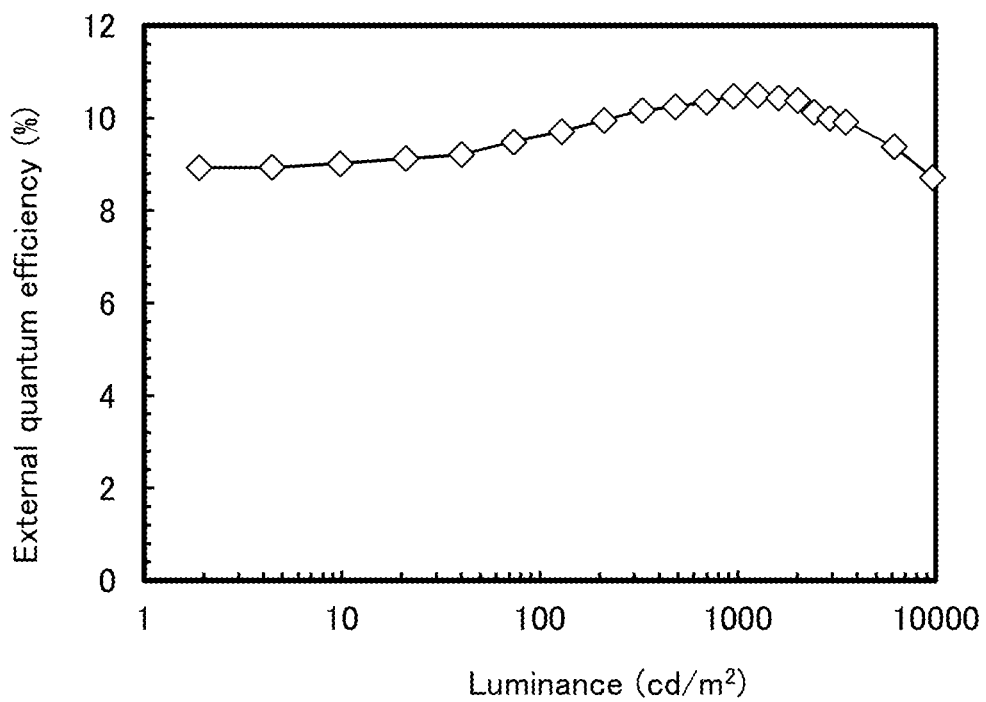
FIG. 60 is a diagram showing external quantum efficiency-luminance characteristics of the light-emitting device 5.
Figure 61:
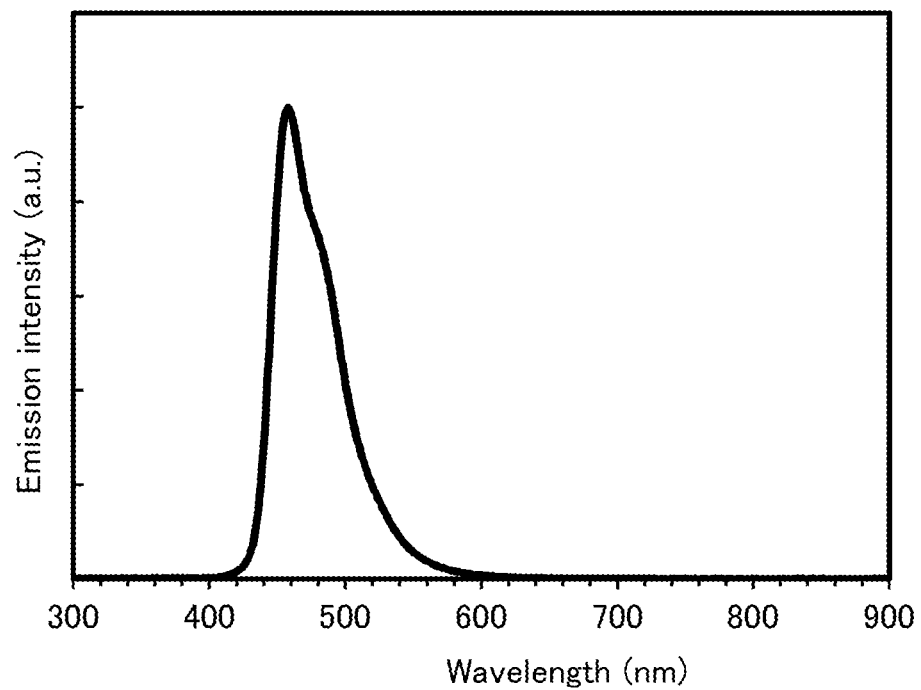
FIG. 61 is an emission spectrum of the light-emitting device 5.

59 shows the current-voltage characteristics thereof; FIG. 60 shows the external quantum efficiency-luminance characteristics thereof; and FIG. 61 shows the emission spectra thereof. In addition, their device characteristics at around a luminance of 1000 cd/m² are listed in Table 10.

TABLE 10

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 5 | 3.1 | 0.31 | 7.8 | 0.14 | 0.15 | 12.3 | 10.5 |

According to FIG. 56 to FIG. 61 and Table 10, the light-emitting device 5 exhibits favorable characteristics, an external quantum efficiency of 10.5% at a luminance of approximately 1000 cd/m².

REFERENCE NUMERALS

101: anode, 102: cathode, 103: EL layer, 111: hole-injection layer, 112: hole-transport layer, 113: light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: first electrode, 502: second electrode, 503: EL layer, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current controlling FET, 613: first electrode, 614: insulator, 616: EL layer, 617: second electrode, 618: light-emitting device, 623: n-channel FET, 624: p-channel FET, 730: insulating film, 770: planarization insulating film, 772: conductive film, 782: light-emitting device, 783: droplet discharge apparatus, 784: droplet, 785: layer, 786: layer containing light-emitting substance, 788: conductive film, 901: housing, 902: liquid crystal layer, 903: backlight unit, 904: housing, 905: driver IC, 906: terminal, 951: substrate, 952: electrode, 953: insulating layer, 954: partition layer, 955: EL layer, 956: electrode, 1001 substrate, 1002 base insulating film, 1003 gate insulating film, 1006 gate electrode, 1007 gate electrode, 1008 gate electrode, 1020 first interlayer insulating film, 1021 second interlayer insulating film, 1022 electrode, 1024W first electrode of light-emitting device, 1024R first electrode of light-emitting device, 1024G first electrode of light-emitting device, 1024B first electrode of light-emitting device, 1025 partition, 1028 EL layer, 1029 cathode, 1031 sealing substrate, 1032 sealant, 1033 transparent base material, 1034R red coloring layer, 1034G green coloring layer, 1034B blue coloring layer, 1035 black layer (black matrix), 1036 overcoat layer, 1037 third interlayer insulating film, 1040 pixel portion, 1041 driver circuit portion, 1042 peripheral portion, 1400: droplet discharge apparatus, 1402: substrate, 1403: droplet discharge means, 1404: imaging means, 1405: head, 1406: dotted line, 1407: control means, 1408: storage medium, 1409: image processing means, 1410: computer, 1411: marker, 1412: head, 1413: material supply source, 1414: material supply source, 1415: material supply source, 1416: head, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9033: fastener, 9034: switch, 9035: power switch, 9036: switch, 9310: portable information terminal, 9311: display panel, 9312: display region, 9313: hinge, 9315: housing, 9630: housing, 9631: display portion, 9631a: display portion, 9631b: display portion, 9632a: touch panel region, 9632b: touch panel region, 9633: solar cell, 9634: charge and discharge control circuit, 9635: battery, 9636: DCDC converter, 9637: operation key, 9638: converter, 9639: button This application is based on Japanese Patent Application Serial No. 2018-092186 filed with Japan Patent Office on May 11, 2018, the entire contents of which are hereby incorporated herein by reference.

What is claimed is:

1. An organic compound represented by a general formula (G1),

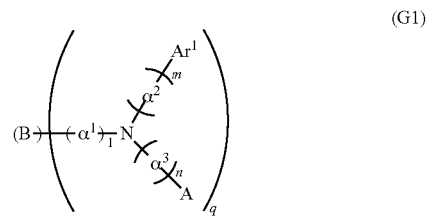

wherein:

B is any of skeletons represented by a general formula (B1) to a general formula (B3),

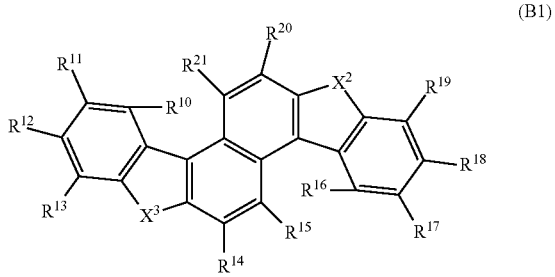

-continued

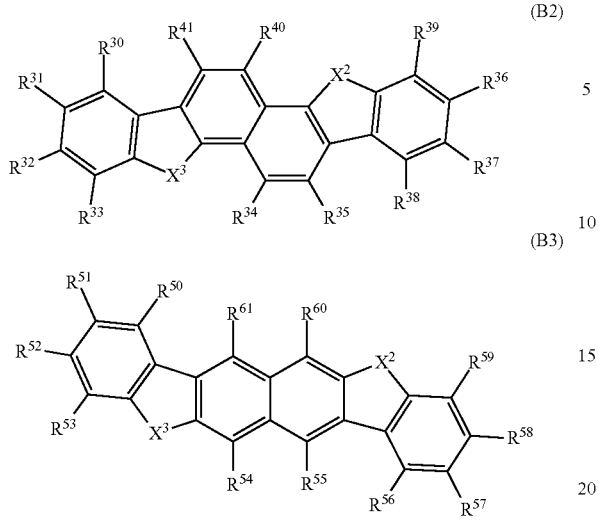

(B2)

(B3)

wherein:

$X^2$ and $X^3$ each independently represent an oxygen atom or a sulfur atom;

any one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms;

any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; and any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms, $Ar^1$ is any one of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group, and the substituted or unsubstituted dibenzofuranyl group, the substituted or unsubstituted dibenzothiophenyl group, and the substituted or unsubstituted carbazolyl group have a structure in which a benzene ring is condensed;

A is any of a substituted or unsubstituted dibenzofuranyl group in which at least one benzene ring is condensed, a substituted or unsubstituted dibenzothiophenyl group in which at least one benzene ring is condensed, and a substituted or unsubstituted carbazolyl group in which at least one benzene ring is condensed, $\alpha^1$ to $\alpha^3$ are each independently a substituted or unsubstituted divalent aromatic hydrocarbon group having 6 to 25 carbon atoms, and l, m, and n each independently represent any of integers from 0 to 2, and q is 1 or 2.

2. The organic compound according to claim 1, wherein q in the general formula (G1) is 2.

3. The organic compound according to claim 1, wherein:

q in the general formula (G1) is 2;

$X^2$ and $X^3$ each independently represent an oxygen atom or a sulfur atom;

$R^{12}$ and $R^{18}$ represent a single bond and $R^{10}$, $R^{11}$, $R^{13}$ to $R^{17}$, and $R^{19}$ to $R^{21}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms;

$R^{32}$ and $R^{38}$ represent a single bond and $R^{30}$, $R^{31}$, $R^{33}$ to $R^{37}$, and $R^{39}$ to $R^{41}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; and $R^{52}$ and $R^{58}$ represent a single bond and $R^{50}$, $R^{51}$, $R^{53}$ to $R^{57}$, and $R^{59}$ to $R^{61}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

4. The organic compound according to claim 1, wherein a molecular weight is less than or equal to 1300.

5. A light-emitting device comprising the organic compound according to claim 1.

6. A light-emitting apparatus comprising the light-emitting device according to claim 5, and a transistor or a substrate.

7. An electronic device comprising the organic compound according to claim 1.

8. An organic compound represented by a general formula (G1),

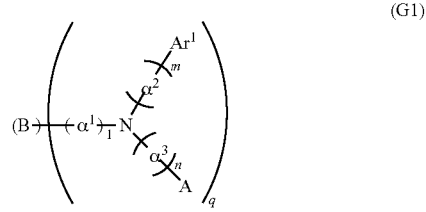

(G1)

wherein:
B is any of skeletons represented by a general formula (B1) to a general formula (B3), (B1)
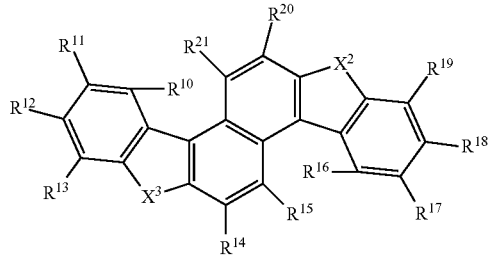

(B2)
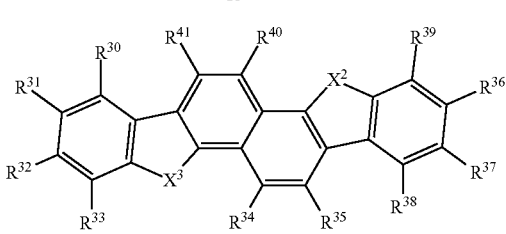

(B3)
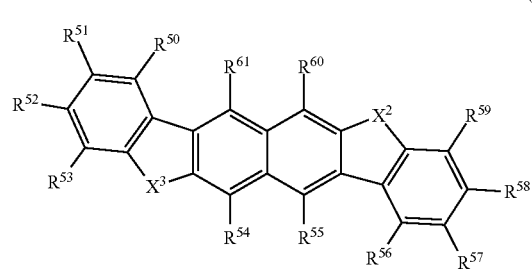

wherein:
$X^2$ and $X^3$ each independently represent an oxygen atom or a sulfur atom;
any one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms;
any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; and
any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms,
$Ar^1$ is any of a substituted or unsubstituted aromatic hydrocarbon group having 6 to 25 carbon atoms and groups represented by general formulae (g1) to (g3);
A is any of the groups represented by the general formulae (g1) to (g3);
$\alpha^1$ to $\alpha^3$ are each independently any of substituted or unsubstituted divalent aromatic hydrocarbon groups having 6 to 14 carbon atoms; and
l, m, and n each independently represent any of integers from 0 to 2, and q is 1 or 2, (g1)
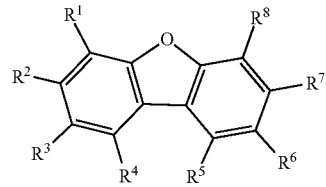

(g2)
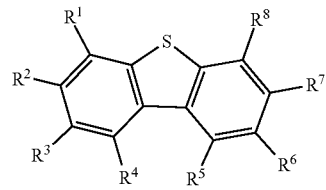

(g3)
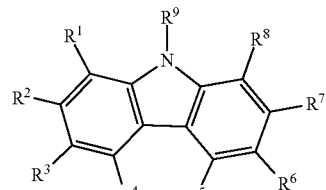

wherein:
any one of $R^1$ to $R^9$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms;
A has a structure in which condensation occurs in at least one of combinations of $R^1$ and $R^2$, $R^2$ and $R^3$, $R^3$ and $R^4$, $R^5$ and $R^6$, $R^6$ and $R^7$, and $R^7$ and $R^8$ among $R^1$ to $R^8$ and a benzene ring is formed;
n is 1 or 2 when A is represented by the general formula (g3) and $R^9$ in (g3) represents a single bond;
$R^1$ and $R^2$, $R^2$ and $R^3$, $R^3$ and $R^4$, $R^5$ and $R^6$, $R^6$ and $R^7$, and $R^7$ and $R^8$ among $R^1$ to $R^8$ are condensed to form a benzene ring when $Ar^1$ is the group represented by the general formulae (g1) to (g3); and
m is 1 or 2 when $Ar^1$ is represented by the general formula (g3) and $R^9$ in (g3) represents a single bond.

9. The organic compound according to claim 8, wherein q in the general formula (G1) is 2.

10. The organic compound according to claim 8, wherein:
q in the general formula (G1) is 2;
$X^2$ and $X^3$ each independently represent an oxygen atom or a sulfur atom;
$R^{12}$ and $R^{18}$ represent a single bond and $R^{10}$, $R^{11}$, $R^{13}$ to $R^{17}$, and $R^{19}$ to $R^{21}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms;
$R^{32}$ and $R^{38}$ represent a single bond and $R^{30}$, $R^{31}$, $R^{33}$ to $R^{37}$, and $R^{39}$ to $R^{41}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; and $R^{52}$ and $R^{58}$ represent a single bond and $R^{50}$, $R^{51}$, $R^{53}$ to $R^{57}$, and $R^{59}$ to $R^{61}$ each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

11. The organic compound according to claim 8, wherein a molecular weight is less than or equal to 1300.

12. A light-emitting device comprising the organic compound according to claim 8.

13. A light-emitting apparatus comprising the light-emitting device according to claim 12, and a transistor or a substrate.

14. An electronic device comprising the organic compound according to claim 8.

15. An organic compound represented by a general formula (G1-1),

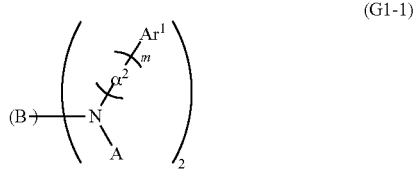

(G1-1)

wherein:

B represents a general formula (B1-1) or (B3-1);

$Ar^1$ is a substituted or unsubstituted aromatic hydrocarbon group having 6 to 25 carbon atoms, and A is a group represented by a general formula (g0);

m represents an integer of 0 to 2, and $\alpha^2$ is a substituted or unsubstituted divalent aromatic hydrocarbon group having 6 to 14 carbon atoms,

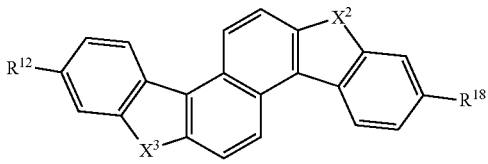

(B1-1)

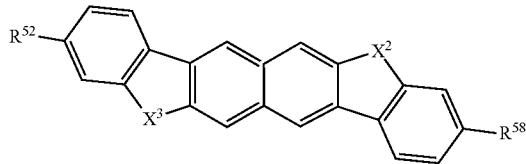

(B3-1)

wherein:

$X^2$ and $X^3$ each independently represent an oxygen atom or a sulfur atom, and $R^{12}$, $R^{18}$, $R^{52}$, and $R^{58}$ represent a single bond,

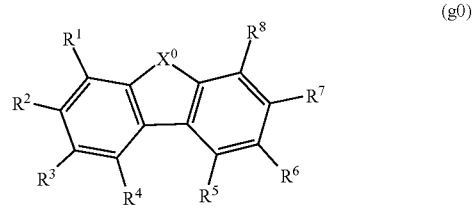

(g0)

wherein:

$X^0$ is an oxygen atom, a sulfur atom, or a nitrogen atom to which a substituted or unsubstituted phenyl group is bonded;

$R^2$ represents a single bond, and condensation occurs in at least one of combinations of $R^3$ and $R^4$, $R^5$ and $R^6$, $R^6$ and $R^7$, and $R^7$ and $R^8$ and a benzene ring is formed, and the others represent a hydrogen atom.

16. The organic compound according to claim 15, wherein a molecular weight is less than or equal to 1300.

17. A light-emitting device comprising the organic compound according to claim 15.

18. A light-emitting apparatus comprising the light-emitting device according to claim 17, and a transistor or a substrate.

19. An electronic device comprising the organic compound according to claim 15.

20. An organic compound represented by either of structural formulae,

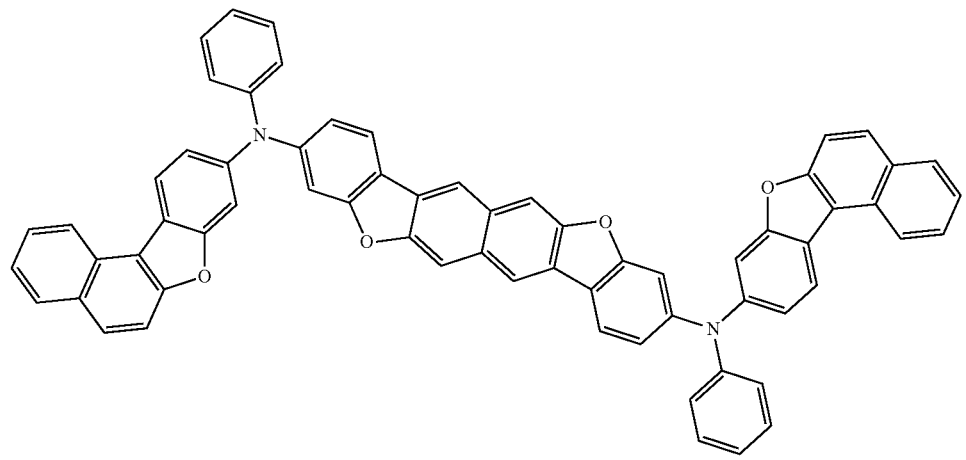

-continued
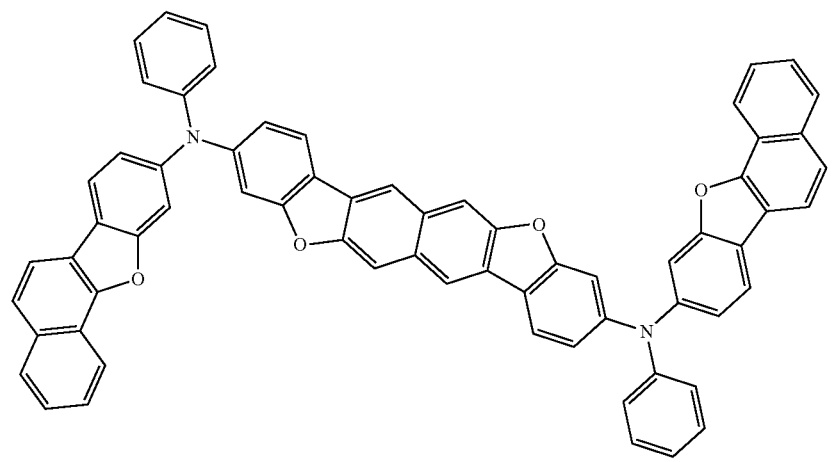
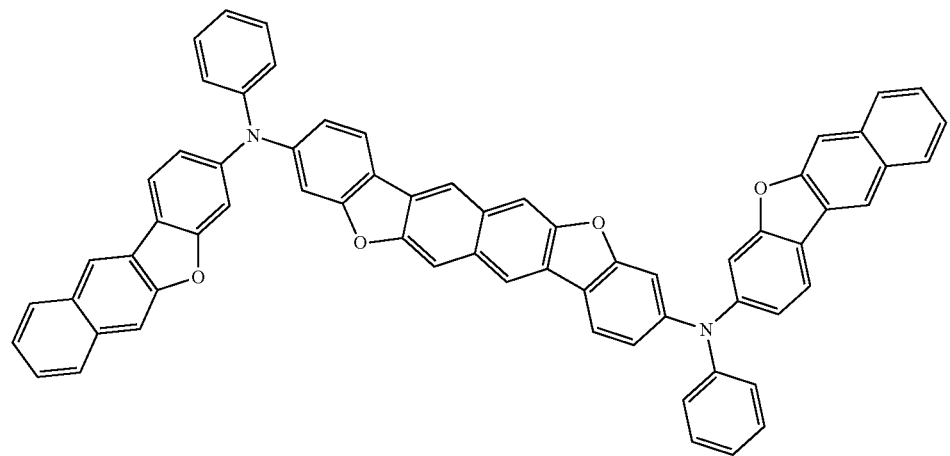
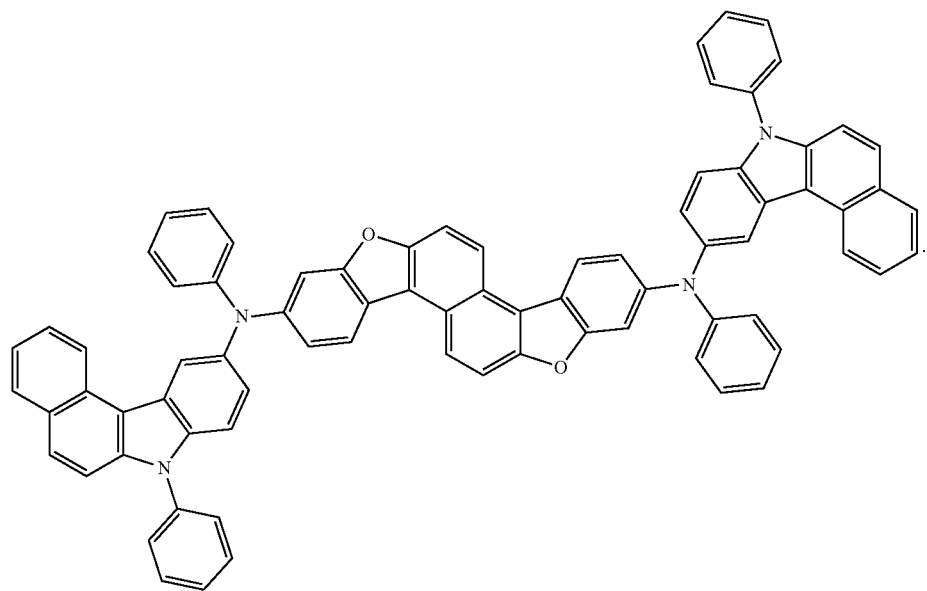 [SMILES: c1ccc(N(c2ccc3c(c2)oc2ccc4c(ccc5oc6cc(N(c7ccccc7)c7ccc8c(c7)c7c9ccccc9ccc7n8-c7ccccc7)ccc6c54)c23)c2ccc3c(c2)c2c4ccccc4ccc2n3-c2ccccc2)cc1]

21. A light-emitting device comprising the organic compound according to claim 20.

22. A light-emitting apparatus comprising the light-emitting device according to claim 21, and a transistor or a substrate.

23. An electronic device comprising the organic compound according to claim 20.

* * * * *